(12) United States Patent
Barry et al.

(10) Patent No.: US 7,972,777 B1
(45) Date of Patent: Jul. 5, 2011

(54) NUCLEIC ACID PROBE-BASED DIAGNOSTIC ASSAYS TARGETING SSRA GENES OF PROKARYOTIC AND EUKARYOTIC ORGANISMS

(75) Inventors: Thomas Gerard Barry, Kinvara (IE); Terence James Smith, Galway (IE)

(73) Assignees: Enterprise Ireland, Dublin (IE); National University of Ireland, Galway, Galway (IE)

( * ) Notice: Subject to any disclaimer, the term of this patent is extended or adjusted under 35 U.S.C. 154(b) by 823 days.

(21) Appl. No.: 09/959,964

(22) PCT Filed: May 15, 2000

(86) PCT No.: PCT/IE00/00066
§ 371 (c)(1),
(2), (4) Date: Jan. 31, 2002

(87) PCT Pub. No.: WO00/70086
PCT Pub. Date: Nov. 23, 2000

(30) Foreign Application Priority Data

May 14, 1999 (WO) .................. PCT/IE99/00043

(51) Int. Cl.
*C12Q 1/68* (2006.01)
*C12P 19/34* (2006.01)
(52) U.S. Cl. .......................... 435/6; 435/91.2
(58) Field of Classification Search ............ 435/6, 91.2
See application file for complete search history.

(56) References Cited

U.S. PATENT DOCUMENTS

| | | | |
|---|---|---|---|
| 6,348,315 B1 * | 2/2002 | Pluckthun et al. | 435/6 |
| 7,115,366 B1 * | 10/2006 | Felden | 435/6 |
| 2006/0216733 A1 | 9/2006 | Felden | |

FOREIGN PATENT DOCUMENTS

| | | |
|---|---|---|
| EP | A 0 395 292 | 10/1990 |
| WO | A 98/48008 | 10/1998 |
| WO | WO 00/59918 | 10/2000 |

OTHER PUBLICATIONS

Williams et al., Nucleic Acids Research, vol. 26, No. 1, pp. 163-165 (1998).
Zwieb et al., Nucleic Acids Research, vol. 26, No. 1, 166-167 (1998).
Sheridan et al., Applied and Environmental Microbiology, vol. 64, No. 4, pp. 1313-1318 (1998).
Watanabe et al., Biochimica and Biophysica Acta, vol. 1396, pp. 97-104 (1998).
Brown et al., Nucleic Acids Research, vol. 18, No. 9, p. 2820 (1990).
Chauhan et al., Molecular Microbiology, vol. 3, No. 11, pp. 1481-1485 (1989).
Ushida et al., Nucleic Acids Research, vol. 22, No. 16, pp. 3392-3396 (1994).
Williams et al., RNA, vol. 2, pp. 1306-1310 (1996).
Tjagi et al., Nucleic Acids Research, vol. 20, No. 1, p. 6. 138 (1991).
Felden et al., Biochimica and Biophysica Acta, vol. 1446, pp. 145-148 (1999).
Keiler, Kenneth C. et al., Science, vol. 271, pp. 990-993, 1996.
Matveeva, Olga et al., Nature Biotechnology, vol. 16, pp. 1374-1375, 1998.

* cited by examiner

*Primary Examiner* — Kenneth R. Horlick
(74) *Attorney, Agent, or Firm* — Birch, Stewart, Kolasch & Birch, LLP.

(57) ABSTRACT

Use of the ssrA gene or tmRNA, an RNA transcript of the ssrA gene, or fragments thereof as target regions in a nucleic acid probe assay for the detection and identification of prokaryotic and/or eukaryotic organisms is described. Nucleotide sequence alignment of tmRNA sequences from various organisms can be used to identify regions of homology and non-homology within the sequences which in turn can be used to design both genus specific and species specific oligonucleotide probes. These newly identified regions of homology and non-homology provide the basis of identifying and detecting organisms at the molecular level. Oligonucleotide probes identified in this way can be used to detect tmRNA in samples thereby giving an indication of the viability of non-viral organisms present in various sample types.

29 Claims, 20 Drawing Sheets

FIG. 1

```
L.m.  ACAGGGATAGTTCGAGCTTGAGTTGCGAGTCGGGGGATCGTCCTCGTTA
L.i.  ACAGGGATAGTTCGAGCTTGAGTTGCGAGTCGGGGGATCGTCCTCGTTA
L.mu. ACAGGGATAGTTCGAGCTTGAGTTGCGAGTCGGGGGATCGTCCTCGTTA
L.w.  ACAGGGATAGTTCGAGCTTGAGTTGCGAGTCGGGGGATCGTCCTCGTTA
L.g.  ACAGGGATAGTTCGAGCTTGAGTTGCGAGCCGGGGATCGGCC-CGTCA
      *********************

L8tm

```
L.m.   TCTGGGGTTAAATAGAGAGCTTAATCAGACTAGCTGAATGGAAGCCTGT
L.i.   TCTGAGGTTAAATAGAAGAGCTTAATCAGACTAGCTGAATGGAAGCCTGT
L.mu.  TCTGAGGTTAAATAGAAGAGCTTAATGAGACTAGCTGAATGGAAGCCTGT
L.w.   TCTGAGGTTAGTTGGAAGAGCTTAATCAGACTAGCTGAATGGAAGCCTGT
L.g.   TCTGGGGCAAACGAGAGAGAC

```
B.s.  ACAGGGATGGATCGAGCTTGAGCTGCGAGCCGAGAGG--CGATCTCGTAA
L.m.  ACAGGGATAGTTCGAGCTTGAGTTGCGAGTCGGAGTCGGGGGATCGTCCTCGTTA
      ****** *  * ******* ** ** * ** **   **  ****** *****

B.s.  ACACGCACTTAAATATAACTGGCAAAACTAACAGTTTAACCAAAACGTA
L.m.  TCA-ACG-TCAAAGCCAA-TAATA--ACTGGCAAAGAAAAACAAAACCTA
       **  *   *****  *  * *    ********  *  *** ** ***

B.s.  GCATTAGCTGCCTAATAAGC-GCAGCGAGACT---CTTCCTGACATTGCC
L.m.  GCTTTCGCTGCCTAATAAGCAGTAGCATAGCTGATCCTCCGTGCATCGCC
      ** ** ************* * ***  *** *  ** **  * *** ***

B.s.  TATGTGT--CTGTGAAGAGCACA-TCCAAGTAGGCTACGCTTGC--GTTC
L.m.  CATGTGCTACGCGGTAAGGGTCTCTCACTCTAAGTGGGCTACACTAGTAATCT
       *****      *   ** *  *  *  * ** ** ******* **  ****

B.s.  CCGTCTGAGAACGTA-AGAAGAGATGAA-CAGACTAGCTCTCGGAAGGCC
L.m.  CCGTCTGGGGGTTAAATAGAAGACTTAATCAGATCAGATCAGAAGCTGAATGGAAGCC
      *******    *  ** *** ***  ** *****  *  *   *** *****

B.s.  CGCCCCGCAGGCAAGAAGATGAGTGAAACCATAAATATGCAGGCTACGCTC
L.m.  TGTTACCGGGGCCGATGTTTATGCGAAAT-GCTAATACGGTGACTACGCTC
       *   ****  *    *  ** *** **   ***** *  * ********

B.s.  G-AGACGCTTAAGTTAATCGATGTTTCTGG
L.m.  GTAGATATTTAAGT--GCCGATATTTCTGG
      * *** * ******    ****  *****
```

FIG. 6

```
Ct1  GGGGGTGTAAAGGTTTCGACTTAGAAATGAAGCGTTAATTGCATGCGGAG
Ct2  GGGGGTGTAAAGGTTTCGACTTAGAAATGAAGCGTTAATTGCATGCGGAG
     **************************************************

Ct1  GGCGTTGGCTGGCCTCCTAAAAAGCCGACAAAACAATAAATGCCGAACCT
Ct2  GGCGTTGGCTGGCCTCCTAAAAAGCCGACAAAACAATAAATGCCGAACCT
     **************************************************

Ct1  AAGGCTGAATGCGAAATTATCAGCTTCGCTGATCTCGAAGATCTAAGAGT
Ct2  AAGGCTGAATGCGAAATTATCAGCTTCGCTGATCTTAATGATCTAAGAGT
     ***********************************  * ***********

Ct1  AGCTGCTTAATTAGCAAAGTTGTTACCTAAATACGGGTGACCCGGTGTTC
Ct2  TGCTGCTTAATTAGCAAAGTTGTTACCTAAGTACTACGGTAACCCGGTGTTC
      *****************************  *** *** **********

Ct1  GCGAGCTCCACCAGAGGTTTTCGAAACACCGTCATGTATCTGGTTAGAAC
Ct2  GCGAGCTCCACCAGAGGTTTTCGAAACGCCGTCATTTATCTGGTTAGAAT
     ***************************  ****** *************
```

FIG. 11A

```
Ct1  TTAGTCCTTTAATTCTCGAGGAAATGAGTTTGAAATTTAATGAGAGTCG
Ct2  TAGGGCCTTTAACTCTCAAGGGAACTAATTTGAATTTTAATGAGAGTCG
     *   *  ***  ***  ****** ****  *** ** **********

Ct1  TTAGTCTCTATAGGGGTTTCTAGCTGAGGAGACATAACGTATAGTAC-CT
Ct2  TTGGTCTCTATAGAGGTTTCTAGCTGAGGAGATATAACGTAAAATATTCT
     ** ********* ******************* ********  *** **

Ct1  AGGAACTAAGCATGTAGAGGTTAGCGGGAGTTTACTAAGGACGAGAGTT
Ct2  AGAAACTAAGCATGTAGAGGTTAGCGGGAGTTTACTAAGGACGAGAGTT
     ** **********************************************

Ct1  CGACTCTCTCCACCTCCACCA
Ct2  CGAATCTCTCCACCTCCACCA
     ***  ****************
```

FIG. 11B

```
Hp1  AGATTTCTGTGCGGCAGATAGCATGCCAAGCGCTGCTTGTAAAACAGCA
Hp2  AGATTTCTGTGCGCACAGATAGCATGCCAAGCGCTGCTTGTAAAACAGCA
     * * * * * * * * * * * * * * * * * * * * * * * * *

Hp1  ACAAAAATAACTGTAAACAACACAGATTACGCTCCAGCTTACGCTAAAGC
Hp2  ACAAAAATAACTGTAAACAACACAGATTACGCTCCAGCTTACGCTAAAGC
     * * * * * * * * * * * * * * * * * * * * * * * * *

Hp1  TGCGTGAGTTAATCTCCTTTGGAGCTGACTGATTAGAATTTCTAGCGT
Hp2  TGCGTGAGTTAATCTCCTTTGGAGCTGACTGATTAGAATTTCTAGCGT
     * * * * * * * * * * * * * * * * * * * * * * * * *

Hp1  TTTAATCGCTCCATAACCTAAGCTAGACGCTTTAAAAGGTGTTCGCC
Hp2  TTTAATCGCTCCATAACCTAAGCTAGACGCTTTAAAAGGTGGTTCGCC
     * * * * * * * * * * * * * * * * * * * * * * * * *

Hp1  TTTTAAACTAAGAAAACAAGAACTCTTGAAACTATCTTAAGTTTTAGAAA
Hp2  TTTTAAACTAAGAAAACAAGAACTCTTGAAACTATCTCAAGTTTTAGAAA
     * * * * * * * * * * * * * * * * * * * * * * * * *

Hp1  GTTGGACCAGAGCTAGTTTTAAGGCTAAAAACTAACCAATTTCTAAGC
Hp2  GTTGGACCAGAGCTAGTTTTAAGGCTAAAACCAACCAATTTCTAAGC
     * * * * * * * * * * * * * * * * * * * * * * * * *

Hp1  ATTGTAGAAGTTTGTGTTTAGGGCAAGATTTTTGGACTGGGG
Hp2  ATTGTAGAAGTTTGTGTTTAGGGCAAGATTTTTGGACTGGGG
     * * * * * * * * * * * * * * * * * * * * *
```

FIG. 12

```
Mc1  ACATAATGCTGATAGACAAACAGTAGCATTGGGGTATGCCCCTTACAGCG
Mc2  ACATAATGCTGATAGACAAACAGTAGCATTGGGGTATGCCCCTTACAGCG
     **************************************************

Mc1  CTAGGTTCAATAACCGACAAAGAAAATAACGAAGTGTTGGTAGAACCAAA
Mc2  CTAGGTTCAATAACCGACAAAGAAAATAACGAAGTGTTGGTAGATCCAAA
     *******************************************  *****

Mc1  TTTGATCATTAACCAACAAGCAAGTGTTAACTTTGCTTTTGCATAAGTAG
Mc2  TTTGATCATTAACCAACAAGCAAGTGTTAACTTTGCTTTTGCATAAGTAG
     **************************************************

Mc1  ATACTAAAGCTACAGCTGGTGAATAGTCATAGTTTGCTAGCTGTCATAGT
Mc2  ATACTAAAGCTACAGCTGGTGAATAGTCATAGTTTGCTAGCTGTCATAGT
     **************************************************

Mc1  TTATGACTCGAGGTTAAATCGTTCAATTTAACCTTTAAAAATAGAACTTG
Mc2  TTATGACTCGAGGTTAAATCGTTCAATTTAACCTTTAAAAATAGAACTTG
     **************************************************

Mc1  TTGTTTCCATGATTGTTTGTGATCAATTGGAAACAAGACAAAAATCCAC
Mc2  TGTTTCCATGATTGTTTGTGATCAATTGGAAACAAGACAAAAATCCAC
     *************************************************

Mc1  AAAACTAAAATGTAGAAGCTGTTGTTGTGTCCTTTATGGAAACGGGTTC
Mc2  AAAACTAAAATGTAGAAGCTGTTGTTGTGTCCTTTATGGAAACGGGTTC
     *************************************************
```

FIG. 13

```
Ng1  GGGGGTTGCGAAGCAGATGCGGGCATACCGGGGTCTCAGATTCCCGTAAA
Ng2  GGGGGTTGCGAAGCAGATGCGGGCATACCGGGGTCTCAGATTCCCGTAAA
     **************************************************

Ng1  ACACTGAATTCAAATAGTCGCAAACGACGAAACTTACGCTTAGCCGCTT
Ng2  ACACTGAATTCAAATAGTCGCAAACGACGAAACTTACGCTTAGCCGCTT
     *************************************************

Ng1  AAGGCTAGCCGTTGCAGCAGTCGGTCAATGGGCTGTGTGGCGAAAGCCAC
Ng2  AAGGCTAGCCGTTGCAGCAGTCGGTCAATGGGCTGTGTGGTGAAAGCCAC
     ****************************************:*********

Ng1  CGCAACGTCATCTTACATTGACTGGTTTCCAGCCGGGTTACTTGGCAGA
Ng2  CGCAACGTCATCTTACATTGACTGGTTTCCAGCCGGGTTACTTGGCAGA
     *************************************************

Ng1  AATAAGACTTAAGGTAACTGGTTTCCAAAAGGCCTGTTGTCGGCATGAT
Ng2  AATAAGACTTAAGGTAACTGGTTTCCAAAAGGCCTGTTGTCGGCATGAT
     *************************************************

Ng1  CGAAATAAGATTTCAAATAGACACAACTAAGTATGTAGAACGCTTTGTA
Ng2  CGAAATAAGATTTCAAATAGACACAACTAAGTATGTAGAACGCTTTGTA
     *************************************************

Ng1  GAGGACTTTCGGACGGGGG
Ng2  GAGGACTTTCGGACGGGGG
     *******************
```

FIG. 14

```
L.m1  CAAAGAAAAACAAAACCTAGCTTTCGCTGCCTAATAAGCAGTAGCATAGC
L.m2  CAAAGAAAAACAAAACCTAGCTTTCGCTGCCTAATAAGCAGTAGCATAGC
      **************************************************

L.m1  TGATCCTCCGTGCATCGCCCATGTCTACGGTAAGGGTCTCACTCTAAGT
L.m2  TGATCCTCCGTGCATCGCCCATGTCTACGGTAAGGGTCTCACTCTAAGT
      *************************************************

L.m1  GGGCTACACTAGTTAATCTCCGTCTGGGGTTAAATAGAAGAGCTTAATCA
L.m2  GGGCTACACTAGTTAATCTCCGTCTGAGGTTAAATAGAAGAGCTTAATCA
      *************************  ***********************

L.m1  GACTAGCTGAATGGAAGCCCTGTTACCGGGC

```
L.m1   CAAAGAAAAACAAAACCTAGCTTTCGCTGCCTAATAAGCAGTAGCATAGC
L.m2   CAAAGAAAAACAAAACCTAGCTTTCGCTGCCTAATAAGCAGTAGCATAGC
L.i    CAAAGAAAAACAAAACCTAGCTTTCGCTGCCTAATAAGCAGTAGCATAGC
       **************************************************

L.m1   TGATCCTCCGTGCATCGCCCATGTGCTACGGTAAGGGTCTCACTCTAAGT
L.m2   TGATCCTCCGTGCATCGCCCATGTGCTACGGTAAGGGTCTCACTCTAAGT
L.i    TGATCCTCCGTGCATCGCCCATGTGCTACGGTAAGGGTCTCACTCTAAGT
       **************************************************

L.m1   GGGCTACACTAGTTAATCTCCGTCTGGGGTTAAATAGAAGAGCTTAATCA
L.m2   GGGCTACACTAGTTAATCTCCGTCTGAGGTTAAATAGAAGAGCTTAATCA
L.i    GGGCTACACTAGTTAATCTCCGTCTGAGGTTAAATAGAAGAGCTTAATCA
       ************************* ************************

L.m1   GACTAGCTGAATGGAAGCCTGTTACCGGGCCGATGTTTATGCGAAATGCT
L.m2   GACTAGCTGAATGGAAGCCTGTTACCGGGCCGATGTTTATGCGAAATGCT
L.i    GACTAGCTGAATGGAAGCCTGTTACCGGGCCGATGTTTATGCGAAATGCT
       **************************************************

L.m1   AATACGGTGACTACGCTCGTAGATATTT
L.m2   AATACGGTGACTACGCTCGTAGATATTT
L.i    AATACGGTGACTACGCTCGTAGATATTC
       *************************** 
```

FIG. 16

NUCLEIC ACID PROBE-BASED DIAGNOSTIC ASSAYS TARGETING SSRA GENES OF PROKARYOTIC AND EUKARYOTIC ORGANISMS

This application is the national phase under 35 U.S.C. §371 of PCT International Application No. PCT/IE00/00066 which has an International filing date of May 15, 2000, which designated the United States of America and was published in English.

TECHNICAL FIELD

This invention relates to the identification of target sequences for use in nucleic acid assays for the detection and identification of prokaryotic and/or eukaryotic organisms.

BACKGROUND ART

The ssrA gene, which encodes a small stable high copy number RNA transcript (tmRNA), is found in all bacteria and has recently been identified in chloroplasts and diatoms. It has a dual function both as a tRNA and as an mRNA molecule and is involved in rescuing truncated mRNAs which have lost stop codons, facilitating trans-translation of truncated peptides prior to protease degradation (Keiler, K. C. et al. (1996), Science, 271, 990-993). The unique function of tmRNAs has directed researchers to analyse the relationship of the secondary structure of these molecules with their function. These studies have focussed on the conservation of the secondary structure of tmRNAs from different microorganisms, and on the evolutionary significance and functional relevance of such structural conservation. Studies were carried out by Matveeva, O et al (1998), Vol. 16, No. 13, 1374-1375 to investigate oligonucleotide binding to RNA molecules using tmRNA as a model of RNA containing secondary structure. The studies did not have as their objective the identification of sites in tmRNA with the goal of designing antisense oligonucleotide for therapeutic purposes.

The number of nucleic acid targets/probes for bacterial diagnostics is currently limited. As such, the need to identify and characterise novel DNA and RNA targets for diagnostic purposes is now seen as a priority. Target nucleic acid sequences for the development of probes can be for example, plasmids, ribosomal RNA genes, intergenic regions, genes encoding virulence factors or random genomic DNA fragments. In addition, a number of RNA molecules have been described which are used as targets for RNA-based detection for example, ribosomal RNA and RNase P.

The basis of any nucleic acid-based probe assay is the requirement for well characterised nucleic acid sequences which are present in all prokaryotes and eukaryotes under study. For reliable detection of a prokaryotic or eukaryotic organism, the nucleic acid probes used should be highly specific (i.e. not cross-react with nucleic acids from other organisms) and highly sensitive (i.e. most or all strains of the organism to be detected should react with the probe). Therefore, preferred target sequences would be present in all strains of the organism concerned. Such sequences would have significant sequence variability to allow differentiation of the species concerned from other closely related species but, on the other hand, have sufficient sequence conservation to allow the detection of all strains of the species concerned. In general, the precise identification of a nucleic acid sequence, which could form the basis of a specific nucleic acid probe assay, is tedious, difficult and uncertain. To date there are few general approaches which would facilitate the development of nucleic acid probes for a wide variety of microorganisms. The nucleic acid sequences which have been identified as potentially useful targets for probe development are, for example, rRNA genes and RNA, and the rRNA 16S/23S intergenic region.

The majority of nucleic acid probe/target assays centre on the high copy number ribosomal RNAs (rRNA) and rRNA 16S/23S spacer regions (European Patent No. 0 395 292) of the bacterial cell for the purposes of detection and identification. A number of successful commercial bacterial diagnostic kits have been marketed based on these rRNA probes/targets for the detection of a variety of microrganisms. These include a range of commercial probe kits based on the 16S rRNA gene marketed by Gen-probe Inc. San Diego Calif., and DNA probes based on the 16S/23S spacer region marketed by Innogenetics N.V. Ghent, Belgium. However, many of these diagnostic kits have limitations, including lack of sensitivity due to low copy-number target sequences and lack of specificity due to sequence identity between closely related organisms in many cases.

Nucleic acid-based methods that could be applied directly to samples to give an indication of the viability of any microbes present therein would be of enormous significance for food, industrial, environmental and medical applications.

A disadvantage of DNA-based methods is that they do not distinguish between living and dead organisms. Some studies have focussed on using rRNA and mRNA as indicators of cell viability (Sheridan, G. E. C. et al. (1998) Applied and Environmental Microbiology, 64, 1313-1318). However, these sequences are not satisfactory targets as rRNA and mRNA can be present in bacterial cells up to 48 hours after cell death.

With the advent of nucleic acid based microarray-like formatting, incorporating simultaneous monitoring of multiple nucleic acid targets, there is now a clear requirement to identify and characterise novel nucleic acid sequences for use as probes and/or target regions to detect and identify viable prokaryotic and eukaryotic cells.

DISCLOSURE OF INVENTION

The invention provides use of the ssrA gene or a fragment thereof as a target region in a nucleic acid probe assay for a prokaryotic or eukaryotic organism.

Thus, the invention has application in relation to all organisms other than viruses.

No other nucleic acid probe assay has been reported which uses regions of the ssrA gene as a target region to detect and identify species of prokaryotes and eukaryotes with the attendant advantages.

According to one embodiment of the invention a fragment of the ssrA gene molecule corresponding to a region of high homology from the 5' end of the DNA molecule can be used as a universal target region.

In an alternative embodiment of the invention a fragment of the ssrA gene molecule corresponding to a region of high homology from the 3' end of the DNA molecule can be used as a universal target region.

In a further embodiment of the invention a fragment of the ssrA gene molecule corresponding to a region of low homology can be used as a target region in a nucleic acid probe assay to distinguish between species.

In a still further embodiment of the invention a fragment of the ssrA gene molecule corresponding to a region of low homology can be used as a target region for the generation of a genus specific probe.

As hereinafter described nucleotide sequence alignments of ssrA gene sequences from different organisms show that the 5' and 3' regions of these molecules demonstrate a high degree of homology and are therefore useful as universal target regions. The ssrA genes also demonstrate a more significant degree of nucleotide sequence variability between closely related organisms than any other bacterial high copy number RNA. These variable regions are ideal targets for nucleic acid assays to distinguish between species.

The invention also provides use of tmRNA, an RNA transcript of the ssrA gene, or a fragment thereof as a target region in a nucleic acid probe assay for a prokaryotic or eukaryotic organism.

According to one embodiment of this aspect of the invention a fragment of a tmRNA molecule corresponding to a region of high homology from the 5' end of the tmRNA molecule can be used as a universal target region.

Alternatively, a fragment of a tmRNA molecule corresponding to a region of high homology from the 3' end of the tmRNA molecule can be used as a universal target region.

According to a further embodiment of this aspect of the invention a fragment of a tmRNA molecule corresponding to a region of low homology can be used as a target region in a nucleic acid probe assay to distinguish between species.

According to a still further embodiment a fragment of a tmRNA molecule corresponding to a region of low homology can be used as a target region for the generation of a genus specific probe.

The nucleic acid probe (DNA or RNA) in accordance with the invention typically consists of at least 10 nucleotides of the ssrA gene and/or tmRNA transcript or their complementary sequence and is used in a nucleic acid probe hybridisation assay for a prokaryotic or eukaryotic organism. Probe hybridisation to its complementary sequence is typically revealed by labelling the nucleic acid probe with a radioactive or non-radioactive (e.g. colorimetric or fluorimetric) label.

In preferred embodiments said ssrA gene fragment or said tmRNA fragment can be used as the basis of a primer to be used in an amplification procedure.

Universal oligonucleotide primers directed to the 5' and 3' regions of either the ssrA gene or the tmRNA sequence can be used in accordance with the invention to amplify the ssrA gene or its encoding tmRNA from a wide variety of bacteria, facilitating amplification of a wide range of organisms simultaneously, whilst also enabling specific nucleic acid probe hybridisation and detection.

Preferably, the product of the amplification procedure is used as a target region in a nucleic probe assay.

Further, preferably, a cDNA transcript of a tmRNA molecule is used as a probe in a nucleic acid hybridisation assay.

Such assays can be carried out in vitro or in situ.

The target region as defined herein can be used as the basis of an assay for distinguishing between living and dead prokaryotic or eukaryotic organisms.

In contrast to rRNA and mRNA which can be present in bacterial cells following cell death, tmRNA is rapidly degraded in dead organisms. Thus, tmRNA can be a useful target for distinguishing between living and dead prokaryotic or eukaryotic organisms either directly by nucleic acid probe hybridisation to isolated bacterial RNA, or by combined RNA amplification and nucleic acid probe hybridisation to the amplified product.

Preferably, the target region is used in a multiple probe format for broad scale detection and/or identification of prokaryotic or eukaryotic organisms.

An ssrA gene probe or a tmRNA transcript probe in accordance with the invention can be linked to a microarray gene chip system for the broad scale high throughput detection and identification of prokaryotic or eukaryotic organisms.

A target region in accordance with the invention can also be used as a probe in an assay to detect prokaryotic or eukaryotic organisms in a sample of matter.

Such a sample of matter can include biological samples such as samples of tissue from the respiratory tract, the urogenital tract or the gastrointestinal tract, or body fluids such as blood and blood fractions, sputum or cerebrospinal fluid.

An assay in accordance with the invention can also be carried out on food samples, environmental samples including air, water, marine and soil samples, and plant and animal derived samples.

According to the invention a fragment of the ssrA gene or the tmRNA transcript can also be used in an assay to obtain a DNA profile of a prokaryotic or eukaryotic organism and, thereby, distinguish between strains of the same species.

Nucleic acid sequence alignments have shown that sequence variation occurs in the ssrA gene and the tmRNA transcript within individual species. This intra-species sequence variation can be used to distinguish between strains of the same species for epidemiology, tracing of infectious agents for example, in outbreaks, or for population studies.

Other applications of the invention include the use of the ssrA gene, the tmRNA transcript or a DNA sequence complementary thereto, or a fragment thereof, to design an agent directed against infectious prokaryotic or eukaryotic organisms for therapeutic purposes.

Such agents can include antisense mRNA or oligonucleotides, ribozymes, and antagonistic peptides and are suitable for use in any kind of medical condition.

Thus, the invention can be used for the detection of viable organisms only in biological samples using the tmRNA target. Thus, during and following any anti-infectious agent drug treatment, the tmRNA target can be used to monitor the efficacy of the therapy on those specific infectious agents (e.g. antimicrobial and/or anti-parasitic treatments).

In one embodiment, the target region is used to monitor the efficacy of drug therapies against infectious agents.

In another embodiment, the target region is used to monitor the viability and level of health-promoting organisms in the gastrointestinal tract.

This aspect of the invention relates, for example, to the introduction into the gut flora of health-promoting (probiotic) organisms contained in for example yoghurt or other food to improve health. There is an interest and need to continuously monitor the presence and levels of these organisms to ensure their continued function in promoting health. The tmRNA region can be used as a target to detect viable organisms, for example in faeces, so as to monitor the presence of the health promoting organisms.

In a further embodiment, the assay is used for the quantification of prokaryotic or eukaryotic organisms.

When using probe hybridisation and/or in vitro amplification to detect organisms in a sample it is possible to determine the number of organisms present, based on the signal intensity. Real-time methods of in vitro amplification can also be used to enable the quantification of organisms in a sample. Thus, the ability to quantify the number of organisms in a sample can be important in clinical situations for treatment purposes, for example for antibiotic or other treatments or for monitoring treatment efficacy.

A still further application of the invention is the use of a database of ssrA gene sequences to identify a prokaryotic or eukaryotic organism.

The invention provides a variety of probes for the 5' and 3' homologous regions and the variable regions of the ssrA gene and tmRNA sequences, the probes being derived from these sequences or sequences complementary thereto. Representative sequences are as follows:

*Actinobacillus actinomycetemcomitans* ssrA

GGGGCTGATTCTGGATTCGACGGGATTAGCGAAGCCCGAAGTGC
ACGTCGAGGTGCGGTAGGCCTCGTAAATAAACCGCAAAAAAATA
GTCGCAAACGACGAACAATACGCTTTAGCAGCTTAATAACCTGC
CTTTAGCCTTCGCTCCCCAGCTTCCGCTCGTAAGACGGGGATAAA
GCGGAGTCAAACCAAAACGAGATCGTGTGGAAGCCACCGTTTGA
GGATCGAAGCATTAAATTAAATCAAAGTAGCTTAATTGTCGCGT
GTCCGTCAGCAGGATTAAGTGAATTTAAAGACCGGACTAAACGT
GTAGTGCTAACGGCAGAGGAATTTCGGACGGGGGTTCAACTCCC
CCCAGCTCCACCA SEQ ID NO: 1

*Actinobacillus actinomycetemcomitans* tmRNA

GGGGCUGAUUCUGGAUUCGACGGGAUUAGCGAAGCCCGAAGU
GCACGUCGAGGUGCGGUAGGCCUCGUAAAUAAACCGCAAAAAA
AUAGUCGCAAACGACGAACAAUACGCUUUAGCAGCUUAAUAAC
CUGCCUUUAGCCUUCGCUCCCCAGCUUCCGCUCGUAAGACGGG
GAUAAAGCGGAGUCAAACCAAAACGAGAUCGUGUGGAAGCCA
CCGUUUGAGGAUCGAAGCAUUAAAUUAAAUCAAAGUAGCUUA
AUUGUCGCGUGUCCGUCAGCAGGAUUAAGUGAAUUUAAAGAC
CGGACUAAACGUGUAGUGCUAACGGGAGAGGAAUUUCGGACG
GGGGUUCAACUCCCCCCAGCUCCACCA SEQ ID NO: 2

*Aeromonas salmonicida* ssrA, Internal Partial

AAGATTCACGAAACCCAAGGTGCATGCCGAGGTGCGGTAGGCCT
CGTTAACAAACCGCAAAAAAATAGTCGCAAACGACGAAAACTA
CGCACTAGCAGCtTAATAACCTGCATAGAGCCCTTCTACCCTAGC
TTGCCTGTGTCCTAGGGAATCGGAAGGTCATCCTTCACAGGATC
GTGTGGAAGTCCTGCTCGGGGCGAAGCATTAAAACCAATCGAG
CTAGTCAATTCGTGGCGTGTCTCTCCGCAGCGGGTTGGCGAATGT
AAAGAGTGACTAAGCATGTAGTACCGAGGATGTAGTAATTTTGG
ACGGGG SEQ ID NO: 3

*Aeromonas salmonicida* tmRNA, Internal Partial

AAGAUUCACGAAACCCAAGGUGCAUGCCGAGGUGCGGUAGGCC
UCGUUAACAAACCGCAAAAAAAUAGUCGCAAACGACGAAAACU
ACGCACUAGCAGCUUAAUAACCUGCAUAGAGCCCUUCUACCCU
AGCUUGCCUGUGUCCUAGGGAAUCGGAAGGUCAUCCUUCACAG
GAUCGUGUGGAAGUCCUGCUCGGGGCGAAGCAUUAAAACCA
AUCGAGCUAGUCAAUUCGUGGCGUGUCUCUCCGCAGCGGGUUG
GCGAAUGUAAAGAGUGACUAAGCAUGUAGUACCGAGGAUGUA
GUAAUUUUGGACGGGG SEQ ID NO: 4

*Alcaligenes eutrophus* ssrA

TGGGCCGACCTGGTTTCGACGTGGTTACAAAGCAGTGAGGCATA
CCGAGGACCCGTCACCTCGTTAATCAATGGAATGCAATAACTGC
TAACGACGAACGTTACGCACTCGCTTAATTGCGGCCGTCCTCGC
ACTGGCTCGCTGACGGGCTAGGGTCGCAAGACCACGCGAGGTAT
TTACGTCAGATAAGCTCCGGAAGGGTCACGAAGCCGGGACGA
AAACCTAGTGACTCGCCGTCGTAGAGCGTGTTCGTCCGATGCGC
CGGTTAAATCAAATGACAGAACTAAGTATGTAGAACTCTCTGTG
GAGGGCTTACGGACGCGGGTTCGATTCCCGCCGGCTCCACCA
SEQ ID NO: 5

*Alcaligenes eutrophus* tmRNA

UGGGCCGACCUGGUUUCGACGUGGUUACAAAGCAGUGAGGCA
UACCGAGGACCCGUCACCUCGUUAAUCAAUGGAAUGCAAUAAC
UGCUAACGACGAACGUUACGCACUCGCUUAAUUGCGGCCGUCC
UCGCACUGGCUCGCUGACGGGCUAGGGUCGCAAGACCACGCGA
GGUAUUUACGUCAGAUAAGCUCCGGAAGGGUCACGAAGCCGG
GACGAAAACCUAGUGACUCGCCGUCGUAGAGCGUGUUCGUCC
GAUGCGCCGGUUAAAUCAAAUGACAGAACUAAGUAUGUAGAA
CUCUCUGUGGAGGGCUUACGGACGCGGGUUCGAUUCCCGCCGG
CUCCACCA SEQ ID NO: 6

*Aquifex aeolicus* ssrA

GGGGGCGGAAAGGATTCGACGGGGACAGGCGGTCCCCGAGGAG
CAGGCCGGGTGGCTCCCGTAACAGCCGCTAAAACAGCTCCCGAA
GCTGAACTCGCTCTCGCTGCCTAATTAAACGGCAGCGCGTCCCC
GGTAGGTTTGCGGGTGGCCTACCGGAGGGCGTCAGAGACACCCG
CTCGGGCTACTCGGTCGCACGGGGCTGAGTAGCTGACACCTAAC
CCGTGCTACCCTCGGGGAGCTTGCCCGTGGGCGACCCGAGGGGA
AATCCTGAACACGGGCTAAGCCTGTAGAGCCTCGGATGTGGCCG
CCGTCCTCGGACGCGGGTTCGATTCCCGCCGCCTCCACCA
SEQ ID NO: 7

*Aquifex aeolicus* tmRNA

GGGGGCGGAAAGGAUUCGACGGGACAGGCGGUCCCCGAGGA
GCAGGCCGGGUGGCUCCCGUAACAGCCGCUAAAACAGCUCCCG
AAGCUGAACUCGCUCUCGCUGCCUAAUUAAACGGCAGCGCGUC
CCCGGUAGGUUUGCGGGUGGCCUACCGGAGGGCGUCAGAGACA
CCCGCUCGGGCUACUCGGUCGCACGGGGCUGAGUAGCUGACAC
CUAACCCGUGCUACCCUCGGGGAGCUUGCCCGUGGGCGACCCG
AGGGGAAAUCCUGAACACGGGCUAAGCCUGUAGAGCCUCGGAU

```
GUGGCCGCCGUCCUCGGACGCGGGUUCGAUUCCCGCCGCCUCC

ACCA SEQ ID NO: 8
```
*Bacillus megaterium* ssrA, Internal Partial

```
AGGGTAGTTCGAGCTTAGGTMCGAGTCGAGGAGATGGCCTCGT

TAAAACATCAACGCCAATAATAACTGGCAAATCTAACAATAACT

TCGCTTTAGCTGCATAATAGTAGCTTAGCGTTCCTCCCTCCATCG

CCCATGTGGTAGGGIAAGGGACTCACTTTAAGTGGGCTACGCCG

GAGTTCGCCGTCTGAGGACGAAGGAAGAGAATAATCAGACTAG

CGACTGGGACGCCTGTTGGTAGGCAGAACAGCTCGCGAATGATC

AATATGCCAACTACACTCGTAGACGCTTAAGTGGCCATATTTCTG

GACGTGG SEQ ID NO: 9
```
*Bacillus megaterium* tmRNA, Internal Partial

```
AGGGUAGUUCGAGCUUAGGUUGCGAGUCGAGGAGAUGGCCUC

GUUAAAACAUCAACGCCAAUAAUAACUGGCAAAUCUAACAAU

AACUUCGCUUUAGCUGCAUAAUAGUAGCUUAGCGUUCCUCCCU

CCAUCGCCCAUGUGGUAGGGUAAGGGACUCACUUUAAGUGGGC

UACGCCGGAGUUCGCCGUCUGAGGACGAAGGAAGAGAAUAAU

CAGACUAGCGACUGGGACGCCUGUUGGUAGGCAGAACAGCUCG

CGAAUGAUCAAUAUGCCAACUACACUCGUAGACGCUUAAGUGG

CCAUAUUUCUGGACGUGG SEQ ID NO: 10
```
*Bacillus subtilis* ssrA

```
GGGGACGTTACGGATTCGACAGGGATGGATCGAGCTTGAGCTGC

GAGCCGAGAGGCGATCTCGTAAACACGCACTTAAATATAACTGG

CAAAACTAACAGTTTTAACCAAAACGTAGCATTAGCTGCCTAAT

AAGCGCAGCGAGCTCTTCCTGACATTGCCTATGTGTCTGTGAAG

AGCACATCCAAGTAGGCTACGCTTGCGTTCCCGTCTGAGAACGT

AAGAAGAGATGAACAGACTAGCTCTCGGAAGGCCCGCCCGCAG

GCAAGAAGATGAGTGAAACCATAAATATGCAGGCTACGCTCGTA

GACGCTTAAGTAATCGATGTTTCTGGACGTGGGTTCGACTCCCAC

CGTCTCCACCA SEQ ID NO: 11
```
*Bacillus subtilis* tmRNA

```
GGGGACGUUACGGAUUCGACAGGGAUGGAUCGAGCUUGAGCU

GCGAGCCGAGAGGCGAUCUCGUAAACACGCACUUAAAUAUAAC

UGGCAAAACUAACAGUUUUAACCAAAACGUAGCAUUAGCUGCC

UAAUAAGCGCAGCGAGCUCUUCCUGACAUUGCCUAUGUGUCUG

UGAAGAGCACAUCCAAGUAGGCUACGCUUGCGUUCCCGUCUGA

GAACGUAAGAAGAGAUGAACAGACUAGCUCUCGGAAGGCCCGC

CCGCAGGCAAGAAGAUGAGUGAAACCAUAAAUAUGCAGGCUA

CGCUCGUAGACGCUUAAGUAAUCGAUGUUUCUGGACGUGGGU

UCGACUCCCACCGUCUCCACCA SEQ ID NO: 12
```
*Bordetella pertussis* ssrA

```
GGGGCCGATCCGGATTCGACGTGGGTCATGAAACAGCTCAGGGC

ATGCCGAGCACCAGTAAGCTCGTTAATCCACTGGAACACTACAA

ACGCCAACGACGAGCGTCTCGCTCTCGCCGCTTAAGCGGTGAGC

CGCTGCACTGATCTGTCCTTGGGTCAGGCGGGGAAGGCAACTT

CACAGGGGGCAACCCCCGAACCGCAGCAGCGACATTCACAAGGA

ATCGGCCACCGCTGGGGTCACACGGCGTTGGTTTAAATTACGTG

AATCGCCCTGGTCCGGCCCGTCGATCGGCTAAGTCCAGGGTTAA

ATCCAAATAGATCGACTAAGCATGTAGAACTGGTTGCGGAGGGC

TTGCGGACGGGGGTTCAATTCCCCCCGGCTCCACCA

SEQ ID NO: 13
```
*Bordetella pertussis* tmRNA

```
GGGGCCGAUCCGGAUUCGACGUGGGUCAUGAAACAGCUCAGGG

CAUGCCGAGCACCAGUAAGCUCGUUAAUCCACUGGAACACUAC

AAACGCCAACGACGAGCGUCUCGCUCUCGCCGCUUAAGCGGUG

AGCCGCUGCACUGAUCUGUCCUUGGGUCAGGCGGGGAAGGCA

ACUUCACAGGGGCAACCCCCGAACCGCAGCAGCGACAUUCACA

AGGAAUCGGCCACCGCUGGGGUCACACGGCGUUGGUUUAAAUU

ACGUGAAUCGCCCUGGUCCGGCCCGUCGAUCGGCUAAGUCCAG

GGUUAAAUCCAAAUAGAUCGACUAAGCAUGUAGAACUGGUUG

CGGAGGGCUUGCGGACGGGGGUUCAAUUCCCCCCGGCUCCACC

A SEQ ID NO: 14
```
*Borrelia burgdorferi* ssrA

```
GGGGATGTTTTGGATTTGACTGAAAATGTTAATATTGTAAGTTGC

AGGCAGAGGGAATCTCTTAAAACTTCTAAAATAAATGCAAAAAA

TAATAACTTTACAAGCTCAAATCTTGTAATGGCTGCTTAAGTTAG

CAGAGGGTTTTGTTGAATTTGGCTTTGAGGTTCACTTATACTCTT

TTCGACATCAAAGCTTGCTTAAAAATGTTTTCAAGITGATTTTTA

GGGACTTTTATACTTGAGAGCAATTTGGTGGTTTGCTAGTATTTC

CAAACCATATTGCTTAATAAAATACTAGATAAGCTTGTAGAAGC

TTATAGTATTATTTTTAGGACGCGGGTTCAATTCCCGCCATCTCC

ACCA SEQ ID NO: 15
```
*Borrelia burgdorferi* tmRNA

```
GGGGAUGUUUUGGAUUUGACUGAAAAUGUUAAUAUUGUAAGU

UGCAGGCAGAGGGAAUCUCUUAAAACUUCUAAAAUAAAUGCA
```

-continued

AAAAAUAAUAACUUUACAAGCUCAAAUCUUGUAAUGGCUGCU

UAAGUUAGCAGAGGGUUUUGUUGAAUUUGGCUUUGAGGUUCA

CUUUAUACUCUUUUCGACAUCAAAGCUUGCUUAAAAAUGUUUU

CAAGUUGAUUUUUAGGGACUUUUAUACUUGAGAGCAAUUUGG

UGGUUUGCUAGUAUUUCCAAACCAUAUUGCUUAAUAAAAUAC

UAGAUAAGCUUGUAGAAGCUUUAUAGUAUUAUUUUUAGGACGC

GGGUUCAAUUCCCGCCAUCUCCACCA SEQ ID NO: 16

*Campylobacter jejuni* ssrA

GGGAGCGACTTGGCTTCGACAGGAGTAAGTCTGCTTAGATGGCA

TGTCGCTTTGGGCAAAGCGTAAAAAGCCCAAATAAAATTAAACG

CAAACAACGTTAAATTCGCTCCTGCTTACGCTAAAGCTGCGTAA

GTTCAGTTGAGCCTGAAATTTAAGTCATACTATCTAGCTTAATTT

TCGGTCATTTTTGATAGTGTAGCCTTGCGTTTGACAAGCGTTGAG

GTGAAATAAAGTCTTAGCCTTGCTTTTGAGTTTTGGAAGATGAGC

GAAGTAGGGTGAAGTAGTCATCTTTGCTAAGCATGTAGAGGTCT

TTGTGGGATTATTTTTGGACAGGGGTTCGATTCCCCTCGCTTCCA

CCA SEQ ID NO: 17

*Campylobacter jejuni* tmRNA

GGGAGCGACUUGGCUUCGACAGGAGUAAGUCUGCUUAGAUGG

CAUGUCGCUUUGGGCAAAGCGUAAAAAGCCCAAAUAAAAUUA

AACGCAAACAACGUUAAAUUCGCUCCUGCUUACGCUAAAGCUG

CGUAAGUUCAGUUGAGCCUGAAAUUUAAGUCAUACUAUCUAG

CUUAAUUUUCGGUCAUUUUUGAUAGUGUAGCCUUGCGUUUGA

CAAGCGUUGAGGUGAAAUAAAGUCUUAGCCUUGCUUUUGAGU

UUUGGAAGAUGAGCGAAGUAGGGUGAAGUAGUCAUCUUUGCU

AAGCAUGUAGAGGUCUUUGUGGGAUUAUUUUUGGACAGGGGU

UCGAUUCCCCUCGCUUCCACCA SEQ ID NO: 18

*Chlamydia trachomatis* (D/UW-3/CX) ssrA

GGGGGTGTAAAGGTTTCGACTTAGAAATGAAGCGTTAATTGCAT

GCGGAGGGCGTTGGCTGGCCTCCTAAAAAGCCGACAAAACAATA

AATGCCGAACCTAAGGCTGAATGCGAAATTATCAGCTTCGCTGA

TCTCGAAGATCTAAGAGTAGCTGCTTAATTAGCAAAGTTGTTACC

TAAATACGGGTGACCCGGTGTTCGCGAGCTCCACCAGAGGTTTT

CGAAACACCGTCATGTATCTGGTTAGAACTTAGGTCCTTTAATTC

TCGAGGAAATGAGTTTGAAATTTAATGAGAGTCGTTAGTCTCTAT

AGGGGTTTCTAGCTGAGGAGACATAACGTATAGTACCTAGGAAC

TAAGCATGTAGAGGTTAGCGGGGAGTTTACTAAGGACGAGAGTT

CGACTCTCTCCACCTCCACCA SEQ ID NO: 19

*Chlamydia trachomatis* (D/UW-3/CX) tmRNA

GGGGGUGUAAAGGUUUCGACUUAGAAAUGAAGCGUUAAUUGC

AUGCGGAGGGCGUUGGCUGGCCUCCUAAAAAGCCGACAAAACA

AUAAAUGCCGAACCUAAGGCUGAAUGCGAAAUUAUCAGCUUC

GCUGAUCUCGAAGAUCUAAGAGUAGCUGCUUAAUUAGCAAAG

UUGUUACCUAAAUACGGGUGACCCGGUGUUCGCGAGCUCCACC

AGAGGUUUUCGAAACACCGUCAUGUAUCUGGUUAGAACUUAG

GUCCUUUAAUUCUCGAGGAAAUGAGUUUGAAAUUUAAUGAGA

GUCGUUAGUCUCUAUAGGGGUUUCUAGCUGAGGAGACAUAAC

GUAUAGUACCUAGGAACUAAGCAUGUAGAGGUUAGCGGGGAG

UUUACUAAGGACGAGAGUUCGACUCUCUCCACCUCCACCA

SEQ ID NO: 20

*Chlamydia trachomatis* (Mouse Pneumonitis) ssrA

GGGGGTGTAAAGGTTTCGACTTAGAAATGAAGCGTTAATTGCAT

GCGGAGGGCGTTGGCTGGCCTCCTAAAAAGCCGACAAAACAATA

AATGCCGAACCTAAGGCTGAATGCGAAATTATCAGCTTCGCTGA

TCTTAATGATCTAAGAGTTGCTGCTTAATTAGCAAAGTTGTTACC

TAAGTACTGGTAACCCGGTGTTCGCGAGCTCCACCAGAGGTTTTC

GAAACGCCGTCATTTATCTGGTTAGAATTAGGGCCTTTTAACTCT

CAAGGGAACTAATTTGAATTTTAATGAGAGTCGTTGGTCTCTATA

GAGGTTTCTAGCTGAGGAGATATAACGTAAAATATTCTAGAAAC

TAAGCATGTAGAGGTTAGCGGGGAGTTTACTAAGGACGAGAGTT

CGAATCTCTCCACCTCCACCA SEQ ID NO: 21

*Chlamydia trachomatis* (Mouse Pneumonitis) tmRNA

GGGGGUGUAAAGGUUUCGACUUAGAAAUGAAGCGUUAAUUGC

AUGCGGAGGGCGUUGGCUGGCCUCCUAAAAAGCCGACAAAACA

AUAAAUGCCGAACCUAAGGCUGAAUGCGAAAUUAUCAGCUUC

GCUGAUCUUAAUGAUCUAAGAGUUGCUGCUUAAUUAGCAAAG

UUGUUACCUAAGUACUGGUAACCCGGUGUUCGCGAGCUCCACC

AGAGGUUUUCGAAACGCCGUCAUUUAUCUGGUUAGAAUUAGG

GCCUUUUAACUCUCAAGGGAACUAAUUUGAAUUUUAAUGAGA

GUCGUUGGUCUCUAUAGAGGUUUCUAGCUGAGGAGAUAUAAC

GUAAAAUAUUCUAGAAACUAAGCAUGUAGAGGUUAGCGGGGA

GUUUACUAAGGACGAGAGUUCGAAUCUCUCCACCUCCACCA

SEQ ID NO: 22

*Chlorobium tepidum* ssrA

GGGGATGACAGGCTATCGACAGGATAGGTGTGAGATGTCGTTGC

ACTCCGAGTTTCAGCATGGACGGACTCGTTAAACAAGTCTATGT

```
ACCAATAGATGCAGACGATTATTCGTATGCAATGGCTGCCTGAT

TAGCACAAGTTAATTCAGAAGCCATCGTCCTGCGGTGAATGCGC

TTACTCTGAAGCCGCCGGATGGCATAACCCGCGCTTGAGCCTAC

GGGTTCGCGCAAGTAAGCTCCGTACATTCATGCCCGAGGGGGTG

TGCGGGTAACCAATCGGGATAAGGGGACGAACGCTGCTGGCGGT

GTAATCGGACCACGAAAAACCAACCACCAGAGATGAGTGTGGT

AACTGCATCGAGCAGTGTCCTGGACGCGGGTTCAAGTCCCGCCA

TCTCCACCA SEQ ID NO: 23
```

*Chlorobium tepidum* tmRNA

```
GGGGAUGACAGGCUAUCGACAGGAUAGGUGUGAGAUGUCGUU

GCACUCCGAGUUUCAGCAUGGACGGACUCGUUAAACAAGUCUA

UGUACCAAUAGAUGCAGACGAUUAUUCGUAUGCAAUGGCUGC

CUGAUUAGCACAAGUUAAUUCAGAAGCCAUCGUCCUGCGGUGA

AUGCGCUUACUCUGAAGCCGCCGGAUGGCAUAACCCGCGCUUG

AGCCUACGGGUUCGCGCAAGUAAGCUCCGUACAUUCAUGCCCG

AGGGGGUGUGCGGGUAACCAAUCGGGAUAAGGGGACGAACGC

UGCUGGCGGUGUAAUCGGACCACGAAKAACCAACCACCAGAGA

UGAGUGUGGUAACUGCAUCGAGCAGUGUCCUGGACGCGGGUU

CAAGUCCCGCCAUCUCCACCA SEQ ID NO: 24
```

*Cyanophora paradoxa* (Alga) Cyanelle ssrA

```
GGGGCTGTTTAGGTTTCGACGTTTTTTTCTAATTATGTTTGTTAAG

CAAGTCGAGGATTTGTTCTATCTCGAAAATCAAGAACTCTCAAA

ATTTAAACGCAACTAATATTGTACGTTTTAACCGTAAAGCAGCTT

TCGCTGTTTAATAATTACTTTTAATTTAAAAACCTAATTTTTTTAG

GAATTTATTTATTTATTGTTTATCCTGCTTAATGAATTAAAAAAA

GCTATACTTGTGAATAAACGCATAATTTAAAAAAACGGACGTGG

GTTCAAATCCCACCAGCTCCACCA SEQ ID NO: 25
```

*Cyanophora paradoxa* (Alga) Cyanelle tmRNA

```
GGGGCUGUUUAGGUUUCGACGCUUUUUUUCUAAUUAUGUUUGU

UAAGCAAGUCGAGGAUUUGUUCUAUCUCGAAAAUCAAGAACU

CUCAAAAUUUAAACGCAACUAAUAUUGUACGUUUUAACCGUA

AAGCAGCUUUCGCUGUUUAAUAAUUACUUUUAAUUUAAAAAC

CUAAUUUUUUUAGGAAUUUAUUUAUUUAUUGUUUAUCCUGCU

UAAUGAAUUAAAAAAAGCUAUACUUGUGAAUAAACGCAUAAU

UUAAAAAAACGGACGUGGGUUCAAAUCCCACCAGCUCCACCA

SEQ ID NO: 26
```

*Clostridium acetobutylicum* ssrA, 3' Partial

```
AATCTGGCGTCGAGAGCGGGGAAACGAGCCTTACAAAGCTTTGA

GTAAGGAACGGAATTTATGAAGCTACTGAAGTGAAAAGCTTGTT

TGTAGGCGTTTCATGGAGGGAATGTTAAAATACAAACTGCACTC

GGAGATGCTTAATGAAACCATTTTCGGACAGGGGTTCGATTCCC

CTCGCCTCCACCA SEQ ID NO: 27
```

*Clostridium acetobutylicum* tmRNA, 3' Partial

```
AAUCUGGCGUCGAGAGCGGGGAAACGAGCCUUACAAAGCUUU

GAGUAAGGAACGGAAUUUAUGAAGCUACUGAAGUGAAAAGCU

UGUUUGUAGGCGUUUCAUGGAGGGAAUGUUAAAAUACAAACU

GCACUCGGAGAUGCUUAAUGAAACCAUUUUCGGACAGGGGUU

CGAUUCCCCUCGCCUCCACCA SEQ ID NO: 28
```

*Deinococcus radiodurans* ssrA

```
GGGGGTGACCCGGTTTCGACAGGGGAACTGAAGGTGATGTTGCG

TGTCGAGGTGCCGTTGGCCTCGTAAACAAACGGCAAAGCCATTT

AACTGGCAACCAGAACTACGCTCTCGCTGCTTAAGTGAGATGAC

GACCGTGCAGCCCGGCCTTTGGCGTCGCGGAAGTCACTAAAAAA

GAAGGCTAGCCCAGGCGATTCTCCATAGCCGACGGCGAAACTTT

ATGGAGCTACGGCCTGCGAGAACCTGCCCACTGGTGAGCGCCGG

CCCGACAATCAAACAGTGGGATACACACGTAGACGCACGCTGGA

CGGACCTTTGGACGGCGGTTCGACTCCGCCCACCTCCACCA

SEQ ID NO: 29
```

*Deinococcus radiodurans* tmRNA

```
GGGGGUGACCCGGUUUCGACAGGGGAACUGAAGGUGAUGUUG

CGUGUCGAGGUGCCGUUGGCCUCGUAAACAAACGGCAAAGCCA

UUUAACUGGCAACCAGAACUACGCUCUCGCUGCUUAAGUGAGA

UGACGACCGUGCAGCCCGGCCUUUGGCGUCGCGGAAGUCACUA

AAAAGAAGGCUAGCCCAGGCGAUUCUCCAUAGCCGACGGCGA

AACUUUAUGGAGCUACGGCCUGCGAGAACCUGCCCACUGGUGA

GCGCCGGCCCGACAAUCAAACAGUGGGAUACACACGUAGACGC

ACGCUGGACGGACCUUUGGACGGCGGUUCGACUCCGCCCACCU

CCACCA SEQ ID NO: 30
```

*Desulfovibrio desulfuricans* ssrA, Internal Partial

```
GGGACTGGAACCGTAGCGGCAGGTCGAGGCGCCGCTGGCCTCGT

AAAAAGCGGCACAAAAGTAATTGCCAACAACGATTACGACTAC

GCTTACGCTGCCTAATAACAGCGAGGCAATGACCGTTTAACGGT

CGCGCCGATCAGGGCCATGCCTGATAACCCTGATTGGCGACACT

TATCAGGCTGGCGAAAACCGGCTCTCGCCGGGGTTTTTCGCGAG

GAGTTTACCGGCGGGATTGCTGCGTTGTGCCTGGTCAGGGGCCA

ACAGCGCGGTGAAATACATACTTGACCTAAACCTGTAATGCTTC

GTGTGGAATGTTCTCGGACGGGG SEQ ID NO: 31
```

*Desulfovibrio desulfuricans* tmRNA, Internal Partial

```
GGGACUGGAACCGUAGCGGCAGGUCGAGGCGCCGCUGGCCUCG
UAAAAAGCGGCACAAAAGUAAUUGCCAACAACGAUUACGACU
ACGCUUACGCUGCCUAAUAACAGCGAGGCAAUGACCGUUUAAC
GGUCGCGCCGAUCAGGGCCAUGCCUGAUAACCCUGAUUGGCGA
CACUUAUCAGGCUGGCGAAAACCGGCUCUCGCCGGGGUUUUUC
GCGAGGAGUUUACCGGCGGGAUUGCUGCGUUGUGCCUGGUCA
GGGGCCAACAGCGCGGUGAAAUACAUACUUGACCUAAACCUGU
AAUGCUUCGUGUGGAAUGUUCUCGGACGGGG          SEQ ID NO: 32
```

*Dichelobacter nodosus* ssrA, 3 Partial

```
CTCGAGGTGCATGTCGAGAATGAGAGAATCTCGTTAAATACTTT
CAAAACTTATAGTTGCAAACGACGACAACTACGCTTTAGCGGCT
TAATTCCCGCTTTCGCTTACCTAGATTTGTCTGTGGGTTTACCGTA
AGCGACATTAACACAGAATCGCTGGTTAACGCGTCCGCTGTTAA
TCGGTTAAATTAAGCGGAATCGCTTGTAAAATGCCTGAGCGTTG
GCTGTTTATGAGTTAAACCTAATTAACTGCTCTAAACATGTAGTA
CCAAAAGTTAAGGATTCGCGGACGGGGGTTCAAATCCCCCGCC
TCCACCA          SEQ ID NO: 33
```

*Dichelobacter nodosus* tmRNA, 3 Partial

```
CUCGAGGUGCAUGUCGAGAAUGAGAGAAUCUCGUUAAAUACU
UUCAAAACUUAUAGUUGCAAACGACGACAAGUACGCUUUAGCG
GCUUAAUUCCCGCUUUCGCUUACCUAGAUUUGUCUGUGGGUUU
ACCGUAAGCGACAUUAACACAGAAUCGCUGGUUAACGCGUCCG
CUGUUAAUCGGUUAAAUUAAGCGGAAUCGCUUGUAAAAUGCC
UGAGCGUUGGCUGUUUAUGAGUUAAACCUAAUUAACUGCUCU
AAACAUGUAGUACCAAAAGUUAAGGAUUCGCGGACGGGGGUU
CAAAUCCCCCGCCUCCACCA          SEQ ID NO: 34
```

*Enterococcus faecalis* ssrA

```
GGGGGCGTTACGGATTCGACAGGCATAGTTGAGCTTGAATTGCG
TTTCGTAGGTTACGGCTACGTTAAAACGTTACAGTTAAATATAAC
TGCTAAAAACGAAACAATTCTTTCGCTTTAGCTGCCTAAAAAC
CAGCTAGCGAAGATCCTCCCGGCATCGCCCATGTGCTCGGGTCA
GGGTCCTAATCGAAGTGGGATACGCTAAATTTTTCCGTCTGTAAA
ATTTAGAGGAGCTTACCAGACTAGCAATACAGAATGCCTGTCAC
TCGGCACGCTGTAAAGCGAACCTTTAAATGAGTGTCTATGAACG
TAGAGATTTAAGTGGCAATATGTTTGGACGCGGGTTCGACTCCC
GCCGTCTCCACCA          SEQ ID NO: 35
```

*Enterococcus faecalis* tmRNA

```
GGGGGCGUUACGGAUUCGACAGGCAUAGUUGAGCUUGAAUUG
CGUUUCGUAGGUUACGGCUACGUUAAAACGUUACAGUUAAAU
AUAACUGCUAAAAACGAAACAAUUCUUUCGCUUUAGCUGCCU
AAAAACCAGCUAGCGAAGAUCCUCCCGGCAUCGCCCAUGUGCU
CGGGUCAGGGUCCUAAUCGAAGUGGGAUACGCUAAAUUUUUC
CGUCUGUAAAAUUUAGAGGAGCUUACCAGACUAGCAAUACAG
AAUGCCUGUCACUCGGCACGCUGUAAAGCGAACCUUUAAAUGA
GUGUCUAUGAACGUAGAGAUUUAAGUGGCAAUAUGUUUGGAC
GCGGGUUCGACUCCCGCCGUCUCCACCA          SEQ ID NO: 36
```

*Escherichia coli* ssrA

```
GGGGCTGATTCTGGATTCGACGGGATTTGCGAAACCCAAGGTGC
ATGCCGAGGGGCGGTTGGCCTCGTAAAAAGCCGCAAAAAATAGT
CGCAAACGACGAAAACTACGCTTTAGCAGCTTAATAACCTGCTT
AGAGCCCTCTCTCCCTAGCCTCCGCTCTTAGGACGGGGATCAAG
AGAGGTCAAACCCAAAAGAGATCGCGTGGAAGCCCTGCCTGGG
GTTGAAGCGTTAAAACTTAATCAGGCTAGTTTGTTAGTGGCGTGT
CCGTCCGCAGCTGGCAAGCGAATGTAAAGACTGACTAAGCATGT
AGTACCGAGGATGTAGGAATTTCGGACGCGGGTTCAACTCCCGC
CAGCTCCACCA          SEQ ID NO: 37
```

*Escherichia coli* tmRNA

```
GGGGCUGAUUCUGGAUUCGACGGGAUUUGCGAAACCCAAGGU
GCAUGCCGAGGGGCGGUUGGCCUCGUAAAAAGCCGCAAAAAAU
AGUCGCAAACGACGAAAACUACGCUUUAGCAGCUUAAUAACCU
GCUUAGAGCCCUCUCUCCCUAGCCUCCGCUCUUAGGACGGGGA
UCAAGAGAGGUCAAACCCAAAAGAGAUCGCGUGGAAGCCCUGC
CUGGGGUUGAAGCGUUAAAACUUAAUCAGGCUAGUUUGUUAG
UGGCGUGUCCGUCCGCAGCUGGCAAGCGAAUGUAAAGACUGAC
UAAGCAUGUAGUACCGAGGAUGUAGGAAUUUCGGACGCGGGU
UGAACUCCGGCCAG          SEQ ID NO: 38
```

*Haemophilus influenzae* ssrA

```
GGGGCTGATTCTGGATTCGACGGGATTAGCGAAGCCCAAGGTGC
ACGTCGAGGTGCGGTAGGCCTCGTAAATAAACCGCAAAAAAATA
GTCGCAAACGACGAACAATACGCTTTAGCAGCTTAATAACCTGC
ATTTAGCCTTCGCGCTCCAGCTTCCGCTCGTAAGACGGGGATAAC
GCGGAGTCAAACCAAAACGAGATCGTGTGGAAGCCACCGTTTGA
GGATCGAAGCACTAAATTGAATCAAACTAGCTTAAGTTTAGCGT
GTCTGTCCGCATGCTTAAGTGAAATTAAAGACGAGACTAAACGT
```

-continued
GTAGTACTGAAGGTAGAGTAATTTCGGACGGGGGTTCAACTCCC

CCCAGCTCCACCA SEQ ID NO: 39

*Haemophilus influenzae* tmRNA

GGGGCUGAUUCUGGAUUCGACGGGAUUAGCGAAGCCCAAGGU

GCACGUCGAGGUGCGGUAGGCCUCGUAAAUAAACCGCAAAAAA

AUAGUCGCAAACGACGAACAAUACGCUUUAGCAGCUUAAUAAC

CUGCAUUUAGCCUUCGCGCUCCAGCUUCCGCUCGUAAGACGGG

GAUAACGCGGAGUCAAACCAAAACGAGAUCGUGUGGAAGCCAC

CGUUUGAGGAUCGAAGCACUAAAUUGAAUCAAACUAGCUUAA

GUUUAGCGUGUCUGUCCGCAUGCUUAAGUGAAAUUAAAGACG

AGACUAAACGUGUAGUACUGAAGGUAGAGUAAUUUCGGACGG

GGGUUCAACUCCCCCCAGCUCCACCA SEQ ID NO: 40

*Helicobacter pylori* (ATCC 43504) ssrA, Internal Partial

SEQ ID NO: 41
AGATTTCTTGTCGCGCAGATAGCATGCCAAGCGCTGCTTGTAAA

ACAGCAACAAAAATAACTGTAAACAACACAGATTACGCTCCAGC

TTACGCTAAAGCTGCGTGAGTTAATCTCCTTTTGGAGCTGGACTG

ATTAGAATTTCTAGCGTTTTAATCGCTCCATAACCTTAAGCTAGA

CGCTTTTAAAGGTGGTTCGCCTTTTAAACTAAGAAACAAGAAC

TCTTGAAACTATCTTAAGGTTTTAGAAAGTTGGACCAGAGCTAGT

TTTAAGGCTAAAAACTAACCAATTTTCTAAGCATTGTAGAAGTTT

GTGTTTAGGGCAAGATTTTTGGACTGGG

*Helicobacter pylori* (ATCC 43504) tmRNA, Internal Partial

SEQ ID NO: 42
AGAUUUCUUGUCGCGCAGAUAGCAUGCCAAGCGCUGCUUGUAA

AACAGCAACAAAAAUAACUGUAAACAACACAGAUUACGCUCCA

GCUUACGCUAAAGCUGCGUGAGUUAAUCUCCUUUUGGAGCUG

GACUGAUUAGAAUUUCUAGCGUUUUAAUCGCUCCAUAACCUU

AAGCUAGACGCUUUUAAAGGUGGUUCGCCUUUUAAACUAAG

AAACAAGAACUCUUGAAACUAUCUUAAGGUUUUAGAAAGUUG

GACCAGAGCUAGUUUUAAGGCUAAAAACUAACCAAUUUUCUA

AGCAUUGUAGAAGUUUGUGUUUAGGGCAAGAUUUUUGGACUG

GG

*Helicobacter pylori* (strain 26695) ssrA

SEQ ID NO: 43
GGGGCTGACTTGGATTTCGACAGATTTCTTGTCGCACAGATAGC

ATGCCAAGCGCTGCTTGTAAAACAGCAACAAAAATAACTGTAAA

CAACACAGATTACGCTCCAGCTTACGCTAAAGCTGCGTGAGTTA

ATCTCCTTTTGGAGCTGGACTGATTAGAATTTCTAGCGTTTTAAT

CGCTCCATAACCTTAAGCTAGACGCTTTTAAAGGTGGTTCGCCT

TTTAAACTAAGAAACAAGAACTCTTGAAACTATCTCAAGGTTTT

AGAAAGTTGGACCAGAGCTAGTTTTAAGGCTAAAAACCAACCA

ATTTTCTAAGCATTGTAGAAGTTTGTGTTTAGGGCAAGATTTTTG

GACTGGGGTTCGATTCCCCACAGCTCCACCA

*Helicobacter pylori* (Strain 26695) tmRNA

SEQ ID NO: 44
GGGGCUGACUUGGAUUUCGACAGAUUUCUUGUCGCACAGAUA

GCAUGCCAAGCGCUGCUUGUAAAACAGCAACAAAAAUAACUGU

AAACAACACAGAUUACGCUCCAGCUUACGCUAAAGCUGCGUGA

GUUAAUCUCCUUUUGGAGCUGGACUGAUUAGAAUUUCUAGCG

UUUUAAUCGCUCCAUAACCUUAAGCUAGACGCUUUUAAAGG

UGGUUCGCCUUUUAAACUAAGAAACAAGAACUCUUGAAACUA

UCUCAAGGUUUUAGAAAGUUGGACCAGAGCUAGUUUUAAGGC

UAAAAACCAACCAAUUUUCUAAGCAUUGUAGAAGUUUGUGU

UUAGGGCAAGAUUUUUGGACUGGGGUUCGAUUCCCCACAGCUC

CACCA

*Klebsiella aerogenes* (NCTC 9528) ssrA, Internal Partial

SEQ ID NO: 45
GGGATTCGCGAAACCCAAGGTGCATGCCGAGGGGCGGTTGGCCT

CGTAAAAAGCCGCAAAAAAATAGTCGCAAACGACGAAAACTAC

GCTTTAGCAGCTTAATAACCTGCTAAGAGCCCTCTCTCCCTAGCT

TCCGCTCCTAAGACGGGGAATAAAGAGAGGTCAAACCCAAAAG

AGATCGCGTGGAAGCCCTGCCTGGGGTTGAAGCGTTAAAACTAA

TCAGGCTAGTTTGTCAGTGGCGTGTCCGTCCGCAGCTGGCCAGC

GAATGTAAAGACTGGACTAAGCATGTAGTGCCGAGGATGTAGGA

ATTTC

*Klebsiella aerogenes* (NCTC 9528) tmRNA, Internal Partial

SEQ ID NO: 46
GGGAUUCGCGAAACCCAAGGUGCAUGCCGAGGGGCGGUUGCC

UCGUAAAAAGCCGCAAAAAAAUAGUCGCAAACGACGAAAACU

ACGCUUUAGCAGCUUAAUAACCUGCUAAGAGCCCUCUCUCCCU

AGCUUCCGCUCCUAAGACGGGGAAUAAAGAGAGGUCAAACCCA

AAAGAGAUCGCGUGGAAGCCCUGCCUGGGGUUGAAGCGUUAA

AACUAAUCAGGCUAGUUUGUCAGUGGCGUGUCCGUCCGCAGCU

GGCCAGCGAAUGUAAAGACUGGACUAAGCAUGUAGUGCCGAG

GAUGUAGGAAUUUC

*Lactobacillus lactis* (NCTC 662) ssrA, Internal Partial

SEQ ID NO: 47
AAGCACAGTTCGAGCTTGAATTGCGTTTCGTAGGTTACGTCTACG

TTAAAACGTTACAGTTAAATATAACTGCTAAAAACGAAAACAAC

```
TCTTACGCTTTAGCTGCCTAAAAACAGTTAGCGTAGATCCTCTCG

GCATCGCCCATGTGCTCGAGTAAGGGTCTCAAATTTAGTGGGAT

ACGTTAAACTTTTCCGTCTGTAAAGTTTAAAAGAGATCATCAGAC

TAGCGATACAGAATGCCTGTCACTCGGCAAGCTGTAAAGCGAAA

CCTCAAATGAGTTGACTATGAACGTAGATTTTTAAGTGTCGATGT

GTTT
```

*Lactobacillus lactis* (NCTC 662) tmRNA, Internal Partial

SEQ ID NO: 48
```
AAGCACAGUUCGAGCUUGAAUUGCGUUUCGUAGGUUACGUCU

ACGUUAAAACGUUACAGUUAAAUAUAACUGCUAAAAACGAAA

ACAACUCUUACGCUUUAGCUGCCUAAAAACAGUUAGCGUAGAU

CCUCUCGGCAUCGCCCAUGUGCUCGAGUAAGGGUCUCAAAUUU

AGUGGGAUACGUUAAACUUUUCCGUCUGUAAAGUUUAAAAGA

GAUCAUCAGACUAGCGAUACAGAAUGCCUGUCACUCGGCAAGC

UGUAAAGCGAAACCUCAAAUGAGUUGACUAUGAACGUAGAUU

UUUAAGUGUCGAUGUGUUU
```

*Legionella pneumophila* ssrA, Internal Partial

SEQ ID NO: 49
```
GTGGGTTGCAAAACCGGAAGTGCATGCCGAGAAGGAGATCTCTC

GTAAATAAGACTCAATTAAATATAAATGCAAACGATGAAAACTT

TGCTGGTGGGAAGCTATCGCTGCCTAATAAGCACTTTAGTTAA

ACCATCACTGTGTACTGGCCAATAAACCCAGTATCCCGTTCGACC

GAGCCCGCTTATCGGTATCGAATCAACGGTCATAAGAGATAAGC

TAGCGTCCTAATCTATCCCGGGTTATGGCGCGAAACTCAGGGAA

TCGCTGTGTATCATCCTGCCCGTCGGAGGAGCCACAGTTAAATTC

AAAAGACAAGGCTATGCATGTAGAGCTAAAGGCAGAGGACTTG

CGGACGCGG
```

*Legionella pneumophila* tmRNA, Internal Partial

SEQ ID NO: 50
```
GUGGGUUGCAAAACCGGAAGUGCAUGCCGAGAAGGAGAUCUC

UCGUAAAUAAGACUCAAUUAAAUAUAAAUGCAAACGAUGAAA

ACUUUGCUGGUGGGAAGCUAUCGCUGCCUAAUAAGCACUUU

AGUUAAACCAUCACUGUGUACUGGCCAAUAAACCCAGUAUCCC

GUUCGACCGAGCCCGCUUAUCGGUAUCGAAUCAACGGUCAUAA

GAGAUAAGCUAGCGUCCUAAUCUAUCCCGGGUUAUGGCGCGAA

ACUCAGGGAAUCGCUGUGUAUCAUCCUGCCCGUCGGAGGAGCC

ACAGUUAAAUUCAAAAGACAAGGCUAUGCAUGUAGAGCUAAA

GGCAGAGGACUUGCGGACGCGG
```

*Listeria grayi* ssrA, Internal Partial

SEQ ID NO: 51
```
ACAGGGATAGGTCGAGCTTGAGTTGCGAGCCGGGGGGATCGGCC

CGTCATCAACGTCAAAGCCAATAATAACTGGCAAACAAAACAAC

AATTTAGCTTTCGCTGCCTAATAGCAGTCTGAATAGCTGATCCTC

CGTGCATCACCCATGTGCTACGGTAAGGGTCTCACTTTTAAGTGG

GTTACGCTGGCTTATCTCCGTCTGGGGCAAACGAGAAGAGCATA

ATCAGACTAGCTAGATAGAGCCCTGACGCCGGGCAGACATCTAT

GCGAAATCCAAATACGGCAACTACGCTCGTAGATGCTCAAGTGC

CGATATTTCTGG
```

*Listeria grayi* tmRNA, Internal Partial

SEQ ID NO: 52
```
ACAGGGAUAGGUCGAGCUUGAGUUGCGAGCCGGGGGGAUCGG

CCCGUCAUCAACGUCAAAGCCAAUAAUAACUGGCAAACAAAAC

AACAAUUUAGCUUUCGCUGCCUAAUAGCAGUCUGAAUAGCUG

AUCCUCCGUGCAUCACCCAUGUGCUACGGUAAGGGUCUCACUU

UUAAGUGGGUUACGCUGGCUUAUCUCCGUCUGGGGCAAACGA

GAAGAGCAUAAUCAGACUAGCUAGAUAGAGCCCUGACGCCGGG

CAGACAUCUAUGCGAAAUCCAAAUACGGCAACUACGCUCGUAG

AUGCUCAAGUGCCGAUAUUUCUGG
```

*Listeria innocua* ssrA, Internal Partial

SEQ ID NO: 53
```
ACAGGGATAGTTCGAGCTTGAGTTGCGAGTCGGGGGATCGTCC

TCGTTATCAACGTCAAAGCCAATAATAACTGGCAAAGAAAACA

AAACCTAGCTTTCGCTGCCTAATAAGCAGTAGCATAGCTGATCCT

CCGTGCATCGCCCATGTGCTACGGTAAGGGTCTCACTCTAAGTG

GGCTACACTAGTTAATCTCCGTCTGAGGTTAAATAGAAGAGCTT

AATCAGACTAGCTGAATGGAAGCCTGTTACCGGGCTGATGTTTA

TGCGAAATGCTAATACGGTGACTACGCTCGTAGATATTCAAGTG

CCGATATTTCTGG
```

*Listeria innocua* tmRNA, Internal Partial

SEQ ID NO: 54
```
ACAGGGAUAGUUCGAGCUUGAGUUGCGAGUCGGGGGAUCGU

CCUCGUUAUCAACGUCAAAGCCAAUAAUAACUGGCAAAGAAAA

ACAAAACCUAGCUUUCGCUGCCUAAUAAGCAGUAGCAUAGCUG

AUCCUCCGUGCAUCGCCCAUGUGCUACGGUAAGGGUCUCACUC

UAAGUGGGCUACACUAGUUAAUCUCCGUCUGAGGUUAAAUAG

AAGAGCUUAAUCAGACUAGCUGAAUGGAAGCCUGUUACCGGG

CUGAUGUUUAUGCGAAAUGCUAAUACGGUGACUACGCUCGUA

GAUAUUCAAGUGCCGAUAUUUCUGG
```

Listeria monocytogenes (NCTC 7973) ssrA, Internal Partial

SEQ ID NO: 55
ACAGGGATAGTTCGAGCTTGAGTTGCGAGTCGGGGGATCGTCC
TCGTTATCAACGTCAAAGCCAATAATAACTGGCAAAGAAAAACA
AAACCTAGCTTTCGCTGCCTAATAAGCAGTAGCATAGCTGATCCT
CCGTGCATCGCCCATGTGCTACGGTAAGGGTCTCACTCTAAGTG
GGCTACACTAGTTAATCTCCGTCTGGGGTTAAATAGAAGAGCTT
AATCAGACTAGCTGAATGGAAGCCTGTTACCGGGCCGATGTTTA
TGCGAAATGCTAATACGGTGACTACGCTCGTAGATATTTAAGTG
CCGATATTTCTGG

Listeria monocytogenes (NCTC 7973) tmRNA, Internal Partial

ACAGGGAUAGUUCGAGCUUGAGUUGCGAGUCGGGGGAUCGU
CCUCGUUAUCAACGUCAAAGCCAAUAAUAACUGGCAAAGAAAA
ACAAAACCUAGCUUUCGCUGCCUAAUAAGCAGUAGCAUAGCUG
AUCCUCCGUGCAUCGCCCAUGUGCUACGGUAAGGGUCUCACUC
UAAGUGGGCUACACUAGUUAAUCUCCGUCUGGGGUUAAAUAG
AAGAGCUUAAUCAGACUAGCUGAAUGGAAGCCUGUUACCGGG
CCGAUGUUUAUGCGAAAUGCUAAUACGGUGACUACGCUCGUA
GAUAUUUAAGUGCCGAUAUUUCUGG SEQ ID NO: 56

Listeria monocytogenes (NCTC 11994) ssrA, Internal Partial

CAAAGCCAATAATAACTGGCAAAGAAAAACAAAACCTAGCTTTC
GCTGCCTAATAAGCAGTAGCATAGCTGATCCTCCGTGCATCGCC
CATGTGCTACGGTAAGGGTCTCACTCTAAGTGGGCTACACTAGTT
AATCTCCGTCTGGGGTTAAATAGAAGAGCTTAATCAGACTAGCT
GAATGGAAGCCTGTTACCGGGCCGATGTTTATGCGAAATGCTAA
TACGGTGACTACGCTCGTAGATATTT SEQ ID NO: 57

Listeria monocytogenes (NCTC 11994) tmRNA, Internal Partial

CAAAGCCAAUAAUAACUGGCAAAGAAAAACAAAACCUAGCUU
UCGCUGCCUAAUAAGCAGUAGCAUAGCUGAUCCUCCGUGCAUC
GCCCAUGUGCUACGGUAAGGGUCUCACUCUAAGUGGGCUACAC
UAGUUAAUCUCCGUCUGGGGUUAAAUAGAAGAGCUUAAUCAG
ACUAGCUGAAUGGAAGCCUGUUACCGGGCCGAUGUUUAUGCG
AAAUGCUAAUACGGUGACUACGCUCGUAGAUAUUU
SEQ ID NO: 58

Listeria murrayi ssrA, Internal Partial

ACAGGGATAGTTCGAGCTTGAGTTGCGAGTCGGGGGATCGTCC
TCGTTATCAACGTCAAAGCCAATAATAACTGGCAAAGAAAAACA
AAACCTAGCTTTCGCTGCCTAATAAGCAGTAGCATAGCTGATCCT
CCGTGCATCGCCCATGTGCTACGGTAAGGGTCTCACTCTAAGTG
GGCTACACTAGTTAATCTCCGTCTGAGGTTAAATAGAAGAGCTT
AATGAGACTAGCTGAATGGAAGCCTGTTACCGGGCTGATGTTTA
TGCGAAATGCTAATACGGTGACTACGCTCGTAGATATTCAAGTG
CCGATATTTCTGG SEQ ID NO: 59

Listeria murrayi tmRNA, Internal Partial

ACAGGGAUAGUUCGAGCUUGAGUUGCGAGUCGGGGGAUCGU
CCUCGUUAUCAACGUCAAAGCCAAUAAUAACUGGCAAAGAAAA
ACAAAACCUAGCUUUCGCUGCCUAAUAAGCAGUAGCAUAGCUG
AUCCUCCGUGCAUCGCCCAUGUGCUACGGUAAGGGUCUCACUC
UAAGUGGGCUACACUAGUUAAUCUCCGUCUGAGGUUAAAUAG
AAGAGCUUAAUGAGACUAGCUGAAUGGAAGCCUGUUACCGGG
CUGAUGUUUAUGCGAAAUGCUAAUACGGUGACUACGCUCGUA
GAUAUUCAAGUGCCGAUAUUUCUGG SEQ ID NO: 60

Listeria welshimeri ssrA, Internal Partial

ACAGGGATAGTTCGAGCTTGAGTTGCGAGTCGGGGGATCGTCC
TCGTTATCAACGTCAAAGCCAATAATAACTGGGAAAGAAAAACA
AAACCTAGCTTTCGCTGCCTAATAAGCAGTAGCATAGCTGATCCT
CCGTGCATCGCCCATGTGCTACGGTAAGGGTCTCACTCTAAGTG
GGCTACACTGGCTAATCTCCGTCTGAGGTTAGTTGGAAGAGCTT
AATCAGACTAGCTGAATGGAAGCCTGTTACCGGGCCGATGTTTA
TGCGAAATGCTAATACGGTGACTACGCTCGTAGATATTTAAGTG
CCGATATTTCTGG SEQ ID NO: 61

Listeria welshimeri tmRNA, Internal Partial

ACAGGGAUAGUUCGAGCUUGAGUUGCGAGUCGGGGGAUCGU
CCUCGUUAUCAACGUCAAAGCCAAUAAUAACUGGCAAAGAAAA
ACAAAACCUAGCUUUCGCUGCCUAAUAAGCAGUAGCAUAGCUG
AUCCUCCGUGCAUCGCCCAUGUGCUACGGUAAGGGUCUCACUC
UAAGUGGGCUACACUGGCUAAUCUCCGUCUGAGGUUAGUUGG
AAGAGCUUAAUCAGACUAGCUGAAUGGAAGCCUGUUACCGGG
CCGAUGUUUAUGCGAAAUGCUAAUACGGUGACUACGCUCGUA
GAUAUUUAAGUGCCGAUAUUUCUGG SEQ ID NO: 62

Marinobacter hydrocarbonoclasticus ssrA, Internal Partial

GCCGGTGACGAACCCTTGGGTGCATGCCGAGATGGCAGCGAATC
TCGTAAATCCAAAGCTGCAACGTAATAGTCGCAAACGACGAAAA
CTACGCACTGGCGGCGTAAGCCGTTCCAGTCGTCCTGGCTGAGG

CGCCTATAACTCAGTAGCAACATCCCAGGACGTCATCGCTTATA

GGCTGCTCCGTTCACCAGAGCTCACTGGTGTTCGGCTAAGATTAA

AGAGCTCGCCTCTTGCACCCTGACCTTCGGGTCGCTTGAGGTTAA

ATCAATAGAAGGACACTAAGGATGTAGACCTCAAGGCCTAGTGC

TGGCGGACGCGG SEQ ID NO: 63

*Marinobacter hydrocarbonoclasticus* tmRNA, Internal Partial

GCCGGUGACGAACCCUUGGGUGCAUGCCGAGAUGGCAGCGAAU

CUCGUAAAUCCAAAGCUGCAACGUAAUAGUCGCAAACGACGAA

AACUACGCACUGGCGGCGUAAGCCGUUCCAGUCGUCCUGGCUG

AGGCGCCUAUAACUCAGUAGCAACAUCCCAGGACGUCAUCGCU

UAUAGGCUGCUCCGUUCACCAGAGCUCACUGGUGUUCGGCUAA

GAUUAAAGAGCUCGCCUCUUGCACCCUGACCUUCGGGUCGCUU

GAGGUUAAAUCAAUAGAAGGACACUAAGCAUGUAGACCUCAA

GGCCUAGUGCUGGCGGACGCGG SEQ ID NO: 64

*Mycobacterium avium* ssrA, Internal Partial

TTCGCGCATCGAATCAAGGGAAGCGTGCCGGTGCAGGCAACTGA

CCACCGTAAGCGTCGTTGCAAATAGATAAGCGCCGATTCACATC

AGCGCGACTTACCTCTCGCTGCCTAAGCGACAGCTAGTCCGTCA

GCCCGGGAACGCCCTCGACCCGGAGCCTGGCGTCAGCTAGAGGG

ATCCACCGATGAGTTCGGTCGCGGGACTCATCGGGACACCAACA

GCGACTGGGATCGTCATCCTGGCTTGTTCGCGTGACCAGGAGAT

CCGAGTAGAGGCATAGCGAACTGCGCACGGAGAAGCCTTGAGG

GAATGCCGTAGAACCCGGGTTCGATTCCCAA SEQ ID NO: 65

*Mycobacterium avium* tmRNA, Internal Partial

UUCGCGCAUCGAAUCAAGGGAAGCGUGCCGGUGCAGGCAACUG

ACCACCGUAAGCGUCGUUGCAAAUAGAUAAGCGCCGAUUCACA

UCAGCGCGACUUACCUCUCGCUGCCUAAGCGACAGCUAGUCCG

UCAGCCCGGGAACGCCCUCGACCCGGAGCCUGGCGUCAGCUAG

AGGGAUCCACCGAUGAGUUCGGUCGCGGGACUCAUCGGGACAC

CAACAGCGACUGGGAUCGUCAUCCUGGCUUGUUCGCGUGACCA

GGAGAUCCGAGUAGAGGCAUAGCGAACUGCGCACGGAGAAGCC

UUGAGGGAAUGCCGUAGAACCCGGGUUCGAUUCCCAA

SEQ ID NO: 66

*Mycobacterium bovis* ssrA, Internal Partial

TTCGCGCATCGAATCAAGGGAAGCGTGCCGGTGCAGGCAAGAG

ACCACCGTAAGCGTCGTTGCGACCAAATAAGCGCCGATTCACAT

CAGCGCGACTACGTCTCGCTGCCTAAGCGACGGCTAGTCTGTCA

GACCGGGAACGCCCTCGGCCCGGACCCTGGCATCAGCTAGAGGG

ATCCACCGATGAGTCCGGTCGCGGGACTCCTCGGGACAACCACA

GCGACTGGGATCGTCATCTCGGCTAGTTCGCGTGACCGGGAGAT

CCGAGCAGAGGCATAGCGAACTGCGCACGGAGAAGCCTTGAGG

GAATGCCGTAGG SEQ ID NO: 67

*Mycobacterium bovis* tmRNA, Internal Partial

UUCGCGCAUCGAAUCAAGGGAAGCGUGCCGGUGCAGGCAAGAG

ACCACCGUAAGCGUCGUUGCGACCAAAUAAGCGCCGAUUCACA

UCAGCGCGACUACGUCUCGCUGCCUAAGCGACGGCUAGUCUGU

CAGACCGGGAACGCCCUCGGCCCGGACCCUGGCAUCAGCUAGA

GGGAUCCACCGAUGAGUCCGGUCGCGGGACUCCUCGGGACAAC

CACAGCGACUGGGAUCGUCAUCUCGGCUAGUUCGCGUGACCGG

GAGAUCCGAGCAGAGGCAUAGCGAACUGCGCACGGAGAAGCCU

UGAGGGAAUGCCGUAGG SEQ ID NO: 68

*Mycobacterium leprae* ssrA

GGGGCTGAAAGGTTTCGACTTCGCGCATCGAATCAAGGGAAGCG

TGCCGGTGCAGGCAAGAGACCACCGTAAGCGTCGTTGCAGCAAT

ATAAGCGCCGATTCATATCAGCGCGACTATGCTCTCGCTGCCTAA

GCGATGGCTAGTCTGTCAGACCGGGAACGCCCTCGTCCCGGAGC

CTGGCATCAGCTAGAGGGATCTACCGATGGGTTCGGTCGCGGGA

CTCGTCGGGACACCAACCGCGACTGGGATCGTCATCCTGGCTAG

TTCGCGTGATCAGGAGATCCGAGTAGAGGCATAGCGAACTACGC

ACGGAGAAGCCTTGAGGGAAATGCCGTAGGACCCGGGTTCGATT

CCCGGCAGCTCCACCA SEQ ID NO: 69

*Mycobacterium leprae* tmRNA

GGGGCUGAAAGGUUUCGACUUCGCGCAUCGAAUCAAGGGAAG

CGUGCCGGUGCAGGCAAGAGACCACCGUAAGCGUCGUUGCAGC

AAUAUAAGCGCCGAUUCAUAUCAGCGCGACUAUGCUCUCGCUG

CCUAAGCGAUGGCUAGUCUGUCAGACCGGGAACGCCCUCGUCC

CGGAGCCUGGCAUCAGCUAGAGGGAUCUACCGAUGGGUUCGGU

CGCGGGACUCGUCGGGACACCAACCGCGACUGGGAUCGUCAUC

CUGGCUAGUUCGCGUGAUCAGGAGAUCCGAGUAGAGGCAUAG

CGAACUACGCACGGAGAAGCCUUGAGGGAAAUGCCGUAGGACC

CGGGUUCGAUUCCCGGCAGCUCCACCA SEQ ID NO: 70

*Mycobacterium paratuberculosis* ssrA, Internal Partial

TTCGCGCATCGAATCAAGGGAAGCGTGCCGGTGCAGGCAACTGA

CCACCGTAAGCGTCGTTGCAAATAGATAAGCGCCGATTCACATC

AGCGCGACTTACCTCTCGCTGCCTAAGCGACAGCTAGTCCGTCA

GCCCGGGAACGCCCTCGACCCGGAGCCTGGCGTCAGCTAGAGGG

ATCCACCGATGAGTTCGGTCGCGGGACTCATCGGGACACCAACA

GCGACTGGGATCGTCATCCTGGCTTGTTCGCGTGACCAGGAGAT

CCGAGTAGAGGCATAGCGAACTGCGCACGGAGAAGCCTTGAGG

GAATGCCGTAGAACCCGGGTTCGATTCCCAA SEQ ID NO: 71

*Mycobacterium paratuberculosis* tmRNA, Internal Partial

UUCGCGCAUCGAAUCAAGGGAAGCGUGCCGGUGCAGGCAACUG

ACCACCGUAAGCGUCGUUGCAAAUAGAUAAGCGCCGAUUCACA

UCAGCGCGACUUACCUCUCGCUGCCUAAGCGACAGCUAGUCCG

UCAGCCCGGGAACGCCCUCGACCCGGAGCCUGGCGUCAGCUAG

AGGGAUCCACCGAUGAGUUCGGUCGCGGGACUCAUCGGGACAC

CAACAGCGACUGGGAUCGUCAUCCUGGCUUGUUCGCGUGACCA

GGAGAUCCGAGUAGAGGCAUAGCGAACUGCGCACGGAGAAGCC

UUGAGGGAAUGCCGUAGAACCCGGGUUCGAUUCCCAA

SEQ ID NO: 72

*Mycobacterium tuberculosis* ssrA

GGGGCTGAACGGTITCGACITCGCGCATCGAATCAAGGGAAGCG

TGCCGGTGCAGGCAAGAGACCACCGTAAGCGTCGTTGCGACCAA

ATAAGCGCCGATTCACATCAGCGCGACTACGCTCTCGCTGCCTA

AGCGACGGCTAGTCTGTCAGACCGGGAACGCCCTCGGCCCGGAC

CCTGGCATCAGCTAGAGGGATCCACCGATGAGTCCGGTCGCGGG

ACTCCTCGGGACAACCACAGCGACTGGGATCGTCATCTCGGCTA

GTTCGCGTGACCGGGAGATCCGAGCAGAGGCATAGCGAACTGCG

CACGGAGAAGCCTTGAGGGAATGCCGTAGGACCCGGGTTCGATT

CCCGGCAGCTCCACCA SEQ ID NO: 73

*Mycobacterium tuberculosis* tmRNA

GGGGCUGAACGGUUUCGACUUCGCGCAUCGAAUCAAGGGAAGC

GUGCCGGUGCAGGCAAGAGACCACCGUAAGCGUCGUUGCGACC

AAAUAAGCGCCGAUUCACAUCAGCGCGACUACGCUCUCGCUGC

CUAAGCGACGGCUAGUCUGUCAGACCGGGAACGCCCUCGGCCC

GGACCCUGGCAUCAGCUAGAGGGAUCCACCGAUGAGUCCGGUC

GCGGGACUCCUCGGGACAACCACAGCGACUGGGAUCGUCAUCU

CGGCUAGUUCGCGUGACCGGGAGAUCCGAGCAGAGGCAUAGCG

AACUGCGCACGGAGAAGCCUUGAGGGAAUGCCGUAGGACCCGG

GUUCGAUUCCCGGCAGCUCCACCA SEQ ID NO: 74

*Mycoplasma capricolumn* ssrA

GGGGATGTCATGGATTTGACAGGATATCTTTAGTACATATAAGC
AGTAGTGTTGTAGACTATAAATACTACTAGGITIAAAAAAACGC

-continued

AAATAAAAACGAAGAAACTTTTGAAATGCCAGCATTTATGATGA
ATAATGCATCAGCTGGAGCAAACTTTATUTTTGCTTAATAACTAC
TAGTTTAGTTATAGTATTTCACGAATTATAGATATTTTAAGCTTT
ATTTATAACCGTATTACCCAAGCTTAATAGAATATATGATTGCAA
TAAATATATTTGAAATCTAATTGCAAATGATATTTAACCTTTAGT
TAATTTTAGTTAAATATTTTAATTAGAAAATTAACTAAACTGTAG
AAAGTATGTATTAATATATCTTGGACGCGAGTTCGATTCTCGCCA
TCTCCACCA SEQ ID NO: 75

*Mycoplasma capricolumn* tmRNA

GGGGAUGUCAUGGAUUUGACAGGAUAUCUUUAGUACAUAUAA
GCAGUAGUGUUGUAGACUAUAAAUACUACUAGGUUUAAAAAA
ACGCAAAUAAAAACGAAGAAACUUUUGAAAUGCCAGCAUUUA
UGAUGAAUAAUGCAUCAGCUGGAGCAAACUUUAUGUUUGCUU
AAUAACUACUAGUUUAGUUAUAGUAUUUCACGAAUUAUAGAU
AUUUUAAGCUUUAUUUAUAACCGUALTUACCCAAGCUUAAUAG
AAUAUAUGAUUGCAAUAAAUAUAUUUGAAAUCUAAUUGCAAA
UGAUAUUUAACCUUUAGUUAAUUUUAGUUAAAUAUUUUAAUU
AGAAAAUUAACUAAACUGUAGAAAGUAUGUAUUAAUAUAUCU
UGGACGCGAGUUCGAUUCUCGCCAUCUCCACCA SEQ ID NO: 76

*Mycoplasma genitalium* (ATTC 33530, #1) ssrA

GGGGATGTTTTGGGTTTGACATAATGCTGATAGACAAACAGTAG
CATTGGGGTATGCCCCTTACAGCGCTAGGTTCAATAACCGACAA
AGAAAATAACGAAGTGTTGGTAGAACCAAATITGATCATTAACC
AACAAGCAAGTGTTAAGCTTTGCTTTTGCATAAGTAGATACTAAA
GCTACAGCTGGTGAATAGTCATAGTTTGCTAGCTGTCATAGTTTA
TGACTCGAGGTTAAATCGTTCAATTTAACCTTTAAAAATAGAACT
TGTTGTTTCCATGATTGTTTTGTGATCAATTGGAAACAAGACAAA
AATCCACAAAACTAAAATGTAGAAGCTGTTTGTTGTGTCCTTTAT
GGAAACGGGTTCGATTCCCGTCATCTCCACCA SEQ ID NO: 77

*Mycoplasma genitalium* (ATTC 33530, #1) tmRNA

GGGGAUGUUUUGGGUUUGACAUAAUGCUGAUAGACAAACAGU
AGCAUUGGGGUAUGCCCCUUACAGCGCUAGGUUCAAUAACCGA
CAAAGAAAAUAACGAAGUGUUGGUAGAACCAAAUUUGAUCAU
UAACCAACAAGCAAGUGUUAACUUUGCUUUUGCAUAAGUAGA
UACUAAAGCUACAGCUGGUGAAUAGUCAUAGUUUGCUAGCUG
UCAUAGLTUUAUGACUCGAGGUUAAAUCGUUCAAUUUAACCUU
UAAAAAUAGAACUUGUUGUUUCCAUGAUUGUUUUGUGAUCAA
UUGGAAACAAGACAAAAAUCCACAAAACUAAAAUGUAGAAGC

-continued
UGUUUGUUGUGUCCUUUAUGGAAACGGGUUCGAUUCCCGUCA

UCUCCACCA SEQ ID NO: 78

*Mycoplasma genitalium* (ATTC 33530, #2) tmRNA, Internal Partial

ACATAATGCTGATAGACAAACAGTAGCATTGGGGTATGCCCCTT

ACAGCGCTAGGTTCAATAACCGACAAAGAAAATAACGAAGTGTT

GGTAGATCCAAATTTGATCATTAACCAACAAGCAAGTGTTAACT

TTGCTTTTGCATAAGTAGATACTAAAGCTACAGCTGGTGAATAGT

CATAGTTTGCTAGCTGTCATAGTTTATGACTCGAGGTTAAATCGT

TCAATTTAACCTTTAAAAATAGAACTTGTTGTTTCCATGATTGTT

TTGTGATCAATTGGAAACAAGACAAAAATCCACAAAACTAAAAT

GTAGAAGCTGTTTGTTGTGTCCTTTATGGAAACGGGTTC

SEQ ID NO: 79

*Mycoplasma genitalium* (ATTC 33530, #2) tmRNA, Internal Partial

ACAUAAUGCUGAUAGACAAACAGUAGCAUUGGGGUAUGCCCC

UUACAGCGCUAGGUUCAAUAACCGACAAAGAAAAUAACGAAG

UGUUGGUAGAUCCAAAUUUGAUCAUUAACCAACAAGCAAGUG

UUAACUUUGCUUUUGCAUAAGUAGAUACUAAAGCUACAGCUG

GUGAAUAGUCAUAGUUUGCUAGCUGUCAUAGUUUAUGACUCG

AGGUUAAAUCGUUCAAUUUAACCUUUAAAAAUAGAACUUGUU

GUUUCCAUGAUUGUUUUGUGAUCAAUUGGAAACAAGACAAAA

AUCCACAAAACUAAAAUGUAGAAGCUGUUUGUUGUGUCCUUU

AUGGAAACGGGUUC SEQ ID NO: 80

*Mycoplasma Pneumophila* ssrA

GGGGATGTAGAGGTTTTGACATAATGTTGAAAGGAAAACAGTTG

CAGTGGGGTATGCCCCTTACAGCTCTAGGTATAATAACCGACAA

AAATAACGACGAAGTTTTGGTAGATCCAATGTTGATCGCTAACC

AACAAGCAAGTATCAACTACGCTTTCGCTTAGAACATACTAAAG

CTACACGAATTGAATCGCCATAGTTTGGTTCGTGTCACAGTTTAT

GGCTCGGGGTTAACTGGTTCAACTTAATCCTTAAATTATGAACTT

ATCGTITACTTGTITGTCTTATGATCTAAAGTAAGCGAGACATTA

AAACATAAGACTAAACTGTAGAAGCTGTTTTACCAATCCTTTATG

GAAACGGGITCGATTCCCGTCATCTCCACCA SEQ ID NO: 81

*Mycoplasma pneumophila* tmRNA

GGGGAUGUAGAGGUUUUGACAUAAUGUUGAAAGGAAAACAGU

UGCAGUGGGGUAUGCCCCUUACAGCUCUAGGUAUAAUAACCGA

CAAAAAUAACGACGAAGUUUUGGUAGAUCCAAUGUUGAUCGC

UAACCAACAAGCAAGUAUCAACUACGCUUUCGCUUAGAACAUA

CUAAAGCUACACGAAUUGAAUCGCCAUAGUUUGGUUCGUGUC

ACAGUUUAUGGCUCGGGGUUAACUGGUUCAACUUAAUCCUUA

AAUUAUGAACUUAUCGUUUACUUGUUUGUCUUAUGAUCUAAA

GUAAGCGAGACAUUAAAACAUAAGACUAAACUGUAGAAGCUG

UUUUACCAAUCCUUUAUGGAAACGGGUUCGAUUCCCGUCAUCU

CCACCA SEQ ID NO: 82

*Neisseria gonorrhoeae* (ATCC 19424) ssrA, Internal Partial

GGGGGTTGCGAAGCAGATGCGGGCATACCGGGGTCTCAGATTCC

CGTAAAACACTGAATTCAAATAGTCGCAAACGACGAAACTTACG

CTTTAGCCGCTTAAGGCTAGCCGTTGCAGCAGTCGGTCAATGGG

CTGTGTGGCGAAAGCCACCGCAACGTCATCTTACATTGACTGGTT

TCCAGCCGGGTTACTTGGCAGGAAATAAGACTTAAGGTAACTGG

TTTCCAAAAGGCCTGTIGGTCGGCATGATGGAAATAAGATTTTC

AAATAGACACAACTAAGTATGTAGAACGCTTTGTAGAGGACTTT

CGGACGGGG SEQ ID NO: 83

*Neisseria gonorrhoeae* (ATCC 19424) tmRNA, Internal Partial

GGGGGUUGCGAAGCAGAUGCGGGCAUACCGGGGUCUCAGAUU

CCCGUAAAACACUGAAUUCAAAUAGUCGCAAACGACGAAACUU

ACGCUUUAGCCGCUUAAGGCUAGCCGUUGCAGCAGUCGGUCAA

UGGGCUGUGUGGCGAAAGCCACCGCAACGUCAUCUUACAUUGA

CUGGUUUCCAGCCGGGUUACUUGGCAGGAAAUAAGACUUAAG

GUAACUGGUUUCCAAAAGGCCUGUUGGUCGGCAUGAUGGAAA

UAAGAUUUUCAAAUAGACACAACUAAGUAUGUAGAACGCUUU

GUAGAGGACUUUCGGACGGGG SEQ ID NO: 84

*Neisseria gonorrhoeae* (FA 1090) ssrA

GGGGGCGACCTTGGTTTCGACGGGGGTTGCGAAGCAGATGCGGG

CATACCGGGGTCTCAGATTCCCGTAAAACACTGAATTCAAATAG

TCGCAAACGACGAAACTTACGCTTTAGCCGCTTAAGGCTAGCCG

TTGCAGCAGTCGGTCAATGGGCTGTGTGGTGAAAGCCACCGCAA

CGTCATCTTACATTGACTGGTTTCCAGCCGGGTTACTTGGCAGGA

AATAAGACTTAAGGTAACTGGTTTCCAAAAGGCCTGTTGGTCGG

CATGATGGAAATAAGATTTTCAAATAGACACAACTAAGTATGTA

GAACGCTTTGTAGAGGACTTTCGGACGGGGGTTCGATTCCCCCC

GCCTCCACCA SEQ ID NO: 85

*Neisseria gonorrhoeae* (FA 1090) tmRNA

SEQ ID NO: 86
GGGGGCGACCUUGGUUUCGACGGGGGUUGCGAAGCAGAUGCG

GGCAUACCGGGGUCUCAGAUUCCCGUAAAACACUGAAUUCAA

-continued

AUAGUCGCAAACGACGAAACUUACGCUUUAGCCGCUUAAGGC

UAGCCGUUGCAGCAGUCGGUCAAUGGGCUGUGUGGCGAAAGC

CACCGCAACGUCAUCUUACAUUGACUGGUUUCCAGCCGGGUU

ACUUGGCAGGAAAUAAGACUUAAGGUAACUGGUUUCCAAAAG

GCCUGUUGGUCGGCAUGAUGGAAAUAAGAUUUUCAAAUAGAC

ACAACUAAGUAUGUAGAACGCUUUGUAGAGGACUUUCGGACG

GGGGUUCGAUUCCCCCCGCCUCCACCA

*Neisseria meningitidis* ssrA

SEQ ID NO: 87
GGGGGCGACCTTGGTTTCGACGGGGGTTGCGAAGCAGATGCGGG

CATACCGGGGTCTCAGATTCCCGTAAAACACTGAATTCAAATAG

TCGCAAACGACGAAACTTACGCTTTAGCCGCTTAAGGCTAGCCG

TTGCAGCAGTCGGTCAATGGGCTGTGTGGCGAAAGCCACCGCAA

CGTCATCTTACATTGACTGGTTTCCTGCCGGGTTATTTGGCAGG

AAATGAGATTTAAGGTAACTGGTTTCCAAAAGGCCTGTTGGTCG

GCATGATGGAAATAAGATTTTCAAATAGACACAACTAAGTATGT

AGAACGCTTTGTAGAGGACTTTCGGACGGGGGTTCGATTCCCCC

CGCCTCCACCA

*Neisseria meningitidis* tmRNA

SEQ ID NO: 88
GGGGGCGACCUUGGUUUCGACGGGGGUUGCGAAGCAGAUGCG

GGCAUACCGGGGUCUCAGAUUCCCGUAAAACACUGAAUUCAA

AUAGUCGCAAACGACGAAACUUACGCUUUAGCCGCUUAAGGC

UAGCCGUUGCAGCAGUCGGUCAAUGGGCUGUGUGGCGAAAGC

CACCGCAACGUCAUCUUACAUUGACUGGUUUCCUGCCGGGUU

AUUUGGCAGGAAAUGAGAUUUAAGGUAACUGGUUUCCAAAAG

GCCUGUUGGUCGGCAUGAUGGAAAUAAGAUUUUCAAAUAGAC

ACAACUAAGUAUGUAGAACGCUUUGUAGAGGACUUUCGGACG

GGGGUUCGAUUCCCCCCGCCUCCACCA

*Nostoc muscorum* PCC7120 ssrA

SEQ ID NO: 89
GGGTCCGTCGGTTTCGACAGGTTGGCGAACGCTACTCTGTGATT

CAGGTCGAGAGTGAGTCTCCTCTGCAAATCAAGGCTCAAAACAA

AAGTAAATGCGAATAACATCGTTAAATTTGCTCGTAAGGACGCT

CTAGTAGCTGCCTAAATAGCCTCTTTCAGGTTCGAGCGTCTTCG

GTTTGACTCCGTTAAGGACTGAAGACCAACCCCCAACGGATGCT

CTAGCAATGTTCTCTGGTTGGCTTGCTAGCTAAGATTTAATCAG

AGCATCCTACGTTCGGGATAATGAACGATTCCCGCCTTGAGGGT

CAGAAAGGCTAAACCTGTGAATGAGCGGGGGTCAATACCCAAT

TTGGACAGCAGTTCGACTCTGCTCGATCCACCA

*Nostoc muscorum* PCC7120 tmRNA

SEQ ID NO: 90
GGGUCCGUCGGUUUCGACAGGUUGGCGAACGCUACUCUGUGA

UUCAGGUCGAGAGUGAGUCUCCUCUGCAAAUCAAGGCUCAAA

ACAAAAGUAAAUGCGAAUAACAUCGUUAAAUUUGCUCGUAAG

GACGUCUAGUAGCUGCCUAAAUAGCCUCUUUCAGGUUCGAGC

GUCUUCGGULTUGACUCCGUUAAGGACUGAAGACCAACCCCC

AACGGAUGCUCUAGCAAUGUUCUCUGGUUGGCUUGCUAGCUA

AGAUUUAAUCAGAGCAUCCUACGUUCGGGAUAAUGAACGAUU

CCCGCCUUGAGGGUCAGAAAGGCUAAACCUGUGAAUGAGCGG

CGGGGUAAUACCCAAUUUGGACAGCAGUUCGACUCUGCUCGA

UCCACCA

*Odontella sinensis* (diatom) Chloroplast ssrA

SEQ ID NO: 91
GGGGCTGACTTGGTTTCGACATTTAAAAATTGTTACAGTATGA

TGCAGGTCGAAGTTTCTAATCTTCGTAAAAAAAGAGAAATTTA

TAATAAATGCTAATAATTTAATTTCTTCTGTGTTTAAAAGTTT

ATCAACTAAGCAAAATAGTTTAAATTTAAGTTTTGCTGTTTAA

GTTTTATGCACATTTAATGATCTAGTAAATAACTTTGTTCGCT

ATAATTTATATTTATAACTAGACTTTTGTCTTTITTATAGTTT

AGAATAACTTTATCATTTCAAACCTCGTTCCATCTAGTTGAAC

TAAACCTGTGAACGAATACTATAATAAAATTTTAGATGGACGT

GGGTTCGACTCCCATCAGCTCCACCA

*Odontella sinensis* (Diatom) Chloroplast tmRNA

SEQ ID NO: 92
GGGGCUGACUUGGUUUCGACALTUUAAAAAUUGUUACAGUAUG

AUGCAGGUCGAAGUUUCUAAUCUUCGUAAAAAAAGAGAAAUUU

UAUAAUAAAUGCUAAUAAUUUAAUUUCUUCUGUGUUUAAAA

GUUUAUCAACUAAGCAAAAUAGUUUAAAUUUAAGUUUUGGC

UGUUUAAGUUUUAUGCACAUUUAAUGAUCUAGUAAAUAACUUU

GUUCGCUAUAAUUUAUAUUUAUAACUAGACUUUUGUCUUUUU

AUAGUUUAGAAUAACULTUAUCAUUUCAAACCUCGUUCCAUC

UAGUUGAACUAAACCUGUGAACGAAUACUAUAAUAAAAUUUU

UAGAUGGACGUGGGUUCGACUCCCAUCAGCUCCACCA

*Porphyra purpureum* (Red Alga) Chloroplast ssrA

SEQ ID NO: 93
GGGGCTGCAAGGTTTCTAGATTGTGAAAAAACAAATATATGAAA

GTAAAACGAGCTCATTAITAGAGCTTTTAGTTAAATAAATGCAG

AAAATAATATTATTGCTTTTTCTCGAAAATTAGCTGTTGCATAA

ATAGTCTCAATTTTTGTAATTCGAAGTGATAGACTCTTATACAC

-continued
TACGAATATTCTGTTAGAGTTGCTCTTAATAAAAGAAAAGTAAA

AAAATACAAATTCTTATGTTTTTTACCTGAATTGATTCAATTTA

AGGTTAGTATTTTTTGATTTTTACAATGGACGTGGGTTCAAGTC

CCACCAGCTCCACCA

*Porphyra purpureum* (Red Alga) Chloroplast tmRNA

SEQ ID NO: 94
GGGGCUGCAAGGUUUCUACAUUGUGAAAAAACAAAUAUAUGA

AAGUAAAACGAGCUCAUUAUUAGAGCUUUUAGUUAAAUAAAU

GCAGAAAAUAAUAUUAUUGCUUUUUCUCGAAAAUUAGCUGUU

GCAUAAAUAGUCUCAAUUUUUGUAAUUCGAAGUGAUAGACUC

UUAUACACUACGAAUAUUCUGUUAGAGUUGCUCUUAAUAAAA

GAAAAGUAAAAAAAUACAAAUUCUUAUGUUUUUUACCUGAAU

UGAUUCAAUUUAAGGUUAGUAUUUUUUGAUUUUUACAAUGGA

CGUGGGUUCAAGUCCCACCAGCUCCACCA

*Porphyromonas gingivalis* ssrA

SEQ ID NO: 95
GGGGCTGACCGGCTTTGACAGCGTGATGAAGCGGTATGTAAGCA

TGTAGTGCGTGGGTGGCTTGCACTATAATCTCAGACATCAAAAG

TTTAATTGGCGAAAATAACTACGCTCTCGCTGCGTAATCGAAGA

ATAGTAGATTAGACGCTTCATCGCCGCCAAAGTGGCAGCGACGA

GACATCGCCCGAGCAGCTTTTTCCCGAAGTAGCTCGATGGTGCG

GTGCTGACAAATCGGGAACCGCTACAGGATGCTTCCTGCCTGTG

GTCAGATCGAACGGAAGATAAGGATCGTGCATTGGGTCGTTTCA

GCCTCCGCTCGCTCACGAAAATTCCAACTGAAACTAAACATGTA

GAAAGCATATTGATTCCATGTTTGGACGAGGGTTCAATTCCCTC

CAGCTCCACCA

*Porphyromonas gingivalis* tmRNA

SEQ ID NO: 96
GGGGCUGACCGGCUUUGACAGCGUGAUGAAGCGGUAUGUAAG

CAUGUAGUGCGUGGGUGGCUUGCACUAUAAUCUCAGACAUCA

AAAGUUUAAUUGGCGAAAAUAACUACGCUCUCGCUGCGUAAU

CGAAGAAUAGUAGAUUAGACGCUUCAUCGCCGCCAAAGUGGC

AGCGACGAGACAUCGCCCGAGCAGCUUUUUCCCGAAGUAGCU

CGAUGGUGCGGUGCUGACAAAUCGGGAACCGCUACAGGAUGC

UUCCUGCCUGUGGUCAGAUCGAACGGAAGAUAAGGAUCGUGC

AUUGGGUCGUUUCAGCCUCCGCUCGCUCACGAAAAUUCCAAC

UGAAACUAAACAUGUAGAAAGCAUAUUGAUUCCAUGUUUGGA

CGAGGGUUCAAUUCCCUCCAGCUCCACCA

*Proteus rettgeri* ssrA (NCTC 10975), Internal Partial

SEQ ID NO: 97
GGGATTTGCGAAACCCAAGGTGCATGCCGAGGGGCGGTTGGCC

TCGTAAAAAGCCGCAAAAAATAGTCGCAAACGACGAAAACTA

CGCTTTAGCAGCTTAATAACCTGCTTAGAGCCCTCTCTCCCTA

GCCTCCGCTCTTGGACGGGGATCAAGAGAGGTCAAACCCAAAA

GAGATCGCGTGGATGCCTTGCCTGGGGTTGAAGCGTTAAACTT

AATCAGGATAGTTTGTTGGTGGCGTGTCTGTCCGCAGCTGGCA

AAATGATTCAAAGACTAGACTAAGCATGTAGTACCGAGGATGT

AGAAATTTC

*Proteus rettgeri* tmRNA (NCTC 10975), Internal Partial

SEQ ID NO: 98
GGGAUUUGCGAAACCCAAGGUGCAUGCCGAGGGGCGGUUGGC

CUCGUAAAAAGCCGCAAAAAAUAGUCGCAAACGACGAAAAC

UACGCUUUAGCAGCUUAAUAACCUGCUUAGAGCCCUCUCUCC

CUAGCCUCCGCUCUUGGACGGGGAUCAAGAGAGGUCAAACCC

AAAAGAGAUCGCGUGGAUGCCUUGCCUGGGGUUGAAGCGUUA

AACUUAAUCAGGAUAGUUUGUUGGUGGCGUGUCUGUCCGCAG

CUGGCAAAUGAAUUCAAAGACUAGACUAAGCAUGUAGUACCG

AGGAUGUAGAAAUUUC

*Pseudoalteromonas haloplanktoni* ssrA, Internal Partial

SEQ ID NO: 99
GGAATTCAAGAAGCCCGAGGTGCATGTCGAGGTGCGGTTTGCCT

CGTAAAAAGCCGCAATTTAAAGTAATCGCAAACGACGATAACT

ACTCTCTAGCAGCTTAGGCTGGCTAGCGCTCCTTCCATGTATTC

TTGTGGACTGGATTTTGGAGTGTCACCCTAACACCTGATCGCGA

CGGAAACCCTGGCCGGGGTTGAAGCGTTAAAACTAAGCGGCCTC

GCCTTTATCTACCGTGTTTGTCCGGGATTTAAAGGTTAATTAAA

TGACAATACTAAACATGTAGTACCGACGGTCGAGGCTTTTCGGA

CGGGG

*Pseudoalteromonas haloplanktoni* tmRNA, Internal Partial

SEQ ID NO: 100
GGAAUUCAAGAAGCCCGAGGUGCAUGUCGAGGUGCGGUUUGC

CUCGUAAAAAGCCGCAAUUUAAAGUAAUCGCAAACGACGAU

AACUACUCUCUAGCAGCUUAGGCUGGCUAGCGCUCCUUCCAU

GUAUUCUUGUGGACUGGAUUUUGGAGUGUCACCCUAACACCU

GAUCGCGACGGAAACCCUGGCCGGGGUUGAAGCGUUAAAACU

AAGCGGCCUCGCCUUUAUCUACCGUGUUUGUCCGGGAUUUAA

AGGUUAAUUAAAUGACAAUACUAAACAUGUAGUACCGACGGU

CGAGGCUUUUCGGACGGGG

Pseudomonas aeruginosa ssrA

SEQ ID NO: 101
```
GGGGCCGATTAGGATTCGACGCCGGTAACAAAAGTTGAGGGGCA
TGCCGAGTTGGTAGCAGAACTCGTAAATTCGCTGCTGCAAACTT
ATAGTTGCCAACGACGACAACTACGCTCTAGCTGCTTAATGCGG
CTAGCAGTCGCTAGGGGATGCCTGTAAACCCGAAACGACTGTCA
GATAGAACAGGATCGCCGCCAAGTTCGCTGTAGACGTAACGGCT
AAAACTCATACAGCTCGCTCCAAGCACCCTGCCACTCGGGCGGC
GCGGAGTTAACTCAGTAGAGCTGGCTAAGCATGTAAAACCGATA
GCGGAAAGCTGGCGGACGGGGGTTCAAATCCCCCCGGTTCCACC
A
```

Pseudomonas aeruginosa tmRNA

SEQ ID NO: 102
```
GGGGCCGAUUAGGAUUCGACGCCGGUAACAAAAGUUGAGGGGCA
UGCCGAGUUGGUAGCAGAACUCGUAAAUUCGCUGCUGCAAACUU
AUAGUUGCCAACGACGACAACUACGCUCUAGCUGCUUAAUGCGG
CUAGCAGUCGCUAGGGGAUGCCUGUAAACCCGAAACGACUGUCA
GAUAGAAGAGGAUCGCCGCCAAGUUCGCUGUAGACGUAACGGCU
AAAACUCAUACAGCUCGCUCCKAGCACCCUGCCACUCGGGCGGC
GCGGAGUUAACUCAGUAGAGCUGGCUAAGCAUGUAAAACCGAUA
GCGGAAAGCUGGCGGACGGGGGUUCAAAUCCCCCCGGUUCCACC
A
```

Salmonella typhimurium ssrA

SEQ ID NO: 103
```
GGGGCTGATTCTGGATTCGACGGGATTTGCGAAACCCAAGGTGC
ATGCCGAGGGGCGGTTGGCCTCGTAAAAAGCCGCAAAAAAATAG
TCGCAAACGACGAAACCTACGCTTTAGCAGCTTAATAACCTGCT
TAGAGCCCTCTCTCCCTAGCCTCCGCTCTTAGGACGGGGATCAA
GAGAGGTCAAACCCAAAAGAGATCGCGCGGATGCCCTGCCTGGG
GTTGAAGCGTTAAAACGAATCAGGCTAGTCTGGTAGTGGCGTGT
CCGTCCGCAGGTGCCAGGCGAATGTAAAGACTGACTAAGCATGT
AGTACCGAGGATGTAGGAATTTCGGACGCGGGTTCAACTCCCGC
CAGCTCCACCA
```

Salmonella typhimurium tmRNA

SEQ ID NO: 104
```
GGGGCUGAUUCUGGAUUCGACGGGAUUUGCGAAACCCAAGGUGC
AUGCCGAGGGGCGGUUGGCCUCGUAAAAAGCCGCAAAAAAUAG
UCGCAAACGACGAAACCUACGCUUUAGCAGCUUAAUAACCUGCU
UAGAGCCCUCUCUCCCUAGCCUCCGCUCUUAGGACGGGGAUCAA
GAGAGGUCAAACCCAAAAGAGAUCGCGCGGAUGCCCUGCCUGGG
GUUGAAGCGUUAAAACGAAUCAGGCUAGUCUGGUAGUGGCGUGU
CCGUCCGCAGGUGCCAGGCGAAUGUAAAGACUGACUAAGCAUGU
AGUACCGAGGAUGUAGGAAUUUCGGACGCGGGUUCAACUCCCGC
CAGCUCCACCA
```

Shewanella putrefaciens ssrA

SEQ ID NO: 105
```
GGGGGCGATTCTGGATTCGACAGGATTCACGAAACCCTGGGAGC
ATGCCGAGGGGCGGTTGGCCTCGTAAAAAGCCGCAAAGTTATAG
TTGCAAACGACGATAACTACGCTCTAGCCGCTTAATGCCGCTAG
CCATCTACCACACGCTTTGCACATGGGCAGTGGATTTGATGGTC
ATCTCACATCGTGCTAGCGAGGGAACCCTGTCTGGGGGTGAACC
GCGAAACAGTACCGGACTCACCGTGTGGGATCCTGTCTTTCGGA
GTTCAAACGGTTAAACAATAGAAAGACTAAGCATGTAGCGCCTT
GGATGTAGGTTTTCTGGACGCGGGTTCAAGTCCCGCCGCCTCCA
CCA
```

Shewanella putrefaciens tmRNA

SEQ ID NO: 106
```
GGGGGCGAUUCUGGAUUCGACAGGAUUCACGAAACCCUGGGAGC
AUGCCGAGGGGCGGUUGGCCUCGUAAAAAGCCGCAAAGUUAUAG
UUGCAAACGACGAUAACUACGCUCUAGCCGCUUAAUGCCGCUAG
CCAUCUACCACACGCUUUGCACAUGGGCAGUGGAUUUGAUGGUC
AUCUCACAUCGUGCUAGCGAGGGAACCCUGUCUGGGGGUGAACC
GCGAAACAGUACCGGACUCACCGUGUGGGAUCCUGUCUUUCGGA
GUUCAAACGGUUAAACAAUAGAAAGACUAAGCAUGUAGCGCCU
UGGAUGUAGGUUUUCUGGACGCGGGUUCAAGUCCCGCCGCCUCC
ACCA
```

Staphylococcus aureus ssrA

SEQ ID NO: 107
```
GGGGACGTTCATGGATTCGACAGGGGTCCCCCGAGCTCATTAAG
CGTGTCGGAGGGTTGTCTTCGTCATCAACACACACAGTTTATAA
TAACTGGCAAATCAAACAATAATTTCGCAGTAGCTGCCTAATCG
CACTCTGCATCGCCTAACAGCATTTCCTATGTGCTGTTAACGCG
ATTCAACCTTAATAGGATATGCTAAACACTGCCGTTTGAAGTCT
GTTTAGAAGAAACTTAATCAAACTAGCATCATGTTGGTTGTTTA
TCACTTTTCATGATGCGAAACCTATCGATAAACTACACACGTAG
AAAGATGTGTATCAGGACCTTTGGACGCGGGTTCAAATCCCGCC
GTCTCCACCA
```

Staphylococcus aureus tmRNA

SEQ ID NO: 108
```
GGGGACGUUCAUGGAUUCGACAGGGGUCCCCCGAGCUCAUUAAG
CGUGUCGGAGGGUUGUCUUCGUCAUCAACACACACAGUUUAUAA
UAACUGGCAAAUCAAACAAUAAUUUCGCAGUAGCUGCCUAAUCG
```

-continued

CACUCUGCAUCGCCUAACAGCAUUUCCUAUGUGCUGUUAACGCG

AUUCAACCUUAAUAGGAUAUGCUAAACACUGCCGUUUGAAGUCU

GUUUAGAAGAAACUUAAUCAAACUAGCAUCAUGUUGGUUGUUUA

UCACUUUUCAUGAUGCGAAACCUAUCGAUAAACUACACACGUAG

AAAGAUGUGUAUCAGGACCUUUGGACGCGGGUUCAAAUCCCGCC

GUCUCCACCA

*Streptococcus gordonii* ssrA

SEQ ID NO: 109
GGGGTCGTTACGGATTCGACAGGCATTATGAGGCATATTTTGCG

ACTCATCTAGCGGATGTAAAACGCCAGTTAAATATAACTGCAAA

AAATAATACTTCTTACGCTTTAGCTGCCTAAAAACCAGCGGGCG

TGACCCGATTCGGATTGCTTGTGTCTGATGACAGGTCTTATTAT

TAGCAAGCTACGGTAGAATCTTGTCTAGTGATTTTACAAGAGAT

TGATAGACTCGCTTGATTTGGGCTTGAGTTATGTGTCAAAATCA

AGTTAAAACAATACATAGCCTATGGTTGTAGACAAATGTGTTGG

CAGATGTTTGGACGTGGGTTCGACTCCCACCGGCTCCACCA

*Streptococcus gordonii* tmRNA

SEQ ID NO: 110
GGGGUCGUUACGGAUUCGACAGGCAUUAUGAGGCAUAUUUUGCG

ACUCAUCUAGCGGAUGUAAAACGCCAGUUAAAUAUAACUGCAAA

AAAUAAUACUUCUUACGCUUUAGCUGCCUAAAAACCAGCGGGCG

UGACCCGAUUCGGAUUGCUUGUGUCUGAUGACAGGUCUUAUUAU

UAGCAAGCUACGGUAGAAUCUUGUCUAGUGAUUUUACAAGAGAU

UGAUAGACUCGCUUGAUUUGGGCUUGAGUUAUGUGUCAAAAUCA

AGUUAAAACAAUACAUAGCCUAUGGUUGUAGACAAAUGUGUUGG

CAGAUGUUUGGACGUGGGUUCGACUCCCACCGGCUCCACCA

*Streptococcus mutans* ssrA

SEQ ID NO: 111
GGGGTCGTTACGGATTCGACAGGCATTATGAGACCTATTTTGCG

ACTCATCTAGCGGATGTAAAACGCCAGTTAAATATAACTGCAAA

AAATACAAATTCTTACGCAGTAGCTGCCTAAAAACCAGCCTGTG

TGATCAATAACAAATTGCTTGTGTTTGTTGATTGGTCTTATTGT

TAACAAGCTACGTTAGAACTGAGTCAGGCTGTTCTAAAAGAGTT

CTACTGACTCGCATCGTTAGAGTTTGAGTTATGTATTGTAACGG

TGTTAAATAAACACATAACCTATAGTTGTAGACAAATGGGTTAG

CAGATGTTTGGACGTGGGTTCGACTCCCACCGGCTCCACCA

*Streptococcus mutans* tmRNA

SEQ ID NO: 112
GGGGUCGUUACGGAUUCGACAGGCAUUAUGAGACCUAUUUUGCG

ACUCAUCUAGCGGAUGUAAAACGCCAGUUAAAUAUAACUGCAAA

-continued

AAAUACAAAUUCUUACGCAGUAGCUGCCUAAAAACCAGCCUGUG

UGAUCAAUAACAAAUUGCUUGUGUUUGUUGAUUGGUCUUAUUGU

UAACAAGCUACGUUAGAACUGAGUCAGGCUGUUCUAAAAGAGUU

CUACUGACUCGCAUCGUUAGAGUUUGAGUUAUGUAUUGUAACGG

UGUUAAAUAAACACAUAACCUAUAGUUGUAGACAAAUGGGUUAG

CAGAUGUUUGGACGUGGGUUCGACUCCCACCGGCUCCACCA

*Streptococcus pneumoniae* ssrA

SEQ ID NO: 113
GGGGTCGTTACGGATTCGACAGGCATTATGAGGCATATTTTGCG

ACTCGTGTGGCGACGTAAACGCTCAGTTAAATATAACTGCAAAA

AATAACACTTCTTACGCTCTAGCTGCCTAAAAACCAGCAGGCGT

GACCCGATTTGGATTGCTCGTGTTCAATGACAGGTCTTATTATT

AGCGAGATACGATTAAGCCTTGTCTAGCGGTTTGATAAGAGATT

GATAGACTCGCAGTTTCTAGACTTGAGTTATGTGTCGAGGGGCT

GTTAAAATAATACATAACCTATGGTTGTAGACAAATATGTTGGC

AGGTGTTTGGACGTGGGTTCGACTCCCACCGGCTCCACCA

*Streptococcus pneumoniae* tmRNA

SEQ ID NO: 114
GGGGUCGUUACGGAUUCGACAGGCAUUAUGAGGCAUAUUUUGCG

ACUCGUGUGGCGACGUAAACGCUCAGUUAAAUAUAACUGCAAAA

AAUAACACUUCUUACGCUCUAGCUGCCUAAAAACCAGCAGGCGU

GACCCGAUUUGGAUUGCUCGUGUUCAAUGACAGGUCUUAUUAUU

AGCGAGAUACGAUUAAGCCUUGUCUAGCGGUUUGAUAAGAGAUU

GAUAGACUCGCAGUUUCUAGACUUGAGUUAUGUGUCGAGGGGCU

GUUAAAAUAAUACAUAACCUAUGGUUGUAGACAAAUAUGUUGGC

AGGUGUUUGGACGUGGGUUCGACUCCCACCGGCUCCACCA

*Streptococcus pyogenes* ssrA

SEQ ID NO: 115
GGGGTTGTTACGGATTCGACAGGCATTATGAGGCATGTTTTGCG

TCCCATCGGCAGATGTAAATTGCCAGTTAAATATAACTGCAAAA

AATACAAACTCTTACGCTTTAGCTGCCTAAAAACCAGCTAGCGT

GACTTCTACAAGATTGCTTGTGTCCTGTTAGAAGTCTCAAAATA

GCAAGCTACGGTTACGAAATTGTCTAGTTTCGTGACAAGAGATT

GATAGACTCGCAAACTAATGGCTTGAGTTATGTGTCTTTAGTTT

GTTAAATGAAGACATAACCTATGGACGTAGACAAATATGTTGGC

AGGTGTTTGGACGTGGGTTCGACTCCCACCAGCTCCACCA

*Streptococcus pyogenes* tmRNA

SEQ ID NO: 116
GGGGUUGUUACGGAUUCGACAGGCAUUAUGAGGCAUGUUUUGCGUCCCAUC

GGCAGAUGUAAAUUGCCAGUUAAAUAUAACUGCAAAAAAUACAAACUCUUA

-continued
CGCUUUAGCUGCCUAAAAACCAGCUAGCGUGACUUCUACAAGAUUGCUUGU

GUCCUGUUAGAAGUCUCAAAAUAGCAAGCUACGGUUACGAAAUUGUCUAGU

UUCGUGACAAGAGAUUGAUAGACUCGCAAACUAAUGGCUUGAGUUAUGUGU

CUUUAGUUUGUUAAAUGAAGACAUAACCUAUGGACGUAGACAAAUAUGUUG

GCAGGUGUUUGGACGUGGGUUCGACUCCCACCAGCUCCACCA

*Synechococcus* sp. PCC6301 ssrA

SEQ ID NO: 117
GGGGCTGTAATGGTTTCGACGTGTTGGTGAATCCTTCACCGTGATTCAGGC

CGAGAGGGAGTCCACTCTCGTAAATCCAGGCTCAACCAAAAGTAACTGCGA

ACAACATCGTTCCTTTCGCTCGTAAGGCTGCTCCTGTAGCTGCTTAAACGC

CACAAACTTTCTGGCTCGAGCGTCTAGTCGTAGACTCCGTTAATACGCCTA

GACTTAAACCCCCAACGGATGCTCGAGTGGCGGCCTCAGGTCCGTCCTCTC

GCTAAGCAAAAACCTGAGCATCCCGCCACGGGGATAATCGTTGGCTCCCGC

ACAGTGGGTCAACCGTGCTAAGCCTGTGAACGAGCGGAAAGTTACTAGTCA

ATGCGGACAGCGGTTCGATTCCGCTCAGCTCCACCA

*Synechococcus* sp. PCC6301 tmRNA

SEQ ID NO: 118
GGGGCUGUAAUGGUUUCGACGUGUUGGUGAAUCCUUCACCGUGAUUCAGGC

CGAGAGGGAGUCCACUCUCGUAAAUCCAGGCUCAACCAAAAGUAACUGCGA

ACAACAUCGUUCCUUUCGCUCGUAAGGCUGCUCCUGUAGCUGCUUAAACGC

CACAAACUUUCUGGCUCGAGCGUCUAGUCGUAGACUCCGUUAAUACGCCUA

GACUUAAACCCCCAACGGAUGCUCGAGUGGCGGCCUCAGGUCCGUCCUCUC

GCUAAGCAAAAACCUGAGCAUCCCGCCAACGGGGAUAAUCGUUGGCUCCCG

CACAGUGGGUCAACCGUGCUAAGCCUGUGAACGAGCGGAAAGUUACUAGUC

AAUGCGGACAGCGGUUCGAUUCCGCUCAGCUCCACCA

*Synechocystis* sp. PCC6803 ssrA

SEQ ID NO: 119
GGGGCCGCAATGGTTTCGACAGGTTGGCGAAAGCTTGCCCGTGATACAGGT

CGAGAGTGAGTCTCCTCTCGCAAATCAAAGGCTCAAAAAAAAGTAACTGCG

AATAACATCGTCAGCTTCAAACGGGTAGCCATAGCAGCCTAGTCTGTAAAA

GCTACATTTTCTTGTCAAAGACCGTTTACTTCTTTTCTGACTCCGTTAAGG

ATTAGAGGTTAACCCCAACGGATGCTTTGTTTGGCTCTTCTCTAGTTAGCT

AAACAATCAAGACTCAGACTAGAGCATCCCACCATCAGGGATAATCGATGG

TCCCCGTCCTAGGGCTAGAAGGACTAAACCTGTGAATGAGCGGAAAGTTAA

TACCCAGTTTGGACAGCAGTTCAATTCTGCTCGGCTCCACCA

*Synechocystis* sp. PCC6803 tmRNA

SEQ ID NO: 120
GGGGCCGCAAUGGUUUCGACAGGUUGGCGAAAGCUUGCCCGUGAUACAGGU

CGAGAGUGAGUCUCCUCUCGCAAAUCAAAGGCUCAAAAAAAAGUAACUGCG

AAUAACAUCGUCAGCUUCAAACGGGUAGCCAUAGCAGCCUAGUCUGUAAAA

GCUACAUUUUCUUGUCAAAGACCGUUUACUUCUUUUCUGACUCCGUUAAGG

AUUAGAGGUUAACCCCAACGGAUGCUUUGUUUGGCUCUUCUCUAGUUAGCU

AAACAAUCAAGACUCAGACUAGAGCAUCCCACCAUCAGGGAUAAUCGAUGG

UCCCCGUCCUAGGGCUAGAAGGACUAAACCUGUGAAUGAGCGGAAAGUUAA

UACCCAGUUUGGACAGCAGUUCAAUUCUGCUCGCUCCACCA

*Thermotoga maritima* ssrA

SEQ ID NO: 121
GGGGGCGAACGGGTTCGACGGGGATGGAGTCCCCTGGGAAGCGAGCCGAGG

TCCCCACCTCCTCGTAAAAAAGGTGGGACAAAGAATAAGTGCCAACGAACC

TGTTGCTGTTGCCGCTTAATAGATAAGCGGCCGTCCTCTCCGAAGTTGGCT

GGGCTTCGGAAGAGGGCGTGAGAGATCCAGCCTACCGATTCAGCTTCGCCT

TCCGGCCTGAATCGGGAAAACTCAGGAAGGCTGTGGGAGAGGACACCCTGC

CCGTGGGAGGTCCCTCCCGAGAGCGAAAACACGGGCTGCGCTCGGAGAAGC

CCAGGGGCCTCCATCTTCGGACGGGGGTTCGAATCCCCCCGCCTCCACCA

*Thermotoga maritima* tmRNA

SEQ ID NO: 122
GGGGGCGAACGGGUUCGACGGGGAUGGAGUCCCCUGGGAAGCGAGCCGAGG

UCCCCACCUCCUCGUAAAAAAGGUGGGACAAAGAAUAAGUGCCAACGAACC

UGUUGCUGLUGCCGCUUAAUAGAUAAGCGGCCGUCCUCUCCGAAGUUGGC

UGGGCUUCGGAAGAGGGCGUGAGAGAUCCAGCCUACCGAUUCAGCUUCGCC

UUCCGGCCUGAAUCGGGAAAACUCAGGAAGGCUGUGGGAGAGGACACCCUG

CCCGUGGGAGGUCCCUCCCGAGAGCGAAAACACGGGCUGCGCUCGGAGAAG

CCCAGGGGCCUCCAUCUUCGGACGGGGGUUCGAAUCCCCCCGCCUCCACCA

*Thermus thermophilus* ssrA

SEQ ID NO: 123
GGGGGTGAAACGGTCTCGACGGGGGTCGCCGAGGGCGTGGCTGCGCGCCGA

GGTGCGGGTGGCCTCGTAAAAACCCGCAACGGCATAACTGCCAACACCAAC

TACGCTCTCGCGGCTTAATGACCGCGACCTCGCCCGGTAGCCCTGCCGGGG

GCTCACCGGAAGCGGGGACACAAACCCGGCTAGCCCGGGGCCACGCCCTCT

AACCCCGGGCGAAGCTTGAAGGGGGCTCGCTCCTGGCCGCCCGTCCGCGGG

CCAAGCCAGGAGGACACGCGAAACGCGGACTACGCGCGTAGAGGCCCGCCG

TAGAGACCTTCGGACGGGGGTTCGACTCCCCCCACCTCCACCA

*Thermus thermophilus* tmRNA

SEQ ID NO: 124
GGGGGUGAAACGGUCUCGACGGGGGUCGCCGAGGGCGUGGCUGCGCGCCGA

GGUGCGGGUGGCCUCGUAAAAACCCGCAACGGCAUAACUGCCAACACCAAC

UACGCUCUCGCGGCUUAAUGACCGCGACCUCGCCCGGUAGCCCUGCCGGGG

GCUCACCGGAAGCGGGGACACAAACCCGGCUAGCCCGGGGCCACGCCCUCU

AACCCCGGGCGAAGCUUGAAGGGGGCUCGCUCCUGGCCGCCCGUCCGCGGG

CCAAGCCAGGAGGACACGCGAAACGCGGACUACGCGCGUAGAGGCCCGCCG

UAGAGACCUUCGGACGGGGGUUCGACUCCCCCCACCUCCACCA

*Treponema pallidum* ssrA

SEQ ID NO: 125
GGGGATGACTAGGTTTCGACTAGGGATGTGGGGTGTTGCGCTGCAGGTGGA

GTGTCGATCTCCTGATTCGGCGCCTTTATAACTGCCAATTCTGACAGTTTC

GACTACGCGCTCGCCGCGTAATCGCGGGCCTGTGTTTGCGCTGCTCTGAGC

GAACATATCGGCCCGACGCCAAACGGAGCTTGCTCTTACGTTGTGCACGGC

GGACGTAGGGGACTTTTGTCTGTGCTAAGACTCTGGCGCGTGCGGTGCAG

GCCTAGCAGAGTCCGACAAACGCAGTACGCACCGCTAAACCTGTAGGCGCG

CAGCACTCGCGCTTTAGGACGGGGGTTCGATTCCCCCCATCTCCACCA

*Treponema pallidum* tmRNA

SEQ ID NO: 126
GGGGAUGACUAGGUUUCGACUAGGGAUGUGGGGUGUUGCGCUGCAGGUGGA

GUGUCGAUCUCCUGAUUCGGCGCCUUUUAUAACUGCCAAUUCUGACAGUUU

CGACUACGCGCUCGCCGCGUAAUCGCGGGCCUGUGUUUGCGCUGCUCUGAG

CGAACAUAUCGGCCCGACGCCAAACGGAGCUUGCUCUUACGUUGUGCACGG

CGGACGUAGGGGACUUUUGUCUGUGCUAAGACUCUGGCGCGUGCGGUGCA

GGCCUAGCAGAGUCCGACAAACGCAGUACGCACCGCUAAACCUGUAGGCGC

GCAGCACUCGCGCUCUUUAGGACGGGGGUUCGAUUCCCCCCAUCUCCACCA

*Vibrio cholerae* ssrA

SEQ ID NO: 127
GGGGCTGATTCAGGATTCGACGGGAATTTTGCAGTCTGAGGTGCATGCCGA

GGTGCGGTAGGCCTCGTTAACAAACCGCAAAAAAATAGTCGCAAACGACGA

AAACTACGCACTAGCAGCTTAATACCCTGCTCAGAGCCCTTCCTCCCTAGC

TTCCGCTTGTAAGACGGGGAAATCAGGAAGGTCAAACCAAATCAAGCTGGC

GTGGATTCCCCCACCTGAGGATGAAGCGCGAGATCTAATTCAGGTTAGCCA

TTAGCGTGTCGGTTCGCAGGCGGTGGTGAAATTAAAGATCGACTAAGCATG

TAGTACCAAAGATGAATGGTTTTCGGACGGGGGTTCAACTCCCCCCAGCTC

CACCA

*Vibrio cholerae* tmRNA

SEQ ID NO: 128
GGGGCUGAUUCAGGAUUCGACGGGAAUUUUGCAGUCUGAGGUGCAUGCCGA

GGUGCGGUAGGCCUCGUUAACAAACCGCAAAAAAAUAGUCGCAAACGACGA

AAACUACGCACUAGCAGCUUAAUACCCUGCUCAGAGCCCUUCCUCCCUAGC

UUCCGCUUGUAAGACGGGGAAAUCAGGAAGGUCAAACCAAAUCAAGCUGGC

GUGGAUUCCCCCACCUGAGGGAUGAAGCGCGAGAUCUAAUUCAGGUUAGCC

AUUCGUUAGCGUGUCGGUUCGCAGGCGGUGGUGAAAUUAAAGAUCGACUAA

GCAUGUAGUACCAAAGAUGAAUGGUUUUCGGACGGGGGUUCAACUCCCCC

AGCUCCACCA

*Yersinia pestis* ssrA

SEQ ID NO: 129
GGGGCTGATTCTGGATTCGACGGGATTCGCGAAACCCAAGGTGCATGCCGA

GGTGCGGTGGCCTCGTAAAAAACCGCAAAAAAAATAGTTGCAAACGACGAA

AACTACGCACTAGCAGCTTAATAACCTGCTTAGAGCCCTCTCTGCCTAGCC

TCCGCTCTTAGGACGGGGATCAAGAGAGGTCAAACCTAAAAGAGCTCGTGT

GGAAACCTTGCCTGGGGTGGAAGCATTAAAACTAATSAGGATAGTTTGTCA

GTAGCGTGTCCATCCGCAGCTGGCCGGCGAATGTAATGATTGGACTAAGCA

TGTAGTGCCGACGGTGTAGTAATTTCGGACGGGGGTTCAAATCCCCCCAGC

TCCACCA

*Yersinia pestis* tmRNA

SEQ ID NO: 130
GGGGCUGAUUCUGGAUUCGACGGGAUUCGCGAAACCCAAGGUGCAUGCCGA

GGUGCGGUGGCCUCGUAAAAAACCGCAAAAAAAAUAGUUGCAAACGACGAA

AACUACGCACUAGCAGCUUAAUAACCUGCUUAGAGCCCUCUCUGCCUAGCC

UCCGCUCUUAGGACGGGGAUCAAGAGAGGUCAAACCUAAAAGAGCUCGUGU

GGAAACCUUGCCUGGGGUGGAAGCAUUAAAACUAAUCAGGAUAGUUUGUCA

GUAGCGUGUCCAUCCGCAGCUGGCCGGCGAAUGUAAUGAUUGGACUAAGCA

UGUAGUGCCGACGGUGUAGUAAUUUCGGACGGGGGUUCAAAUCCCCCCAGC

UCCACCA

*Campylobacter fetus* ssrA, Internal Partial

SEQ ID NO: 131
AGGAGTAAGTCTGCTTAGATGGCATGTCGCTTTGGGCAAAGCGTAAAAAGC

CCAAATAAAATTAAACGCAAACAACGTTAAATTCGCTCCTGCTTACGCTAA

AGCTGCGTAAGTTCAGTTGAGCCTGAAATTTAAGTCATACTATCTAGCTTA

ATTTTCGGTCATCTTTGATAGTGTAGCCTTGCGTTTGACAAGCGTTGAGGT

GAAATAAAGTCTTAGCCTTGCTTTTGAGTTTTGGAAGATGAGCGAAGTAGG

GTGAAGTAGTCATCTTTGCTAAGCATGTAGAGGTCTTTGTGGGATTATTTT

TGG

*Campylobacter fetus* tmRNA, Internal Partial

SEQ ID NO: 132
AGGAGUAAGUCUGCUUAGAUGGCAUGUCGCUUUGGGCAAAGCGUAAAAAGC

CCAAAUAAAAUUAAACGCAAACAACGUUAAAUUCGCUCCUGCUUACGCUAA

AGCUGCGUAAGUUCAGUUGAGCCUGAAAUUUAAGUCAUACUAUCUAGCUUA

AUUUUCGGUCAUCUUUGAUAGUGUAGCCUUGCGUUUGACAAGCGUUUGAG

GUGAAAUAAAGUCUUAGCCUUGCUUUUGAGUUUUGGAAGAUGAGCGAAGUA

GGGUGAAGUAGUCAUCUUUGCUAAGCAUGUAGAGGUCUUUGUGGGAUUAUU

UUUGG

*Campylobacter coli* (BM2509) ssrA, Internal Partial

SEQ ID NO: 133
AGGAGTAAGTCTGCTTAGATGGCATGTCGCTTTGGACAAAGCGTAAAAGT

CCAAATTAAAATTAAACGCAAATAACGTTAAATTTGCTCCTGCTTACGCTA

AAGCTGCGTAAGTTCAGTTGAGCCCGAAACTCAAGTGATGCTATCTAGCTT

GAATTTTGGTCATCTTTGATAGTGTAGATTGAAAATTGACAACTTTTAATC

GAAGTTAAAGTCTTAGTCTAGCTTGAAATTTTGGAAGGTGAGTTTAGCCAG

ATGAAGTTTTCACCTTTGCTAAACATGTAGAAGTCTTTGTGGGGTTATTTT

TGG

*Campylobacter coli* (BM2509) tmRNA, Internal Partial

SEQ ID NO: 134
AGGAGUAAGUCUGCUUAGAUGGCAUGUCGCUUUGGACAAAGCGUAAAAG

UCCAAAUUAAAAUUAAACGCAAAUAACGUUAAAUUUGCUCCUGCUUACGCU

AAAGCUGCGUAAGUUCAGUUGAGCCCGAAACUCAAGUGAUGCUAUCUAGCU

UGAAUUUUGGUCAUCUUUGAUAGUGUAGAUUGAAAAUUGACAACUUUUAAU

CGAAGUUAAAGUCUUAGUCUAGCUUGAAAUUUUGGAAGGUGAGUUUAGCCA

GAUGAAGUUUUCACCUUUGCUAAACAUGUAGAAGUCUUUGUGGGGUUAUUU

UUGG

*Camplyobacter* Chicken Isolate ssrA, Internal Partial

SEQ ID NO: 135
ACAGGAGTAAGTCTGCTTAGATGGCATGTCGCTTTGGGCAAAGCGTAAAAA

GCCCAAATAAAATTAAACGCAAACAACGTTAAATTCGCTCCTGCTTACGCT

AAAGCTGCGTAAGTTCAGTTGAGCCTGAAATTTAAGTCATACTATCTAGCT

TAATTTTCGGTCATTTTTGATAGTGTAGCCTTGCGTTTGACAAGCGTTGAG

GTGAAATAAGGTCTTAGCCTTGCTTTTGAGTTTTGGAAGATGAGCGAAGTA

GGGTGAAGTAGTCATCTTTGCTAAGCATGTAGAGGTCTTTGTGGGATTATT

TTTGG

*Camplyobacter* Chicken Isolate tmRNA, Internal Partial

SEQ ID NO: 136
ACAGGAGUAAGUCUGCUUAGAUGGCAUGUCGCUUUGGGCAAAGCGUAAAAA

GCCCAAAUAAAAUUAAACGCAAACAACGUUAAAUUCGCUCCUGCUUACGCU

AAAGCUGCGUAAGUUCAGUUGAGCCUGAAAUUUAAGUCAUACUAUCUAGCU

UAAUUUUCGGUCAUUUUUGAUAGUGUAGCCUUGCGUUUGACAAGCGUUGA

GGUGAAAUAAGGUCUUAGCCUUGCUUUUGAGUUUUGGAAGAUGAGCGAAG

UAGGGUGAAGUAGUCAUCUUUGCUAAGCAUGUAGAGGUCUUUGUGGGAUUA

UUUUUGG

*Clostridium perfringens* ssrA, Internal Partial

SEQ ID NO: 137
ACGGGGGTAGGATGGGTTTGATAAGCGAGTCGAGGGAAGCATGGTGCCTCG

ATAATAAAGTATGCATTAAAGATAAACGCACGAGATAATTTTGCATTAGCA

GCTTAAGTTAGCGCTGCTCATCCTTCCTCAATTGCCCACGGTTGAGAGTAA

GGGTGTCATTTAAAAGTGGGGAACCGAGCCTAGCAAAGCTTTGAGCTAGGA

ACGGAATTTATGAAGCTTACCAAAGAGGAAGTTTGTCTGTGGACGTTCTCT

GAGGGAATTTTAAAACACAAGACTACACTCGTAGAAAGTCTTACTGGTCTG

CTTTCGG

*Clostridium perfringens* tmRNA, Internal Partial

SEQ ID NO: 138
ACGGGGGUAGGAUGGGUUUGAUAAGCGAGUCGAGGGAAGCAUGGUGCCUCG

AUAAUAAAGUAUGCAUUAAAGAUAAACGCACGAGAUAAUUUUGCAUUAGCA

GCUUAAGUUAGCGCUGCUCAUCCUUCCUCAAUUGCCCACGGUUGAGAGUAA

GGGUGUCAUUUAAAAGUGGGGAACCGAGCCUAGCAAAGCUUUGAGCUAGGA

ACGGAAUUUAUGAAGCUUACCAAAGAGGAAGUUUGUCUGUGGACGUUCUCU

GAGGGAAUUUUAAAACACAAGACUACACUCGUAGAAAGUCUUACUGGUCUG

CUUUCGG

*Haemophilus ducreyi* (NCTC 10945) ssrA, Internal Partial

SEQ ID NO: 139
ACGGGATTAGCGAAGTCCAAGGTGCACGTCGAGGTGCGGTAGGCCTCGTAA

CAAACCGCAAAAAAATAGTCGCAAACGACGAACAATACGCTTTAGCAGCTT

AATAACCTGCATTTAGCCTTCGCGCCCTAGCTTTCGCTCGTAAGACGGGGA

GCACGCGGAGTCAAACCAAAACGAGATCGTGTGGACGCTTCCGCTTGTAGA

TGAAACACTAAATTGAATCAAGCTAGTTTATTTCTTGCGTGTCTGTCCGCT

GGAGATAAGCGAAATTAAAGACCAGACTAAACGTGTAGTACTGAAGATAGA

GTAATTTCGGACCCGGGTTCGACTC

*Haemophilus ducreyi* (NCTC 10945) tmRNA, Internal Partial

SEQ ID NO: 140
ACGGGAUUAGCGAAGUCCAAGGUGCACGUCGAGGUGCGGUAGGCCUCGUAA

CAAACCGCAAAAAAAUAGUCGCAAACGACGAACAAUACGCUUUAGCAGCUU

AAUAACCUGCAUUUAGCCUUCGCGCCCUAGCUUUCGCUCGUAAGACGGGG

AGCACGCGGAGUCAAACCAAAACGAGAUCGUGUGGACGCUUCCGCUUGUAG

AUGAAACACUAAAUUGAAUCAAGCUAGUUUAUUUCUUUGCGUGUCUGUCCG

CUGGAGAUAAGCGAAAUUAAAGACCAGACUAAACGUGUAGUACUGAAGAUA

UAGUAAUUUCGGACCCGGGUUCGACUC

*Listeria innocua* (Food Isolate #1) ssrA, Internal Partial

SEQ ID NO: 141
GGCAAAGAAAAACAAAACCTAGCTTTCGCTGCCTAATAACCAGTAGCATAG

CTGATCCTCCGTGCATCGCCCATGTGCTACGGTAAGGGTCTCACTCTAAGT

GGGCTACACTAGTTAATCTCCGTCTGAGGTAAATAGAAGAGCTTAATCAGA

CTAGCTGAATGGAAGCCTGTTACCGGGCTGATGTTTATGCGAAATGCTAAT

ACGGTGACTACGCTCGTAGATATTCAA

*Listeria innocua* (Food Isolate #1) tmRNA, Internal Partial

SEQ ID NO: 142
GGCAAAGAAAAACAAAACCUAGCUUUCGCUGCCUAAUAACCAGUAGCAUAG
CUGAUCCUCCGUGCAUCGCCCAUGUGCUACGGUAAGGGUCUCACUCUAAGU
GGGCUACACUAGUUAAUCUCCGUCUGAGGUUAAAUAGAAGAGCUUAAUCAG
ACUAGCUGAAUGGAAGCCUGUUACCGGGCUGAUGUUUAUGCGAAAUGCUAA
UACGGUGACUACGCUCGUAGAUAUUCAA

*Listeria innocua* (Food Isolate #2) ssrA, Internal Partial

SEQ ID NO: 143
GGCAAAGAAAAACAAAACCTAGCTTTCGCTGCCTAATAAGCAGTAGCATAG
CTGATCCTCCGTGCATCGCCCATGTGCTACGGTAAGGGTCTCACTCTAAGT
GGGCTACACTAGTTAATCTCCGTCTGAGGTTAAATAGAAGAGCTTAATCAG
ACTAGCTGAATGGAAGCCTGTTACCGGGCCGATGTTTATGCGAAATGCTAA
TACGGTGACTACGCTCGTAGATATTTAA

*Listeria innocua* (Food Isolate #2) tmRNA, Internal Partial

SEQ ID NO: 144
GGCAAAGAAAAACAAAACCUAGCUUUCGCUGCCUAAUAAGCAGUAGCAUAG
CUGAUCCUCCGUGCAUCGCCCAUGUGCUACGGUAAGGGUCUCACUCUAAGU
GGGCUACACUAGUUAAUCUCCGUCUGAGGUUAAAUAGAAGAGCUUAAUCAG
ACUAGCUGAAUGGAAGCC

*Listeria innocua* (Food Isolate #3) ssrA, Internal Partial

SEQ ID NO: 145
GGCAAAGAAAAACAAAACCTAGCTTTCGCTGCCTAATAAGCAGTAGAATAG
CTGATCCTCCGTGCATCGCCCATGTGCTACGGTAAGGGTCTCACTCTAAGT
GGGCTACACTAGTTAATCTCCGTCTGAGGTTAAATAGAAGAGCTTAATCGG
ACTAGCTGAATGGAAGCCTGTTACCGGGCCGATGTTTATGCGAAATGCTAA
TACGGTGACTACGCTCGTAGATATTTAA

*Listeria innocua* (Food Isolate #3) tmRNA, Internal Partial

GGCAAAGAAAAACAAAACCUAGCUUUCGCUGCCUAAUAAGCAG
UAGAAUAGCUGAUCCUCCGUGCAUCGCCCAUGUGCUACGGUAA
GGGUCUCACUCUAAGUGGGCUACACUAGUUAAUCUCCGUCUGA
GGUUAAAUAGAAGAGCUUAAUCGGACUAGCUGAAUGGAAGCC
UGUUACCGGGCCGAUGUUUAUGCGAAAUGCUAAUACGGUGAC
UACGCUCGUAGAUAUUUAA SEQ ID NO: 146

*Listeria innocua* (ATCC 12210) ssrA, Internal Partial

GGCAAAGAAAAACAAAACCTAGCCGCTGCCTAATAAGCAGT
AGCATAGCTGATCCTCCGTGCATCGCCCATGTGCTACGGTAAGG
GTCTCACTCTAAGTGGGCTACACTAGTTAATCTCCGTCTGGGTT
AAATAGAAGAGCTTAATCAGACTAGCTGAATGGAAGCCTGTTAC
TGGGCCGATGTTTATGCGAAATGCTAATACGGTGACTACGCTCG
TAGATATTTA SEQ ID NO: 147

*Listeria innocua* (ATCC 12210) tmRNA, Internal Partial

GGCAAAGAAAAACAAAACCUAGCUUUCGCUGCCUAAUAAGCAG
UAGCAUAGCUGAUCCUCCGUGCAUCGCCCAUGUGCUACGGUAA
GGGUCUCACUCUAAGUGGGCUACACUAGUUAAUCUCCGUCUGG
GGUUAAAUAGAAGAGCUUAAUCAGACUAGCUGAAUGGAAGCC
UGUUACUGGGCCGAUGUUUAUGCGAAAUGCUAAUACGGUGAC
UACGCUCGUAGAUAUUUAA SEQ ID NO: 148

*Listeria ivanovii* (NCTC 11846) ssrA, Internal Partial

ACAGGGATAGTTCGAGCTTGAGTTGCGAGTCGGGGGGATCGTCC
TCGTTATTAACGTCAAAGCCAATAATAACTGGCAAAGAAAACA
AAACCTAGCTTTCGCTGCCTAATAAGCAGTAGCATAGCTGATCCT
CCGTGCATCGCCCATGTGCTACGGTAAGGGTCTCACTTTAAGTGG
GCTACACTAAATAATCTCCGTCTGGGGTTAGTTAGAAGAGCTTA
ATCAGACTAGCTGAATGGAAGCCTGTTACCGGGCTGATGTTTAT
GCGAAATGCTAATACGGTGACTACGCTCGTAGATATTTAAGTGC
CGATATTTCTGG SEQ ID NO: 149

*Listeria ivanovii* (NCTC 11846) tmRNA, Internal Partial

ACAGGGAUAGUUCGAGCUUGAGUUGCGAGUCGGGGGGAUCGU
CCUCGUUAUUAACGUCAAAGCCAAUAAUAACUGGCAAAGAAA
AACAAAACCUAGCUUUCGCUGCCUAAUAAGCAGUAGCAUAGCU
GAUCCUCCGUGCAUCGCCCAUGUGCUACGGUAAGGGUCUCACU
UUAAGUGGGCUACACUAAAUAAUCUCCGUCUGGGGUUAGUUA
GAAGAGCUUAAUCAGACUAGCUGAAUGGAAGCCUGUUACCGG
GCUGAUGUUUAUGCGAAAUGCUAAUACGGUGACUCGCUCGUA
GAUAUUUAAGUGCCGAUAUUUCUGG SEQ ID NO: 150

*Listeria seeligeri* (NCTC 11856) ssrA, Internal Partial

ACAGGGATAGTTCGAGCTTGAGTTGCGAGTCGGGGGATCGTCC
TCGTTATCAACGTCAAAGCCAATAATAACTGGCAAAGAAAAACA
AAACCTAGCTTTCGCTGCCTAATAAGCAGTAGCATAGCTGATCCT
CCGTGCATCGCCCATGTGCTACGGAAAGGGTCTCACTTTAAGTG
GGCTACACTAAATAATCTCCGTCTGGGGTTAGTTAGAAGAGCTT
AATCAGACTAGCTGAATGGAAGCCTTTACCGGGCTGATGTTTA
TGCGAATACTAATACGGTGACTACGCTCGTAGATATTTAAGTG
CCCATATTTCTGG SEQ ID NO: 151

Listeria seeligeri (NCTC 11856) tmRNA, Internal Partial

```
ACAGGGAUAGUUCGAGCUUGAGUUGCGAGUCGGGGGAUCGU
CCUCGUUAUCAACGUCAAAGCCAAUAAUAACUGGCAAAGAAAA
ACAAAACCUAGCUUUCGCUGCCUAAUAAGCAGUAGCAUAGCUG
AUCCUCCGUGCAUCGCCCAUGUGCUACGGAAAGGGUCUCACUU
UAAGUGGGCUACACUAAAUAAUCUCCGUCUGGGGUUAGUUAG
AAGAGCUUAAUCAGACUAGCUGAAUGGAAGCCUGUUACCGGG
CUGAUGUUUAUGCGAAAUACUAAUACGGUGACUACGCUCGUA
GAUAUUUAAGUGCCCAUAUUUCUGG SEQ ID NO: 152
```

Salmonella enteritidis ssrA, Internal Partial

```
ACGGGATTTGCGAAACCCAAGGTGCATGCCGAGGGGCGGTTGGC
CTCGTAAAAAGCCGCAAAAAAATAGTCGCAAACGACGAAACCT
ACGCTTTAGCAGCTTAATAACCTGCTTAGAGCCCTCTCTCCCTAG
CCTCCGCTCTTAGGACGGGGATCAAGAGAGGTCAAACCCAAAAG
AGATCGCGTGGATGCCCTGCCTGGGGTTGAAGCGTTAAAACGAA
TCAGGCTAGTCTGGTAGTGGCGTGTCCGTCCGCAGGTGCCAGGC
GAATGTAAAGACTGACTAAGCATGTAGTACCGAGGATGTAGGAA
TTTCGG SEQ ID NO: 153
```

Salmonella enteritidis tmRNA, Internal Partial

```
ACGGGAUUUGCGAAACCCAAGGUGCAUGCCGAGGGGCGGUUG
GCCUCGUAAAAGCCGCAAAAAAUAGUCGCAAACGACGAAAC
CUACGCUUUAGCAGCUUAAUAACCUGCUUAGAGCCCUCUCUCC
CUAGCCUCCGCUCUUAGGACGGGGAUCAAGAGAGGUCAAACCC
AAAAGAGAUCGCGUGGAUGCCCUGCCUGGGGUUGAAGCGUUA
AAACGAAUCAGGCUAGUCUGGUAGUGGCGUGUCCGUCCGCAGG
UGCCAGGCGAAUGUAAAGACUGACUAAGCAUGUAGUACCGAG
GAUGUAGGAAUUUCGG SEQ ID NO: 154
```

Staphylococcus epidermidis (NCTC 11047) ssrA, Internal Partial

```
ACAGGGGTCCCCCGAGCTTATTAAGCGTGTCGGAGGGTTGGCTC
CGTCATCAACACATTTCGGTTAAATATAACTGACAAATCAAACA
ATAATTTCGCAGTAGCTGCGTAATAGCCACTGCATCGCCTAACA
GCATCTCCTACGTGCTGTTAACGCGATTCAACCCTAGTAGGATAT
GCTAAACACTGCCGCTTGAAGTCTGTTTAGATGAAATATAATCA
HGCTAGTATC+TGTTGGTTGTTTATTGCTTAGCATGATGCGAAAA
TTATCAATAAACTACACACGTAGAAAGATTTGTATCAGGACCTC
TGG SEQ ID NO: 155
```

Staphylococcus epidermidis (NCTC 11047) tmRNA, Internal Partial

```
ACAGGGGUCCCCCGAGCUUAUUAAGCGUGUCGGAGGGUUGGCU
CCGUCAUCAACACAUUUCGGUUAAAUAUAACUGACAAAUCAAA
4AAUAAUUUCJ3CAGUAGCUGCGUAAUAGCCACUGCAUCGCCUA
ACAGCAUCUCCUACGUGCUGUUAACGCGAUUCAACCCUAGUAG
GAUAUGCUAAACACUGCCGCUUGAAGUCUGUUUAGAUGAAAU
AUAAUCAAGCUAGUAUCAUGUUGGUUGUUUALnjGCUUAGCAU
GAUGCGAAAAUUAUCAAUAAACUACACACGUAGAAAGAUUUG
UAUCAGGACCUCUGG SEQ ID NO: 156
```

Streptococcus agalactiae (NCTC 8181) ssrA, Internal Partial

```
ACAGGCATTATGAGGTATATTTTGCGACTCATCGGCAGATGTAA
AATGCCAGTTAAATATAACTGCAAAAAATACAAATTCTTACGCA
TTAGCTGCCTAAAAAACAGCCTGCGTGATCTTCACAAGATTGTTT
GCGTTTTGCTAGAAGGTCTTATTTATCAGCAAACTACGTTTGGCT
ACTGTCTAGTTAGTTAAAAAGAGATTTATAGACTCGCTATGTGA
GGGCTTGAGTTATGTGTCATCACCTAGTTAAATCAATACATAACC
TATAGTTGTAGACAAATATATTAGCAGATGTTTGG
SEQ ID NO: 157
```

Streptococcus agalactiae (NCTC 8181) tmRNA, Internal Partial

```
ACAGGCAUUAUGAGGUAUAUUUUGCGACUCAUCGGCAGAUGU
AAAAUGCCAGUUAAAUAUAACUGCAAAAAAUACAAAUUCUUA
CGCAUUAGCUCCUAAAAAACAGCCUGCGUGAUCUUCACAAGA
UUGUUUGCGUUUUGCUAGAAGGUCUUAUUUAUCAGCAAACUA
CGUUUGGCUACUGUCUAGUUAGUUAAAAAGAGAUUUAUAGAC
UCGCUAUGUGAGGGCUUGAGUUAUGUGUCAUCACCUAGUUAA
AUCAAUACAUAACCUAUAGUUGUAGACAAAUAUAUUAGCAGA
UGUUUGG SEQ ID NO: 158
```

Bordetella bronchiseptica ssrA

```
GGGGCCGATCCGGATTCGACGTGGGTCATGAAACAGCTCAAGGC
ATGCCGAGCACCAGTAAGCTCGTTAATCCACTGGAACACTACAA
ACGCCAACGACGAGCGITICGCTCTCGCCGCTTAAGCGGTGAGC
CGCTGCACTGATCTGTCCTTGGGTCACGCGGGGAA
SEQ ID NO: 159
```

Bordetella bronchiseptica tmRNA

```
GGGGCCGAUCCGGAUUCGACGUGGGUCAUGAAACAGCUCAAGGC
AUGCCGAGCACCAGUAAGCUCGUUAAUCCACUGGAACACUACAA
```

-continued
ACGCCAACGACGAGCGUUUCGCUCUCGCCGCUUAAGCGGUGAGC

CGCUGCACUGAUCUGUCCUUGGGUCACGCGGGGAA

SEQ ID NO: 160

*Chlamydia pneumoniae* (CWL029), ssrA

GGGGGTGTATAGGTTTCGACTTGAAAATGAAGTGTTAATTGCAT
GCGGAGGGCGTTGGCTGGCCTCCTAAAAAGCCAACAAAACAATA
AATGCCGAACCTAAGGCTGAATGCGAAATTATTAGCTTGTTTGA
CTCAGTAGAGGAAAGACTAGCTGCTTAATTAGCAAAAGTTGTTA
GCTAGATAATCTCTAGGTAACCCGGTATCTGCGAGCTCCACCAG
AGGCTTGCAAAATACCGTCATTTATCTGGTTGGAACTTACTTTCT
CTAATTCTCAAGGAAGTTCGTTCGAGATTTTTGAGAGTCATTGGC
TGCTATAGAGGCTTCTAGCTAAGGGAGTCCAATGTAAACAATTC
TAGAAGATAAGCATGTAGAGGTTAGCAGGGAGTTTGTCAAGGAC
GAGAGTTCGAGTCTCTCCACCTCCACCA SEQ ID NO: 161

*Chlamydia pneumoniae* (CWL029) tmRNA

GGGGGUGUAUAGGUUUCGACUUGAAAAUGAAGUGUUAAUUGC
AUGCGGAGGGCGUUGGCUGGCCUCCUAAAAAGCCAACAAAACA
AUAAAUGCCGAACCUAAGGCUGAAUGCGAAAUUAUUAGCUUG
UUUGACUCAGUAGAGGAAAGACUAGCUGCUUAAUUAGCAAAA
GUUGUUAGCUAGAUAAUCUCUAGGUAACCCGGUAUCUGCGAG
CUCCACCAGAGGCUUGCAAAAUACCGUCAUUUAUCUGGUUGGA
ACUUACUUUCUCUAAUUCUCAAGGAAGUUCGUUCGAGAUUUU
UGAGAGUCAUUGGCUGCUAUAGAGGCUUCUAGCUAAGGGAGU
CCAAUGUAAACAAUUCUAGAAGAUAAGCAUGUAGAGGUUAGC
AGGGAGUUUGUCAAGGACGAGAGUUCGAGUCUCUCCACCUCCA
CCA SEQ ID NO: 162

*Francisella tularensis* ssrA

GGGGGCGAATATGGTTTCGACATGAATGTCAAAATCTAAGGTGC
ATGCCGAGGAAGTACCGTAACCTCGTTAATAACAGTACAAATGC
CAATAATAACTGGCAACAAAAAAGCAAACCGCGTAGCGGCTAA
CGACAGCAACTTTGCTGCTGTTGCTAAAGCTGCCTAGTCTAGCTT
AATAATCTAGATGCGCACGGATATGATAGTCTTTCTTATGACACT
ATCTATACATCCGTTCATATTCCGCATAAGACGGTCTTTGCTTTTT
GTCTGGGAGTTAAGGCTGTATTTAACAGACTCGCTAACTATTACC
CTGGCTAATTGGGAATAGTCAAGCTAAACTCAAATAGATTAGC
CTAAGCATGTAGATCCAAAGATCTAGAGTTTGTGGACGCGGGTT
CAAATCCCGCCGCCTCCACCA SEQ ID NO: 163

*Francisella tularensis* tmRNA

GGGGGCGAAUAUGGUUUCGACAUGAAUGUCAAAAUCUAAGGU
GCAUGCCGAGGAAGUACCGUAACCUCGUUAAUAACAGUACAAA
UGCCAAUAAUAACUGGCAACAAAAAAGCAAACCGCGUAGCGGC
UAACGACAGCAACUUUGCUGCUGUUGCUAAAGCUGCCUAGUCU
AGCUUAAUAAUCUAGAUGCGCACGGAUAUGAUAGUCUUUCUU
AUGACACUAUCUAUACAUCCGUUCAUAUUCCGCAUAAGACGGU
CUUUGCUUUUUGUCUGGGAGUUAAGGCUGUAUUUAACAGACU
CGCUAACUAUUACCCUGGCUAAUUGGGGAAUAGUCAAGCUAA
ACUCAAAUAGAUUAGCCUAAGCAUGUAGAUCCAAAGAUCUAG
AGUUUGUGGACGCGGGUUCAAAUCCCGCCGCCUCCACCA

SEQ ID NO: 164

*Guillardia theta* (Plastid) ssrA

GGGGCTGATTTGGATTCGACATATAAATTTGCGTGTTTCATTATG
AAGCAAGTCAAGTTTAATGATCTTGTAAAAAACATTAAAGTACA
AATAAATGCAAGCAATATAGTTTCATTTAGTTCAAAACGTTTAGT
CTCTTTTGCATAAGCAAAATGTGTTAATAACTTTCTTAGTAGAAA
TTGGAGAAGTTTACTAAGATTTATATTTACTCCATAATTATTTTA
AAGATGGTAAAAAGGTGATTCATCATTTGTATGTTTCTAAACTTT
GTGAAAGAATAGTGGGCTCCATTTATAATGAACGTGGGTTCAAA
TCCCACCAGCTCCACCA SEQ ID NO: 165

*Guillardia theta* (Plastid) tmRNA

GGGGCUGAUUUGGAUUCGACAUAUAAAUUUGCGUGUUUCAUU
AUGAAGCAAGUCAAGUUUAAUGAUCUUGUAAAAAACAUUAAA
GUACAAAUAAAUGCAAGCAAUAUAGUUUCAUUUAGUUCAAAA
CGUUUAGUCUCUUUUGCAUAAGCAAAAUGUGUUAAUAACUUU
CUUAGUAGAAAUUGGAGAAGUUUACUAAGAUUUAUAUUUACU
CCAUAAUUAUUUUAAAGAUGGUAAAAAGGUGAUUCAUCAUUU
GUAUGUUUCUAAACUUUGUGAAAGAAUAGUGGGCUCCAUUUA
UAAUGAACGUGGGUUCAAAUCCCACCAGCUCCACCA

SEQ ID NO: 166

*Thalassiosira Weissflogii* (Plastid) ssrA

GGGGCTGATTTGGTTTCGACATTTAAAACTTCTTTCTATGTGTCA
GGTCAAAGTTTGTATTCTTTGTAAAAAAATACTAAAATACTAATA
AATGCTAATAATATAATACCGTTTATTTTTAAAGCAGTAAAAAC
AAAAAAGAAGCAATGGCTTTAAATTTTGCTGTATAGTTCATTA
ACTTAGGTTATTAAATATTTTTTCATTATAACTGGACTTTTCTCTA
GTTTATAGTTTAGAATAAATTTAAATTTTGCAAAACTCGTTCGAA

```
AATTTTCGGGCTAAACCTGTAAACGCAAATACTAAGAAATTTTA

GATGGACATGGGTTCAATTCCCATCAGTTCCACCA

SEQ ID NO: 167
```

*Thalassiosira Weissflogii* (Plastid) tmRNA

```
GGGGCUGAUUUGGUUUCGACAUUUAAAACUUCUUUCUAUGUG

UCAGGUCAAAGUUUGUAUUCUUUGUAAAAAAAUACUAAAAUA

CUAAUAAAUGCUAAUAAUAUAAUACCGUUUAUUUUUAAAGCA

GUAAAAACAAAAAAAGAAGCAAUGGCUUUAAAUUUUGCUGUA

UAGUUCAUUAACUUAGGUUAUUAAAUAUUUUUUCAUUAUAAC

UGGACUUUUCUCUAGUUUAUAGUUUAGAAUAAAUUUAAAUUU

UGCAAAACUCGUUCGAAAAUUUUCGGGCUAAACCUGUAAACGC

AAAUACUAAGAAAUUUUAGAUGGACAUGGGUUCAAUUCCCAU

CAGUUCCACCA SEQ ID NO: 168
```

*Helicobacter pylori* ssrA, (Clinical Isolate 1), Internal Partial

```
TGGGGATGTTACGGTTTCGACAGGGGTAGTTCGAGCTTAGGTGG

CGAGTCGAGGGGATCGGCCTCGTTAAAACGTCAAAGCCTATAAC

TGGCAAACAACAAAACAACTTCGCTTTAGCAGCTTAATAAGCTC

TTAGCGGTTCCTCCCTCCATCGCCCATGTGGTAGGGTAAGGGACT

CAAATTAAGTGGGCTACGCTGGATTCCACCGTCTGAGGATGAAA

GAAGAGAACAACCAGACTAGCTACCCGGACGCCCGTCGATAGG

CAGATGGAGTAGCGAATCGCGAATATATCGACTACACTCGTAGA

AGCTTAAGTGCCGATATTCTTGGACGTGGGTTCGACTCCC

SEQ ID NO: 176
```

*Helicobacter pylori* tmRNA, (Clinical Isolate 1), Internal Partial

```
UGGGGAUGUUACGGUUUCGACAGGGGUAGUUCGAGCUUAGGU

GGCGAGUCGAGGGGAUCGGCCUCGUUAAAACGUCAAAGCCUAU

AACUGGCAAACAACAAAACAACUUCGCUUUAGCAGCUUAAUAA

GCUCUUAGCGGUUCCUCCCUCCAUCGCCCAUGUGGUAGGGUAA

GGGACUCAAAUUAAGUGGGCUACGCUGGAUUCCACCGUCUGAG

GAUGAAAGAAGAGAACAACCAGACUAGCUACCCGGACGCCCGU

CGAUAGGCAGAUGGAGUAGCGAAUCGCGAAUAUAUCGACUAC

ACUCGUAGAAGCUUAAGUGCCGAUAUUCUUGGACGUGGGUUC

GACUCCC SEQ ID NO: 177
```

*Helicobacter pylori* ssrA, (Clinical Isolate 2), Internal Partial

```
TGGGGACGTTACGGTTTCGACAGGGATAGTTCGAGCTTAGGTTG

CGAGTCGAGGGGATCGGCCTCGTTAAAACGTCAAAGCCTATAAT

TGGCAAACAAAACAATCTTTCTTTAGCTGCTTAATTGCACTAAAG

GTTCCTCCCTCCATCGTCCATGTGGTAGGGTAAGGGACTCAAACT

AAGTGGACTACGCCGGAGTTCGCCGTCTGAGGACAAAGGAAGA

GAACAACCAGACTAGCAACTTGGAAGCCTGTCGATAGGCCGAAG

AGTTCGCGAAATGCTAATATATCGACTACACTCGTAGAAGCTTA

AGTGCCGATATTTTTGGACGTGGGTTCGATTCCCT SEQ ID

NO: 178
```

*Helicobacter pylori* tmRNA, (Clinical Isolate 2), Internal Partial

```
UGGGGACGUUACGGUUUCGACAGGGAUAGUUCGAGCUUAGGU

UGCGAGUCGAGGGGAUCGGCCUCGUUAAAACGUCAAAGCCUAU

AAUUGGCAAACAAAACAAUCUUUCUUUAGCUGCUUAAUUGCA

CUAAAGGUUCCUCCCUCCAUCGUCCAUGUGGUAGGGUAAGGGA

CUCAAACUAAGUGGACUACGCCGGAGUUCGCCGUCUGAGGACA

AAGGAAGAGAACAACCAGACUAGCAACUUGGAAGCCUGUCGA

UAGGCCGAAGAGUUCGCGAAAUGCUAAUAUAUCGACUACACUC

GUAGAAGCUUAAGUGCCGAUAUUUUUGGACGUGGGUUCGAUU

CCCU SEQ ID NO: 179
```

*Listeria seeligeri* (NCTC 11856) ssrA, Internal Partial

```
ACAGGGATAGTTCGAGCTTGAGTTGCGAGTCGGGGGATCGTCC

TCGTTATCAACGTCAAAGCCAATAATAACTGGCAAAGAAAACA

AAACCTAGCTTTCGCTGCCTAATAAGCAGTAGCATAGCTGATCCT

CCGTGCATCGCCCATGTGCTACGGAAAGGGTCTCACTTTAAGTG

GGCTACACTAAATAATCTCCGTCTGGGGTTAGTTAGAAGAGCTT

AATCAGACTAGCTGAATGGAAGCCTGTTACCGGGCTGATGTTTA

TGCGAAATACTAATACGGTGACTACGCTCGTAGATATTTAAGTG

CCCATATTTCTGG SEQ ID NO: 180
```

*Listeria seeligeri* (NCTC 11856) tmRNA, Internal Partial

```
ACAGGGAUAGUUCGAGCUUGAGUUGCGAGUCGGGGGAUCGU

CCUCGUUAUCAACGUCAAAGCCAAUAAUAACUGGCAAAGAAAA

ACAAAACCUAGCUUUCGCUGCCUAAUAAGCAGUAGCAUAGCUG

AUCCUCCGUGCAUCGCCCAUGUGCUACGGAAAGGGUCUCACUU

UAAGUGGGCUACACUAAAUAAUCUCCGUCUGGGGUUAGUUAG

AAGAGCUUAAUCAGACUAGCUGAAUGGAAGCCUGUUACCGGG

CUGAUGUUUAUGCGAAAUACUAAUACGGUGACUACGCUCGUA

GAUAUUUAAGUGCCCAUAUUUCUGG SEQ ID NO: 181
```

*Listeria ivanovii* (NCTC 11846) ssrA, Internal Partial

```
ACAGGGATAGTTCGAGCTTGAGTTGCGAGTCGGGGGATCGTCC

TCGTTATTAACGTCAAAGCCAATAATAACTGGCAAAGAAAACA
```

-continued

AAACCTAGCTTTCGCTGCCTAATAAGCAGTAGCATAGCTGATCCT

CCGTGCATCGCCCATGTGCTACGGTAAGGGTCTCACTTTAAGTGG

GCTACACTAAATAATCTCCGTCTGGGGTTAGTTAGAAGAGCTTA

ATCAGACTAGCTGAATGGAAGCCTGTTACCGGGCTGATGTTTAT

GCGAAATGCTAATACGGTGACTACGCTCGTAGATATTTAAGTGC

CGATATTTCTGG SEQ ID NO: 182

*Listeria ivanovii* (NCTC 11846) tmRNA, Internal Partial

ACAGGGAUAGUUCGAGCUUGAGUUGCGAGUCGGGGGAUCGU

CCUCGUUAUUAACGUCAAAGCCAAUAAUAACUGGCAAAGAAA

AACAAAACCUAGCUUUCGCUGCCUAAUAAGCAGUAGCAUAGCU

GAUCCUCCGUGCAUCGCCCAUGUGCUACGGUAAGGGUCUCACU

UUAAGUGGGCUACACUAAAUAAUCUCCGUCUGGGGUUAGUUA

GAAGAGCUUAAUCAGACUAGCUGAAUGGAAGCCUGUUACCGG

GCUGAUGUUUAUGCGAAAUGCUAAUACGGUGACUCGCUCGUA

GAUAUUUAAGUGCCGAUAUUUCUGG SEQ ID NO: 183

*Mycobacterium africanum* (Clinical Isolate) ssrA, Internal Partial

ACTTCGCGCATCGAATCAAGGGAAGCGTGCCGGTGCAGGCAAGA

GACCACCGTAAGCGTCGTTGCGACCAAATAAGCGCCGATTCACA

TCAGCGCGACTACGCTCTCGCTGCCTAAGCGACGGCTAGTCTGTC

AGACCGGGAACGCCCTCGGCCCGGACCCTGGCATCAGCTAGAGG

GATCCACCGATGAGTCCGGTCGCGGGACTCCTCGGGACAACCAC

AGCGACTGGGATCGTCATCTCGGCTAGTTCGCGTGACCGGGAGA

TCCGAGCAGAGGCATAGCGAACTGCGCACGGAGAAGCCTTGAG

GGAATGCCGTA SEQ ID NO: 184

*Mycobacterium africanum* (Clinical Isolate) tmRNA, Internal Partial

ACUUCGCGCAUCGAAUCAAGGGAAGCGUGCCGGUGCAGGCAAG

AGACCACCGUAAGCGUCGUUGCGACCAAAUAAGCGCCGAUUCA

CAUCAGCGCGACUACGCUCUCGCUGCCUAAGCGACGGCUAGUC

UGUCAGACCGGGAACGCCCUCGGCCCGGACCCUGGCAUCAGCU

AGAGGGAUCCACCGAUGAGUCCGGUCGCGGGACUCCUCGGGAC

AACCACAGCGACUGGGAUCGUCAUCUCGGCUAGUUCGCGUGAC

CGGGAGAUCCGAGCAGAGGCAUAGCGAACUGCGCACGGAGAAG

CCUUGAGGGAAUGCCGUA SEQ ID NO: 185

*Mycobacterium gordonae* (Clinical Isolate) ssrA, Internal Partial

ACTTCGCGCATCGAATCAAGGGAAGCGTGCCGGTGCAGGCAAGA

GACCACCGTAAGCGTCGTTGCAACCATATAAGCGCCGATTCACA

-continued

TCAGCGCGACTACGCTCTCGCTGCCTAAGCGACGGCTAGTCTGTC

GGACCGGGAACGCCCTCGCCCCGGACCCCGGCATCAGCTAGAGG

GATCAACCGATGAGTTCGGTCGCGGGACTCATCGGGACACCAAC

AGCGACTGGGATCGTCATCCTGGCTAGTCCGTGTGACCAGGAGA

TCCGAGCAGAGACATAGCGGACTGCGCACGGAGAAGCCTTGAG

GGAATGCCGTA SEQ ID NO: 186

*Mycobacterium gordonae* (Clinical Isolate) tmRNA, Internal Partial

ACUUCGCGCAUCGAAUCAAGGGAAGCGUGCCGGUGCAGGCAAG

AGACCACCGUAAGCGUCGUUGCAACCAUAUAAGCGCCGAUUCA

CAUCAGCGCGACUACGCUCUCGCUGCCUAAGCGACGGCUAGUC

UGUCGGACCGGGAACGCCCUCGCCCCGGACCCCGGCAUCAGCU

AGAGGGAUCAACCGAUGAGUUCGGUCGCGGGACUCAUCGGGAC

ACCAACAGCGACUGGGAUCGUCAUCCUGGCUAGUCCGUGUGAC

CAGGAGAUCCGAGCAGAGACAUAGCGGACUGCGCACGGAGAAG

CCUUGAGGGAAUGCCGUA SEQ ID NO: 187

*Mycobacterium kansasii* (Clinical Isolate) ssrA, Internal Partial

ACTTCGCGCATCGAATCAAGGGAAGCGTGCCGGTGCAGGCAAGA

GACCACCGTAAGCGTCGTTGCAACCAAATAAGCGCCGATTCACA

TCAGCGCGACTACGCTCTCGCTGCCTAAGCGACGGCTAGTCTGTC

AGACCGGGACCGCCCTCGACCCGGACTCTGGCATCAGCTAGAGG

GATCAACCGATGAGTTCGGTCGCGGGACTCGTCGGGACACCAAC

AGCGACTGGGATCGTCATCCTGGCTAGTTCGCGTGACCAGGAGA

TCCGAGCAGAGGCATAGCGAACTGCGCACGGAGAAGCCTTGAG

GGAATGCCGTA SEQ ID NO: 188

*Mycobacterium kansasii* (Clinical Isolate) tmRNA, Internal Partial

ACUUCGCGCAUCGAAUCAAGGGAAGCGUGCCGGUGCAGGCAAG

AGACCACCGUAAGCGUCGUUGCAACCAAAUAAGCGCCGAUUCA

CAUCAGCGCGACUACGCUCUCGCUGCCUAAGCGACGGCUAGUC

UGUCAGACCGGGACCGCCCUCGACCCGGACUCUGGCAUCAGCU

AGAGGGAUCAACCGAUGAGUUCGGUCGCGGGACUCGUCGGGAC

ACCAACAGCGACUGGGAUCGUCAUCCUGGCUAGUUCGCGUGAC

CAGGAGAUCCGAGCAGAGGCAUAGCGAACUGCGCACGGAGAAG

CCUUGAGGGAAUGCCGUA SEQ ID NO: 189

*Mycobacterium chelonae* ssrA, Internal Partial

ACAGCGAGTCTCGACTTAAGGGAAGCGTGCCGGTGCAGGCAAG

AGACCACCGTAAGCGTCATTGCAACCAATTAAGCGCCGATTCTC

```
ATCAGCGCGACTACGCACTCGCTGCCTAAGCGACTGCGTGTCTG

TCAGACCGGGAGCGCCCTCAGCCCGGACCCTGGCATCAGCTAGA

GGGACAAACTACGGGTTCGGTCGCGGGACCCGTAGGGACATCAA

ACAGCGACTGGGATCGTCATCTCGGCTTGTTCGCGGGACCGAGA

GATCCAAGTAGAGGCATAGCGAACTGCGCACGGAGAAGCCTTA

ATGAACGGCCGTTG SEQ ID NO: 190
```

*Mycobacterium chelonae* tmRNA, Internal Partial

```
ACAGCGAGUCUCGACUUAAGGGAAGCGUGCCGGUGCAGGCAAG

AGACCACCGUAAGCGUCAUUGCAACCAAUUAAGCGCCGAUUCU

CAUCAGCGCGACUACGCACUCGCUGCCUAAGCGACUGCGUGUC

UGUCAGACCGGGAGCGCCCUCAGCCCGGACCCUGGCAUCAGCU

AGAGGGACAAACUACGGGUUCGGUCGCGGGACCCGUAGGGACA

UCAAACAGCGACUGGGAUCGUCAUCUCGGCUUGUUCGCGGGAC

CGAGAGAUCCAAGUAGAGGCAUAGCGAACUGCGCACGGAGAA

GCCUUAAUGAACGGCCGUUG SEQ ID NO: 191
```

*Mycobacterium szulgai* (ATCC 35799) ssrA, Internal Partial

```
ACTTCGCGCATCGAATCAAGGGAAGCGTGCCGGTGCAGGCAAGA

GACCACCGTAAGCGTCGTTGCAACCAATTAAGCGCCGAGAACAC

TCAGCGCGACTTCGCTCTCGCTGCCTAAGCGACAGCAAGTCCGT

CAGACCGGGAAAGCCCTCGACCCGGACCCTGGCGTCATCTAGAG

GGATCCACCGGTGAGTTCGGTCGCGGGACTCATCGGGACACCAA

CAGCGACTGGGATCGTCATCCTGGCTAGTTCGCGTGACCAGGAG

ATCCGAGTAGAGACATAGCGAACTGCGCACGGAGAAGCCTTGA

GGGAATGCCGTAG SEQ ID NO: 192
```

*Mycobacterium szulgai* (ATCC 35799) tmRNA, Internal Partial

```
ACUUCGCGCAUCGAAUCAAGGGAAGCGUGCCGGUGCAGGCAAG

AGACCACCGUAAGCGUCGUUGCAACCAAUUAAGCGCCGAGAAC

ACUCAGCGCGACUUCGCUCUCGCUGCCUAAGCGACAGCAAGUC

CGUCAGACCGGGAAAGCCCUCGACCCGGACCCUGGCGUCAUCU

AGAGGGAUCCACCGGUGAGUUCGGUCGCGGGACUCAUCGGGAC

ACCAACAGCGACUGGGAUCGUCAUCCUGGCUAGUUCGCGUGAC

CAGGAGAUCCGAGUAGAGACAUAGCGAACUGCGCACGGAGAA

GCCUUGAGGGAAUGCCGUAG SEQ ID NO: 193
```

*Mycobacterium malmoense* (Clinical Isolate) ssrA, Internal Partial

```
ACTTCGCGCATCGAATCAAGGGAAGCGTGCCGGTGCAGGCAAGA

GACCACCGTAAGCGTCGTTGCAACCATATAAGCGCCGTTTCAAC
```

```
ACAGCGCGACTACGCTCTCGCTGCCTAAGCGACAGCTAGTCCGT

CAGACCGGGAACGCCCTCGACCCGGAGCCTGGCGTCAGCTGGAG

GGATCCACCGGTGAGTCCGGTCGCGGGACTCATCGGGACATACA

CAGCGACTGGGATCGTCATCCTGGCTGGTTCGCGTGACCGGGAG

ATCCGAGCAGAGGCATAGCGAACTGCGCACGGAGAAGCCTTGA

GGGAATGCCGTAG SEQ ID NO: 194
```

*Mycobacterium malmoense* (Clinical Isolate) tmRNA, Internal Partial

```
ACUUCGCGCAUCGAAUCAAGGGAAGCGUGCCGGUGCAGGCAAG

AGACCACCGUAAGCGUCGUUGCAACCAUAUAAGCGCCGUUUCA

ACACAGCGCGACUACGCUCUCGCUGCCUAAGCGACAGCUAGUC

CGUCAGACCGGGAACGCCCUCGACCCGGAGCCUGGCGUCAGCU

GGAGGGAUCCACCGGUGAGUCCGGUCGCGGGACUCAUCGGGAC

AUACACAGCGACUGGGAUCGUCAUCCUGGCUGGUUCGCGUGAC

CGGGAGAUCCGAGCAGAGGCAUAGCGAACUGCGCACGGAGAAG

CCUUGAGGGAAUGCCGUAG SEQ ID NO: 195
```

*Mycobacterium flavescens* ssrA, Internal Partial

```
ACTTCGAGCGTCGAATCAAGGGAAGCGTGCCGGTGCAGGCAAG

AGACCACCGTAAGCGTCGTTGCAACCAATTAAGCGCCGATTCCA

ATCAGCGCGACTACGCACTCGCTGCCTAAGCGACTGCGTGTCTG

TCAGCCCGGGAGAGCCCTCGACCCGGTGTCTGGCATCAGCTAGA

GGGATAAACCGGTGGGTCCGGTCGCGGGACTCATCGGGACATCA

AACAGCGACTGGGATCGTCATCCTGACTTGTTCGCGTGATCAGG

AGATCCGAGTAGAGACATAGCGAACTGCGCACGGAGAAGCCTT

GAGGGAACGCCGTAG SEQ ID NO: 196
```

*Mycobacterium flavescens* tmRNA, Internal Partial

```
ACUUCGAGCGUCGAAUCAAGGGAAGCGUGCCGGUGCAGGCAAG

AGACCACCGUAAGCGUCGUUGCAACCAAUUAAGCGCCGAUUCC

AAUCAGCGCGACUACGCACUCGCUGCCUAAGCGACUGCGUGUC

UGUCAGCCCGGGAGAGCCCUCGACCCGGUGUCUGGCAUCAGCU

AGAGGGAUAAACCGGUGGGUCCGGUCGCGGGACUCAUCGGGAC

AUCAAACAGCGACUGGGAUCGUCAUCCUGACUUGUUCGCGUGA

UCAGGAGAUCCGAGUAGAGACAUAGCGAACUGCGCACGGAGA

AGCCUUGAGGGAACGCCGUAG SEQ ID NO: 197
```

*Mycobacterium marinum* ssrA, Internal Partial

```
ACTTCGCGCATCGAATCAAGGGAAGCGTGCCGGTGCAGGCAAGA

GACCACCGTAAGCGTCGATGCAACTAGATAAGCGCCGATTCACA

TCAGCGCGACTACGCTCTCGCTGCCTAAGCGACGGCTAGTCTGTC
```

```
GGACCGGGAACGCCCTCGCCCCGGACCCCGGCATCAGCTAGAGG

GATCAACCGATGAGTTCGGTCGCGGGGCTCATCGGGACATCAAC

AGCGACTGGGATCGTCATCCTGGCTAGTTCGCGTGACCAGGAGA

TCCGAGCAGAGACCTAGCGGACTGCGCACGGAGAAGCCTTGAG

GGAATGCCGTAG         SEQ ID NO: 198
```

*Mycobacterium marinum* tmRNA, Internal Partial

```
ACUUCGCGCAUCGAAUCAAGGGAAGCGUGCCGGUGCAGGCAAG

AGACCACCGUAAGCGUCGAUGCAACUAGAUAAGCGCCGAUUCA

CAUCAGCGCGACUACGCUCUCGCUGCCUAAGCGACGGCUAGUC

UGUCGACCGGGAACGCCCUCGCCCCGGACCCCGGCAUCAGCU

AGAGGGAUCAACCGAUGAGUUCGGUCGCGGGGCUCAUCGGGAC

AUCAACAGCGACUGGGAUCGUCAUCCUGGCUAGUUCGCGUGAC

CAGGAGAUCCGAGCAGAGACCUAGCGGACUGCGCACGGAGAAG

CCUUGAGGGAAUGCCGUAG         SEQ ID NO: 199
```

*Mycobacterium microti* (Environmental Isolate) ssrA, Internal Partial

```
ACTTCGCGCATCGAATCAAGGGAAGCGTGCCGGTGCAGGCAAGA

GACCACCGTAAGCGTCGTTGCGACCAAATAAGCGCCGATTCACA

TCAGCGCGACTACGCTCTCGCTGCCTAAGCGACGGCTAGTCTGTC

AGACCGGGAACGCCCTCGGCCCGGACCCTGGCATCAGCTAGAGG

GATCCACCGATGAGTCCGGTCGCGGGACTCCTCGGGACAGCCAC

AGCGACTGGGATCGTCATCTCGGCTAGTTCGCGTGACCGGGAGA

TCCGAGCAGAGGCATAGCGAACTGCGCACGGAGAAGCCTTGAG

GGAATGCCGTA         SEQ ID NO: 200
```

*Mycobacterium microti* (Environmental Isolate) tmRNA, Internal Partial

```
ACUUCGCGCAUCGAAUCAAGGGAAGCGUGCCGGUGCAGGCAAG

AGACCACCGUAAGCGUCGUUGCGACCAAAUAAGCGCCGAUUCA

CAUCAGCGCGACUACGCUCUCGCUGCCUAAGCGACGGCUAGUC

UGUCAGACCGGGAACGCCCUCGGCCCGGACCCUGGCAUCAGCU

AGAGGGAUCCACCGAUGAGUCCGGUCGCGGGACUCCUCGGGAC

AGCCACAGCGACUGGGAUCGUCAUCUCGGCUAGUUCGCGUGAC

CGGGAGAUCCGAGCAGAGGCAUAGCGAACUGCGCACGGAGAAG

CCUUGAGGGAAUGCCGUA         SEQ ID NO: 201
```

*Mycobacterium smegmatis* (ATCC 10143) ssrA, Internal Partial

```
ACTTCGAGCATCGAATCCAGGGAAGCGTGCCGGTGCAGGCAAGA

GACCACCGTAAGCGTCGTTGCAACCAATTAAGCGCCGATTCCAA
```

```
TCAGCGCGACTACGCCCTCGCTGCCTAAGCGACGGCTGGTCTGT

CAGACCGGGAGTGCCCTCGGCCCGGATCCTGGCATCAGCTAGAG

GGACCCACCCACGGGTTCGGTCGCGGGACCTGTGGGGACATCAA

ACAGCGACTGGGATCGTCATCTCGGCTTGTTCGTGTGACCGGGA

GATCCGAGTAGAGACATAGCGAACTGCGCACGGAGAAGCCTCG

AGGACATGCCGTAG         SEQ ID NO: 202
```

*Mycobacterium smegmatis* (ATCC 10143) ssrA, Internal Partial

```
ACUUCGAGCAUCGAAUCCAGGGAAGCGUGCCGGUGCAGGCAAG

AGACCACCGUAAGCGUCGUUGCAACCAAUUAAGCGCCGAUUCC

AAUCAGCGCGACUACGCCCUCGCUGCCUAAGCGACGGCUGGUC

UGUCAGACCGGGAGUGCCCUCGGCCCGGAUCCUGGCAUCAGCU

AGAGGGACCCACCCACGGGUUCGGUCGCGGGACCUGUGGGGAC

AUCAAACAGCGACUGGGAUCGUCAUCUCGGCUUGUUCGUGUGA

CCGGGAGAUCCGAGUAGAGACAUAGCGAACUGCGCACGGAGAA

GCCUCGAGGACAUGCCGUAG         SEQ ID NO: 203
```

*Mycobacterium xenopi* (Clinical Isolate) ssrA, Internal Partial

```
ACTTCGCGCATCGAATCAAGGGAAGCGTGCCGGTGCAGGCAAGA

GACCACCGTAAGCGTCGTTGCAACTAAATAAGCGCCGATTCACA

TCAGCGCGACTACGCTCTCGCTGCCTAAGCGACAGCTAGTCCGT

CAGGCCGGGAGTTCCCTCGACCCGGATCCTGGCGTCAGCTAGAG

GGATCCACCGATGGGTTCGGTCGCGGGACCCATCGGGACACCAC

ACAGCGACTGGGATCGCCGTCCCGGCTAGTTCGCGAGACCGGGA

GATCCGAGTAAGGGCAAAGCGAACTGCGCACGGAGAAGCCTTG

AGGGTATGCCGTA         SEQ ID NO: 204
```

*Mycobacterium xenopi* (Clinical Isolate) tmRNA, Internal Partial

```
ACUUCGCGCAUCGAAUCAAGGGAAGCGUGCCGGUGCAGGCAAG

AGACCACCGUAAGCGUCGUUGCAACUAAAUAAGCGCCGAUUCA

CAUCAGCGCGACUACGCUCUCGCUGCCUAAGCGACAGCUAGUC

CGUCAGGCCGGGAGUUCCCUCGACCCGGAUCCUGGCGUCAGCU

AGAGGGAUCCACCGAUGGGUUCGGUCGCGGGACCCAUCGGGAC

ACCACAGCGACUGGGAUCGCCGUCCCGGCUAGUUCGCGAGA

CCGGGAGAUCCGAGUAAGGGCAAAGCGAACUGCGCACGGAGAA

GCCUUGAGGGUAUGCCGUA         SEQ ID NO: 205
```

*Mycobacterium intracellulare* (NCTC 10425) ssrA, Internal Partial

```
ACTTCGCGCATCGAATCAAGGGAAGCGTGCCGGTGCAGGCAACC

GACCACCGTAAGCGTCGTTGCAAACAGATAAGCGCCGATTCACA
```

```
TCAGCGCGACTACGCTCTCGCTGCCTAAGCGACAGCTAGTCCGT

CAGACCGGGAACGCCCTCGACCCGGAGCCTGGCGTCAGCTAGAG

GGATCCACCGATGAGTCCGGTCGCGGGACTTATCGGGACACCAA

CAGCGACTGGGATCGTCATCTCGGCTTGTTCGCGTGACCGGGAG

ATCCGAGTAGAGGCATAGCGAACTGCGCACGGAGAAGTCTTGAG

GGAATGCCGTAG SEQ ID NO: 206
```

*Mycobacterium intracellulare* (NCTC 10425) tmRNA, Internal Partial

```
ACUUCGCGCAUCGAAUCAAGGGAAGCGUGCCGGUGCAGGCAAC

CGACCACCGUAAGCGUCGUUGCAAACAGAUAAGCGCCGAUUCA

CAUCAGCGCGACUACGCUCUCGCUGCCUAAGCGACAGCUAGUC

CGUCAGACCGGGAACGCCCUCGACCCGGAGCCUGGCGUCAGCU

AGAGGGAUCCACCGAUGAGUCCGGUCGCGGGACUUAUCGGGAC

ACCAACAGCGACUGGGAUCGUCAUCUCGGCUUGUUCGCGUGAC

CGGGAGAUCCGAGUAGAGGCAUAGCGAACUGCGCACGGAGAA

GUCUUGAGGGAAUGCCGUAG SEQ ID NO: 207
```

*Mycobacterium scrofulaceum* (NCTC 10803) ssrA, Internal Partial

```
ACATCGCGCATCGAATCAAGGGAAGCGTGCCGGTGCAGGCAAG

AGACCACCGTAAGCGTCGTTGCAACCAATTAAGCGCCGATTCAC

ATCAGCGCGACTACGCTCTCGCTGCCTAAGCGACAGCTAGTCCG

TCAGACCGGGAAAGCCCTCGACCCGGAGCCTGGCGTCAGCTAGA

GGGATCAACCGATGAGTTCGGTCGCGGGACTCATCGGGACACCA

ACAGCGACTGGGATCGTCATCCTGGCTAGTCCGCGTGACCAGGA

GATCCGAGCAGAGGCATAGCGGACTGCGCACGGAGAAGTCTTG

AGGGAATGCCGTTG SEQ ID NO: 208
```

*Mycobacterium scrofulaceum* (NCTC 10803) tmRNA, Internal Partial

```
ACAUCGCGCAUCGAAUCAAGGGAAGCGUGCCGGUGCAGGCAAG

AGACCACCGUAAGCGUCGUUGCAACCAAUUAAGCGCCGAUUCA

CAUCAGCGCGACUACGCUCUCGCUGCCUAAGCGACAGCUAGUC

CGUCAGACCGGGAAAGCCCUCGACCCGGAGCCUGGCGUCAGCU

AGAGGGAUCAACCGAUGAGUUCGGUCGCGGGACUCAUCGGGAC

ACCAACAGCGACUGGGAUCGUCAUCCUGGCUAGUCCGCGUGAC

CAGGAGAUCCGAGCAGAGGCAUAGCGGACUGCGCACGGAGAAG

UCUUGAGGGAAUGCCGUUG SEQ ID NO: 209
```

*Nocardia asteroides* ssrA, Internal Partial

```
ACTGTGTGCGCCGAGGTAGGGAAGCGTGTCGGTGCAGGCTGGA

GACCACCGTTAAGCGTCGCGGCAACCAATTAAGCGCCGATTCCA

ATCAGCGCGACTACGCCCTCGCTGCCTGATCAGCGACGGCTAGC

TGTCGGCCCGGGTTGTGTTCCCGAACCCGGATGCCGGCATCATCT

CAGGGAACTCACCGTGTTCGCCGGTCGCGGACGGACACGGGACA

GCAAACAGCGACTGGGATCGTCATCTCGGCTTGTTCGCGTGACC

GGGAGATCCAAGTAGAGACATAGCGGACTGCACACGGAGAAGC

CCTACTGACTCGACACAG SEQ ID NO: 210
```

*Nocardia asteroides* tmRNA, Internal Partial

```
ACUGUGUGCGCCGAGGUAGGGGAAGCGUGUCGGUGCAGGCUG

GAGACCACCGUUAAGCGUCGCGGCAACCAAUUAAGCGCCGAUU

CCAAUCAGCGCGACUACGCCCUCGCUGCCUGAUCAGCGACGGC

UAGCUGUCGGCCCGGGUUGUGUUCCCGAACCCGGAUGCCGGCA

UCAUCUCAGGGAACUCACCGUGUUCGCCGGUCGCGGACGGACA

CGGGACAGCAAACAGCGACUGGGAUCGUCAUCUCGGCUUGUUC

GCGUGACCGGGAGAUCCAAGUAGAGACAUAGCGGCUGCACACG

GAGAAGCCCUACUGACUCGACACAG SEQ ID NO: 211
```

*Salmonella enteritidis* ssrA, Internal Partial

```
ACGGGATTTGCGAAACCCAAGGTGCATGCCGAGGGGCGGTTGGC

CTCGTAAAAAGCCGCAAAAAAATAGTCGCAAACGACGAAACCT

ACGCTTTAGCAGCTTAATAACCTGCTTAGAGCCCTCTCTCCCTAG

CCTCCGCTCTTAGGACGGGGATCAAGAGAGGTCAAACCCAAAAG

AGATCGCGTGGATGCCCTGCCTGGGGTTGAAGCGTTAAAACGAA

TCAGGCTAGTCTGGTAGTGGCGTGTCCGTCCGCAGGTGCCAGGC

GAATGTAAAGACTGACTAAGCATGTAGTACCGAGGATGTAGGAA

TTTCGG SEQ ID NO: 212
```

*Salmonella enteritidis* tmRNA, Internal Partial

```
ACGGGAUUUGCGAAACCCAAGGUGCAUGCCGAGGGGCGGUUG

GCCUCGUAAAAAGCCGCAAAAAAAUAGUCGCAAACGACGAAAC

CUACGCUUUAGCAGCUUAAUAACCUGCUUAGAGCCCUCUCUCC

CUAGCCUCCGCUCUUAGGACGGGGAUCAAGAGAGGUCAAACCC

AAAAGAGAUCGCGUGGAUGCCCUGCCUGGGGUUGAAGCGUUA

AAACGAAUCAGGCUAGUCUGGUAGUGGCGUGUCCGUCCGCAGG

UGCCAGGCGAAUGUAAAGACUGACUAAGCAUGUAGUACCGAG

GAUGUAGGAAUUUCGG SEQ ID No: 213
```

*Staphylococcus epidermidis* (NCTC 11047) ssrA, Internal Partial

```
ACAGGGGTCCCCCGAGCTTATTAAGCGTGTCGGAGGGTTGGCTC

CGTCATCAACACATTTCGGTTAAATATAACTGACAAATCAAACA
```

```
ATAATTTCGCAGTAGCTGCGTAATAGCCACTGCATCGCCTAACA

GCATCTCCTACGTGCTGTTAACGCGATTCAACCCTAGTAGGATAT

GCTAAACACTGCCGCTTGAAGTCTGTTTAGATGAAATATAATCA

AGCTAGTATCATGTTGGTTGTTTATTGCTTAGCATGATGCGAAAA

TTATCAATAAACTACACACGTAGAAAGATTTGTATCAGGACCTC

TGG SEQ ID NO: 214
```

*Staphylococcus epidermidis* (NCTC 11047) tmRNA, Internal Partial

```
ACAGGGGUCCCCCGAGCUUAUUAAGCGUGUCGGAGGGUUGGCU

CCGUCAUCAACACAUUUCGGUUAAAUAUAACUGACAAAUCAAA

CAAUAAUUUCGCAGUAGCUGCGUAAUAGCCACUGCAUCGCCUA

ACAGCAUCUCCUACGUGCUGUUAACGCGAUUCAACCCUAGUAG

GAUAUGCUAAACACUGCCGCUUGAAGUCUGUUUAGAUGAAAU

AUAAUCAAGCUAGUAUCAUGUUGGUUGUUUAUUGCUUAGCAU

GAUGCGAAAAUUAUCAAUAAACUACACACGUAGAAAGAUUUG

UAUCAGGACCUCUGG SEQ ID NO: 215
```

*Streptococcus agalactiae* (NCTC 8181) ssrA, Internal Partial

```
ACAGGCATTATGAGGTATATTTTGCGACTCATCGGCAGATGTAA

AATGCCAGTTAAATATAACTGCAAAAAATACAAATTCTTACGCA

TTAGCTGCCTAAAAAACAGCCTGCGTGATCTTCACAAGATTGTTT

GCGTTTTGCTAGAAGGTCTTATTTATCAGCAAACTACGTTTGGCT

ACTGTCTAGTTAGTTAAAAAGAGATTTATAGACTCGCTATGTGA

GGGCTTGAGTTATGTGTCATCACCTAGTTAAATCAATACATAACC

TATAGITGTAGACAAATATATTAGCAGATGTTTGG SEQ ID

NO: 216
```

*Streptococcus agalactiae* (NCTC 8181) tmRNA, Internal Partial

```
ACAGGCAUUAUGAGGUAUAUUUUGCGACUCAUCGGCAGAUGU

AAAAUGCCAGUUAAAUAUAACUGCAAAAAAUACAAAUUCUUA

CGCAUUAGCUGCCUAAAAAACAGCCUGCGUGAUCUUCACAAGA

LUGUUUGCGUUUUGCUAGAAGGUCUUAUUUAUCAGCAAACUA

CGUUUGGCUACUGUCUAGUUAGUUAAAAAGAGAUUUAUAGAC

UCGCUAUGUGAGGGCUUGAGUUAUGUGUCAUCACCUAGUUAA

AUCAAUACAUAACCUAUAGUUGUAGACAAAUAUAUUAGCAGA

UGUUUGG SEQ ID NO: 217
```

Of the above sequences SEQ ID NOs 47 to 62, 65 to 68, 71 and 72, and 99, 159 to 168 and 176-217 are novel sequences.

The above mentioned sequences can be used to form a database of ssrA gene sequences which can be used to identify a bacterial species, or for the generation of nucleic acid diagnostic assays.

Representative probes identified in accordance with the invention are as follows:

*Salmonella:*
1) Genius specific probe:

```
5'-CGAATCAGGCTAGTCTGGTAG-3' SEQ ID NO: 218
```

*Mycobacteria:*
2) Oligonucleotide probe for detection of tuberculosis complex

```
                                     SEQ ID NO: 219
    TB01
    5'-ACTCCTCGGACA (A/G) CCACAGCGA-3'
```

3) Oligonucleotide probes for detection of *M. avium* and *M. paratuberculosis* Sequences

```
    Probe 1:
    PAV1-5'-GTTGCAAATAGATAAGCGCC-3' SEQ ID NO: 220

Probe 2:
    PAV2-5'-TCCGTCAGCCCGGGAACGCC-3' SEQ ID NO: 221
```

*Listeria:*
4) Oligonucleotide probe used in the determination of tmRNA integrity after heat killing treatment of cells:

```
    LVtm: 5'-TTTTGTTTTTCTTTGCCA-3' SEQ ID NO: 222
```

*Escherichia coli:*
5) Oligonucleotide probe used in the determination of tmRNA integrity after heat killing treatment of cells:

```
    Evtm: 5'-AGTTTTCGTCGTTTGCGA-3' SEQ ID NO: 223
```

Further representative primers identified in accordance with the invention are as follows:

*Mycobacteria:*
1) Degenerative oligonucleotide primers for the amplification of all mycobacterial sequences
5' Primer

```
                                     SEQ ID NO: 224
    10SAAM3-5'-CAGGCAA (G/C) (A/T/C) GACCACCGTAA-3'
```

3' Primer

```
                                     SEQ ID NO: 225
    10SAAM4-5'GGATCTCC(C/T)G(A/G)TC(A/T)C(A/G)CG (A/G)AC(A/T)A-3'
```

2) Oligonucleotide primers for the amplification of *M. avium* and *M. paratuberculosis*

```
                                     SEQ ID NO: 226
    5'Primer: API for-5'-TGCCGGTGCAGGCAACTG-3'

SEQ ID NO: 227
    3'Primer: AP2rev-5'-CACGCGAACAAGCCAGGA-3'
```

BRIEF DESCRIPTION OF THE DRAWINGS

In the accompanying drawings:

FIG. 1 is a clustal alignment of *E. coli* and *V. cholerae* ssrA gene sequences;

FIG. 5 is a clustal alignment of the ssrA gene sequences from the *Listeria* species;

FIG. 6 is a clustal alignment of the *L. monocytogenes* and *B. subtilis* ssrA/tmRNA gene sequences;

FIG. 11 is a clustal alignment of ssrA gene sequences from *C. trachomatis* strains;

FIG. 12 is a clustal alignment of ssrA gene sequences from *H. pylori* strains;

FIG. 13 is a clustal alignment of ssrA gene sequences from *M. genitalium* strains;

FIG. 14 is a clustal alignment of ssrA gene sequences from *N. gonorrhoeae* strains;

FIG. 15 is a clustal alignment of ssrA gene sequences from *L. monocytogenes* strains;

FIG. 16 is a clustal alignment of ssrA gene sequences from *L. monocytogenes* strains and the *L. innocua* strain;

The invention will be further illustrated by the following Examples.

MODES FOR CARRYING OUT THE INVENTION

Example 1

Examination of the Primary Nucleotide Sequences of Available tmRNA Sequences

A comparative primary nucleotide sequence alignment of available tmRNA sequences using the Clustal W nucleic acid alignment programme demonstrated that tmRNA sequences from prokaryotes show a more significant degree of nucleotide sequence variability and non-homology than other bacterial high copy number RNA, as demonstrated in Table 1.

TABLE 1

Percentage nucleotide sequence homology between RNA molecules from different bacteria.

|  | *Escherichia coli* vs. *Vibrio cholerae* | *Bacillus subtilis* vs. *Mycobacterium tuberculosis* |
|---|---|---|
| rRNA % homology | 88 | 66 |
| tmRNA % homology | 68 | 25 |

These regions of non-homology between tmRNA sequences from different bacteria are located in the middle of the molecule, and the extent of nucleotide sequence non-homology within the tmRNA molecule indicated that genus as well as species specific probes could be generated to distinguish between and/or detect bacteria.

Nucleotide sequence alignments had previously shown that the 5' and 3' flanking regions of the tmRNA molecules share a high degree of homology both within species and within genus. This observation indicated that universal oligonucleotide primers could be generated to amplify the ssrA gene or its encoding tmRNA from a wide variety of bacteria.

We have now demonstrated that these regions of homology and non-homology within the nucleotide sequence of tmRNA molecules from different organisms can be used as the basis of identifying and detecting organisms at the molecular level.

Example 2

Development of a *V. cholerae* tmRNA Specific Probe

A nucleotide sequence alignment of the *E. coli* (SEQ ID NO. 37) and *V. cholerae* (SEQ ID NO. 127) ssrA sequences as depicted in FIG. 1, shows that these two bacterial species are phylogenetically closely related. There are however, regions of non-homology between the sequences as evidenced by the absence of asterix marks. An oligonucleotide probe, complementary to the variable region of the *V. cholerae* ssrA nucleotide sequence underlined in FIG. 1, was synthesised.

The sequence of the *V. cholerae* tmRNA specific probe is

```
                                         SEQ ID NO. 169
           5'-AACGAATGGCTAACCTGAA-3'
```

Figure 2:
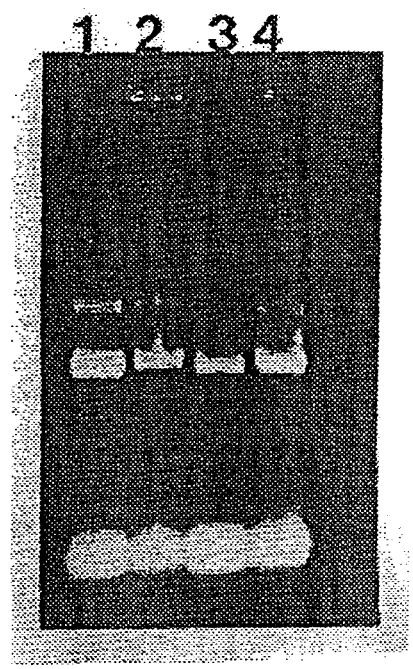
FIG. 2 is a photograph of an agarose gel of total cellular RNA prepared from *E. coli* and *V. cholerae* cells.
Figure 3:
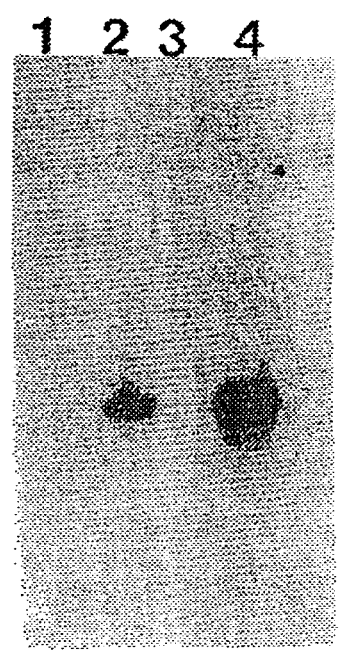
FIG. 3 is a photograph of an autoradiogram of hybridisation of a *V. cholerae* oligonucleotide probe to tmRNA transcripts of *E. coli* and *V. cholerae*.

Total RNA was isolated from liquid cultures of *E. coli* and *V. cholerae* at the mid-exponential phase and the stationary phase of growth. Equivalent amounts of the isolated total RNA were electrophoresed on a denaturing formaldehyde agarose gel and blotted onto HYBOND-N nylon membrane as shown in FIG. 2 in which the Lanes 1-4 represent the following:

Lane 1: Total *E. coli* RNA mid-log phase
Lane 2: Total *V. cholerae* RNA mid-log phase
Lane 3: Total *E. coli* RNA stationary phase
Lane 4: Total *V. cholerae* RNA stationary phase The resulting Northern blot was then hybridised with the *V. cholerae* tmRNA specific probe end-labelled with $\gamma P^{32}$. The results of the hybridisation experiment shown in FIG. 3 demonstrate the specificity of the probe as only *V. cholerae* tmRNAs were detected. Moreover, a greater degree of hybridisation signal intensity was observed with the *V. cholerae* tmRNA isolated from cultures during the stationary phase of growth, indicating that a higher copy number of the tmRNA molecule is present in *V. cholerae* cells during this phase.

Example 3

Generation of Universal ssrA/tmRNA Oligonucleotide Amplification Primers for the Characterisation of Unknown ssrA Gene and tmRNA Sequences Clustal W alignment of all available ssrA gene and tmRNA sequences indicated that degenerate oligonucleotide primers could be designed to amplify ssrA gene and tmRNA nucleotide sequences for a wide variety of organisms.

Degenerate oligonucleotide primers were synthesised to PCR amplify ssrA gene sequences from total genomic DNA preparations from a broad range of bacteria.

The sequences of the synthesised degenerate oligonucleotides are as follows:

(a) tmU5': 5' in vitro PCR amplification primer
5'- GGG(A/C)(C/T)TACGG(A/T)TTCGAC- 3'
SEQ ID NO: 170

(b) tmU3': 3' in vitro PCR amplification primer
5'- GGGA(A/G)TCGAACC(A/G)(C/G)GTCC- 3'
SEQ ID NO: 171

Degenerate base positions are in parentheses.

The products of PCR reactions were electrophoresed on an agarose gel and a 350 base pair (approx.) PCR product was amplified in all cases, as shown in FIG. 4, demonstrating the "universality" of the degenerate tmRNA primers.

Figure 4:
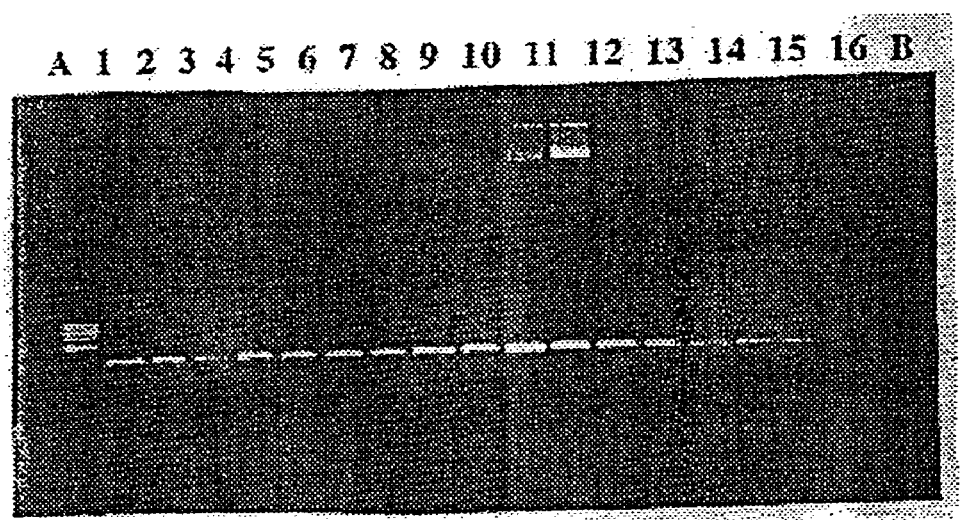
FIG. 4 is a photograph of an agarose gel of the amplified products of universal ssrA gene amplification primers from a panel of organisms.

In FIG. 4 the lanes represent the following:
Lane A: Molecular weight marker V
Lane 1: *Escherichia coli*
Lane 2: *Salmonella poona*
Lane 3: *Klebsiella aerogenes*
Lane 4: *Proteus mirabilis*
Lane 5: *Proteus rettgeri*
Lane 6: *Aeromonas hydrophilia*
Lane 7: *Staphylococcus aureus*
Lane 8: *Enterococcus faecalis*
Lane 9: *Lactobacillus lactis*
Lane 10: *Bacillus subtilus*
Lane 11: *Listeria monocytogenes*
Lane 12: *Listeria innocua*
Lane 13: *Listeria murrayi*
Lane 14: *Listeria welshimeri*
Lane 15: *Listeria grayi*
Lane 16: *Mycobacterium bovis*
Lane B: Molecular weight marker V The universal primers amplified the ssrA gene from both Gram positive and Gram negative bacteria, as shown in Table 2.

TABLE 2

Bacterial species tested with universal amplification primers.

| | | PCR Product |
|---|---|---|
| Gram Negative Bacteria | *Escherichia coli* | + |
| | *Salmonella poona* | + |
| | *Klebsiella aerogenes* | + |
| | *Proteus mirabilis* | + |
| | *Proteus rettgeri* | + |
| | *Aeromonas hydrophilia* | + |

TABLE 2-continued

Bacterial species tested with universal amplification primers.

| | | PCR Product |
|---|---|---|
| Gram Positive Bacteria | *Staphyloccus aureus* | + |
| | *Enterococcus faecalis* | + |
| | *Lactobacillus lactis* | + |
| | *Bacillus subtilus* | + |
| | *Listeria monocytogenes* | + |
| | *Listeria innocua* | + |
| | *Listeria murrayi* | + |
| | *Listeria welshimeri* | + |
| | *Listeria grayi* | + |
| | *Mycobacterium bovis* | + |

Example 4

Isolation and Characterisation of Previously Unknown Bacterial ssrA/tmRNA Nucleotide Sequences The PCR products amplified from genomic DNA from the *Listeria* species of bacteria and that from the *M. bovis* bacterium, from Example 2, were subcloned into a T-tailed plasmid vector for the purposes of DNA sequencing. Three recombinant clones were selected for each species and sequenced by the di-deoxy sequencing method. The sequence of both DNA strands for each subclone was determined.

The nucleotide sequence determined for the *M. bovis* ssrA gene shared 100% homology with the *Mycobacterium tuberculosis* ssrA gene sequence.

A clustal W alignment of the novel ssrA gene sequences obtained for the *Listeria* species (SEQ ID NOS 51, 53, 55, 59 and 61) is shown in FIG. 5. This analysis indicated that genus-specific probes and oligonucleotide amplification primers can be generated for *Listeria* bacteria. Furthermore, the alignment also indicated that a species specific oligonucleotide probe can be generated which will distinguish *L. monocytogenes* from the other *Listeria* species.

In FIG. 5 the proposed genus specific oligonucleotide primers, Ltm 1 and Ltm 2, are boxed, as is the genus specific *Listeria* oligonucleotide probe, LGtm. The proposed *L. monocytogenes* species specific oligonucleotide probe sequence, LStm, is underlined and italicised.

To further illustrate that the ssrA gene/tmRNA nucleic acid target is a suitable target for bacterial diagnostics, a comparative alignment of the *L. monocytogenes* ssrA gene nucleotide sequence (SEQ ID NO. 55) with the available *B. subtilis* ssrA gene nucleotide sequence (SEQ ID NO. 11) (a phylogenetically closely related bacteria to *Listeria*) was carried out as shown in FIG. 6. Analysis of the sequence alignment showed a percentage nucleotide sequence homology of 41%, whereas the corresponding 16S rRNA alignment exhibits a nucleotide sequence percentage homology of 87%, (data not shown).

Example 5

Generation and Application of ssrA Gene/tmRNA Genus-Specific Amplification Primers, Genus-Specific and Species-Specific Probes for the *Listeria* Bacterial Species Using the *Listeria* genus ssrA gene/tmRNA nucleotide sequence alignment of Example 4, regions of the ssrA gene/tmRNA nucleotide sequence were analysed to determine their suitability for the generation of genus-specific amplification primers, and genus-specific and species-specific oligonucleotide probes. In this analysis, regions which demonstrated the greatest sequence differences to *B. subtilis*, were selected in the design of these amplification primers and probes.

The sequences of the synthesised oligonucleotides are as follows:

| | | |
|---|---|---|
| (a) | Ltm1: | 5' *Listeria* genus specific amplification primer<br>5'-AAAGCCAATAATAACTGG- 3'<br>SEQ ID NO: 172 |
| (b) | Ltm2: | 3' *Listeria* genus specific amplification primer<br>5'-CCAGAAATATCGGCACTT- 3'<br>SEQ ID NO: 173 |
| (c) | LGtm: | *Listeria* genus specific hybridisation probe<br>5'-GTGAGACCCTTACCGTAG- 3'<br>SEQ ID NO: 174 |
| (d) | LStm: | *L. monocytogenes* species specific hybridisation probe<br>5'-TCTATTTAACCCCAGACG- 3'<br>SEQ ID NO: 175 |

The genus specific amplification primers Ltm1 and Ltm2 were used in a series of PCR reactions with total genomic DNA from twenty different strains as the template in each case. Only ssrA gene sequences from the *Listeria* species were amplified (260 base pair product) with these primers (FIG. 7 and Table 3) demonstrating that the ssrA gene/tmRNA is a suitable target for specific in vitro amplification of a bacterial genus. No amplification products were observed for any other bacterial species tested, although PCR products were obtained from the DNA from these bacterial species using the universal primers (tmU5' and tmU3') described in Example 2.

Figure 7:
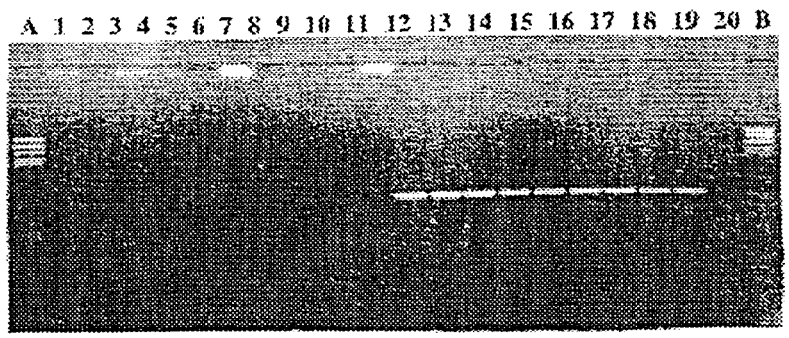
FIG. 7 is a photograph of an agarose gel of the amplified products of *Listeria* genus specific PCR amplification primers from a panel of organisms.

In FIG. 7 the lanes represent the following:
Lane A: Molecular weight marker V
Lane 1: *E. coli*
Lane 2: *S. poona*
Lane 3: *K. aerogenes*
Lane 4: *P. mirabilis*
Lane 5: *P. rettgeri*
Lane 6: *A. hydrophilia*
Lane 7: *S. aureus*
Lane 8: *E. faecalis*
Lane 9: *L. lactis*
Lane 10: *B. subtilus*
Lane 11: *L. monocytogenes* strain 1
Lane 12: *L. monocytogenes* strain 2
Lane 13: *L. monocytogenes* strain 3
Lane 14: *L. monocytogenes* strain 4
Lane 15: *L. monocytogenes* clinical isolate
Lane 16: *L. innocua*
Lane 17: *L. murrayi*
Lane 18: *L. welshimeri*
Lane 19: *L. grayi*
Lane 20: *M. bovis*
Lane B: Molecular weight marker V

TABLE 3

Bacterial species tested with *Listeria* specific amplification primers.

| | | PCR Product |
|---|---|---|
| Gram<br>Negative<br>Bacteria | *Escherichia coli*<br>*Salmonella poona*<br>*Klebsiella aerogenes*<br>*Proteus mirabilis*<br>*Proteus rettgeri*<br>*Aeromonas hydrophilia* | –<br>–<br>–<br>–<br>–<br>– |

TABLE 3-continued

Bacterial species tested with *Listeria* specific amplification primers.

| | | PCR Product |
|---|---|---|
| Gram<br>positive<br>bacteria | *Staphyloccus aureus*<br>*Entrococcus faecalis*<br>*Lactobacillus lacus*<br>*Bacillus subtilus*<br>*Listeria monocytogenes* strain 1<br>*Listeria monocytogenes* strain 2<br>*Listeria monocytogenes* strain 3<br>*Listeria monocytogenes* strain 4<br>*Listeria monocytogenes* clinical isolate<br>*Listeria innocua*<br>*Listeria murrayi*<br>*Listeria welshimeri*<br>*Listeria grayi*<br>*Mycobacterium bovis* | –<br>–<br>–<br>–<br>+<br>+<br>+<br>+<br>+<br>+<br>+<br>+<br>+<br>– |

The *Listeria* genus specific oligonucleotide probe, LGtm, was hybridised to the Southern blot depicted in FIG. 4. Positive hybridisation signals were observed only with *Listeria* species as shown in FIG. 8 and Table 4, demonstrating the utility of the tmRNA sequence as a target in detecting a specific genus.

Figure 8:
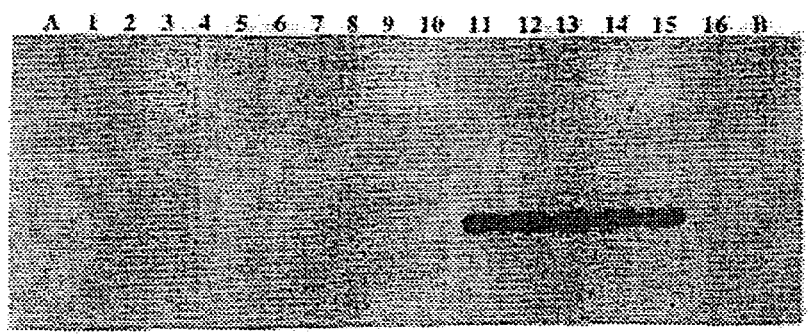
FIG. 8 is a photograph of an autoradiogram of hybridised *Listeria* genus specific oligonucleotide probe to a panel of organisms as prepared in Example 4.

In FIG. 8 the lanes represent the following:
Lane A: Molecular weight marker V
Lane 1: *Escherichia coli*
Lane 2: *Salmonella poona*
Lane 3: *Klebsiella aerogenes*
Lane 4: *Proteus mirabilis*
Lane 5: *Proteus rettgeri*
Lane 6: *Aeromonas hydrophilia*
Lane 7: *Staphyloccus aureus*
Lane 8: *Enterococcus faecalis*
Lane 9: *Lactobacillus lactis*
Lane 10: *Bacillus subtilus*
Lane 11: *Listeria monocytogenes*
Lane 12: *Listeria innocua*
Lane 13: *Listeria murrayi*
Lane 14: *Listeria welshimeri*
Lane 15: *Listeria grayi*
Lane 16: *Mycobacterium bovis*
Lane B: Molecular weight marker V The PCR products generated using the genus-specific amplification described in this Example, and shown in FIG. 7, were Southern blotted and hybridised to the *L. monocytogenes* species-specific oligonucleotide probe. A positive hybridisation signal was observed with three of the four typed strains and the clinical isolate of *L. monocytogenes* as shown in FIG. 9 and Table 4.

Figure 9:
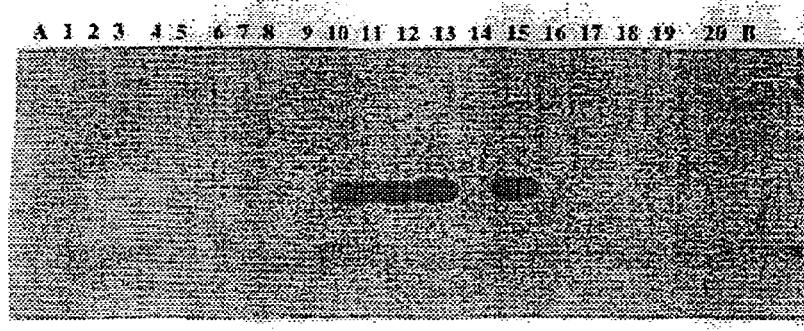
FIG. 9 is a photograph of an autoradiogram of hybridised *L. monocytogenes* species specific probe to a panel of organisms as prepared in Example 7.

In FIG. 9 the lanes represent the following:
Lane A: Molecular weight marker V
Lane 1: *E. coli*
Lane 2: *S. poona*
Lane 3: *K. aerogenes*
Lane 4: *P. mirabilis*
Lane 5: *P. rettgeri*
Lane 6: *A. hydrophilia*
Lane 7: *S. aureus*
Lane 8: *E. faecalis*
Lane 9: *L. lactis*
Lane 10: *B. subtilus*
Lane 11: *L. monocytogenes* strain 1
Lane 12: *L. monocytogenes* strain 2
Lane 13: *L. monocytogenes* strain 3
Lane 14: *L. monocytogenes* strain 4

Lane 15: *L. monocytogenes* clinical isolate
Lane 16: *L. innocua*
Lane 17: *L. murrayi*
Lane 18: *L. welshimeri*
Lane 19: *L. grayi*
Lane 20: *M. bovis*
Lane B: Molecular weight marker V

TABLE 4

Specificity of the *Listeria* genus-specific probe and the *L. monocytogenes* species-specific probe.

|  |  | LGtm Genus-specific probe | LStm Species-specific probe |
|---|---|---|---|
| Gram negative bacteria | *Escherichia coli* | − | − |
| | *Salmonella poona* | − | − |
| | *Klebsiella aerogenes* | − | − |
| | *Proteus mirabilis* | − | − |
| | *Proteus rettgeri* | − | − |
| | *Aeromonas hydrophilia* | − | − |
| Gram positive bacteria | *Staphyloccus aureus* | − | − |
| | *Entrococcus aecalis* | − | − |
| | *Lactobacillus lactis* | − | − |
| | *Bacillus subtilus* | − | − |
| | *Listeria monocytogenes* strain 1 | + | + |
| | *Listeria monocytogenes* strain 2 | + | + |
| | *Listeria monocytogenes* strain 3 | + | + |
| | *Listeria monocytogenes* strain 4 | + | − |
| | *Listeria monocytogenes* clinical isolate | + | + |
| | *Listeria innocua* | + | − |
| | *Listeria murrayi* | + | − |
| | *Listeria welshimeri* | + | − |
| | *Listeria grayi* | + | − |
| | *Mycobacterium bovis* | − | − |

One of the typed *L. monocytogenes* strains, strain 4, failed to generate a positive signal with this probe. DNA sequencing of the PCR amplified ssrA gene from this strain demonstrated that it contained a probe target region identical to *L. innocua*. It should be noted however that the ssrA gene from this strain contains other regions where the sequence is identical to the previously characterised *L. monocytogenes* strain and that these sequences are different to the *L. innocua* sequence, as shown in FIG. 15. Therefore a species specific oligonucleotide directed to one of these variable regions can be synthesised which would recognise each strain type (isolate) within the species, for example *L. monocytogenes*.

Example 6

Multiple Colorimetric Probe Detection of *Listeria* ssrA Gene Sequences

Figure 10:
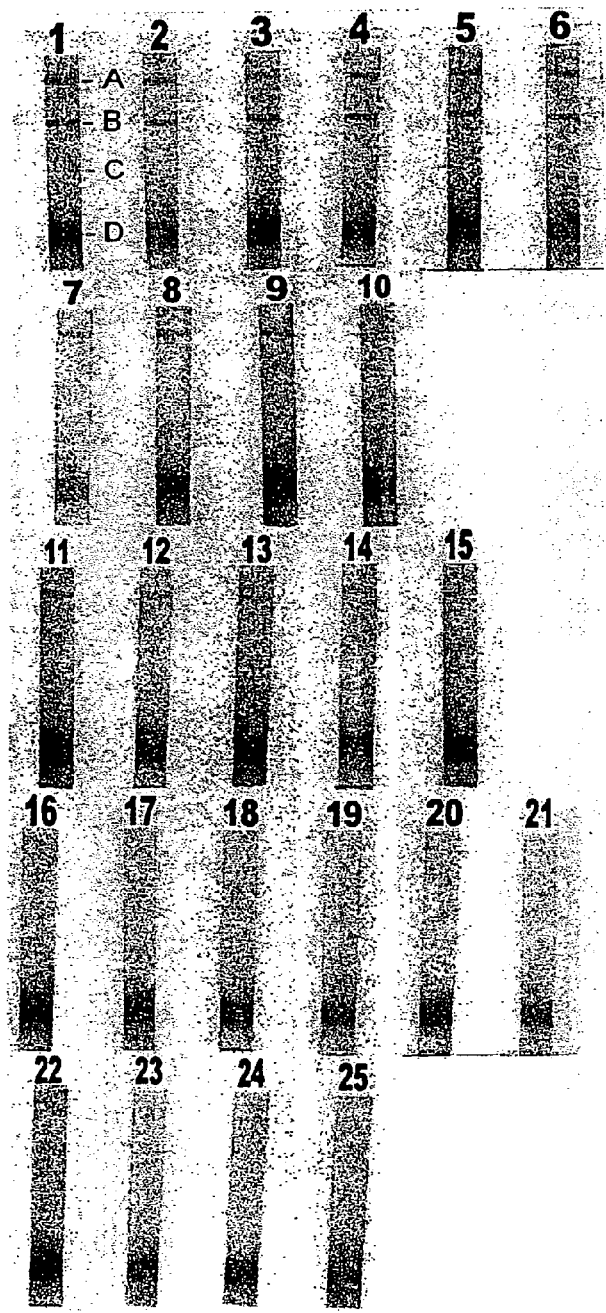
FIG. 10 is a computer scanned image of a nylon membrane strip used in the multiple colorimetric probe detection of *Listeria* ssrA gene sequences as described in Example 6.

LGTm (A), LStm (B) and a *Campylobacter upsaliensis* 16S-23S rRNA spacer (C-5' CATTAAACTTTAGCAAG-GAAGTG 3') SEQ ID NO: 228 oligonucleotide probe were irreversibly bound to nylon membrane strips and hybridised to with amplified ssrA PCR product, using the genus specific primers Ltm1 and Ltm2 (Ltm1 was labelled with biotin at the 5' end), from *L. monocytogenes* (1-6), *L. innocua* (7-10), *Z. ivanovii* (11), *L. murrayi* (12), *L. seeligeri* (13), *L. welshmeri* (14) and *L. grayii* (15). The ssrA amplified PCR products, using tmU5' and tmU3' (tmU5' was labelled with biotin at the 5' end), were also hybridised to the nylon membrane strips from the Gram-positive bacteria, *B. subtilus, L. lactis, S. aureus, S. epidermis, E. faecalis, C. perfringins* (16-21) and the Gram-negative bacteria *E. coli, S. enteritidis, P. Rettgeri, K. aerogenes* (22-25). As shown in FIG. 10 after hybridisation, development of the colorimetric assay to biotin revealed the following: Strips 1-6 demonstrates that the ssrA amplified PCR product originated from *L. monocytogenes* combined with the confirmation that the PCR product amplified is from the genus *Listeria*—A and B give colour detection; Strips 7-15 demonstrate that these PCR products originated from the genus *Listeria*—only A gives colour detection; and Strips 16-25 demonstrate that the PCR products are not from the genus *Listeria*—no colour detection. C is a negative oligonucleotide control probe and D is a positive control colorimetric detection assay for all samples.

Example 7

Use of ssrA/tmRNA Sequences to Distinguish Between Species of Organisms

Clustal W alignments as shown in FIGS. 11 (SEQ ID NOS:19 and 21), 12 (SEQ ID NOS:41 and 43), 13 (SEQ ID NOS:77 and 79), 14 (SEQ ID NOS:83 and 85), 15 (SEQ ID NOS: 229 (L.m.2) and 57, residues 20-247 (L.m.1)), and 16 (SEQ ID NOS:53 (L.i.=Res. Nos. 77 to 304), 229 (L.m.2), and 57 (L.m1), indicate that there are nucleotide differences within the ssrA/tmRNA sequences of different strains of the same bacteria. This suggests that the ssrA/tmRNA sequences could potentially be used to discriminate between individual and/or groups of strains within a bacterial species. This may have useful applications in epidemiology and bacterial population analysis.

Example 8 tmRNA Integrity Analysis After Medium and Extreme Heat Treatment of Bacterial Cells

Figure 17:
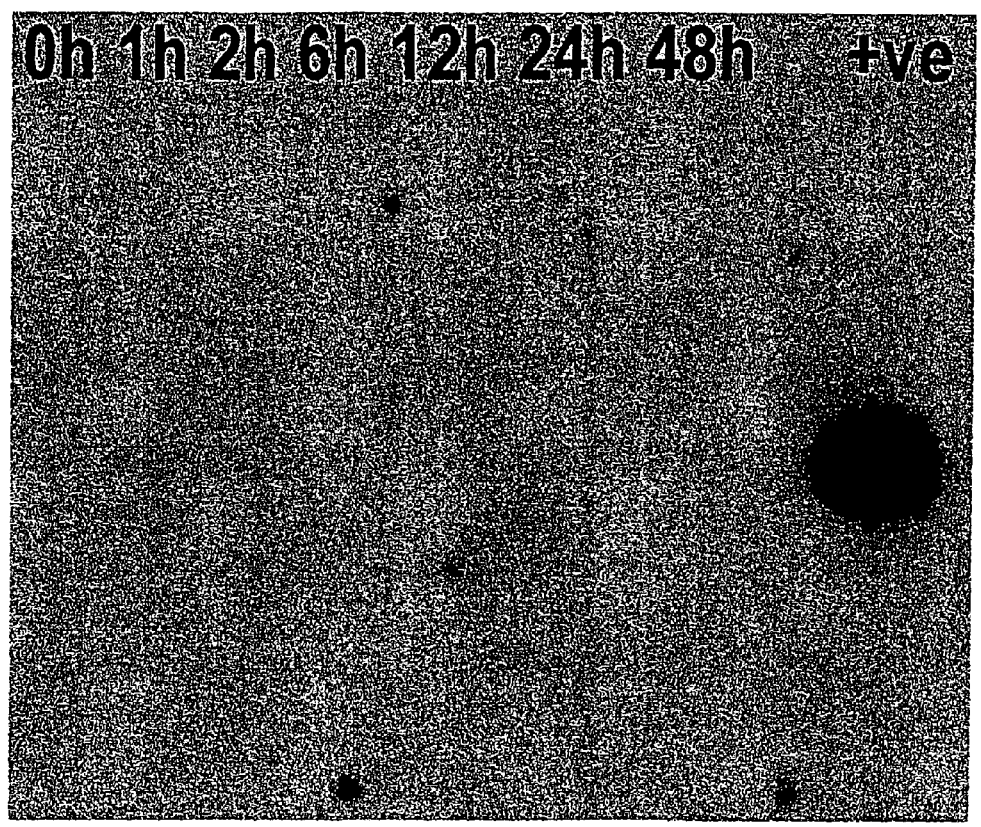
FIG. 17 is a photograph of an autoradiogram hybridised *Listeria* oligonucleotide probe (Evtm) to total RNA samples isolated after medium heat treatment of *E. coli* cells.
Figure 18:
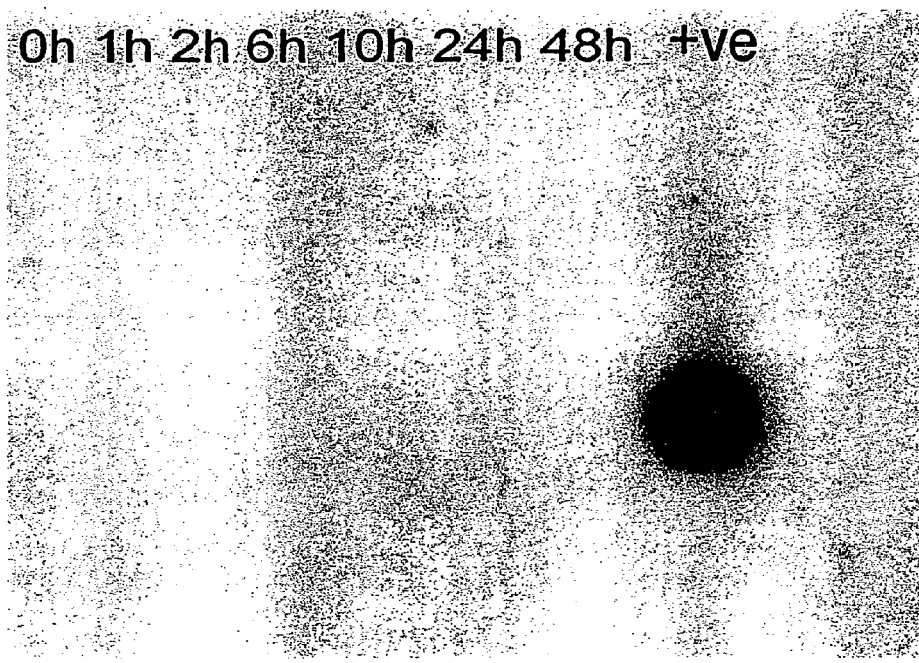
FIG. 18 is a photograph of an autoradiogram hybridised *Listeria* oligonucleotide probe (Evtm) to total RNA samples isolated after extreme heat treatment of *E. coli* cells.
Figure 19:
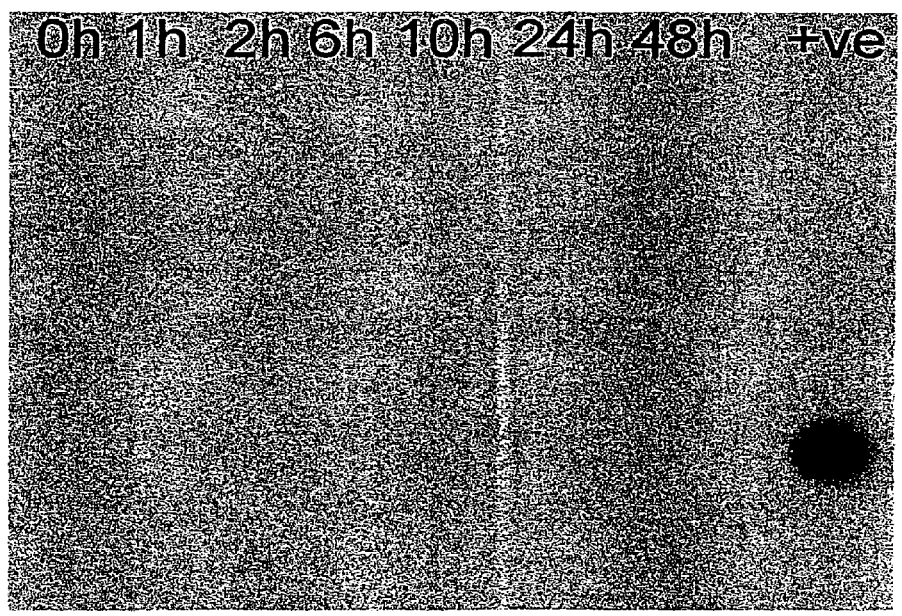
FIG. 19 is a photograph of an autoradiogram hybridised *Listeria* oligonucleotide probe (Lvtm) to total RNA samples isolated after medium heat treatment of *L. monocytogenes* cells.
Figure 20:
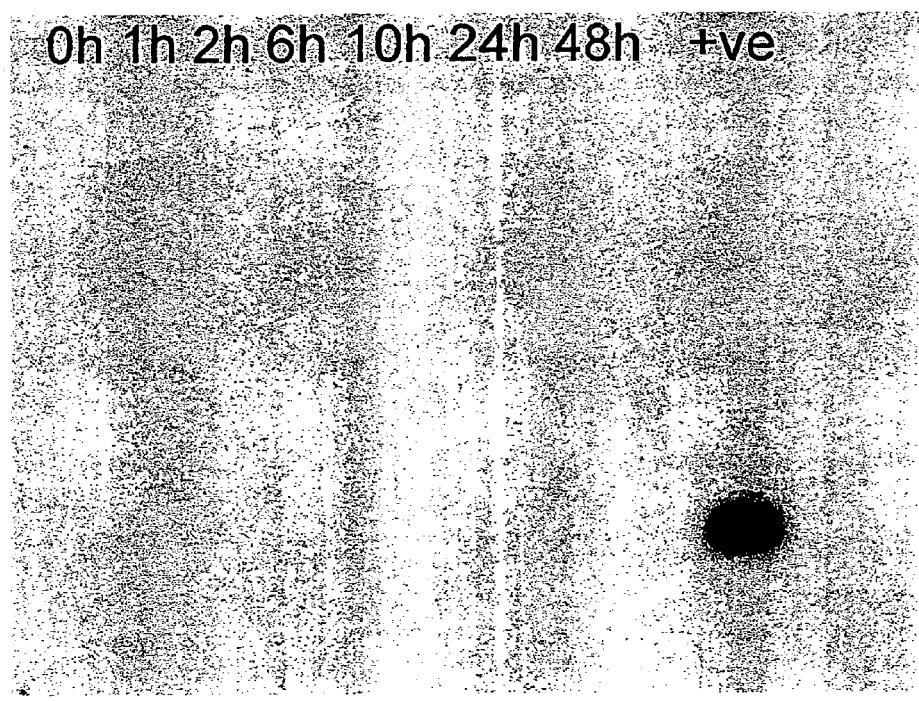
FIG. 20 is a photograph of an autoradiogram hybridised *Listeria* oligonucleotide probe (Lvtm) to total RNA samples isolated after extreme heat treatment of *L. monocytogenes* cells.

*E. coli* and *L. monocytogenes* cultures were heat treated at 80° C., for 20 min. in the case of *E. coli* and 40 min. in the case of *L. monocytogenes* and at 120° C. for 15 min. (autoclaving) after overnight growth and tested for viability at 0 h, 1 h, 2 h, 6 h, 12 h, 24 h and 48 h after heat treatment. No viability was observed at each time period tested. Total RNA was also isolated at these time periods and electrophoresed on denaturing 1.2% agarose gels and Northern blotted. Each blot was hybridised to, in the case of *E. coli* (FIGS. 17 and 18) with a radioactively labelled oligonucleotide probe Evtm and in the case of *L. monocytogenes* (FIGS. 19 and 20) with a radiolabelled LVtm. No tmRNA transcript was detected with each sample tested, demonstrating that tmRNA transcript is degraded after heat treatment. The lanes represented with the notation +ve is a positive control total RNA sample.

Example 9

Use of the tmRNA Transcript in Distinguishing Between Viable and Non-Viable Bacteria A 100 ml culture of *L. monocytogenes* was grown overnight in liquid culture. After growth, serial dilutions of the cells were carried out and viability was determined by spread plating on nutrient agar plates. Simultaneously, total RNA was isolated from a 1 ml aliquot of these cells. The remainder of the cells were heated at 65° C. for 20 min. Cells were then removed for both viability analysis and total RNA isolation. Samples were taken for viability and RNA isolation at time periods of 0 h, 2 h, 6 h and 24 h after treatment.

Spread plating on nutrient agar plates indicated that heat treatment killed *L. monocytogenes* cells, with no viable colony forming units observed. Each RNA sample isolated was then treated with DNase to remove any contaminating DNA and total RNA samples (100 ng) were subjected to Reverse Transcriptase-PCR amplification using the *Listeria* genus specific ssrA/tmRNA oligonucleotide primers Ltm1 and Ltm2. Negative control amplification reactions included primers, target, and Taq polymerase, but no Reverse Transcriptase. The results of the amplification reactions are shown in FIG. 12.

Amplified tmRNA RT-PCR products were only observed with the RNA sample which was not heat treated. All other samples gave no RT-PCR product indicating that the tmRNA molecules in these samples may have been degraded in the non-viable heat treated cells.

Figure 21:
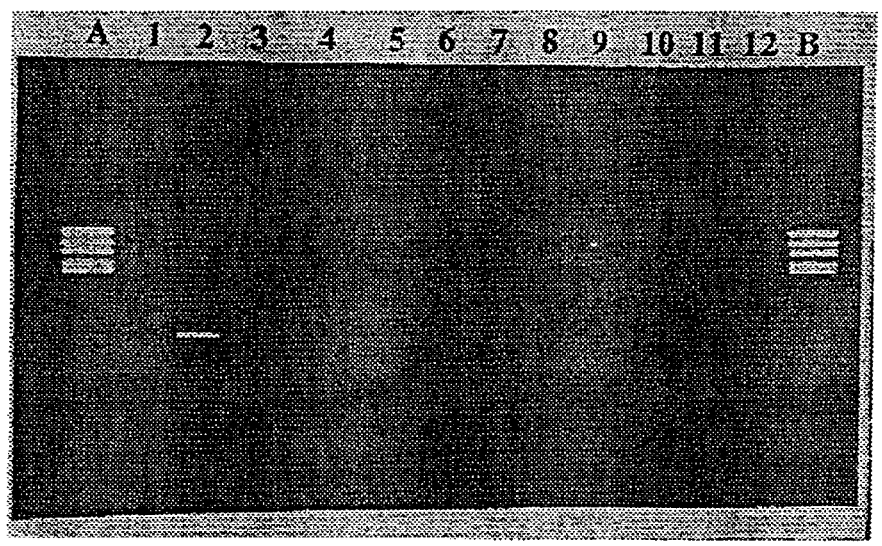
FIG. 21 is a photograph of an agarose gel of RT-PCR generated tmRNA products at various time points post heat treatment.

In FIG. 21 the lanes represent the following:

| | |
|---|---|
| Lane A: | Molecular weight marker V; |
| Lane 1: | PCR amplification of RNA (no heat treatment treatment of cells) −Reverse Transcriptase (RT), +Taq polymerase (TP); |
| Lane 2: | RT-PCR of RNA (no heat treatment of cells), +RT, +TP; |
| Lane 3: | PCR amplification of RNA (at 0 time after heat treatment), −RT, +TP; |
| Lane 4: | RT-PCR of RNA (at 0 time after heat treatment), +RT, +TP; |
| Lane 5: | PCR amplification of RNA (at 1 h time after heat treatment), −RT, +TP; |
| Lane 6: | RT-PCR of RNA (at 1 h time after heat treatment), +RT, +TP; |
| Lane 7: | PCR amplification of RNA (at 2 h time after heat treatment), −RT, +TP; |
| Lane 8: | RT,PCR of RNA (at 2 h time after heat treatment) +RT, +TP; |
| Lane 9: | PCR amplification of RNA (at 6 h time after heat treatment), −RT, +TP; |
| Lane 10: | RT-PCR of RNA (at 6 h time after heat treatment), +RT, +TP; |
| Lane 11: | PCR amplification of RNA (at 24 h time after heat treatment), −RT, +TP; |
| Lane 12: | RT-PCR of RNA (at 24 h time after heat treatment), +RT, +TP; |
| Lane B: | Molecular weight marker V. |

SEQUENCE LISTING

```
<160> NUMBER OF SEQ ID NOS: 239

<210> SEQ ID NO 1
<211> LENGTH: 366
<212> TYPE: DNA
<213> ORGANISM: Actinobacillus actinomycetemcomitans

<400> SEQUENCE: 1
ggggctgatt ctggattcga cgggattagc gaagcccgaa gtgcacgtcg aggtgcggta      60
ggcctcgtaa ataaaccgca aaaaaatagt cgcaaacgac gaacaatacg ctttagcagc     120
ttaataacct gcctttagcc ttcgctcccc agcttccgct cgtaagacgg ggataaagcg     180
gagtcaaacc aaaacgagat cgtgtggaag ccaccgtttg aggatcgaag cattaaatta     240
aatcaaagta gcttaattgt cgcgtgtccg tcagcaggat taagtgaatt taaagaccgg     300
actaaacgtg tagtgctaac ggcagaggaa tttcggacgg gggttcaact ccccccagct     360
ccacca                                                                366

<210> SEQ ID NO 2
<211> LENGTH: 366
<212> TYPE: RNA
<213> ORGANISM: Actinobacillus actinomycetemcomitans

<400> SEQUENCE: 2
ggggcugauu cuggauucga cgggauuagc gaagcccgaa gugcacgucg aggugcggua      60
ggccucguaa auaaaccgca aaaaauagu cgcaaacgac gaacaauacg cuuuagcagc     120
uuaauaaccu gccuuuagcc uucgcucccc agcuuccgcu cguaagacgg ggauaaagcg     180
gagucaaacc aaaacgagau cguguggaag ccaccguuug aggaucgaag cauuaaauua     240
aaucaaagua gcuuaauugu cgcguguccg ucagcaggau uaagugaauu uaaagaccgg     300
acuaaacgug uagugcuaac ggcagaggaa uuucggacgg ggguucaacu ccccccagcu     360
ccacca                                                                366

<210> SEQ ID NO 3
<211> LENGTH: 315
```

```
<212> TYPE: DNA
<213> ORGANISM: Aeromonas salmonicida

<400> SEQUENCE: 3
aagattcacg aaacccaagg tgcatgccga ggtgcggtag gcctcgttaa caaaccgcaa      60
aaaaatagtc gcaaacgacg aaaactacgc actagcagct taataacctg catagagccc     120
ttctacccta gcttgcctgt gtcctaggga atcggaaggt catccttcac aggatcgtgt     180
ggaagtcctg ctcggggcgg aagcattaaa accaatcgag ctagtcaatt cgtggcgtgt     240
ctctccgcag cgggttggcg aatgtaaaga gtgactaagc atgtagtacc gaggatgtag     300
taattttgga cgggg                                                      315

<210> SEQ ID NO 4
<211> LENGTH: 315
<212> TYPE: RNA
<213> ORGANISM: Aeromonas salmonicida

<400> SEQUENCE: 4
aagauucacg aacccaagg ugcaugccga ggugcgguag gccucguuaa caaaccgcaa       60
aaaaauaguc gcaaacgacg aaaacuacgc acuagcagcu uauaaccug cauagagccc      120
uucuacccua gcuugccugu guccuaggga aucggaaggu cauccuucac aggaucgugu     180
ggaaguccug cucggggcgg aagcauuaaa accaaucgag cuagucaauu cguggcgugu     240
cucuccgcag cgggguuggcg aauguaaaga gugacuaagc auguaguacc gaggauguag    300
uaauuuugga cgggg                                                      315

<210> SEQ ID NO 5
<211> LENGTH: 349
<212> TYPE: DNA
<213> ORGANISM: Alcaligenes eutrophus

<400> SEQUENCE: 5
tgggccgacc tggtttcgac gtggttacaa agcagtgagg cataccgagg acccgtcacc      60
tcgttaatca atggaatgca ataactgcta acgacgaacg ttacgcactc gcttaattgc     120
ggccgtcctc gcactggctc gctgacgggc tagggtcgca agaccacgcg aggtatttac     180
gtcagataag ctccggaagg gtcacgaagc cggggacgaa aacctagtga ctcgccgtcg     240
tagagcgtgt tcgtccgatg cgccggttaa atcaaatgac agaactaagt atgtagaact     300
ctctgtggag ggcttacgga cgcgggttcg attcccgccg gctccacca                 349

<210> SEQ ID NO 6
<211> LENGTH: 349
<212> TYPE: RNA
<213> ORGANISM: Alcaligenes eutrophus

<400> SEQUENCE: 6
ugggccgacc ugguuucgac gugguuacaa agcagugagg cauaccgagg acccgucacc      60
ucguuaauca auggaaugca auaacugcua acgacgaacg uuacgcacuc gcuuaauugc     120
ggccguccuc gcacuggcuc gcugacgggc uaggucgca agaccacgcg agguauuuac      180
gucagauaag cuccggaagg gucacgaagc cggggacgaa aaccuaguga cucgccgucg     240
uagagcgugu ucguccgaug cgccgguuaa aucaaaugac agaacuaagu auguagaacu     300
cucuguggag ggcuuacgga cgcggguucg auucccgccg gcuccacca                 349

<210> SEQ ID NO 7
<211> LENGTH: 347
```

<212> TYPE: DNA
<213> ORGANISM: Aquifex aeolicus

<400> SEQUENCE: 7

```
gggggcggaa aggattcgac ggggacaggc ggtccccgag gagcaggccg ggtggctccc    60
gtaacagccg ctaaaacagc tcccgaagct gaactcgctc tcgctgccta attaaacggc   120
agcgcgtccc cggtaggttt gcgggtggcc taccggaggg cgtcagagac acccgctcgg   180
gctactcggt cgcacggggc tgagtagctg acacctaacc cgtgctaccc tcggggagct   240
tgcccgtggg cgaccgagg ggaaatcctg aacacgggct aagcctgtag agcctcggat    300
gtggccgccg tcctcggacg cgggttcgat tcccgccgcc tccacca                 347
```

<210> SEQ ID NO 8
<211> LENGTH: 347
<212> TYPE: RNA
<213> ORGANISM: Aquifex aeolicus

<400> SEQUENCE: 8

```
gggggcggaa aggauucgac ggggacaggc gguccccgag gagcaggccg ggugcuccc     60
guaacagccg cuaaaacagc ucccgaagcu gaacucgcuc ucgcugccua auuaaacggc   120
agcgcguccc cgguagguuu gcggguggcc uaccggaggg cgucagagac acccgcucgg   180
gcuacucggu cgcacggggc ugaguagcug acaccuaacc cgugcuaccc ucggggagcu   240
ugcccguggg cgaccgagg ggaaauccug aacacgggcu aagccuguag agccucggau    300
guggccgccg uccucggacg cggguucgau ucccgccgcc uccacca                 347
```

<210> SEQ ID NO 9
<211> LENGTH: 316
<212> TYPE: DNA
<213> ORGANISM: Bacillus megaterium

<400> SEQUENCE: 9

```
agggtagttc gagcttaggt tgcgagtcga ggagatggcc tcgttaaaac atcaacgcca    60
ataataactg gcaaatctaa caataacttc gctttagctg cataatagta gcttagcgtt   120
cctccctcca tcgcccatgt ggtagggtaa gggactcact ttaagtgggc tacgccggag   180
ttcgccgtct gaggacgaag gaagagaata atcagactag cgactgggac gcctgttggt   240
aggcagaaca gctcgcgaat gatcaatatg ccaactacac tcgtagacgc ttaagtggcc   300
atatttctgg acgtgg                                                   316
```

<210> SEQ ID NO 10
<211> LENGTH: 316
<212> TYPE: RNA
<213> ORGANISM: Bacillus megaterium

<400> SEQUENCE: 10

```
agggu aguuc gagcuuaggu ugcgagucga ggagauggcc ucguuaaaac aucaacgcca    60
auauaacug gcaaaucuaa caauaacuuc gcuuuagcug cauaauagua gcuuagcguu    120
ccucccucca ucgcccaugu gguaggguaa gggacucacu uuaagugggc uacgccggag   180
uucgccgucu gaggacgaag gaagagaaua aucagacuag cgacugggac gccuguuggu   240
aggcagaaca gcucgcgaau gaucaauaug ccaacuacac ucguagacgc uuaaguggcc   300
auauuucugg acgugg                                                   316
```

<210> SEQ ID NO 11
<211> LENGTH: 363

-continued

<212> TYPE: DNA
<213> ORGANISM: Bacillus subtilis

<400> SEQUENCE: 11

```
ggggacgtta cggattcgac agggatggat cgagcttgag ctgcgagccg agaggcgatc     60
tcgtaaacac gcacttaaat ataactggca aaactaacag ttttaaccaa aacgtagcat    120
tagctgccta ataagcgcag cgagctcttc ctgacattgc ctatgtgtct gtgaagagca    180
catccaagta ggctacgctt gcgttcccgt ctgagaacgt aagaagagat gaacagacta    240
gctctcggaa ggcccgcccg caggcaagaa gatgagtgaa accataaata tgcaggctac    300
gctcgtagac gcttaagtaa tcgatgtttc tggacgtggg ttcgactccc accgtctcca    360
cca                                                                  363
```

<210> SEQ ID NO 12
<211> LENGTH: 363
<212> TYPE: RNA
<213> ORGANISM: Bacillus subtilis

<400> SEQUENCE: 12

```
ggggacguua cggauucgac agggauggau cgagcuugag cugcgagccg agaggcgauc     60
ucguaaacac gcacuuaaau auaacuggca aaacuaacag uuuuaaccaa aacguagcau    120
uagcugccua auaagcgcag cgagcucuuc cugacauugc cuaugugucu gugaagagca    180
cauccaagua ggcuacgcuu gcguucccgu cugagaacgu aagaagagau gaacagacua    240
gcucucggaa ggcccgcccg caggcaagaa gaugagugaa accauaaaua ugcaggcuac    300
gcucguagac gcuuaaguaa ucgauguuuc uggacguggg uucgacuccc accgucucca    360
cca                                                                  363
```

<210> SEQ ID NO 13
<211> LENGTH: 387
<212> TYPE: DNA
<213> ORGANISM: Bordetella pertussis

<400> SEQUENCE: 13

```
ggggccgatc cggattcgac gtgggtcatg aaacagctca gggcatgccg agcaccagta     60
agctcgttaa tccactggaa cactacaaac gccaacgacg agcgtctcgc tctcgccgct    120
taagcggtga gccgctgcac tgatctgtcc ttgggtcagg cgggggaagg caacttcaca    180
gggggcaacc ccgaaccgca gcagcgacat tcacaaggaa tcggccaccg ctggggtcac    240
acggcgttgg tttaaattac gtgaatcgcc ctggtccggc ccgtcgatcg gctaagtcca    300
gggttaaatc caaatagatc gactaagcat gtagaactgg ttgcggaggg cttgcggacg    360
ggggttcaat tccccccggc tccacca                                        387
```

<210> SEQ ID NO 14
<211> LENGTH: 387
<212> TYPE: RNA
<213> ORGANISM: Bordetella pertussis

<400> SEQUENCE: 14

```
ggggccgauc cggauucgac gugggucaug aaacagcuca gggcaugccg agcaccagua     60
agcucguuaa uccacuggaa cacuacaaac gccaacgacg agcgucucgc ucucgccgcu    120
uaagcgguga gccgcugcac ugaucugucc uugggucagg cgggggaagg caacuucaca    180
gggggcaacc ccgaaccgca gcagcgacau ucacaaggaa ucggccaccg cuggggucac    240
acggcguugg uuuaaauuac gugaaucgcc cugguccggc ccgucgaucg gcuaagucca    300
```

```
ggguuaaauc caaauagauc gacuaagcau guagaacugg uugcggaggg cuugcggacg    360
ggggnucaau ucccccggc uccacca                                          387

<210> SEQ ID NO 15
<211> LENGTH: 362
<212> TYPE: DNA
<213> ORGANISM: Borrelia burgdorferi

<400> SEQUENCE: 15
ggggatgttt tggatttgac tgaaaatgtt aatattgtaa gttgcaggca gagggaatct     60
cttaaaactt ctaaaataaa tgcaaaaaat aataacttta caagctcaaa tcttgtaatg   120
gctgcttaag ttagcagagg gttttgttga atttggcttt gaggttcact tatactcttt   180
tcgacatcaa agcttgctta aaatgttttt caagttgatt tttagggact tttatacttg   240
agagcaattt ggtggtttgc tagtattccc aaaccatatt gcttaataaa atactagata   300
agcttgtaga agcttatagt attatttttta ggacgcgggt tcaattcccg ccatctccac   360
ca                                                                    362

<210> SEQ ID NO 16
<211> LENGTH: 362
<212> TYPE: RNA
<213> ORGANISM: Borrelia burgdorferi

<400> SEQUENCE: 16
ggggauguuu uggauuugac ugaaaauguu aauauuguaa guugcaggca gagggaaucu     60
cuuaaaacuu cuaaaauaaa ugcaaaaaau aauaacuuua caagcucaaa ucuuguaaug   120
gcugcuuaag uuagcagagg guuuuguuga auuggcuuu gagguucacu uauacucuuu   180
ucgacaucaa agcuugcuua aaauguuuu caaguugauu uuuagggacu uuuauacuug   240
agagcaauuu gguggunugc uaguanuucc aaaccauauu gcuuaauaaa auacagauaa   300
agcuuguaga agcuuauagu auuauuuuua ggacgcgggu ucaauucccg ccaucuccac   360
ca                                                                    362

<210> SEQ ID NO 17
<211> LENGTH: 359
<212> TYPE: DNA
<213> ORGANISM: Campylobacter jejuni

<400> SEQUENCE: 17
gggagcgact tggcttcgac aggagtaagt ctgcttagat ggcatgtcgc tttgggcaaa     60
gcgtaaaaag cccaaataaa attaaacgca aacaacgtta aattcgctcc tgcttacgct    120
aaagctgcgt aagttcagtt gagcctgaaa tttaagtcat actatctagc ttaattttcg    180 gtcattttg atagtgtagc cttgcgtttg acaagcgttg aggtgaaata aagtcttagc    240
cttgcttttg agttttggaa gatgagcgaa gtagggtgaa gtagtcatct ttgctaagca    300
tgtagaggtc tttgtgggat tattttttgga caggggttcg attcccctcg cttccacca    359

<210> SEQ ID NO 18
<211> LENGTH: 359
<212> TYPE: RNA
<213> ORGANISM: Campylobacter jejuni

<400> SEQUENCE: 18
gggagcgacu uggcuucgac aggaguaagu cugcuuagau ggcaugucgc uuugggcaaa     60
gcguaaaaag cccaaauaaa auuaaacgca aacaacguua aauucgcucc ugcuuacgcu    120
```

-continued

```
aaagcugcgu aaguucaguu gagccugaaa uuuaagucau acuaucuagc uuaauuuucg    180
gucauuuuug auaguguagc cuugcguuug acaagcguug aggugaaaua aagucuuagc    240
cuugcuuuug aguuuuggaa gaugagcgaa guagggugaa guagucaucu ugcuaagca    300 uguagagguc uuuguggau auuuuugga caggggu ucg auucccc ucg cuuccacca    359
```

```
<210> SEQ ID NO 19
<211> LENGTH: 420
<212> TYPE: DNA
<213> ORGANISM: Chlamydia trachomatis (D/UW-3/CX)

<400> SEQUENCE: 19
gggggtgtaa aggtttcgac ttagaaatga agcgttaatt gcatgcggag ggcgttggct    60
ggcctcctaa aaagccgaca aaacaataaa tgccgaacct aaggctgaat gcgaaattat   120
cagcttcgct gatctcgaag atctaagagt agctgcttaa ttagcaaagt tgttacctaa   180
atacgggtga cccggtgttc gcgagctcca ccagaggttt cgaaacacc gtcatgtatc   240 tggttagaac ttaggtcctt taattctcga ggaaatgagt ttgaaattta atgagagtcg   300
ttagtctcta taggggtttc tagctgagga gacataacgt atagtaccta ggaactaagc   360
atgtagaggt tagcggggag tttactaagg acgagagttc gactctctcc acctccacca   420
```

```
<210> SEQ ID NO 20
<211> LENGTH: 420
<212> TYPE: RNA
<213> ORGANISM: Chlamydia trachomatis (D/UW-3/CX)

<400> SEQUENCE: 20 gggggguguaa agguuucgac uuagaaauga agcguuaauu gcaugcggag ggcguuggcu    60
ggccuccuaa aaagccgaca aaacaauaaa ugccgaaccu aaggcugaau gcgaaauuau   120
cagcuucgcu gaucucgaag aucuaagagu agcugcuuaa uuagcaaagu uguuaccuaa   180
auacggguga cccgguguuc gcgagcucca ccagagguuu cgaaacacc gucauguauc   240 ugguuagaac uuagguccuu uaauucucga ggaaaugagu uugaaauuua augagagucg   300
uuagucucua uaggguuuc uagcugagga gacauaacgu auaguaccua ggaacuaagc   360
auguagaggu uagcggggag uuuacuaagg acgagaguuc gacucucucc accuccacca   420
```

```
<210> SEQ ID NO 21
<211> LENGTH: 421
<212> TYPE: DNA
<213> ORGANISM: Chlamydia trachomatis (mouse pneumonitis)

<400> SEQUENCE: 21
gggggtgtaa aggtttcgac ttagaaatga agcgttaatt gcatgcggag ggcgttggct    60
ggcctcctaa aaagccgaca aaacaataaa tgccgaacct aaggctgaat gcgaaattat   120
cagcttcgct gatcttaatg atctaagagt tgctgcttaa ttagcaaagt tgttacctaa   180
gtactggtaa cccggtgttc gcgagctcca ccagaggttt cgaaacgcc gtcatttatc   240 tggttagaat tagggccttt taactctcaa ggaactaat ttgatttta atgagagtcg   300 ttggtctcta tagaggtttc tagctgagga gatataacgt aaaatattct agaaactaag   360
catgtagagg ttagcgggga gtttactaag gacgagagtt cgaatctctc cacctccacc   420
a                                                                    421
```

```
<210> SEQ ID NO 22
<211> LENGTH: 421
```

```
<212> TYPE: RNA
<213> ORGANISM: Chlamydia trachomatis (mouse pneumonitis)

<400> SEQUENCE: 22 gggggnguuaa agguuucgac uuagaaauga agcguuaauu gcaugcggag ggcguuggcu      60
ggccuccuaa aaagccgaca aaacaauaaa ugccgaaccu aaggcugaau gcgaaauuau     120
cagcuucgcu gaucuuaaug aucuaagagu ugcugcuuaa uuagcaaagu uguuaccuaa     180
guacugguaa cccgguguuc gcgagcucca ccagagguuu ucgaaacgcc gucauuuauc     240
ugguuagaau uagggccuuu uaacucucaa gggaacuaau uugaauuuua augagagucg     300
uuggucucua uagagguuuc uagcugagga gauauaacgu aaaauauucu agaaacuaag     360
cauguagagg uuagcgggga guuuacuaag gacgagaguu cgaaucucuc caccuccacc     420
a                                                                   421

<210> SEQ ID NO 23
<211> LENGTH: 404
<212> TYPE: DNA
<213> ORGANISM: Chlorobium tepidum

<400> SEQUENCE: 23
ggggatgaca ggctatcgac aggataggtg tgagatgtcg ttgcactccg agtttcagca      60
tggacggact cgttaaacaa gtctatgtac caatagatgc agacgattat tcgtatgcaa     120
tggctgcctg attagcacaa gttaattcag aagccatcgt cctgcggtga atgcgcttac     180
tctgaagccg ccggatggca taacccgcgc ttgagcctac ggttcgcgc aagtaagctc      240
cgtacattca tgcccgaggg ggtgtgcggg taaccaatcg ggataagggg acgaacgctg     300
ctggcggtgt aatcggacca cgaaaaacca accaccagag atgagtgtgg taactgcatc     360
gagcagtgtc ctggacgcgg gttcaagtcc cgccatctcc acca                      404

<210> SEQ ID NO 24
<211> LENGTH: 404
<212> TYPE: RNA
<213> ORGANISM: Chlorobium tepidum

<400> SEQUENCE: 24
ggggaugaca ggcuaucgac aggauaggug ugagaugucg uugcacuccg aguuucagca      60
uggacggacu cguuaaacaa gucuauguac caauagaugc agacgauuau ucguaugcaa     120
uggcugccug auuagcacaa guuaauucag aagccaucgu ccugcgguga augcgcuuac     180
ucugaagccg ccggauggca uaacccgcgc uugagccuac gguucgcgc aaguaagcuc      240
cguacauuca ugcccgaggg ggugugcggg uaaccaaucg ggauaagggg acgaacgcug     300
cuggcggugu aaucggacca cgaaaaacca accaccagag augagugugg uaacugcauc     360
gagcagnguc cuggacgcgg guucaaguce cgccaucucc acca                      404

<210> SEQ ID NO 25
<211> LENGTH: 294
<212> TYPE: DNA
<213> ORGANISM: Cyanophora paradoxa (alga) cyanelle

<400> SEQUENCE: 25
ggggctgttt aggtttcgac gttttttttct aattatgttt gttaagcaag tcgaggattt     60
gttctatctc gaaaatcaag aactctcaaa atttaaacgc aactaatatt gtacgttta     120
accgtaaagc agctttcgct gtttaataat tactttaat ttaaaaacct aattttttta     180
ggaatttatt tatttattgt ttatcctgct taatgaatta aaaaaagcta tacttgtgaa     240
```
taaacgcata atttaaaaaa acggacgtgg gttcaaatcc caccagctcc acca        294

<210> SEQ ID NO 26
<211> LENGTH: 294
<212> TYPE: RNA
<213> ORGANISM: Cyanophora paradoxa (alga) cyanelle

<400> SEQUENCE: 26
ggggcuguuu agguuucgac guuuuuucu aauuauguuu guuaagcaag ucgaggauuu     60
guucuaucuc gaaaaucaag aacucucaaa auuuaaacgc aacuaauauu guacguuuua  120
accguaaagc agcuuucgcu guuuaauaau uacuuuuaau uuaaaaaccu aauuuuuuua  180
ggaauuuauu uauuuauugu uuauccugcu uaaugaauua aaaaaagcua acuugugaa   240 uaaacgcaua auuuaaaaaa acggacgugg guucaaaucc caccagcucc acca        294

<210> SEQ ID NO 27
<211> LENGTH: 189
<212> TYPE: DNA
<213> ORGANISM: Clostridium acetobutylicum

<400> SEQUENCE: 27
aatctggcgt cgagagcggg gaaacgagcc ttacaaagct ttgagtaagg aacggaattt   60
atgaagctac tgaagtgaaa agcttgtttg taggcgtttc atggagggaa tgttaaaata  120
caaactgcac tcggagatgc ttaatgaaac cattttcgga caggggttcg attcccctcg  180
cctccacca                                                         189

<210> SEQ ID NO 28
<211> LENGTH: 189
<212> TYPE: RNA
<213> ORGANISM: Clostridium acetobutylicum

<400> SEQUENCE: 28
aaucuggcgu cgagagcggg gaaacgagcc uuacaaagcu uugaguaagg aacggaauuu   60
augaagcuac ugaagugaaa agcuuguuug uaggcguuuc auggagggaa uguuaaaaua  120
caaacugcac ucggagaugc uuaaugaaac cauuuucgga cagggguucg auucccucg   180 ccuccacca                                                         189

<210> SEQ ID NO 29
<211> LENGTH: 349
<212> TYPE: DNA
<213> ORGANISM: Deinococcus radiodurans

<400> SEQUENCE: 29
gggggtgacc cggtttcgac aggggaactg aaggtgatgt tgcgtgtcga ggtgccgttg   60
gcctcgtaaa caaacggcaa agccatttaa ctggcaacca gaactacgct ctcgctgctt  120
aagtgagatg acgaccgtgc agcccggcct ttggcgtcgc ggaagtcact aaaaaagaag  180
gctagcccag cgattctcc atagccgacg gcgaaacttt atggagctac ggcctgcgag   240
aacctgccca ctggtgagcg ccggcccgac aatcaaacag tggatacac acgtagacgc   300 acgctggacg gacctttgga cggcggttcg actccgccca cctccacca              349

<210> SEQ ID NO 30
<211> LENGTH: 349
<212> TYPE: RNA
<213> ORGANISM: Deinococcus radiodurans

<400> SEQUENCE: 30

```
gggggugacc cgguuucgac aggggaacug aagguagugu ugcgugucga ggugccguug      60
gccucguaaa caaacggcaa agccauuuaa cuggcaacca gaacuacgcu cucgcugcuu     120
aagugagaug acgaccguge agcccggccu uuggcgucgc ggaagucacu aaaaaagaag     180
gcuagcccag gcgauucucc auagccgacg gcgaaacuuu auggagcuac ggccugcgag     240
aaccugccca cuggugagcg ccggcccgac aaucaaacag ugggauacac acguagacgc     300
acgcuggacg gaccuuugga cggcgguucg acuccgccca ccuccacca                 349
```

```
<210> SEQ ID NO 31
<211> LENGTH: 330
<212> TYPE: DNA
<213> ORGANISM: Desulfovibrio desulfuricans

<400> SEQUENCE: 31
gggactggaa ccgtagcggc aggtcgaggc gccgctggcc tcgtaaaaag cggcacaaaa      60
gtaattgcca acaacgatta cgactacgct tacgctgcct aataacagcg aggcaatgac     120
cgtttaacgg tcgcgccgat cagggccatg cctgataacc ctgattggcg acacttatca     180
ggctggcgaa aaccggctct cgccggggtt tttcgcgagg agtttaccgg cgggattgct     240
gcgttgtgcc tggtcagggg ccaacagcgc ggtgaaatac atacttgacc taaacctgta     300
atgcttcgtg tggaatgttc tcggacgggg                                      330
```

```
<210> SEQ ID NO 32
<211> LENGTH: 330
<212> TYPE: RNA
<213> ORGANISM: Desulfovibrio desulfuricans

<400> SEQUENCE: 32
gggacuggaa ccguagcggc aggucgaggc gccgcuggcc ucguaaaaag cggcacaaaa      60
guaauugcca acaacgauua cgacuacgcu uacgcugccu aauaacagcg aggcaaugac     120
cguuuaacgg ucgcgccgau cagggccaug ccugauaacc cugauuggcg acacuuauca     180
ggcuggcgaa aaccggcucu cgccgggguu uuucgcgagg aguuuaccgg cgggauugcu     240
gcguugugcc uggucagggg ccaacagcgc ggugaaauac auacuugacc uaaaccugua     300
augcuucgug uggaauguuc ucggacgggg                                      330
```

```
<210> SEQ ID NO 33
<211> LENGTH: 318
<212> TYPE: DNA
<213> ORGANISM: Dichelobacter nodosus

<400> SEQUENCE: 33
ctcgaggtgc atgtcgagaa tgagagaatc tcgttaaata ctttcaaaac ttatagttgc      60
aaacgacgac aactacgctt tagcggctta attcccgctt tcgcttacct agatttgtct     120
gtgggtttac cgtaagcgac attaacacag aatcgctggt taacgcgtcc gctgttaatc     180
ggttaaatta agcggaatcg cttgtaaaat gcctgagcgt tggctgttta tgagttaaac     240
ctaattaact gctctaaaca tgtagtacca aaagttaagg attcgcggac gggggttcaa     300
atccccccgc ctccacca                                                   318
```

```
<210> SEQ ID NO 34
<211> LENGTH: 318
<212> TYPE: RNA
<213> ORGANISM: Dichelobacter nodosus

<400> SEQUENCE: 34
```

```
cucgaggugc augucgagaa ugagagaauc ucguuaaaua cuuucaaaac uuauaguugc    60
aaacgacgac aacuacgcuu uagcggcuua auucccgcuu ucgcuuaccu agauuugucu   120 gugguuuac cguaagcgac auuaacacag aaucgcuggu uaacgcgucc gcuguuaauc   180
gguuaaauua agcggaaucg cuuguaaaau gccugagcgu uggcuguuua ugaguuaaac   240
cuaauuaacu gcucuaaaca uguaguacca aaaguuaagg auucgcggac ggggguucaa   300
auccccccgc cuccacca                                                 318

<210> SEQ ID NO 35
<211> LENGTH: 367
<212> TYPE: DNA
<213> ORGANISM: Enterococcus faecalis

<400> SEQUENCE: 35
gggggcgtta cggattcgac aggcatagtt gagcttgaat tgcgtttcgt aggttacggc    60
tacgttaaaa cgttacagtt aaatataact gctaaaaacg aaaacaattc tttcgcttta   120
gctgcctaaa aaccagctag cgaagatcct cccggcatcg cccatgtgct cgggtcaggg   180
tcctaatcga agtgggatac gctaaatttt tccgtctgta aaatttagag gagcttacca   240
gactagcaat acagaatgcc tgtcactcgg cacgctgtaa agcgaacctt taaatgagtg   300
tctatgaacg tagagattta agtggcaata tgtttggacg cgggttcgac tcccgccgtc   360
tccacca                                                            367

<210> SEQ ID NO 36
<211> LENGTH: 367
<212> TYPE: RNA
<213> ORGANISM: Enterococcus faecalis

<400> SEQUENCE: 36
gggggcguua cggauucgac aggcauaguu gagcuugaau ugcguuucgu agguuacggc    60
uacguuaaaa cguuacaguu aaauauaacu gcuaaaaacg aaaacaauuc uuucgcuuua   120
gcugccuaaa aaccagcuag cgaagauccu cccggcaucg cccaugugcu cgggucaggg   180
uccuaaucga aguggggauac gcuaaauuuu uccgucugua aaauuuagag gagcuuacca   240
gacuagcaau acagaaugcc ugucacucgg cacgcguaa agcgaaccuu uaaaugagug   300
ucuaugaacg uagagauuua aguggcaaua uguuuggacg cggguucgac ucccgccguc   360
uccacca                                                            367

<210> SEQ ID NO 37
<211> LENGTH: 363
<212> TYPE: DNA
<213> ORGANISM: Escherichia coli

<400> SEQUENCE: 37
ggggctgatt ctggattcga cgggatttgc gaaacccaag gtgcatgccg aggggcggtt    60
ggcctcgtaa aaagccgcaa aaatagtcg caaacgacga aaactacgct ttagcagctt   120
aataacctgc ttagagccct ctctccctag cctccgctct taggacgggg atcaagagag   180
gtcaaaccca aaagagatcg cgtggaagcc ctgcctgggg ttgaagcgtt aaaacttaat   240
caggctagtt tgttagtggc gtgtccgtcc gcagctggca agcgaatgta aagactgact   300
aagcatgtag taccgaggat gtaggaattt cggacgcggg ttcaactccc gccagctcca   360
cca                                                                363
```

-continued

```
<210> SEQ ID NO 38
<211> LENGTH: 363
<212> TYPE: RNA
<213> ORGANISM: Escherichia coli

<400> SEQUENCE: 38
ggggcugauu cuggauucga cgggauuugc gaaacccaag gugcaugccg aggggcgguu      60
ggccucguaa aaagccgcaa aaauagucg caaacgacga aaacuacgcu uuagcagcuu     120
aauaaccugc uuagagcccu cucucccuag ccuccgcucu uaggacgggg aucaagagag    180
gucaaaccca aagagaucg cguggaagcc cugccugggg uugaagcguu aaaacuuaau    240
caggcuaguu uguuagugc gugucgucc gcagcuggca agcgaaugua aagacugacu     300
aagcauguag uaccgaggau guaggaauuu cggacgcggg uucaacuccc gccagcucca    360
cca                                                                  363

<210> SEQ ID NO 39
<211> LENGTH: 366
<212> TYPE: DNA
<213> ORGANISM: Haemophilus influenzae

<400> SEQUENCE: 39
ggggctgatt ctggattcga cgggattagc gaagcccaag gtgcacgtcg aggtgcggta      60
ggcctcgtaa ataaaccgca aaaaatagt cgcaaacgac gaacaatacg ctttagcagc     120
ttaataacct gcatttagcc ttcgcgctcc agcttccgct cgtaagacgg ggataacgcg    180
gagtcaaacc aaaacgagat cgtgtggaag ccaccgtttg aggatcgaag cactaaattg    240
aatcaaacta gcttaagttt agcgtgtctg tccgcatgct taagtgaaat taagacgag     300 actaaacgtg tagtactgaa ggtagagtaa tttcggacgg gggttcaact cccccagct    360 ccacca                                                               366

<210> SEQ ID NO 40
<211> LENGTH: 366
<212> TYPE: RNA
<213> ORGANISM: Haemophilus influenzae

<400> SEQUENCE: 40
ggggcugauu cuggauucga cgggauuagc gaagcccaag gugcacgucg aggugcggua      60
ggccucguaa auaaaccgca aaaaauagu cgcaaacgac gaacaauacg cuuuagcagc     120
uuaauaaccu gcauuuagcc uucgcgcucc agcuuccgcu cguaagacgg ggauaacgcg    180
gagucaaacc aaaacgagau cguguggaag ccaccguuug aggaucgaag cacuaaauug    240
aaucaaacua gcuuaaguuu agcgugucug uccgcaugcu uaagugaaau uaagacgag     300 acuaaacgug uaguacugaa gguagaguaa uuucggacgg ggguucaacu cccccagcu    360 ccacca                                                               366

<210> SEQ ID NO 41
<211> LENGTH: 340
<212> TYPE: DNA
<213> ORGANISM: Helicobacter pylori (ATC 43504)

<400> SEQUENCE: 41
agatttcttg tcgcgcagat agcatgccaa gcgctgcttg taaaacagca acaaaaataa      60
ctgtaaacaa cacagattac gctccagctt acgctaaagc tgcgtgagtt aatctccttt    120
tggagctgga ctgattagaa tttctagcgt tttaatcgct ccataacctt aagctagacg    180 ctttttaaaag gtggttcgcc ttttaaacta agaaacaaga actcttgaaa ctatcttaag    240
```

```
gttttagaaa gttggaccag agctagtttt aaggctaaaa actaaccaat tttctaagca       300
ttgtagaagt ttgtgtttag ggcaagattt ttggactggg                            340

<210> SEQ ID NO 42
<211> LENGTH: 340
<212> TYPE: RNA
<213> ORGANISM: Helicobacter pylori (ATC 43504)

<400> SEQUENCE: 42
agauuucuug ucgcgcagau agcaugccaa gcgcugcuug uaaaacagca acaaaaauaa       60
cuguaaacaa cacagauuac gcuccagcuu acgcuaaagc ugcgugaguu aaucuccuuu      120
uggagcugga cugauuagaa uuucuagcgu uuuaaucgcu ccauaaccuu aagcuagacg      180
cuuuuaaaag gugguucgcc uuuuaaacua agaaacaaga acucuugaaa cuaucuuaag      240
guuuuagaaa guuggaccag agcuaguuuu aaggcuaaaa acuaaccaau uuucuaagca      300
uuguagaagu uuguguuuag ggcaagauuu uuggacuggg                            340

<210> SEQ ID NO 43
<211> LENGTH: 386
<212> TYPE: DNA
<213> ORGANISM: Helicobacter pylori (strain 26695)

<400> SEQUENCE: 43
ggggctgact tggatttcga cagatttctt gtcgcacaga tagcatgcca agcgctgctt       60
gtaaaacagc aacaaaaata actgtaaaca acacagatta cgctccagct tacgctaaag      120
ctgcgtgagt taatctcctt ttggagctgg actgattaga atttctagcg ttttaatcgc      180
tccataacct taagctagac gcttttaaaa ggtggttcgc cttttaaact aagaaacaag      240
aactcttgaa actatctcaa ggttttagaa agttggacca gagctagttt taaggctaaa      300
aaaccaacca attttctaag cattgtagaa gtttgtgttt agggcaagat ttttggactg      360
gggttcgatt ccccacagct ccacca                                           386

<210> SEQ ID NO 44
<211> LENGTH: 386
<212> TYPE: RNA
<213> ORGANISM: Helicobacter pylori (strain 26695)

<400> SEQUENCE: 44
ggggcugacu uggauuucga cagauuucuu gucgcacaga uagcaugcca agcgcugcuu       60
guaaaacagc aacaaaaaua acuguaaaca acacagauua cgcuccagcu uacgcuaaag      120
cugcgugagu uaaucuccuu uuggagcugg acugauuaga auuucuagcg uuuuaaucgc      180
uccauaaccu uaagcuagac gcuuuuaaaa ggugguucgc cuuuuaaacu aagaaacaag      240
aacucuugaa acuaucucaa gguuuuagaa aguuggacca gagcuaguuu uaaggcuaaa      300
aaaccaacca auuuucuaag cauuguagaa guuuguguuu agggcaagau uuuuggacug      360
ggguucgauu ccccacagcu ccacca                                           386

<210> SEQ ID NO 45
<211> LENGTH: 312
<212> TYPE: DNA
<213> ORGANISM: Klebsiella aerogenes (NCTC 9528)

<400> SEQUENCE: 45
gggattcgcg aaacccaagg tgcatgccga ggggcggttg gcctcgtaaa aagccgcaaa       60
aaaatagtcg caaacgacga aaactacgct ttagcagctt aataacctgc taagagccct      120
```

-continued

| ctctccctag cttccgctcc taagacgggg aataaagaga ggtcaaaccc aaaagagatc | 180 |
| gcgtggaagc cctgcctggg gttgaagcgt taaaactaat caggctagtt tgtcagtggc | 240 |
| gtgtccgtcc gcagctggcc agcgaatgta aagactggac taagcatgta gtgccgagga | 300 |
| tgtaggaatt tc | 312 |

<210> SEQ ID NO 46
<211> LENGTH: 312
<212> TYPE: RNA
<213> ORGANISM: Klebsiella aerogenes (NCTC 9528)

<400> SEQUENCE: 46

| gggauucgcg aaacccaagg ugcaugccga ggggcgguug gccucguaaa aagccgcaaa | 60 |
| aaaauagucg caaacgacga aaacuacgcu uuagcagcuu aauaaccugc uaagagcccu | 120 |
| cucucccuag cuuccgcucc uaagacgggg aauaaagaga ggucaaaccc aaaagagauc | 180 |
| gcguggaagc ccugccuggg guugaagcgu uaaaacuaau caggcuaguu ugucaguggc | 240 |
| guguccgucc gcagcuggcc agcgaaugua aagacuggac uaagcaugua gugccgagga | 300 |
| uguaggaauu uc | 312 |

<210> SEQ ID NO 47
<211> LENGTH: 316
<212> TYPE: DNA
<213> ORGANISM: Lactobacillus lactis (NCTC 662)

<400> SEQUENCE: 47

| aagcacagtt cgagcttgaa ttgcgtttcg taggttacgt ctacgttaaa acgttacagt | 60 |
| taaatataac tgctaaaaac gaaacaact cttacgcttt agctgcctaa aaacagttag | 120 |
| cgtagatcct ctcggcatcg cccatgtgct cgagtaaggg tctcaaattt agtgggatac | 180 |
| gttaaacttt tccgtctgta agtttaaaa gagatcatca gactagcgat acagaatgcc | 240 |
| tgtcactcgg caagctgtaa agcgaaacct caaatgagtt gactatgaac gtagattttt | 300 |
| aagtgtcgat gtgttt | 316 |

<210> SEQ ID NO 48
<211> LENGTH: 316
<212> TYPE: RNA
<213> ORGANISM: Lactobacillus lactis (NCTC 662)

<400> SEQUENCE: 48

| aagcacaguu cgagcuugaa uugcguuucg uagguuacgu cuacguuaaa acguuacagu | 60 |
| uaaauauaac ugcuaaaaac gaaacaacu cuuacgcuuu agcugccuaa aaacaguuag | 120 |
| cguagauccu cucggcaucg cccaugugcu cgaguaaggg ucucaaauuu aguggggauac | 180 |
| guuaaacuuu uccgucugua aguuuaaaa gagaucauca gacuagcgau acagaaugcc | 240 |
| ugucacucgg caagcuguaa agcgaaaccu caaaugaguu gacuaugaac guagauuuuu | 300 |
| aagugucgau guguuu | 316 |

<210> SEQ ID NO 49
<211> LENGTH: 362
<212> TYPE: DNA
<213> ORGANISM: Legionella pneumophila

<400> SEQUENCE: 49

| gtgggttgca aaaccggaag tgcatgccga gaaggagatc tctcgtaaat aagactcaat | 60 |
| taaatataaa tgcaaacgat gaaaactttg ctggtgggga agctatcgct gcctaataag | 120 | cactttagtt aaaccatcac tgtgtactgg ccaataaacc cagtatcccg ttcgaccgag 180 cccgcttatc ggtatcgaat caacggtcat aagagataag ctagcgtcct aatctatccc 240 gggttatggc gcgaaactca gggaatcgct gtgtatcatc ctgcccgtcg gaggagccac 300 agttaaattc aaaagacaag gctatgcatg tagagctaaa ggcagaggac ttgcggacgc 360 gg 362

<210> SEQ ID NO 50
<211> LENGTH: 362
<212> TYPE: RNA
<213> ORGANISM: Legionella pneumophila

<400> SEQUENCE: 50 gugggguugca aaaccggaag ugcaugccga gaaggagauc ucucguaaau aagacucaau 60
uaaauauaaa ugcaaacgau gaaaacuuug cugguggga agcuaucgcu gccuaauaag 120
cacuuuaguu aaaccaucac uguguacugg ccaauaaacc caguaucccg uucgaccgag 180
cccgcuuauc gguaucgaau caacggucau aagagauaag cuagcguccu aaucuauccc 240
ggguuauggc gcgaaacuca gggaaucgcu guguaucauc cugcccgucg gaggagccac 300
aguuaaauuc aaaagacaag gcuaugcaug uagagcuaaa ggcagaggac uugcggacgc 360
gg 362

<210> SEQ ID NO 51
<211> LENGTH: 322
<212> TYPE: DNA
<213> ORGANISM: Listeria grayi

<400> SEQUENCE: 51
acagggatag gtcgagcttg agttgcgagc cggggggatc ggcccgtcat caacgtcaaa 60
gccaataata actggcaaac aaaacaacaa tttagctttc gctgcctaat agcagtctga 120
atagctgatc ctccgtgcat cacccatgtg ctacggtaag ggtctcactt ttaagtgggt 180
tacgctggct tatctccgtc tggggcaaac gagaagagca taatcagact agctagatag 240
agccctgacg ccgggcagac atctatgcga aatccaaata cggcaactac gctcgtagat 300
gctcaagtgc cgatatttct gg 322

<210> SEQ ID NO 52
<211> LENGTH: 322
<212> TYPE: RNA
<213> ORGANISM: Listeria grayi

<400> SEQUENCE: 52
acagggauag gucgagcuug aguugcgagc cggggggauc ggcccgucau caacgucaaa 60
gccaauaaua acuggcaaac aaaacaacaa uuuagcuuuc gcugccuaau agcagucuga 120
auagcugauc cuccgugcau cacccaugug cuacgguaag ggucucacuu uuaagugggu 180
uacgcuggcu uaucuccguc uggggcaaac gagaagagca uaaucagacu agcuagauag 240
agcccugacg ccgggcagac aucuaugcga aauccaaaua cggcaacuac gcucguagau 300
gcucaagugc cgauauuucu gg 322

<210> SEQ ID NO 53
<211> LENGTH: 322
<212> TYPE: DNA
<213> ORGANISM: Listeria innocua

<400> SEQUENCE: 53

```
acagggatag ttcgagcttg agttgcgagt cgggggatc gtcctcgtta tcaacgtcaa      60
agccaataat aactggcaaa gaaaacaaa acctagcttt cgctgcctaa taagcagtag     120
catagctgat cctccgtgca tcgcccatgt gctacggtaa gggtctcact ctaagtgggc    180
tacactagtt aatctccgtc tgaggttaaa tagaagagct taatcagact agctgaatgg   240
aagcctgtta ccgggctgat gtttatgcga aatgctaata cggtgactac gctcgtagat   300
attcaagtgc cgatatttct gg                                            322

<210> SEQ ID NO 54
<211> LENGTH: 322
<212> TYPE: RNA
<213> ORGANISM: Listeria innocua

<400> SEQUENCE: 54
acagggauag uucgagcuug aguugcgagu cgggggauc guccucguua ucaacgucaa      60
agccauuaau aacuggcaaa gaaaacaaa accuagcuuu cgcugccuaa uaagcaguag     120
cauagcugau ccuccgugca ucgcccaugu gcuacgguaa ggucucacu cuaagugggc    180 uacacuaguu aaucuccguc ugagguuaaa uagaagagcu uaaucagacu agcugaaugg   240
aagccuguua ccgggcugau guuuaugcga aaugcuaaua cggugacuac gcucguagau   300
auucaagugc cgauauuucu gg                                            322

<210> SEQ ID NO 55
<211> LENGTH: 322
<212> TYPE: DNA
<213> ORGANISM: Listeria monocytogenes (NCTC 7973)

<400> SEQUENCE: 55
acagggatag ttcgagcttg agttgcgagt cgggggatc gtcctcgtta tcaacgtcaa      60
agccaataat aactggcaaa gaaaacaaa acctagcttt cgctgcctaa taagcagtag     120
catagctgat cctccgtgca tcgcccatgt gctacggtaa gggtctcact ctaagtgggc    180
tacactagtt aatctccgtc tggggttaaa tagaagagct taatcagact agctgaatgg   240
aagcctgtta ccgggccgat gtttatgcga aatgctaata cggtgactac gctcgtagat   300
atttaagtgc cgatatttct gg                                            322

<210> SEQ ID NO 56
<211> LENGTH: 322
<212> TYPE: RNA
<213> ORGANISM: Listeria monocytogenes (NCTC 7973)

<400> SEQUENCE: 56
acagggauag uucgagcuug aguugcgagu cgggggauc guccucguua ucaacgucaa      60
agccauuaau aacuggcaaa gaaaacaaa accuagcuuu cgcugccuaa uaagcaguag     120
cauagcugau ccuccgugca ucgcccaugu gcuacgguaa gggucucacu cuaagugggc    180
uacacuaguu aaucuccguc uggguuaaa uagaagagcu uaaucagacu agcugaaugg    240
aagccuguua ccgggccgau guuuaugcga aaugcuaaua cggugacuac gcucguagau   300
auuuaagugc cgauauuucu gg                                            322

<210> SEQ ID NO 57
<211> LENGTH: 247
<212> TYPE: DNA
<213> ORGANISM: Listeria monocytogenes (NCTC 11994)

<400> SEQUENCE: 57
```

```
caaagccaat aataactggc aaagaaaaac aaaacctagc tttcgctgcc taataagcag        60
tagcatagct gatcctccgt gcatcgccca tgtgctacgg taagggtctc actctaagtg       120
ggctacacta gttaatctcc gtctggggtt aaatagaaga gcttaatcag actagctgaa       180
tggaagcctg ttaccgggcc gatgtttatg cgaaatgcta atacggtgac tacgctcgta       240
gatattt                                                                 247

<210> SEQ ID NO 58
<211> LENGTH: 247
<212> TYPE: RNA
<213> ORGANISM: Listeria monocytogenes (NCTC 11994)

<400> SEQUENCE: 58
caaagccaau aauaacuggc aaagaaaaac aaaaccuagc uuucgcugcc uaauaagcag        60
uagcauagcu gauccuccgu gcaucgccca ugugcuacgg uaagggucuc acucuaagug       120
ggcuacacua guuaaucucc gucuggdguu aaauagaaga gcuuaaucag acuagcugaa       180
uggaagccug uuaccgggcc gauguuuaug cgaaaugcua auacggugac uacgcucgua       240
gauauuu                                                                 247

<210> SEQ ID NO 59
<211> LENGTH: 322
<212> TYPE: DNA
<213> ORGANISM: Listeria murrayi

<400> SEQUENCE: 59
acagggatag ttcgagcttg agttgcgagt cgggggatc gtcctcgtta tcaacgtcaa         60
agccaataat aactggcaaa gaaaacaaa acctagcttt cgctgcctaa taagcagtag        120
catagctgat cctccgtgca tcgcccatgt gctacggtaa gggtctcact ctaagtgggc       180
tacactagtt aatctccgtc tgaggttaaa tagaagagct taatgagact agctgaatgg       240
aagcctgtta ccgggctgat gtttatgcga aatgctaata cggtgactac gctcgtagat       300
attcaagtgc cgatatttct gg                                                322

<210> SEQ ID NO 60
<211> LENGTH: 322
<212> TYPE: RNA
<213> ORGANISM: Listeria murrayi

<400> SEQUENCE: 60
acagggauag uucgagcuug aguugcgagu cgggggauc guccucguua ucaacgucaa         60
agccaauaau aacuggcaaa gaaaacaaa accuagcuuu cgcugccuaa uaagcaguag        120
cauagcugau ccuccgugca ucgcccaugu gcuacgguaa ggguacucu cuaagugggc       180 uacacuaguu aaucuccguc ugagguuaaa uagaagagcu uaaugagacu agcugaaugg       240
aagccuguua ccgggcugau guuuaugcga aaugcuaaua cggugacuac gcucguagau       300
auucaagugc cgauauuucu gg                                                322

<210> SEQ ID NO 61
<211> LENGTH: 322
<212> TYPE: DNA
<213> ORGANISM: Listeria welshimeri

<400> SEQUENCE: 61
acagggatag ttcgagcttg agttgcgagt cgggggatc gtcctcgtta tcaacgtcaa         60
agccaataat aactggcaaa gaaaacaaa acctagcttt cgctgcctaa taagcagtag        120
```

```
catagctgat cctccgtgca tcgcccatgt gctacggtaa gggtctcact ctaagtgggc    180
tacactggct aatctccgtc tgaggttagt tggaagagct taatcagact agctgaatgg    240
aagcctgtta ccgggccgat gtttatgcga aatgctaata cggtgactac gctcgtagat    300
atttaagtgc cgatatttct gg                                             322

<210> SEQ ID NO 62
<211> LENGTH: 322
<212> TYPE: RNA
<213> ORGANISM: Listeria welshimeri

<400> SEQUENCE: 62
acagggauag uucgagcuug aguugcgagu cgggggggauc guccucguua ucaacgucaa    60
agccaauaau aacuggcaaa gaaaaacaaa accuagcuuu cgcugccuaa uaagcaguag    120
cauagcugau ccuccgugca ucgcccaugu gcuacgguaa gggucucacu cuaagugggc    180
uacacuggcu aaucuccguc ugagguuagu uggaagagcu uaaucagacu agcugaaugg    240
aagccuguua ccgggccgau guuuaugcga aaugcuaaua cggugacuac gcucguagau    300
auuuaagugc cgauauuucu gg                                             322

<210> SEQ ID NO 63
<211> LENGTH: 322
<212> TYPE: DNA
<213> ORGANISM: Marinobacter hydrocarbonoclasticus

<400> SEQUENCE: 63
gccggtgacg aacccttggg tgcatgccga gatggcagcg aatctcgtaa atccaaagct    60
gcaacgtaat agtcgcaaac gacgaaaact acgcactggc ggcgtaagcc gttccagtcg    120
tcctggctga ggcgcctata actcagtagc aacatcccag gacgtcatcg cttataggct    180
gctccgttca ccagagctca ctggtgttcg gctaagatta aagagctcgc tcttgcacc    240 ctgaccttcg ggtcgcttga ggttaaatca atagaaggac actaagcatg tagacctcaa    300
ggcctagtgc tggcggacgc gg                                             322

<210> SEQ ID NO 64
<211> LENGTH: 322
<212> TYPE: RNA
<213> ORGANISM: Marinobacter hydrocarbonoclasticus

<400> SEQUENCE: 64
gccggugacg aacccuuggg ugcaugccga gauggcagcg aaucucguaa auccaaagcu    60
gcaacguaau agucgcaaac gacgaaaacu acgcacuggc ggcguaagcc guuccagucg    120
uccuggcuga ggcgccuaua acucaguagc aacaucccag gacgucaucg cuuauaggcu    180
gcuccguuca ccagagcuca cugguguucg gcuaagauua aagagcucgc ucuugcacc    240 cugaccuucg ggucgcuuga gguuaaauca auagaaggac acuaagcaug uagaccucaa    300
ggccuagugc uggcggacgc gg                                             322

<210> SEQ ID NO 65
<211> LENGTH: 338
<212> TYPE: DNA
<213> ORGANISM: Mycobacterium avium

<400> SEQUENCE: 65
ttcgcgcatc gaatcaaggg aagcgtgccg gtgcaggcaa ctgaccaccg taagcgtcgt    60
tgcaaataga taagcgccga ttcacatcag cgcgacttac ctctcgctgc ctaagcgaca    120
```

```
gctagtccgt cagcccggga acgccctcga cccggagcct ggcgtcagct agagggatcc      180
accgatgagt tcggtcgcgg gactcatcgg acaccaaca gcgactggga tcgtcatcct       240
ggcttgttcg cgtgaccagg agatccgagt agaggcatag cgaactgcgc acggagaagc     300
cttgagggaa tgccgtagaa cccgggttcg attcccaa                              338
```

<210> SEQ ID NO 66
<211> LENGTH: 338
<212> TYPE: RNA
<213> ORGANISM: Mycobacterium avium

<400> SEQUENCE: 66

```
uucgcgcauc gaaucaaggg aagcgugccg gugcaggcaa cugaccaccg uaagcgucgu      60
ugcaaauaga uaagcgccga uucacaucag cgcgacuuac cucucgcugc cuaagcgaca     120
gcuagcccgu cagcccggga acgcccucga cccggagccu ggcgucagcu agagggauccu   180 accgaugagu ucggucgcgg gacucaucgg acaccaaca gcgacuggga ucgucauccu       240
ggcuuguucg cgugaccagg agauccgagu agaggcauag cgaacugcgc acggagaagc    300
cuugagggaa ugccguagaa cccggguucg auucccaa                              338
```

<210> SEQ ID NO 67
<211> LENGTH: 318
<212> TYPE: DNA
<213> ORGANISM: Mycobacterium bovis

<400> SEQUENCE: 67

```
ttcgcgcatc gaatcaaggg aagcgtgccg gtgcaggcaa gagaccaccg taagcgtcgt      60
tgcgaccaaa taagcgccga ttcacatcag cgcgactacg tctcgctgcc taagcgacgg    120
ctagtctgtc agaccgggaa cgccctcggc ccggaccctg gcatcagcta gagggatcca    180
ccgatgagtc cggtcgcggg actcctcggg acaaccacag cgactgggat cgtcatctcg    240
gctagttcgc gtgaccggga gatccgagca gaggcatagc gaactgcgca cggagaagcc   300
ttgagggaat gccgtagg                                                   318
```

<210> SEQ ID NO 68
<211> LENGTH: 318
<212> TYPE: RNA
<213> ORGANISM: Mycobacterium bovis

<400> SEQUENCE: 68

```
uucgcgcauc gaaucaaggg aagcgugccg gugcaggcaa gagaccaccg uaagcgucgu      60
ugcgaccaaa uaagcgccga uucacaucag cgcgacuacg ucucgcugcc uaagcgacgg    120
cuagucuguc agaccgggaa cgcccucggc ccggacccug gcaucagcua gagggauccu    180
ccgaugaguc ggucgcggg acuccucggg acaaccacag cgacugggau cgucaucucg     240
gcuaguucgc gugaccggga gauccgagca gaggcauagc gaacugcgca cggagaagcc    300
uugagggaau gccguagg                                                   318
```

<210> SEQ ID NO 69
<211> LENGTH: 369
<212> TYPE: DNA
<213> ORGANISM: Mycobacterium leprae

<400> SEQUENCE: 69

```
ggggctgaaa ggtttcgact tcgcgcatcg aatcaaggga agcgtgccgg tgcaggcaag     60
agaccaccgt aagcgtcgtt gcagcaatat aagcgccgat tcatatcagc gcgactatgc   120
```

-continued

```
tctcgctgcc taagcgatgg ctagtctgtc agaccgggaa cgccctcgtc ccggagcctg    180
gcatcagcta gagggatcta ccgatgggtt cggtcgcggg actcgtcggg acaccaaccg    240
cgactgggat cgtcatcctg gctagttcgc gtgatcagga gatccgagta gaggcatagc    300
gaactacgca cggagaagcc ttgagggaaa tgccgtagga cccgggttcg attcccggca    360
gctccacca                                                           369
```

<210> SEQ ID NO 70
<211> LENGTH: 369
<212> TYPE: RNA
<213> ORGANISM: Mycobacterium leprae

<400> SEQUENCE: 70

```
ggggcugaaa gguuucgacu ucgcgcaucg aaucaaggga agcgugccgg ugcaggcaag     60
agaccaccgu aagcgucguu gcagcaauau aagcgccgau ucauaucagc gcgacuaugc    120
ucucgcugcc uaagcgaugg cuagucuguc agaccgggaa cgcccucguc ccggagccug    180
gcaucagcua gagggaucua ccgauggguu cggucgcggg acucgucggg acaccaaccg    240
cgacugggau cgucauccug gcuaguucgc gugaucagga gauccgagua gaggcauagc    300
gaacuacgca cggagaagcc uugagggaaa ugccguagga cccggguucg auucccggca    360
gcuccacca                                                           369
```

<210> SEQ ID NO 71
<211> LENGTH: 338
<212> TYPE: DNA
<213> ORGANISM: Mycobacterium paratuberculosis

<400> SEQUENCE: 71

```
ttcgcgcatc gaatcaaggg aagcgtgccg gtgcaggcaa ctgaccaccg taagcgtcgt     60
tgcaaataga taagcgccga ttcacatcag cgcgacttac ctctcgctgc ctaagcgaca    120
gctagtccgt cagcccggga acgccctcga cccggagcct ggcgtcagct agagggatcc    180
accgatgagt tcggtcgcgg gactcatcgg gacaccaaca cgactgggat cgtcatcct    240 ggcttgttcg cgtgaccagg agatccgagt agaggcatag cgaactgcgc acggagaagc    300
cttgagggaa tgccgtagaa cccgggttcg attcccaa                           338
```

<210> SEQ ID NO 72
<211> LENGTH: 338
<212> TYPE: RNA
<213> ORGANISM: Mycobacterium paratuberculosis

<400> SEQUENCE: 72

```
uucgcgcauc gaaucaaggg aagcgugccg gugcaggcaa cugaccaccg uaagcgucgu     60
ugcaaauaga uaagcgccga uucacaucag cgcgacuuac cucucgcugc cuaagcgaca    120
gcuaguccgu cagcccggga acgcccucga cccggagccu ggcgucagcu agagggaucc    180
accgaugagu ucggucgcgg gacucaucgg gacaccaaca cgacugggau cgucauccu    240 ggcuuguucg cgugaccagg agauccgagu agaggcauag cgaacugcgc acggagaagc    300
cuugagggaa ugccguagaa cccggguucg auucccaa                           338
```

<210> SEQ ID NO 73
<211> LENGTH: 368
<212> TYPE: DNA
<213> ORGANISM: Mycobacterium tuberculosis

<400> SEQUENCE: 73

```
ggggctgaac ggtttcgact tcgcgcatcg aatcaaggga agcgtgccgg tgcaggcaag     60
agaccaccgt aagcgtcgtt gcgaccaaat aagcgccgat tcacatcagc gcgactacgc    120
tctcgctgcc taagcgacgg ctagtctgtc agaccgggaa cgccctcggc ccggaccctg    180
gcatcagcta gagggatcca ccgatgagtc cggtcgcggg actcctcggg acaaccacag    240
cgactgggat cgtcatctcg gctagttcgc gtgaccggga gatccgagca gaggcatagc    300
gaactgcgca cggagaagcc ttgagggaat gccgtaggac ccgggttcga ttcccggcag    360
ctccacca                                                             368
```

<210> SEQ ID NO 74
<211> LENGTH: 368
<212> TYPE: RNA
<213> ORGANISM: Mycobacterium tuberculosis

<400> SEQUENCE: 74

```
ggggcugaac gguuucgacu ucgcgcaucg aaucaaggga agcgugccgg ugcaggcaag     60
agaccaccgu aagcgucguu gcgaccaaau aagcgccgau ucacaucagc gcgacuacgc    120
ucucgcugcc uaagcgacgg cuagucuguc agaccgggaa cgcccucggc ccggacccug    180
gcaucagcua gagggaucca ccgaugaguc cggucgcggg acuccucggg acaaccacag    240
cgacugggau cgucaucucg gcuaguucgc gugaccggga gauccgagca gaggcauagc    300
gaacugcgca cggagaagcc uugagggaau gccguaggac ccggguucga uucccggcag    360
cuccacca                                                             368
```

<210> SEQ ID NO 75
<211> LENGTH: 411
<212> TYPE: DNA
<213> ORGANISM: Mycoplasma capricolum

<400> SEQUENCE: 75

```
ggggatgtca tggatttgac aggatatctt tagtacatat aagcagtagt gttgtagact     60
ataaatacta ctaggtttaa aaaaacgcaa ataaaaacga agaaactttt gaaatgccag    120
catttatgat gaataatgca tcagctggag caaactttat gtttgcttaa taactactag    180
tttagttata gtatttcacg aattatagat attttaagct ttatttataa ccgtattacc    240
caagcttaat agaatatatg attgcaataa atatatttga aatctaattg caaatgatat    300
ttaaccttta gttaatttta gttaaatatt ttaattagaa aattaactaa actgtagaaa    360
gtatgtatta atatatcttg gacgcgagtt cgattctcgc catctccacc a             411
```

<210> SEQ ID NO 76
<211> LENGTH: 411
<212> TYPE: RNA
<213> ORGANISM: Mycoplasma capricolum

<400> SEQUENCE: 76

```
ggggauguca uggauuugac aggauaucuu uaguacauau aagcaguagu guuguagacu     60
auaaauacua cuagguuuaa aaaaacgcaa auaaaaacga agaaacuuuu gaaaugccag    120
cauuuaugau gaauaaugca ucagcuggag caaacuuuau guuugcuuaa uaacuacuag    180
uuuaguuaua guauuucacg aauuauagau auuuuaagcu uuauuuauaa ccguauuacc    240
caagcuuaau agaauauaug auugcaauaa auauauuuga aaucuaauug caaaugauau    300
uuaaccuuua guuaauuuua guuaaauauu uuaauuagaa aauuaacuaa acuguagaaa    360
guauguauua auauaucuug gacgcgaguu cgauucucgc caucuccacc a             411
```

<210> SEQ ID NO 77
<211> LENGTH: 388
<212> TYPE: DNA
<213> ORGANISM: Mycoplasma genitalium (ATTC 33530, #1)

<400> SEQUENCE: 77

```
ggggatgttt tgggtttgac ataatgctga tagacaaaca gtagcattgg ggtatgcccc      60
ttacagcgct aggttcaata accgacaaag aaaataacga agtgttggta gaaccaaatt    120
tgatcattaa ccaacaagca agtgttaact ttgcttttgc ataagtagat actaaagcta    180
cagctggtga atagtcatag tttgctagct gtcatagttt atgactcgag gttaaatcgt    240
tcaatttaac ctttaaaaat agaacttgtt gtttccatga ttgttttgtg atcaattgga    300
aacaagacaa aaatccacaa aactaaaatg tagaagctgt ttgttgtgtc ctttatggaa    360
acgggttcga ttcccgtcat ctccacca                                       388
```

<210> SEQ ID NO 78
<211> LENGTH: 388
<212> TYPE: RNA
<213> ORGANISM: Mycoplasma genitalium (ATTC 33530, #1)

<400> SEQUENCE: 78

```
ggggauguuu uggguuugac auaaugcuga uagacaaaca guagcauugg gguaugcccc      60
uuacagcgcu agguucaaua accgacaaag aaaauaacga aguguuggua gaaccaaauu    120
ugaucauuaa ccaacaagca aguguuaacu uugcuuuugc auaaguagau acuaaagcua    180
cagcugguga auagucauag uuugcuagcu gucauaguuu augacucgag guuaaaucgu    240
ucaauuuaac cuuuaaaaau agaacuuguu guuccauga uuguuuugug aucaauugga    300
aacaagacaa aaauccacaa aacuaaaaug uagaagcugu uuguugugu cuuuauggaa    360
acgguucga uucccgucau cuccacca                                         388
```

<210> SEQ ID NO 79
<211> LENGTH: 243
<212> TYPE: RNA
<213> ORGANISM: Mycoplasma genitalium (ATTC 33530, #2)

<400> SEQUENCE: 79

```
acaaagcgaa gacaaacaga gcaggggagc cccacagcgc aggcaaaacc gacaaagaaa      60
aaacgaaggg gagaccaaag acaaccaac aagcaaggaa cgcgcaaaga gaacaaagca    120
cagcgggaaa gcaaggcagc gcaagagacc gaggaaacgc aaaaccaaaa aagaacggcc    180
agagggacaa ggaaacaaga caaaaaccac aaaacaaaag agaagcgggg ccaggaaacg    240
ggc                                                                   243
```

<210> SEQ ID NO 80
<211> LENGTH: 350
<212> TYPE: RNA
<213> ORGANISM: Mycoplasma genitalium (ATTC 33530, #2)

<400> SEQUENCE: 80

```
acauaaugcu gauagacaaa caguagcauu gggguaugcc ccuuacagcg cuagguucaa      60
uaaccgacaa agaaaauaac gaaguguugg uagauccaaa uuugaucauu aaccaacaag    120
caaguguuaa cuuugcuuuu gcauaaguag auacuaaagc uacagcuggu gaauagucau    180
aguuugcuag cugucauagu uuaugacucg agguuaaauc gucaauuua accuuuaaaa    240
auagaacuug uuguuuccau gauuguuuug ugaucaauug gaaacaagac aaaaauccac    300
```
aaaacuaaaa uguagaagcu guuuguugug uccuuuaugg aaacggguuc 350

<210> SEQ ID NO 81
<211> LENGTH: 387
<212> TYPE: DNA
<213> ORGANISM: Mycoplasma pneumophila

<400> SEQUENCE: 81
ggggatgtag aggttttgac ataatgttga aaggaaaaca gttgcagtgg ggtatgcccc 60
ttacagctct aggtataata accgacaaaa ataacgacga agttttggta gatccaatgt 120
tgatcgctaa ccaacaagca agtatcaact acgctttcgc ttagaacata ctaaagctac 180
acgaattgaa tcgccatagt ttggttcgtg tcacagttta tggctcgggg ttaactggtt 240
caacttaatc cttaaattat gaacttatcg tttacttgtt tgtcttatga tctaaagtaa 300
gcgagacatt aaaacataag actaaactgt agaagctgtt ttaccaatcc tttatggaaa 360
cgggttcgat tcccgtcatc tccacca 387

<210> SEQ ID NO 82
<211> LENGTH: 387
<212> TYPE: RNA
<213> ORGANISM: Mycoplasma pneumophila

<400> SEQUENCE: 82
ggggauguag agguuuugac auaauguuga aaggaaaaca guugcagugg gguaugcccc 60
uuacagcucu agguauaaua accgacaaaa auaacgacga aguuuuggua gauccaaugu 120
ugaucgcuaa ccaacaagca aguaucaacu acgcuuucgc uuagaacaua cuaaagcuac 180
acgaauugaa ucgccauagu uugguucgug ucacaguuua uggcucgggg uuaacugguu 240
caacuuaauc cuuaaauuau gaacuuaucg uuuacuuguu ugucuuauga ucuaaaguaa 300
gcgagacauu aaaacauaag acuaaacugu agaagcuguu uuaccaaucc uuuauggaaa 360
cggguucgau ucccgucauc uccacca 387

<210> SEQ ID NO 83
<211> LENGTH: 318
<212> TYPE: DNA
<213> ORGANISM: Neisseria gonorrhoeae (ATCC 19424)

<400> SEQUENCE: 83
gggggttgcg aagcagatgc gggcataccg ggtctcaga ttcccgtaaa acactgaatt 60
caaatagtcg caaacgacga aacttacgct ttagccgctt aaggctagcc gttgcagcag 120
tcggtcaatg ggctgtgtgg cgaaagccac cgcaacgtca tcttacattg actggtttcc 180
agccgggtta cttggcagga aataagactt aaggtaactg gtttccaaaa ggcctgttgg 240
tcggcatgat ggaaataaga ttttcaaata gacacaacta agtatgtaga acgctttgta 300
gaggactttc ggacgggg 318

<210> SEQ ID NO 84
<211> LENGTH: 318
<212> TYPE: RNA
<213> ORGANISM: Neisseria gonorrhoeae (ATCC 19424)

<400> SEQUENCE: 84 gggggguugcg aagcagaugc gggcauaccg ggucucaga uucccguaaa acacugaauu 60
caaauagucg caaacgacga aacuuacgcu uuagccgcuu aaggcuagcc guugcagcag 120
ucggucaaug ggcugugugg cgaaagccac cgcaacguca ucuuacauug acugguuucc 180

```
agccggguua cuuggcagga aauaagacuu aagguaacug guuuccaaaa ggccuguugg    240
ucggcaugau ggaaauaaga uuuucaaaua gacacaacua aguauguaga acgcuuugua    300
gaggacuuuc ggacgggg                                                  318
```

<210> SEQ ID NO 85
<211> LENGTH: 363
<212> TYPE: DNA
<213> ORGANISM: Neisseria gonorrhoeae (FA 1090)

<400> SEQUENCE: 85

```
gggggcgacc ttggtttcga cggggttgc gaagcagatg cggcatacc ggggtctcag     60 attcccgtaa aacactgaat tcaaatagtc gcaaacgacg aaacttacgc tttagccgct   120
taaggctagc cgttgcagca gtcggtcaat gggctgtgtg gtgaaagcca ccgcaacgtc   180
atcttacatt gactggtttc cagccgggtt acttggcagg aaataagact taaggtaact   240
ggtttccaaa aggcctgttg gtcggcatga tggaaataag attttcaaat agacacaact   300
aagtatgtag aacgctttgt agaggacttt cggacggggg ttcgattccc cccgcctcca   360
cca                                                                 363
```

<210> SEQ ID NO 86
<211> LENGTH: 363
<212> TYPE: RNA
<213> ORGANISM: Neisseria gonorrhoeae (FA 1090)

<400> SEQUENCE: 86

```
gggggcgacc uugguuucga cggggguugc gaagcagaug cggcauacc ggggucucag    60 auucccguaa aacacugaau ucaaauaguc gcaaacgacg aaacuuacgc uuuagccgcu   120
uaaggcuagc cguugcagca gucggucaau gggcugugug gugaaagcca ccgcaacguc   180
aucuuacauu gacugguuuc cagccggguu acuggcagg aaauaagacu uaagguaacu    240
gguuuccaaa aggccuguug gucggcauga uggaaauaag auuuucaaau agacacaacu   300
aaguauguag aacgcuuugu agaggacuuu cggacggggg uucgauuccc cccgccucca   360
cca                                                                 363
```

<210> SEQ ID NO 87
<211> LENGTH: 363
<212> TYPE: DNA
<213> ORGANISM: Neisseria meningitidis

<400> SEQUENCE: 87

```
gggggcgacc ttggtttcga cggggttgc gaagcagatg cggcatacc ggggtctcag     60 attcccgtaa aacactgaat tcaaatagtc gcaaacgacg aaacttacgc tttagccgct   120
taaggctagc cgttgcagca gtcggtcaat gggctgtgtg gcgaaagcca ccgcaacgtc   180
atcttacatt gactggtttc ctgccgggtt atttggcagg aaatgagatt taaggtaact   240
ggtttccaaa aggcctgttg gtcggcatga tggaaataag attttcaaat agacacaact   300
aagtatgtag aacgctttgt agaggacttt cggacggggg ttcgattccc cccgcctcca   360
cca                                                                 363
```

<210> SEQ ID NO 88
<211> LENGTH: 363
<212> TYPE: RNA
<213> ORGANISM: Neisseria meningitidis

<400> SEQUENCE: 88

-continued

```
gggggcgacc uugguuucga cggggguugc gaagcagaug cgggcauacc ggggucucag      60
auucccguaa aacacugaau ucaaauaguc gcaaacgacg aaacuuacgc uuuagccgcu     120
uaaggcuagc cguugcagca gucggucaau gggcugugug gcgaaagcca ccgcaacguc     180
aucuuacauu gacugguuuc cugccggguu auuuggcagg aaaugagauu uaagguaacu     240
gguuuccaaa aggccuguug gucggcauga uggaaauaag auuuucaaau agacacaacu     300
aaguauguag aacgcuuugu agaggacuuu cggacggggg uucgauuccc cccgccucca     360
cca                                                                   363
```

<210> SEQ ID NO 89
<211> LENGTH: 385
<212> TYPE: DNA
<213> ORGANISM: Nostoc muscorum PCC7120

<400> SEQUENCE: 89

```
gggtccgtcg gtttcgacag gttggcgaac gctactctgt gattcaggtc gagagtgagt      60
ctcctctgca aatcaaggct caaaacaaaa gtaaatgcga ataacatcgt taaatttgct     120
cgtaaggacg ctctagtagc tgcctaaata gcctcttca ggttcgagcg tcttcggttt      180
gactccgtta aggactgaag accaaccccc aacggatgct ctagcaatgt tctctggttg     240
gcttgctagc taagatttaa tcagagcatc ctacgttcgg gataatgaac gattcccgcc     300
ttgagggtca gaaaggctaa acctgtgaat gagcgggggg tcaatacca atttggacag     360 cagttcgact ctgctcgatc cacca                                           385
```

<210> SEQ ID NO 90
<211> LENGTH: 385
<212> TYPE: RNA
<213> ORGANISM: Nostoc muscorum PCC7120

<400> SEQUENCE: 90

```
ggguccgucg guuucgacag guuggcgaac gcuacucugu gauucagguc gagagugagu      60
cuccucugca aaucaaggcu caaaacaaaa guaaaugcga auaacaucgu uaaauuugcu     120
cguaaggacg cucuaguagc ugccuaaaua gccucuuuca gguucgagcg ucuucgguuu     180
gacuccguua aggacugaag accaaccccc aacggaugcu cuagcaaugu ucucugguug     240
gcuugcuagc uaagauuuaa ucagagcauc cuacguucgg gauaaugaac gauucccgcc     300
uugaggguca gaaaggcuaa accugugaau gagcgggggg ucauaccca auuggacag     360 caguucgacu cugcucgauc cacca                                           385
```

<210> SEQ ID NO 91
<211> LENGTH: 371
<212> TYPE: DNA
<213> ORGANISM: Odontella sinensis (diatom) chloroplast

<400> SEQUENCE: 91

```
ggggctgact tggtttcgac atttaaaaat tgttacagta tgatgcaggt cgaagtttct      60
aatcttcgta aaaaagaga aatttataat aaatgctaat aatttaattt cttctgtgtt     120
taaaagttta tcaactaagc aaaatagttt aaatttaagt tttgctgttt aagtttatg     180 cacatttaat gatctagtaa ataactttgt tcgctataat ttatatttat aactagactt     240
ttgtcttttt tatagtttag ataactttta tcatttcaaa cctcgttcca tctagttgaa     300
ctaaacctgt gaacgaatac tataataaaa ttttagatg gacgtgggtt cgactcccat     360
cagctccacc a                                                          371
```

<210> SEQ ID NO 92
<211> LENGTH: 371
<212> TYPE: RNA
<213> ORGANISM: Odontella sinensis (diatom) chloroplast

<400> SEQUENCE: 92

| | | | | | |
|---|---|---|---|---|---|
| ggggcugacu | ugguuucgac | auuuaaaaau | uguuacagua | ugaugcaggu | cgaaguuucu | 60 |
| aaucuucgua | aaaaaagaga | aauuuauaau | aaaugcuaau | aauuuaauuu | cuucuguguu | 120 |
| uaaaaguuua | ucaacuaagc | aaaauaguuu | aaauuuaagu | uuugcuguuu | aaguuuaug | 180 |
| cacauuuaau | gaucuaguaa | auaacuuugu | ucgcuauaau | uuauauuuau | aacuagacuu | 240 |
| uugucuuuuu | uauaguuuag | aauaacuuua | ucauuucaaa | ccucguucca | ucuaguugaa | 300 |
| cuaaaccugu | gaacgaauac | uauaauaaaa | uuuuuagaug | gacgugggu | cgacucccau | 360 |
| cagcuccacc | a | | | | | 371 |

<210> SEQ ID NO 93
<211> LENGTH: 323
<212> TYPE: DNA
<213> ORGANISM: Porphyra purpureum (red alga) chloroplast

<400> SEQUENCE: 93

| | | | | | |
|---|---|---|---|---|---|
| ggggctgcaa | ggtttctaca | ttgtgaaaaa | acaaatatat | gaaagtaaaa | cgagctcatt | 60 |
| attagagctt | ttagttaaat | aaatgcagaa | aataatatta | ttgctttttc | tcgaaaatta | 120 |
| gctgttgcat | aaatagtctc | aattttgta | attcgaagtg | atagactctt | atacactacg | 180 |
| aatattctgt | tagagttgct | cttaataaaa | gaaagtaaa | aaaatacaaa | ttcttatgtt | 240 |
| ttttacctga | attgattcaa | tttaaggtta | gtattttttg | attttacaa | tggacgtggg | 300 |
| ttcaagtccc | accagctcca | cca | | | | 323 |

<210> SEQ ID NO 94
<211> LENGTH: 323
<212> TYPE: RNA
<213> ORGANISM: Porphyra purpureum (red alga) chloroplast

<400> SEQUENCE: 94

| | | | | | |
|---|---|---|---|---|---|
| ggggcugcaa | gguuucuaca | uugugaaaaa | acaaauauau | gaaaguaaaa | cgagcucauu | 60 |
| auuagagcuu | uuaguuaaau | aaaugcagaa | aauaauauua | uugcuuuuuc | ucgaaaauua | 120 |
| gcuguugcau | aaauagucuc | aauuuuugua | auucgaagug | auagacucuu | auacacuacg | 180 |
| aauauucugu | uagaguugcu | cuuaauaaaa | gaaaguaaa | aaaauacaaa | uucuuauguu | 240 |
| uuuuaccuga | auugauucaa | uuuaagguua | guauuuuuug | auuuuuacaa | uggacgugggg | 300 |
| uucaagucccc | accagcucca | cca | | | | 323 |

<210> SEQ ID NO 95
<211> LENGTH: 407
<212> TYPE: DNA
<213> ORGANISM: Porphyromonas gingivalis

<400> SEQUENCE: 95

| | | | | | |
|---|---|---|---|---|---|
| ggggctgacc | ggctttgaca | gcgtgatgaa | gcggtatgta | agcatgtagt | gcgtgggtgg | 60 |
| cttgcactat | aatctcagac | atcaaaagtt | taattggcga | aaataactac | gctctcgctg | 120 |
| cgtaatcgaa | gaatagtaga | ttagacgctt | catcgccgcc | aaagtggcag | cgacgagaca | 180 |
| tcgcccgagc | agctttttcc | cgaagtagct | cgatggtgcg | gtgctgacaa | atcgggaacc | 240 |
| gctacaggat | gcttcctgcc | tgtggtcaga | tcgaacggaa | gataaggatc | gtgcattggg | 300 |

```
tcgtttcagc ctccgctcgc tcacgaaaat tccaactgaa actaaacatg tagaaagcat        360
attgattcca tgtttggacg agggttcaat tccctccagc tccacca                      407

<210> SEQ ID NO 96
<211> LENGTH: 407
<212> TYPE: RNA
<213> ORGANISM: Porphyromonas gingivalis

<400> SEQUENCE: 96
ggggcugacc ggcuuugaca gcgugaugaa gcgguaugua agcauguagu gcgugggugg         60
cuugcacuau aaucucagac aucaaaaguu uaauuggcga aaauaacuac gcucucgcug        120
cguaaucgaa gaauaguaga uuagacgcuu caucgccgcc aaaguggcag cgacgagaca        180
ucgcccgagc agcuuuucc cgaaguagcu cgaugguggcg gugcugacaa aucgggaacc        240
gcuacaggau gcuuccugcc uguggucaga ucgaacggaa gauaaggauc gugcauuggg        300
ucguuucagc cuccgcucgc ucacgaaaau uccaacugaa acuaaacaug uagaaagcau        360
auugauucca uguuuggacg agggucaau ucccuccagc uccacca                       407

<210> SEQ ID NO 97
<211> LENGTH: 310
<212> TYPE: DNA
<213> ORGANISM: Proteus rettgeri (NCTC 10975)

<400> SEQUENCE: 97
gggatttgcg aaacccaagg tgcatgccga ggggcggttg gcctcgtaaa aagccgcaaa         60
aaaatagtcg caaacgacga aaactacgct ttagcagctt aataacctgc ttagagccct        120 ctctcccctag cctccgctct tggacgggga tcaagagagg tcaaacccaa aagagatcgc       180
gtggatgcct tgcctggggt tgaagcgtta aacttaatca ggatagtttg ttggtggcgt       240
gtctgtccgc agctggcaaa tgaattcaaa gactagacta agcatgtagt accgaggatg        300
tagaaatttc                                                              310

<210> SEQ ID NO 98
<211> LENGTH: 310
<212> TYPE: RNA
<213> ORGANISM: Proteus rettgeri (NCTC 10975)

<400> SEQUENCE: 98
gggauuugcg aaacccaagg ugcaugccga ggggcgguug gccucguaaa aagccgcaaa         60
aaaauagucg caaacgacga aaacuacgcu uuagcagcuu aauaaccugc uuagagcccu        120
cucucccuag ccuccgcucu uggacgggga ucaagagagg ucaaacccaa aagagaucgc        180
guggaugccu ugccugggu ugaagcguua aacuuaauca ggauaguuug uuggugcgu         240 gucuguccgc agcuggcaaa ugaauucaaa gacuagacua agcauguagu accgaggaug        300
uagaaauuuc                                                              310

<210> SEQ ID NO 99
<211> LENGTH: 241
<212> TYPE: DNA
<213> ORGANISM: Pseudoalteromonas haloplanktis

<400> SEQUENCE: 99
gggagcgaaa cccaagggca gccgaggggc ggggcccgaa aaagccgcaa aaaaagcgc          60 aaacgacgaa aacacgcagc agcaaaaccg cagagccccc cccagcccg ccggacgggg         120 acaagagagg caaacccaaa agagacgcgg gagccgccgg gggaagcgaa acaacaggaa        180
```

```
gggggcggc cccgcagcgg caaagaacaa agacagacaa gcagagaccg aggagagaaa    240
c                                                                  241
```

<210> SEQ ID NO 100
<211> LENGTH: 313
<212> TYPE: RNA
<213> ORGANISM: Pseudoalteromonas haloplanktis

<400> SEQUENCE: 100

```
ggaauucaag aagcccgagg ugcaugucga ggugcgguuu gccucguaaa aaagccgcaa    60
uuuaaaguaa ucgcaaacga cgauaacuac ucucuagcag cuuaggcugg cuagcgcucc   120
uuccauguau ucuuguggac uggauuuugg agugucaccc uaacaccuga ucgcgacgga   180
aacccuggcc gggguugaag cguuaaaacu aagcggccuc gccuuuaucu accguguuug   240
uccgggauuu aaagguuaau uaaaugacaa uacuaaacau guaguaccga cggucgaggc   300
uuuucggacg ggg                                                      313
```

<210> SEQ ID NO 101
<211> LENGTH: 353
<212> TYPE: DNA
<213> ORGANISM: Pseudomonas aeruginosa

<400> SEQUENCE: 101

```
ggggccgatt aggattcgac gccggtaaca aaagttgagg ggcatgccga gttggtagca    60
gaactcgtaa attcgctgct gcaaacttat agttgccaac gacgcaaact acgctctagc   120
tgcttaatgc ggctagcagt cgctagggga tgcctgtaaa cccgaaacga ctgtcagata   180
gaacaggatc gccgccaagt tcgctgtaga cgtaacggct aaaactcata cagctcgctc   240
caagcaccct gccactcggg cggcgcggag ttaactcagt agagctggct aagcatgtaa   300
aaccgatagc ggaaagctgg cggacggggg ttcaaatccc cccggatcca cca          353
```

<210> SEQ ID NO 102
<211> LENGTH: 353
<212> TYPE: RNA
<213> ORGANISM: Pseudomonas aeruginosa

<400> SEQUENCE: 102

```
ggggccgauu aggauucgac gccgguaaca aaaguugagg ggcaugccga guugguagca    60
gaacucguaa auucgcugcu gcaaacuuau aguugccaac gacgcaaacu acgcucuagc   120
ugcuuaaugc ggcuagcagu cgcuaggggg ugccuguaaa cccgaaacga cugucagaua   180
gaacaggauc gccgccaagu ucgcuguaga cguaacggcu aaaacucaua cagcucgcuc   240
caagcacccu gccacucggg cggcgcggag uuaacucagu agagcuggcu aagcauguaa   300
aaccgauagc ggaaagcugg cggacggggg uucaaauccc cccggcucca cca          353
```

<210> SEQ ID NO 103
<211> LENGTH: 363
<212> TYPE: DNA
<213> ORGANISM: Salmonella typhimurium

<400> SEQUENCE: 103

```
ggggctgatt ctggattcga cgggatttgc gaaacccaag gtgcatgccg aggggcggtt    60
ggcctcgtaa aaagccgcaa aaaatagtc gcaaacgacg aaacctacgc tttagcagct    120
taataacctg cttagagccc tctctcccta gcctccgctc ttaggacggg atcaagaga   180
ggtcaaaccc aaaagagatc gcgcggatgc cctgcctggg gttgaagcgt taaaacgaat   240
```

```
caggctagtc tggtagtggc gtgtccgtcc gcaggtgcca ggcgaatgta aagactgact      300
aagcatgtag taccgaggat gtaggaattt cggacgcggg ttcaactccc gccagctcca      360
cca                                                                   363

<210> SEQ ID NO 104
<211> LENGTH: 363
<212> TYPE: RNA
<213> ORGANISM: Salmonella typhimurium

<400> SEQUENCE: 104
ggggcugauu cuggauucga cgggauuugc gaaacccaag gugcaugccg aggggcgguu       60
ggccucguaa aaagccgcaa aaaauaguc gcaaacgacg aaaccuacgc uuuagcagcu      120
uaauaaccug cuuagagccc ucucuccccua gccuccgcuc uuaggacggg gaucaagaga    180
ggucaaaccc aaaagagauc gcgcggaugc ccugccuggg guugaagcgu aaaaacgaau    240
caggcuaguc ugguagugc guguccgucc gcaggugcca ggcgaaugua aagacugacu     300
aagcauguag uaccgaggau guaggaauuu cggacgcggg uucaacuccc gccagcucca    360
cca                                                                   363

<210> SEQ ID NO 105
<211> LENGTH: 355
<212> TYPE: DNA
<213> ORGANISM: Shewanella putrefaciens

<400> SEQUENCE: 105
gggggcgatt ctggattcga caggattcac gaaaccctgg gagcatgccg aggggcggtt       60
ggcctcgtaa aaagccgcaa agttatagtt gcaaacgacg ataactacgc tctagccgct    120
taatgccgct agccatctac cacacgcttt gcacatgggc agtggatttg atggtcatct    180
cacatcgtgc tagcgaggga accctgtctg ggggtgaacc gcgaaacagt accggactca    240
ccgtgtggga tcctgtcttt cggagttcaa acggttaaac aatagaaaga ctaagcatgt    300
agcgccttgg atgtaggttt tctggacgcg ggttcaagtc ccgccgcctc cacca         355

<210> SEQ ID NO 106
<211> LENGTH: 355
<212> TYPE: RNA
<213> ORGANISM: Shewanella putrefaciens

<400> SEQUENCE: 106
gggggcgauu cuggauucga caggauucac gaaacccugg gagcaugccg aggggcgguu       60
ggccucguaa aaagccgcaa aguuauaguu gcaaacgacg auaacuacgc ucuagccgcu    120
uaaugccgcu agccaucuac cacacgcuuu gcacaugggc aguggauuug auggucaucu    180
cacaucgugc uagcgaggga acccugucug ggguugaacc gcgaaacagu accggacuca    240
ccguguggga uccugucuuu cggaguucaa acgguuaaac aauagaaaga cuaagcaugu    300
agcgccuugg auguagguuu ucuggacgcg gguucaaguc ccgccgccuc cacca         355

<210> SEQ ID NO 107
<211> LENGTH: 362
<212> TYPE: DNA
<213> ORGANISM: Staphylococcus aureus

<400> SEQUENCE: 107
ggggacgttc atggattcga caggggtccc ccgagctcat taagcgtgtc ggagggttgt       60
cttcgtcatc aacacacaca gtttataata actggcaaat caaacaataa tttcgcagta    120
```

```
gctgcctaat cgcactctgc atcgcctaac agcatttcct atgtgctgtt aacgcgattc    180
aaccttaata ggatatgcta aacactgccg tttgaagtct gtttagaaga aacttaatca    240
aactagcatc atgttggttg tttatcactt tcatgatgc gaaacctatc gataaactac     300
acacgtagaa agatgtgtat caggacctttt ggacgcgggt tcaaatcccg ccgtctccac   360
ca                                                                   362

<210> SEQ ID NO 108
<211> LENGTH: 362
<212> TYPE: RNA
<213> ORGANISM: Staphylococcus aureus

<400> SEQUENCE: 108
ggggacguuc auggauucga caggggucccc ccgagcucau uaagcguguc ggagggutugu   60 cuucgucauc aacacacaca guuuauaaua acuggcaaau caaacaauaa uuucgcagua   120
gcugccuaau cgcacucugc aucgccuaac agcauuccu augugcuguu aacgcgauuc    180
aaccuuaaua ggauaugcua aacacugccg uuugaagucu guuuagaaga aacuuaauca   240
aacuagcauc auguuggutug uuuaucacuu ucaugaugc gaaaccuauc gauaaacuac    300
acacguagaa agauguguau caggaccuuu ggacgcgggu ucaaaucccg ccgucuccac   360
ca                                                                   362

<210> SEQ ID NO 109
<211> LENGTH: 349
<212> TYPE: DNA
<213> ORGANISM: Streptococcus gordonii

<400> SEQUENCE: 109
ggggtcgtta cggattcgac aggcattatg aggcatattt tgcgactcat ctagcggatg     60
taaaacgcca gttaaatata actgcaaaaa ataatacttc ttacgcttta gctgcctaaa   120
aaccagcggg cgtgacccga ttcggattgc ttgtgtctga tgacaggtct tattattagc   180
aagctacggt agaatcttgt ctagtgattt tacaagagat tgatagactc gcttgatttg   240
ggcttgagtt atgtgtcaaa atcaagttaa aacaatacat agcctatggt tgtagacaaa   300
tgtgttggca gatgtttgga cgtgggttcg actcccaccg gctccacca              349

<210> SEQ ID NO 110
<211> LENGTH: 349
<212> TYPE: RNA
<213> ORGANISM: Streptococcus gordonii

<400> SEQUENCE: 110
ggggucguua cggauucgac aggcauuaug aggcauauuu ugcgacucau cuagcggaug     60
uaaaacgcca guuaaauaua acugcaaaaa auaauacuuc uuacgcuuua gcugccuaaa   120
aaccagcggg cgugacccga uucggauugc uuguguucuga ugcaggucu uauuauuagc   180 aagcuacggu agaaucuugu cuagugauuu uacaagagau ugauagacuc gcuugauuug   240
ggcuugaguu augugucaaa aucaaguuaa aacaauacau agccuauggu uguagacaaa   300
uguguuggca gauguuugga cguggguucg acucccaccg gcuccacca              349

<210> SEQ ID NO 111
<211> LENGTH: 349
<212> TYPE: DNA
<213> ORGANISM: Streptococcus mutans

<400> SEQUENCE: 111
```

```
gggtcgtta cggattcgac aggcattatg agacctattt tgcgactcat ctagcggatg    60
taaaacgcca gttaaatata actgcaaaaa atacaaattc ttacgcagta gctgcctaaa   120
aaccagcctg tgtgatcaat aacaaattgc ttgtgtttgt tgattggtct tattgttaac   180
aagctacgtt agaactgagt caggctgttc taaaagagtt ctactgactc gcatcgttag   240
agtttgagtt atgtattgta acggtgttaa ataaacacat aacctatagt tgtagacaaa   300
tgggttagca gatgtttgga cgtgggttcg actcccaccg gctccacca              349
```

```
<210> SEQ ID NO 112
<211> LENGTH: 349
<212> TYPE: RNA
<213> ORGANISM: Streptococcus mutans

<400> SEQUENCE: 112
ggggucguua cggauucgac aggcauuaug agaccuauuu ugcgacucau cuagcggaug    60
uaaaacgcca guuaaauaua acugcaaaaa auacaaauuc uuacgcagua gcugccuaaa   120
aaccagccug ugugaucaau aacaaauugc uugugucugu ugauggucu uauuguuaac    180 aagcuacguu agaacugagu caggcuguuc uaaaagaguu cuacugacuc gcaucguuag   240
aguuugaguu auguauugua acggucguuaa auaaacacau aaccuauagu uguagacaaa   300
uggguuagca gauguuugga cgugggucg acucccaccg gcuccacca               349
```

```
<210> SEQ ID NO 113
<211> LENGTH: 348
<212> TYPE: DNA
<213> ORGANISM: Streptococcus pneumoniae

<400> SEQUENCE: 113
ggggtcgtta cggattcgac aggcattatg aggcatattt tgcgactcgt gtggcgacgt   60
aaacgctcag ttaaatataa ctgcaaaaaa taacacttct tacgctctag ctgcctaaaa   120
accagcaggc gtgacccgat ttggattgct cgtgttcaat gacaggtctt attattagcg   180
agatacgatt aagccttgtc tagcggtttg ataagagatt gatagactcg cagtttctag   240
acttgagtta tgtgtcgagg ggctgttaaa ataatacata acctatggtt gtagacaaat   300
atgttggcag gtgtttggac gtgggttcga ctcccaccgg ctccacca               348
```

```
<210> SEQ ID NO 114
<211> LENGTH: 348
<212> TYPE: RNA
<213> ORGANISM: Streptococcus pneumoniae

<400> SEQUENCE: 114
ggggucguua cggauucgac aggcauuaug aggcauauuu ugcgacucgu guggcgacgu   60
aaacgcucag uuaaauauaa cugcaaaaaa uaacacuucu uacgcucuag cugccuaaaa   120
accagcaggc gugacccgau uuggauugcu cguguucaau gacaggucuu auuauuagcg   180
agauacgauu aagccuuguc uagcgguuug auaagagauu gauagacucg caguuucuag   240
acuugaguua ugugucgagg ggcuguuaaa auaauacaua accuaugguu guagacaaau   300
auguuggcag guguuuggac gugggucga cucccaccgg cuccacca               348
```

```
<210> SEQ ID NO 115
<211> LENGTH: 348
<212> TYPE: DNA
<213> ORGANISM: Streptococcus pyogenes

<400> SEQUENCE: 115
```

-continued

```
ggggttgtta cggattcgac aggcattatg aggcatgttt tgcgtcccat cggcagatgt    60
aaattgccag ttaaatataa ctgcaaaaaa tacaaactct tacgctttag ctgcctaaaa   120
accagctagc gtgacttcta caagattgct tgtgtcctgt tagaagtctc aaaatagcaa   180
gctacggtta cgaaattgtc tagtttcgtg acaagagatt gatagactcg caaactaatg   240
gcttgagtta tgtgtcttta gtttgttaaa tgaagacata acctatggac gtagacaaat   300
atgttggcag gtgtttggac gtgggttcga ctcccaccag ctccacca               348
```

<210> SEQ ID NO 116
<211> LENGTH: 348
<212> TYPE: RNA
<213> ORGANISM: Streptococcus pyogenes

<400> SEQUENCE: 116

```
ggggttguuua cggauucgac aggcauuaug aggcaugutu ugcgucccau cggcagaugu    60
aaauugccag uuaaauauaa cugcaaaaaa uacaaacucu uacgcuuuag cugccuaaaa   120
accagcuagc gugacuucua caagauugcu uguguccugu uagaagucuc aaaauagcaa   180
gcuacgguua cgaaauuguc uaguuucgug caagagauu gauagacucg caaacuaaug   240
gcuugaguua uguegucuuua guugguuaaa ugaagacaua accuauggac guagacaaau   300
auguuggcag guguuuggac gugggucga cucccaccag cuccacca               348
```

<210> SEQ ID NO 117
<211> LENGTH: 394
<212> TYPE: DNA
<213> ORGANISM: Synechococcus sp. PCC6301

<400> SEQUENCE: 117

```
ggggctgtaa tggtttcgac gtgttggtga atccttcacc gtgattcagg ccgagaggga    60
gtccactctc gtaaatccag gctcaaccaa aagtaactgc gaacaacatc gttcctttcg   120
ctcgtaaggc tgctcctgta gctgcttaaa cgccacaaac tttctggctc gagcgtctag   180
tcgtagactc cgttaatacg cctagactta aaccccaac ggatgctcga gtggcggcct   240
caggtccgtc ctctcgctaa gcaaaaacct gagcatcccg ccaacgggga taatcgttgg   300
ctcccgcaca gtgggtcaac cgtgctaagc ctgtgaacga gcggaaagtt actagtcaat   360
gcggacagcg gttcgattcc gctcagctcc acca                              394
```

<210> SEQ ID NO 118
<211> LENGTH: 394
<212> TYPE: RNA
<213> ORGANISM: Synechococcus sp. PCC6301

<400> SEQUENCE: 118

```
ggggcuguaa ugguuucgac guguugguga auccuucacc gugauucagg ccgagaggga    60
guccacucuc guaaauccag gcucaaccaa aaguaacugc gaacaacauc guuccuuucg   120
cucguaaggc ugcuccugua gcugcuuaaa cgccacaaac uuucuggcuc gagcgucuag   180
ucguagacuc cguuaauacg ccuagacuua aaccccccaac ggaugcucga guggcggccu   240
cagguccguc cucucgcuaa gcaaaaaccu gagcaucccg ccaacgggga uaaucguugg   300
cucccgcaca gugggucaac cgugcuaagc cugugaacga gcggaaaguu acuagucaau   360
gcggacagcg guucgauucc gcucagcucc acca                              394
```

<210> SEQ ID NO 119
<211> LENGTH: 399

```
<212> TYPE: DNA
<213> ORGANISM: Synechocystis PCC6803

<400> SEQUENCE: 119
ggggccgcaa tggtttcgac aggttggcga aagcttgccc gtgatacagg tcgagagtga      60
gtctcctctc gcaaatcaaa ggctcaaaaa aaagtaactg cgaataacat cgtcagcttc     120
aaacgggtag ccatagcagc ctagtctgta aaagctacat tttcttgtca agaccgttt      180 acttcttttc tgactccgtt aaggattaga ggttaacccc aacggatgct tgtttggct     240 cttctctagt tagctaaaca atcaagactc agactagagc atcccaccat cagggataat    300
cgatggtccc cgtcctaggg ctagaaggac taaacctgtg aatgagcgga aagttaatac    360
ccagtttgga cagcagttca attctgctcg gctccacca                           399

<210> SEQ ID NO 120
<211> LENGTH: 399
<212> TYPE: RNA
<213> ORGANISM: Synechocystis PCC6803

<400> SEQUENCE: 120
ggggccgcaa ugguuucgac agguuggcga aagcuugccc gugauacagg ucgagaguga     60
gucuccucuc gcaaaucaaa ggcucaaaaa aaaguaacug cgaauaacau cgucagcuuc    120
aaacgggaug ccauagcagc cuagucugua aaagcuacau uuucuuguca agaccguuu    180 acuucuuuuc ugacuccguu aaggauuaga gguuaacccc aacggaugcu uguuuggcu    240 cuucucuagu uagcuaaaca aucaagacuc agacuagagc aucccaccau cagggauaau   300
cgauggcccc cguccuaggg cuagaaggac uaaaccugug aaugagcgga aaguuaauac   360
ccaguuugga cagcaguuca auucugcucg gcuccacca                          399

<210> SEQ ID NO 121
<211> LENGTH: 356
<212> TYPE: DNA
<213> ORGANISM: Thermotoga maritima

<400> SEQUENCE: 121
gggggcgaac gggttcgacg gggatggagt ccctgggaa gcgagccgag gtccccacct      60
cctcgtaaaa aaggtgggac aaagaataag tgccaacgaa cctgttgctg ttgccgctta    120
atagataagc ggccgtcctc tccgaagttg gctgggcttc ggaagagggc gtgagagatc    180
cagcctaccg attcagcttc gccttccggc ctgaatcggg aaaactcagg aaggctgtgg    240
gagaggacac cctgcccgtg ggaggtccct cccgagagcg aaaacacggg ctgcgctcgg    300
agaagcccag gggcctccat cttcggacgg gggttcgaat cccccgcct ccacca         356

<210> SEQ ID NO 122
<211> LENGTH: 356
<212> TYPE: RNA
<213> ORGANISM: Thermotoga maritima

<400> SEQUENCE: 122
gggggcgaac ggguucgacg gggauggagu cccugggaa gcgagccgag guccccaccu       60
ccucguaaaa aaggugggac aaagaauaag ugccaacgaa ccuguugcug uugccgcuua    120
auagauaagc ggccguccuc uccgaaguug gcugggcuuc ggaagagggc gugagagauc    180
cagccuaccg auucagcuuc gccuuccggc cugaaucggg aaaacucagg aaggcugugg    240
gagaggacac ccugcccgug ggagguccu cccgagagcg aaaacacggg cugcgcucgg    300
agaagcccag gggccuccau cuucggacgg ggguucgaau cccccgccu ccacca         356
```

<210> SEQ ID NO 123
<211> LENGTH: 349
<212> TYPE: DNA
<213> ORGANISM: Thermus thermophilus

<400> SEQUENCE: 123

```
gggggtgaaa cggtctcgac ggggtcgcc gagggcgtgg ctgcgcgccg aggtgcgggt      60
ggcctcgtaa aaacccgcaa cggcataact gccaacacca actacgctct cgcggcttaa   120
tgaccgcgac ctcgcccggt agccctgccg ggggctcacc ggaagcgggg acacaaaccc   180
ggctagcccg gggccacgcc ctctaacccc gggcgaagct tgaaggggc tcgctcctgg    240
ccgcccgtcc gcgggccaag ccaggaggac acgcgaaacg cggactacgc gcgtagaggc   300
ccgccgtaga gaccttcgga cggggttcg actccccca cctccacca                 349
```

<210> SEQ ID NO 124
<211> LENGTH: 349
<212> TYPE: RNA
<213> ORGANISM: Thermus thermophilus

<400> SEQUENCE: 124

```
gggggugaaa cggucucgac ggggucgcc gagggcgugg cugcgcgccg aggugcgggu      60
ggccucguaa aaacccgcaa cggcauaacu gccaacacca acuacgcucu cgcggcuuaa   120
ugaccgcgac cucgcccggu agcccugccg ggggcucacc ggaagcgggg acacaaaccc   180
ggcuagcccg gggccacgcc cucuaacccc gggcgaagcu ugaaggggc ucgcuccugg    240
ccgcccgucc gcgggccaag ccaggaggac acgcgaaacg cggacuacgc gcguagaggc   300
ccgccguaga gaccuucgga cggggguucg acucccccca ccuccacca               349
```

<210> SEQ ID NO 125
<211> LENGTH: 354
<212> TYPE: DNA
<213> ORGANISM: Treponema pallidum

<400> SEQUENCE: 125

```
ggggatgact aggtttcgac tagggatgtg gggtgttgcg ctgcaggtgg agtgtcgatc    60
tcctgattcg gcgcctttat aactgccaat tctgacagtt tcgactacgc gctcgccgcg  120
taatcgcggg cctgtgtttg cgctgctctg agcgaacata tcggcccgac gccaaacgga  180
gcttgctctt acgttgtgca cggcggacgt aggggact ttgtctgtgc taagactctg    240
gcgcgtgcgg tgcaggccta gcagagtccg acaaacgcag tacgcaccgc taaacctgta  300
ggcgcgcagc actcgctctt taggacgggg gttcgattcc ccccatctcc acca         354
```

<210> SEQ ID NO 126
<211> LENGTH: 354
<212> TYPE: RNA
<213> ORGANISM: Treponema pallidum

<400> SEQUENCE: 126

```
ggggaugacu agguuucgac uagggaugug ggguguugcg cugcaggugg agugucgauc    60
uccugauucg gcgccuuuau aacugccaau ucugacaguu ucgacuacgc gcucgccgcg  120
uaaucgcggg ccuguguuug cgcugcucug agcgaacaua ucggcccgac gccaaacgga  180
gcuugcucuu acguugugca cggcggacgu aggggacuu uugucugugc uaagacucug   240
gcgcgugcgg ugcaggccua gcagaguccg acaaacgcag uacgcaccgc uaaaccugua  300
ggcgcgcagc acucgcucuu uaggacgggg guucgauucc ccccaucucc acca         354
```

<210> SEQ ID NO 127
<211> LENGTH: 367
<212> TYPE: DNA
<213> ORGANISM: Vibrio cholerae

<400> SEQUENCE: 127
ggggctgatt caggattcga cgggaatttt gcagtctgag gtgcatgccg aggtgcggta 60
ggcctcgtta acaaaccgca aaaaaatagt cgcaaacgac gaaaactacg cactagcagc 120
ttaataccct gctcagagcc cttcctccct agcttccgct tgtaagacgg ggaaatcagg 180
aaggtcaaac caaatcaagc tggcgtggat tcccccacct gagggatgaa gcgcgagatc 240
taattcaggt tagccattcg ttagcgtgtc ggttcgcagg cggtggtgaa attaaagatc 300
gactaagcat gtagtaccaa agatgaatgg ttttcggacg gggttcaac tccccccagc 360 tccacca 367

<210> SEQ ID NO 128
<211> LENGTH: 367
<212> TYPE: RNA
<213> ORGANISM: Vibrio cholerae

<400> SEQUENCE: 128
ggggcugauu caggauucga cgggaauuuu gcagucugag gugcaugccg aggugcggua 60
ggccucguua acaaaccgca aaaaaauagu cgcaaacgac gaaaacuacg cacuagcagc 120
uuaauacccu gcucagagcc cuuccucccu agcuuccgcu uguaagacgg ggaaaucagg 180
aaggucaaac caaaucaagc uggcguggau ucccccaccu gagggaugaa gcgcgagauc 240
uaauucaggu uagccauucg uuagcguguc gguucgcagg cgguggugaa auuaaagauc 300
gacuaagcau guaguaccaa agaugaaugg uuuucggacg gggguucaac ucccccagc 360 uccacca 367

<210> SEQ ID NO 129
<211> LENGTH: 364
<212> TYPE: DNA
<213> ORGANISM: Yersinia pestis

<400> SEQUENCE: 129
ggggctgatt ctggattcga cgggattcgc gaaacccaag gtgcatgccg aggtgcggtg 60
gcctcgtaaa aaaccgcaaa aaaaatagtt gcaaacgacg aaaactacgc actagcagct 120
taataacctg cttagagccc tctctgccta gcctccgctc ttaggacggg gatcaagaga 180
ggtcaaacct aaaagagctc gtgtggaaac cttgcctggg gtggaagcat taaaactaat 240
caggatagtt tgtcagtagc gtgtccatcc gcagctggcc ggcgaatgta atgattggac 300
taagcatgta gtgccgacgg tgtagtaatt tcggacgggg gttcaaatcc ccccagctcc 360
acca 364

<210> SEQ ID NO 130
<211> LENGTH: 364
<212> TYPE: RNA
<213> ORGANISM: Yersinia pestis

<400> SEQUENCE: 130
ggggcugauu cuggauucga cgggauucgc gaaacccaag gugcaugccg aggugcggug 60
gccucguaaa aaaccgcaaa aaaaauaguu gcaaacgacg aaaacuacgc acuagcagcu 120
uaauaaccug cuuagagccc ucucugccua gccuccgcuc uuaggacggg gaucaagaga 180

```
ggucaaaccu aaaagagcuc guguggaaac cuugccuggg guggaagcau uaaaacuaau    240
caggauaguu ugucaguagc guguccaucc gcagcuggcc ggcgaaugua augauuggac    300
uaagcaugua gugccgacgg uguaguaauu ucggacgggg guucaaaucc ccccagcucc    360
acca                                                                 364
```

<210> SEQ ID NO 131
<211> LENGTH: 309
<212> TYPE: DNA
<213> ORGANISM: Campylobacter fetus

<400> SEQUENCE: 131

```
aggagtaagt ctgcttagat ggcatgtcgc tttgggcaaa gcgtaaaaag cccaaataaa     60
attaaacgca aacaacgtta aattcgctcc tgcttacgct aaagctgcgt aagttcagtt    120
gagcctgaaa tttaagtcat actatctagc ttaattttcg gtcatctttg atagtgtagc    180
cttgcgtttg acaagcgttg aggtgaaata aagtcttagc cttgcttttg agttttggaa    240
gatgagcgaa gtagggtgaa gtagtcatct ttgctaagca tgtagaggtc tttgtgggat    300
tattttttgg                                                           309
```

<210> SEQ ID NO 132
<211> LENGTH: 309
<212> TYPE: RNA
<213> ORGANISM: Campylobacter fetus

<400> SEQUENCE: 132

```
aggaguaagu cugcuuagau ggcaugucgc uuugggcaaa gcguaaaaag cccaaauaaa     60
auuaaacgca aacaacguua aauucgcucc ugcuuacgcu aaagcugcgu aaguucaguu    120
gagccugaaa uuuaagucau acuaucuagc uuaauuuucg gucaucuuug auagugagc    180 cuugcguuug acaagcguug aggugaaaua aagucuuagc cuugcuuuug aguuuuggaa    240
gaugagcgaa guagggugaa guagucaucu uugcuaagca uguagagguc uuuguggaau    300
uauuuuugg                                                            309
```

<210> SEQ ID NO 133
<211> LENGTH: 309
<212> TYPE: DNA
<213> ORGANISM: Campylobacter coli (BM2509)

<400> SEQUENCE: 133

```
aggagtaagt ctgcttagat ggcatgtcgc tttggacaaa gcgtaaaaag tccaaattaa     60
aattaaacgc aaataacgtt aaatttgctc ctgcttacgc taaagctgcg taagttcagt    120
tgagcccgaa actcaagtga tgctatctag cttgaatttt ggtcatcttt gatagtgtag    180
attgaaaatt gacaacttt  aatcgaagtt aaagtcttag tctagcttga aattttggaa    240
ggtgagttta gccagatgaa gttttcacct ttgctaaaca tgtagaagtc tttgtggggt    300
tattttggg                                                            309
```

<210> SEQ ID NO 134
<211> LENGTH: 309
<212> TYPE: RNA
<213> ORGANISM: Campylobacter coli (BM2509)

<400> SEQUENCE: 134

```
aggaguaagu cugcuuagau ggcaugucgc uuuggacaaa gcguaaaaag uccaaauuaa     60
aauuaaacgc aaauaacguu aaauuugcuc cugcuuacgc uaaagcugcg uaaguucagu    120
```
ugagcccgaa acucaaguga ugcuaucuag cuugaauuuu ggucaucuuu gauaguguag 180
auugaaaauu gacaacuuuu aaucgaaguu aaagucuuag ucuagcuuga aauuuuggaa 240
ggugaguuua gccagaugaa guuuucaccu uugcuaaaca uguagaaguc uuuguggggu 300
uauuuuugg 309

<210> SEQ ID NO 135
<211> LENGTH: 311
<212> TYPE: DNA
<213> ORGANISM: Unknown
<220> FEATURE:
<223> OTHER INFORMATION: Description of Unknown Organism:Campylobacter chicken isolate

<400> SEQUENCE: 135
acaggagtaa gtctgcttag atggcatgtc gctttgggca aagcgtaaaa agcccaaata 60
aaattaaacg caaacaacgt taaattcgct cctgcttacg ctaaagctgc gtaagttcag 120
ttgagcctga aatttaagtc atactatcta gcttaatttt cggtcatttt tgatagtgta 180
gccttgcgtt tgacaagcgt tgaggtgaaa taaggtctta gccttgcttt tgagttttgg 240
aagatgagcg aagtagggtg aagtagtcat ctttgctaag catgtagagg tctttgtggg 300
attatttttg g 311

<210> SEQ ID NO 136
<211> LENGTH: 311
<212> TYPE: RNA
<213> ORGANISM: Unknown
<220> FEATURE:
<223> OTHER INFORMATION: Description of Unknown Organism:Campylobacter chicken isolate

<400> SEQUENCE: 136
acaggaguaa gucugcuuag auggcauguc gcuuugggca aagcguaaaa agcccaaaua 60
aaauuaaacg caaacaacgu uaaauucgcu ccugcuuacg cuaaagcugc guaaguucag 120
uugagccuga aauuuaaguc auacuaucua gcuuaauuuu cggucauuuu ugauagugua 180
gccuugcguu ugacaagcgu ugaggugaaa uaaggucuua gccuugcuuu ugaguuuugg 240
aagaugagcg aaguagggug aaguagucau cuuugcuaag cauguagagg ucuuuguggg 300
auuauuuuug g 311

<210> SEQ ID NO 137
<211> LENGTH: 313
<212> TYPE: DNA
<213> ORGANISM: Clostridium perfringens

<400> SEQUENCE: 137
acgggggtag gatgggtttg ataagcgagt cgagggaagc atggtgcctc gataataaag 60
tatgcattaa agataaacgc acgagataat tttgcattag cagcttaagt tagcgctgct 120
catccttcct caattgccca cggttgagag taagggtgtc atttaaaagt ggggaaccga 180
gcctagcaaa gctttgagct aggaacggaa tttatgaagc ttaccaaaga ggaagtttgt 240
ctgtggacgt tctctgaggg aattttaaaa cacaagacta cactcgtaga aagtcttact 300
ggtctgcttt cgg 313

<210> SEQ ID NO 138
<211> LENGTH: 313
<212> TYPE: RNA
<213> ORGANISM: Clostridium perfringens

```
<400> SEQUENCE: 138 acgggguag gauggguuug auaagcgagu cgagggaagc auggugccuc gauaauaaag     60
uaugcauuaa agauaaacgc acgagauaau uuugcauuag cagcuuaagu uagcgcugcu   120
cauccuuccu caauugccca cgguugagag uaagggguguc auuuaaaagu ggggaaccga   180
gccuagcaaa gcuuugagcu aggaacgaaa uuuaugaagc uuaccaaaga ggaaguuugu   240
cuguggacgu ucucugaggg aauuuuaaaa cacaagacua cacucguaga aagucuuacu   300
ggucugcuuu cgg                                                      313

<210> SEQ ID NO 139
<211> LENGTH: 331
<212> TYPE: DNA
<213> ORGANISM: Haemophilus ducreyi (NCTC 10945)

<400> SEQUENCE: 139
acgggattag cgaagtccaa ggtgcacgtc gaggtgcggt aggcctcgta acaaaccgca    60
aaaaaatagt cgcaaacgac gaacaatacg ctttagcagc ttaataaccct gcatttagcc  120 ttcgcgccct agctttcgct cgtaagacgg ggagcacgcg gagtcaaacc aaaacgagat   180
cgtgtggacg cttccgcttg tagatgaaac actaaattga atcaagctag tttatttctt   240
gcgtgtctgt ccgctggaga taagcgaaat taaagaccag actaaacgtg tagtactgaa   300
gatagagtaa tttcggaccc gggttcgact c                                  331

<210> SEQ ID NO 140
<211> LENGTH: 331
<212> TYPE: RNA
<213> ORGANISM: Haemophilus ducreyi (NCTC 10945)

<400> SEQUENCE: 140
acgggauuag cgaaguccaa ggugcacguc gaggugcggu aggccucgua acaaaccgca    60
aaaaaauagu cgcaaacgac gaacaauacg cuuuagcagc uuaauaaccu gcauuuagcc  120
uucgcgcccu agcuuucgcu cguaagacgg ggagcacgcg gagucaaacc aaaacgagau   180
cguguggacg cuuccgcuug uagaugaaac acuaaauuga aucaagcuag uuuauuucuu   240
gcgugucugu ccgcuggaga uaagcgaaau uaaagaccag acuaaacgug uaguacugaa   300
gauagaguaa uuucggaccc ggguucgacu c                                  331

<210> SEQ ID NO 141
<211> LENGTH: 232
<212> TYPE: DNA
<213> ORGANISM: Listeria innocua (food isolate #1)

<400> SEQUENCE: 141
ggcaaagaaa aacaaaacct agctttcgct gcctaataac cagtagcata gctgatcctc    60
cgtgcatcgc ccatgtgcta cggtaagggt ctcactctaa gtgggctaca ctagttaatc   120
tccgtctgag gttaaataga agagcttaat cagactagct gaatggaagc ctgttaccgg   180
gctgatgttt atgcgaaatg ctaatacggt gactacgctc gtagatattc aa           232

<210> SEQ ID NO 142
<211> LENGTH: 232
<212> TYPE: RNA
<213> ORGANISM: Listeria innocua (food isolate #1)

<400> SEQUENCE: 142
ggcaaagaaa aacaaaaccu agcuuucgcu gccuaauaac caguagcaua gcugauccuc    60
```
cgugcaucgc ccaugugcua cgguaagggu cucacucuaa gugggcuaca cuaguuaauc    120
uccgucugag guuaaauaga agagcuuaau cagacuagcu gaauggaagc cuguuaccgg    180
gcugauguuu augcgaaaug cuauacgggu gacuacgcuc guagauauuc aa            232

<210> SEQ ID NO 143
<211> LENGTH: 232
<212> TYPE: DNA
<213> ORGANISM: Listeria innocua (food isolate #2)

<400> SEQUENCE: 143
ggcaaagaaa aacaaaacct agctttcgct gcctaataag cagtagcata gctgatcctc    60
cgtgcatcgc ccatgtgcta cggtaagggt ctcactctaa gtgggctaca ctagttaatc    120
tccgtctgag gttaaataga agagcttaat cagactagct gaatggaagc ctgttaccgg    180
gccgatgttt atgcgaaatg ctaatacggt gactacgctc gtagatattt aa            232

<210> SEQ ID NO 144
<211> LENGTH: 232
<212> TYPE: RNA
<213> ORGANISM: Listeria innocua (food isolate #2)

<400> SEQUENCE: 144
ggcaaagaaa aacaaaaccu agcuuucgcu gccuaauaag caguagcaua gcugauccuc    60
cgugcaucgc ccaugugcua cgguaagggu cucacucuaa gugggcuaca cuaguuaauc    120
uccgucugag guuaaauaga agagcuuaau cagacuagcu gaauggaagc cuguuaccgg    180
gccgauguuu augcgaaaug cuauacgggu gacuacgcuc guagauauuu aa            232

<210> SEQ ID NO 145
<211> LENGTH: 232
<212> TYPE: DNA
<213> ORGANISM: Listeria innocua (food isolate #3)

<400> SEQUENCE: 145
ggcaaagaaa aacaaaacct agctttcgct gcctaataag cagtagaata gctgatcctc    60
cgtgcatcgc ccatgtgcta cggtaagggt ctcactctaa gtgggctaca ctagttaatc    120
tccgtctgag gttaaataga agagcttaat cggactagct gaatggaagc ctgttaccgg    180
gccgatgttt atgcgaaatg ctaatacggt gactacgctc gtagatattt aa            232

<210> SEQ ID NO 146
<211> LENGTH: 232
<212> TYPE: RNA
<213> ORGANISM: Listeria innocua (food isolate #3)

<400> SEQUENCE: 146
ggcaaagaaa aacaaaaccu agcuuucgcu gccuaauaag caguagaaua gcugauccuc    60
cgugcaucgc ccaugugcua cgguaagggu cucacucuaa gugggcuaca cuaguuaauc    120
uccgucugag guuaaauaga agagcuuaau cggacuagcu gaauggaagc cuguuaccgg    180
gccgauguuu augcgaaaug cuauacgggu gacuacgcuc guagauauuu aa            232

<210> SEQ ID NO 147
<211> LENGTH: 232
<212> TYPE: DNA
<213> ORGANISM: Listeria innocua (ATCC 12210)

<400> SEQUENCE: 147
ggcaaagaaa aacaaaacct agctttcgct gcctaataag cagtagcata gctgatcctc    60

```
cgtgcatcgc ccatgtgcta cggtaagggt ctcactctaa gtgggctaca ctagttaatc    120
tccgtctggg gttaaataga agagcttaat cagactagct gaatggaagc ctgttactgg    180
gccgatgttt atgcgaaatg ctaatacggt gactacgctc gtagatattt aa            232

<210> SEQ ID NO 148
<211> LENGTH: 232
<212> TYPE: RNA
<213> ORGANISM: Listeria innocua (ATCC 12210)

<400> SEQUENCE: 148
ggcaaagaaa aacaaaaccu agcuuucgcu gccuaauaag caguagcaua gcugauccuc    60
cgugcaucgc ccaugugcua cgguaagggu cucacucuaa gugggcuaca cuaguuaauc    120
uccgucuggg guuaaauaga agagcuuaau cagacuagcu gaauggaagc cuguuacugg    180
gccgauguuu augcgaaaug cuauacggu gacuacgcuc guagauauuu aa             232

<210> SEQ ID NO 149
<211> LENGTH: 322
<212> TYPE: DNA
<213> ORGANISM: Listeria ivanovii (NCTC 11846)

<400> SEQUENCE: 149
acagggatag ttcgagcttg agttgcgagt cgggggatc gtcctcgtta ttaacgtcaa     60
agccaataat aactggcaaa gaaaaacaaa acctagcttt cgctgcctaa taagcagtag    120
catagctgat cctccgtgca tcgcccatgt gctacggtaa gggtctcact ttaagtgggc    180
tacactaaat aatctccgtc tggggttagt tagaagagct taatcagact agctgaatgg    240
aagcctgtta ccgggctgat gtttatgcga aatgctaata cggtgactac gctcgtagat    300
atttaagtgc cgatatttct gg                                             322

<210> SEQ ID NO 150
<211> LENGTH: 321
<212> TYPE: RNA
<213> ORGANISM: Listeria ivanovii (NCTC 11846)

<400> SEQUENCE: 150
acagggauag uucgagcuug aguugcgagu cgggggauc guccucguua uuaacgucaa     60
agccaauaau aacuggcaaa gaaaaacaaa accuagcuuu cgcugccuaa uaagcaguag    120
cauagcugau ccuccgugca ucgcccaugu gcuacgguaa gggucucacu uuaagugggc    180
uacacuaaau aaucuccguc uggg guuagu uagaagagcu uaaucagacu agcugaaugg    240
aagccuguua ccgggcugau guuuaugcga aaugcuaaua cggugacucg cucguagaua    300
uuuaagugcc gauauuucug g                                              321

<210> SEQ ID NO 151
<211> LENGTH: 322
<212> TYPE: DNA
<213> ORGANISM: Listeria seeligeri (NCTC 11856)

<400> SEQUENCE: 151
acagggatag ttcgagcttg agttgcgagt cgggggatc gtcctcgtta tcaacgtcaa     60
agccaataat aactggcaaa gaaaaacaaa acctagcttt cgctgcctaa taagcagtag    120
catagctgat cctccgtgca tcgcccatgt gctacggaaa gggtctcact ttaagtgggc    180
tacactaaat aatctccgtc tggggttagt tagaagagct taatcagact agctgaatgg    240
aagcctgtta ccgggctgat gtttatgcga aatactaata cggtgactac gctcgtagat    300
```

```
atttaagtgc ccatatttct gg                                              322

<210> SEQ ID NO 152
<211> LENGTH: 322
<212> TYPE: RNA
<213> ORGANISM: Listeria seeligeri (NCTC 11856)

<400> SEQUENCE: 152
acagggauag uucgagcuug aguugcgagu cgggggauc guccucguua ucaacgucaa       60
agccaauaau aacuggcaaa gaaaaacaaa accuagcuuu cgcugccuaa uaagcaguag     120
cauagcugau ccuccgugca ucgcccaugu gcuacggaaa gggucucacu uuaagugggc    180
uacacuaaau aaucuccguc uggguuagu uagaagagcu uaaucagacu agcugaaugg     240
aagccuguua ccgggcugau guuuaugcga aauacuaaua cggugacuac gcucguagau    300
auuuaagugc ccauauuucu gg                                              322

<210> SEQ ID NO 153
<211> LENGTH: 314
<212> TYPE: DNA
<213> ORGANISM: Salmonella enteritidis

<400> SEQUENCE: 153
acgggatttg cgaacccaa ggtgcatgcc gaggggcggt tggcctcgta aaagccgca        60 aaaaatagt cgcaaacgac gaaacctacg ctttagcagc ttaataaccct gcttagagcc    120 ctctctcct agcctccgct cttaggacgg ggatcaagag aggtcaaacc caaaagagat    180
cgcgtggatg ccctgcctgg ggttgaagcg ttaaaacgaa tcaggctagt ctggtagtgg    240
cgtgtccgtc cgcaggtgcc aggcgaatgt aaagactgac taagcatgta gtaccgagga    300
tgtaggaatt tcgg                                                       314

<210> SEQ ID NO 154
<211> LENGTH: 314
<212> TYPE: RNA
<213> ORGANISM: Salmonella enteritidis

<400> SEQUENCE: 154
acgggauuug cgaacccaa ggugcaugcc gaggggcggu uggccucgua aaagccgca        60 aaaaauagu cgcaaacgac gaaaccuacg cuuuagcagc uuaauaaccu gcuuagagcc    120
cucucucccu agccuccgcu cuuaggacgg ggaucaagag aggucaaacc caaaagagau    180
cgcguggaug cccugccugg gguugaagcg uuaaaacgaa ucaggcuagu cugguagugg    240
cguguccguc cgcaggugcc aggcgaaugu aaagacugac uaagcaugua guaccgagga    300
uguaggaauu ucgg                                                       314

<210> SEQ ID NO 155
<211> LENGTH: 313
<212> TYPE: DNA
<213> ORGANISM: Staphylococcus epidermidis (NCTC 11047)

<400> SEQUENCE: 155 acagggtcc cccgagctta ttaagcgtgt cggagggttg gctccgtcat caacacattt       60
cggttaaata taactgacaa atcaaacaat aatttcgcag tagctgcgta atagccactg    120
catcgcctaa cagcatctcc tacgtgctgt taacgcgatt caaccctagt aggatatgct    180
aaacactgcc gcttgaagtc tgtttagatg aaatataatc aagctagtat catgttggtt    240
gtttattgct tagcatgatg cgaaaattat caataaacta cacacgtaga aagatttgta    300
```

```
tcaggacctc tgg                                                   313

<210> SEQ ID NO 156
<211> LENGTH: 313
<212> TYPE: RNA
<213> ORGANISM: Staphylococcus epidermidis (NCTC 11047)

<400> SEQUENCE: 156
acaggggucc cccgagcuua uuaagcgugu cggaggguug gcuccgucau caacacauuu    60
cgguuaaaua uaacugacaa aucaaacaau aauuucgcag uagcugcgua auagccacug   120
caucgccuaa cagcaucucc uacgugcugu uaacgcgauu caacccuagu aggauaugcu   180
aaacacugcc gcuugaaguc uguuuagaug aaauauaauc aagcuaguau cauguugguu   240
guuuauugcu uagcaugaug cgaaaauuau caauaaacua cacacguaga agauuugua    300 ucaggaccuc ugg                                                   313

<210> SEQ ID NO 157
<211> LENGTH: 302
<212> TYPE: DNA
<213> ORGANISM: Streptococcus agalactiae (NCTC 8181)

<400> SEQUENCE: 157
acaggcatta tgaggtatat tttgcgactc atcggcagat gtaaaatgcc agttaaatat    60
aactgcaaaa aatacaaatt cttacgcatt agctgcctaa aaaacagcct gcgtgatctt   120
cacaagattg tttgcgtttt gctagaaggt cttatttatc agcaaactac gtttggctac   180
tgtctagtta gttaaaaaga gatttataga ctcgctatgt gagggcttga gttatgtgtc   240
atcacctagt taaatcaata cataacctat agttgtagac aaatatatta gcagatgttt   300
gg                                                              302

<210> SEQ ID NO 158
<211> LENGTH: 302
<212> TYPE: RNA
<213> ORGANISM: Streptococcus agalactiae (NCTC 8181)

<400> SEQUENCE: 158
acaggcauua ugagguauau uuugcgacuc aucggcagau guaaaaugcc aguuaaauau    60
aacugcaaaa aauacaaauu cuuacgcauu agcugccuaa aaaacagccu gcgugaucuu   120
cacaagauug uuugcguuuu gcuagaaggu cuuauuuauc agcaaacuac guuuggcuac   180
ugucuaguua guuaaaaaga gauuuauaga cucgcuaugu gagggcuuga guuauguguc   240
aucaccuagu uaaaucaaua cauaaccuau aguuguagac aaauauauua gcagauguuu   300
gg                                                              302

<210> SEQ ID NO 159
<211> LENGTH: 168
<212> TYPE: DNA
<213> ORGANISM: Bordetella bronchiseptica

<400> SEQUENCE: 159
ggggccgatc cggattcgac gtgggtcatg aaacagctca aggcatgccg agcaccagta    60
agctcgttaa ccactggaa cactacaaac gccaacgacg agcgtttcgc tctcgccgct    120
taagcggtga gccgctgcac tgatctgtcc ttgggtcacg cggggggaa             168

<210> SEQ ID NO 160
<211> LENGTH: 168
```

```
<212> TYPE: RNA
<213> ORGANISM: Bordetella bronchiseptica

<400> SEQUENCE: 160
ggggccgauc cggauucgac gugggucaug aaacagcuca aggcaugccg agcaccagua 60
agcucguuaa uccacuggaa cacuacaaac gccaacgacg agcguuucgc ucucgccgcu 120
uaagcgguga gccgcugcac ugaucugucc uugggucacg cgggggaa 168

<210> SEQ ID NO 161
<211> LENGTH: 426
<212> TYPE: DNA
<213> ORGANISM: Chlamydia pneumoniae (CWL029)

<400> SEQUENCE: 161
gggggtgtat aggtttcgac ttgaaaatga agtgttaatt gcatgcggag ggcgttggct 60
ggcctcctaa aaagccaaca aaacaataaa tgccgaacct aaggctgaat gcgaaattat 120
tagcttgttt gactcagtag aggaaagact agctgcttaa ttagcaaaag ttgttagcta 180
gataatctct aggtaacccg gtatctgcga gctccaccag aggcttgcaa aataccgtca 240
tttatctggt tggaacttac tttctctaat tctcaaggaa gttcgttcga gatttttgag 300
agtcattggc tgctatagag gcttctagct aagggagtcc aatgtaaaca attctagaag 360
ataagcatgt agaggttagc agggagtttg tcaaggacga gagttcgagt ctctccacct 420
ccacca 426

<210> SEQ ID NO 162
<211> LENGTH: 426
<212> TYPE: RNA
<213> ORGANISM: Chlamydia pneumoniae (CWL029)

<400> SEQUENCE: 162
gggggguguau agguuucgac uugaaaauga aguguuaauu gcaugcggag ggcguuggcu 60
ggccuccuaa aaagccaaca aaacaauaaa ugccgaaccu aaggcugaau gcgaaauuau 120
uagcuuguuu gacucaguag aggaaagacu agcugcuuaa uuagcaaaag uuguuagcua 180
gauaaucucu agguaacccg guaucugcga gcuccaccag aggcuugcaa aauaccguca 240
uuuaucuggu uggaacuuac uuucucuaau ucucaaggaa guucguucga gauuuuugag 300
agucauuggc ugcuauagag gcuucuagcu aagggagucc aauguaaaca auucuagaag 360
auaagcaugu agagguuagc agggaguuug ucaaggacga gaguucgagu cucuccaccu 420
ccacca 426

<210> SEQ ID NO 163
<211> LENGTH: 421
<212> TYPE: DNA
<213> ORGANISM: Francisella tularensis
<400> SEQUENCE: 163
gggggcgaat atggtttcga catgaatgtc aaaatctaag gtgcatgccg aggaagtacc 60
gtaacctcgt taataacagt acaaatgcca ataataactg gcaacaaaaa agcaaaccgc 120
gtagcggcta acgacagcaa ctttgctgct gttgctaaag ctgcctagtc tagcttaata 180
atctagatgc gcacggatat gatagtcttt cttatgacac tatctataca tccgttcata 240
ttccgcataa gacggtcttt gctttttgtc tgggagttaa ggctgtattt aacagactcg 300
ctaactatta ccctggctaa ttggggaata gtcaagctaa actcaaatag attagcctaa 360
gcatgtagat ccaaagatct agagtttgtg gacgcgggtt caaatcccgc cgcctccacc 420

<210> SEQ ID NO 164
<211> LENGTH: 421
<212> TYPE: RNA
<213> ORGANISM: Francisella tularensis

<400> SEQUENCE: 164

| | |
|---|---|
| gggggcgaau augguuucga caugaauguc aaaucuaag gugcaugccg aggaaguacc | 60 |
| guaaccucgu uaauaacagu acaaaugcca auaauaacug gcaacaaaaa agcaaaccgc | 120 |
| guagcggcua acgacagcaa cuuugcugcu guugcuaaag cugccuaguc uagcuuaaua | 180 |
| aucuagaugc gcacggauau gauagucuuu cuuaugacac uaucuauaca uccguucaua | 240 |
| uuccgcauaa gacggucuuu gcuuuugucu ugggaguuaa ggcuguauuu aacagacucg | 300 |
| cuaacuauua cccuggcuaa uuggggaaua gucaagcuaa acucaaauag auuagccuaa | 360 |
| gcauguagau ccaaagaucu agaguuugug gacgcgegguu caaauccege cgccuccacc | 420 |
| a | 421 |

<210> SEQ ID NO 165
<211> LENGTH: 330
<212> TYPE: DNA
<213> ORGANISM: Guillardia theta (plastid)

<400> SEQUENCE: 165

| | |
|---|---|
| ggggctgatt tggattcgac atataaattt gcgtgtttca ttatgaagca agtcaagttt | 60 |
| aatgatcttg taaaaaacat taaagtacaa ataaatgcaa gcaatatagt ttcatttagt | 120 |
| tcaaaacgtt tagtctcttt tgcataagca aaatgtgtta ataactttct tagtagaaat | 180 |
| tggagaagtt tactaagatt tatatttact ccataattat tttaaagatg gtaaaaaggt | 240 |
| gattcatcat ttgtatgttt ctaaactttg tgaaagaata gtgggctcca tttataatga | 300 |
| acgtgggttc aaatcccacc agctccacca | 330 |

<210> SEQ ID NO 166
<211> LENGTH: 330
<212> TYPE: RNA
<213> ORGANISM: Guillardia theta (plastid)

<400> SEQUENCE: 166

| | |
|---|---|
| ggggcugauu uggauucgac auauaaauuu gcguguuuca uuaugaagca agucaaguuu | 60 |
| aaugaucuug uaaaaaacau uaaaguacaa auaaaugcaa gcaauauagu uucauuuagu | 120 |
| ucaaaacguu uagucucuuu ugcauaagca aaaugguguua auaacuuucu uaguagaaau | 180 |
| uggagaaguu uacuaagauu uauauuuacu ccauaauuau uuuaaagaug guaaaaaggu | 240 |
| gauucaucau uuguauguuu cuaaacuuug ugaaagaaua gugggcucca uuuauaauga | 300 |
| acgugggguuc aaaucccacc agcuccacca | 330 |

<210> SEQ ID NO 167
<211> LENGTH: 348
<212> TYPE: DNA
<213> ORGANISM: Thalassiosira Weissflogii (plastid)

<400> SEQUENCE: 167

| | |
|---|---|
| ggggctgatt tggtttcgac atttaaaact tctttctatg tgtcaggtca agtttgtat | 60 |
| tctttgtaaa aaaatactaa aatactaata aatgctaata atataatacc gtttattttt | 120 |
| aaagcagtaa aaacaaaaaa agaagcaatg gctttaaatt ttgctgtata gttcattaac | 180 |

-continued

```
ttaggttatt aaatattttt tcattataac tggactttc tctagtttat agtttagaat    240
aaatttaaat tttgcaaaac tcgttcgaaa attttcgggc taaacctgta aacgcaaata    300
ctaagaaatt ttagatggac atgggttcaa ttcccatcag ttccacca                348
```

<210> SEQ ID NO 168
<211> LENGTH: 348
<212> TYPE: RNA
<213> ORGANISM: Thalassiosira Weissflogii (plastid)

<400> SEQUENCE: 168

```
ggggcugauu ugguuucgac auuuaaaacu ucuuucuaug ugucagguca aguuuguau     60 ucuuuguaaa aaaauacuaa aauacuaaua aaugcuaaua auauaauacc guuuauuuuu    120
aaagcaguaa aaacaaaaaa agaagcaaug gcuuuaaauu uugcuguaua guucauuaac    180
uuagguuauu aaauauuuuu ucauuauaac uggacuuuuc ucuaguuuau aguuuagaau    240
aaauuuaaau uuugcaaaac ucguucgaaa auuuucgggc uaaaccugua aacgcaaaua    300
cuaagaaauu uuagauggac auggguucaa uucccaucag uuccacca                348
```

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence:V. cholerae
      tmRNA specific probe

<400> SEQUENCE: 169

```
aacgaatggc taacctgaa                                                 19
```

<210> SEQ ID NO 170
<211> LENGTH: 17
<212> TYPE: DNA
<213> ORGANISM: Artificial Sequence
<220> FEATURE:
<223> OTHER INFORMATION: Description of Artificial Sequence:Universal
      ssrA/tmRNA 5'  in vitro amplification primer

<400> SEQUENCE: 170

```
gggmytacgg wttcgac                                                   17
```

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence:Universal
      ssrA/tmRNA 3' in vitro amplification primer

<400> SEQUENCE: 171

```
gggartcgaa ccrsgtcc                                                  18
```

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence:5' Listeria
      genus specific PCR amplification primer

<400> SEQUENCE: 172

```
aaagccaata ataactgg                                                  18
```

```
<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence:3' Listeria
      genus specific amplification primer

<400> SEQUENCE: 173
ccagaaatat cggcactt                                                    18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence:Listeria
      genus specific hybridisation probe

<400> SEQUENCE: 174
gtgagaccct taccgtag                                                    18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence:Listeria
      monocytogenes species specific hybridisation probe

<400> SEQUENCE: 175
tctatttaac cccagacg                                                    18

<210> SEQ ID NO 176
<211> LENGTH: 348
<212> TYPE: DNA
<213> ORGANISM: Helicobacter pylori

<400> SEQUENCE: 176
tggggatgtt acggtttcga caggggtagt tcgagcttag gtggcgagtc gaggggatcg       60
gcctcgttaa aacgtcaaag cctataactg gcaaacaaca aaacaacttc gctttagcag      120
cttaataagc tcttagcggt tcctccctcc atcgcccatg tggtagggta agggactcaa      180
attaagtggg ctacgctgga ttccaccgtc tgaggatgaa agaagagaac aaccagacta      240
gctacccgga cgcccgtcga taggcagatg gagtagcgaa tcgcgaatat atcgactaca      300
ctcgtagaag cttaagtgcc gatattcttg gacgtgggtt cgactccc                  348

<210> SEQ ID NO 177
<211> LENGTH: 348
<212> TYPE: RNA
<213> ORGANISM: Helicobacter pylori

<400> SEQUENCE: 177
uggggauguu acguuucga caggggtagu ucgagcuuag guggcgaguc gaggggaucg       60
gccucguuaa aacgucaaag ccuauaacug gcaaacaaca aaacaacuuc gcuuuagcag      120
cuuaauaagc ucuuagcggu uccucccucc aucgcccaug ugguagggua agggacucaa      180 auuaagugggg cuacgcugga uuccaccguc ugaggaugaa agaagagaac aaccagacua     240
gcuacccgga cgcccgucga uaggcagaug gaguagcgaa ucgcgaauau aucgacuaca      300
cucguagaag cuuaagugcc gauauucuug gacgugggu cgacuccc                   348

<210> SEQ ID NO 178
```

-continued

```
<211> LENGTH: 344
<212> TYPE: DNA
<213> ORGANISM: Helicobacter pylori

<400> SEQUENCE: 178
tggggacgtt acggtttcga cagggatagt tcgagcttag gttgcgagtc gaggggatcg      60
gcctcgttaa aacgtcaaag cctataattg gcaaacaaaa caatctttct ttagctgctt     120
aattgcacta aaggttcctc cctccatcgt ccatgtggta gggtaaggga ctcaaactaa     180
gtggactacg ccggagttcg ccgtctgagg acaaggaag agaacaacca gactagcaac      240
ttggaagcct gtcgataggc cgaagagttc gcgaaatgct aatatatcga ctacactcgt     300
agaagcttaa gtgccgatat ttttggacgt gggttcgatt ccct                      344

<210> SEQ ID NO 179
<211> LENGTH: 344
<212> TYPE: RNA
<213> ORGANISM: Helicobacter pylori

<400> SEQUENCE: 179 ugggacguu acgguuucga cagggauagu ucgagcuuag guugcgaguc gaggggaucg       60
gccucguuaa aacgucaaag ccuauaauug gcaaacaaaa caaucuuucu uuagcugcuu     120
aauugcacua aagguuccuc ccuccaucgu ccauguggua ggguaaggga cucaaacuaa     180
guggacuacg ccggaguucg ccgucugagg acaaggaag agaacaacca gacuagcaac      240
uuggaagccu gucgauaggc cgaagaguuc gcgaaaugcu aauauaucga cuacacucgu     300
agaagcuuaa gugccgauau uuuuggacgu ggguucgauu cccu                      344

<210> SEQ ID NO 180
<211> LENGTH: 322
<212> TYPE: DNA
<213> ORGANISM: Listeria seeligeri (NCTC 11856)

<400> SEQUENCE: 180
acagggatag ttcgagcttg agttgcgagt cgggggggatc gtcctcgtta tcaacgtcaa     60
agccaataat aactggcaaa gaaaacaaa acctagcttt cgctgcctaa taagcagtag     120
catagctgat cctccgtgca tcgcccatgt gctacggaaa gggtctcact ttaagtgggc     180
tacactaaat aatctccgtc tggggttagt tagaagagct taatcagact agctgaatgg     240
aagcctgtta ccgggctgat gtttatgcga aatactaata cggtgactac gctcgtagat     300
atttaagtgc ccatatttct gg                                              322

<210> SEQ ID NO 181
<211> LENGTH: 322
<212> TYPE: RNA
<213> ORGANISM: Listeria seeligeri (NCTC 11856)

<400> SEQUENCE: 181
acagggauag uucgagcuug aguugcgagu cgggggggauc gucccucguua ucaacgucaa    60 agccaauaau aacuggcaaa gaaaacaaa accuagcuuu cgcugccuaa uaagcaguag     120
cauagcugau ccuccgugca ucgcccaugu gcuacggaaa ggguccucacu uuaagugggc     180 uacacuaaau aaucuccguc uggguuagu uagaagagcu uaaucagacu agcugaaugg      240
aagccuguua ccgggcugau guuuaugcga aauacuaaua cggugacuac gcucguagau     300
auuuaagugc ccauauuucu gg                                              322

<210> SEQ ID NO 182
```

<211> LENGTH: 322
<212> TYPE: DNA
<213> ORGANISM: Listeria ivanovii (NCTC 11846)

<400> SEQUENCE: 182
acagggatag ttcgagcttg agttgcgagt cgggggggatc gtcctcgtta ttaacgtcaa 60
agccaataat aactggcaaa gaaaaacaaa acctagcttt cgctgcctaa taagcagtag 120
catagctgat cctccgtgca tcgcccatgt gctacggtaa gggtctcact ttaagtgggc 180
tacactaaat aatctccgtc tggggttagt tagaagagct taatcagact agctgaatgg 240
aagcctgtta ccgggctgat gtttatgcga aatgctaata cggtgactac gctcgtagat 300
atttaagtgc cgatatttct gg 322

<210> SEQ ID NO 183
<211> LENGTH: 321
<212> TYPE: RNA
<213> ORGANISM: Listeria ivanovii (NCTC 11846)

<400> SEQUENCE: 183
acagggauag uucgagcuug aguugcgagu cggggggauc guccucguua uuaacgucaa 60
agccaauaau aacuggcaaa gaaaaacaaa accuagcuuu cgcugccuaa uaagcaguag 120
cauagcugau ccuccgugca ucgcccaugu gcuacgguaa gggucucacu uuaagugggc 180
uacacuaaau aaucuccguc ugggguuagu uagaagagcu uaaucagacu agcugaaugg 240
aagccuguua ccgggcugau guuuaugcga aaugcuaaua cggugacucg cucguagaua 300
uuuaagugcc gauauuucug g 321

<210> SEQ ID NO 184
<211> LENGTH: 319
<212> TYPE: DNA
<213> ORGANISM: Mycobacterium africanum

<400> SEQUENCE: 184
acttcgcgca tcgaatcaag ggaagcgtgc cggtgcaggc aagagaccac cgtaagcgtc 60
gttgcgacca aataagcgcc gattcacatc agcgcgacta cgctctcgct gcctaagcga 120
cggctagtct gtcagaccgg gaacgccctc ggcccggacc ctggcatcag ctagagggat 180
ccaccgatga gtccggtcgc gggactcctc gggacaacca cagcgactgg gatcgtcatc 240
tcggctagtt cgcgtgaccg ggagatccga gcagaggcat agcgaactgc gcacggagaa 300
gccttgaggg aatgccgta 319

<210> SEQ ID NO 185
<211> LENGTH: 319
<212> TYPE: RNA
<213> ORGANISM: Mycobacterium africanum

<400> SEQUENCE: 185
acuucgcgca ucgaaucaag ggaagcgugc cggugcaggc aagagaccac cguaagcguc 60
guugcgacca aauaagcgcc gauucacauc agcgcgacua cgcucucgcu gccuaagcga 120
cggcuagucu gucagaccgg gaacgcccuc ggcccggacc cuggcaucag cuagagggau 180
ccaccgauga guccggucgc gggacuccuc gggacaacca cagcgacugg gaucgucauc 240
ucggcuaguu cgcgugaccg ggagauccga gcagaggcau agcgaacugc gcacggagaa 300
gccuugaggg aaugccgua 319

<210> SEQ ID NO 186

```
<211> LENGTH: 319
<212> TYPE: DNA
<213> ORGANISM: Mycobacterium gordonae

<400> SEQUENCE: 186
acttcgcgca tcgaatcaag ggaagcgtgc cggtgcaggc aagagaccac cgtaagcgtc    60
gttgcaacca tataagcgcc gattcacatc agcgcgacta cgctctcgct gcctaagcga   120
cggctagtct gtcggaccgg gaacgccctc gccccggacc ccggcatcag ctagagggat   180
caaccgatga gttcggtcgc gggactcatc gggacaccaa cagcgactgg gatcgtcatc   240
ctggctagtc cgtgtgacca ggagatccga gcagagacat agcggactgc gcacggagaa   300
gccttgaggg aatgccgta                                                319

<210> SEQ ID NO 187
<211> LENGTH: 319
<212> TYPE: RNA
<213> ORGANISM: Mycobacterium gordonae

<400> SEQUENCE: 187
acuucgcgca ucgaaucaag ggaagcgugc cggugcaggc aagagaccac cguaagcguc    60
guugcaacca uauaagcgcc gauucacauc agcgcgacua cgcucucgcu gccuaagcga   120
cggcuagucu gucggaccgg gaacgcccuc gccccggacc ccggcaucag cuagagggau   180
caaccgauga guucggucgc gggacucauc gggacaccaa cagcgacugg gaucgucauc   240
cuggcuaguc cgugugacca ggagauccga gcagagacau agcggacugc gcacggagaa   300
gccuugaggg aaugccgua                                                319

<210> SEQ ID NO 188
<211> LENGTH: 319
<212> TYPE: DNA
<213> ORGANISM: Mycobacterium kansasii

<400> SEQUENCE: 188
acttcgcgca tcgaatcaag ggaagcgtgc cggtgcaggc aagagaccac cgtaagcgtc    60
gttgcaacca aataagcgcc gattcacatc agcgcgacta cgctctcgct gcctaagcga   120
cggctagtct gtcagaccgg gaccgccctc gacccggact ctggcatcag ctagagggat   180
caaccgatga gttcggtcgc gggactcgtc gggacaccaa cagcgactgg gatcgtcatc   240
ctggctagtt cgcgtgacca ggagatccga gcagaggcat agcgaactgc gcacggagaa   300
gccttgaggg aatgccgta                                                319

<210> SEQ ID NO 189
<211> LENGTH: 319
<212> TYPE: RNA
<213> ORGANISM: Mycobacterium kansasii

<400> SEQUENCE: 189
acuucgcgca ucgaaucaag ggaagcgugc cggugcaggc aagagaccac cguaagcguc    60
guugcaacca aauaagcgcc gauucacauc agcgcgacua cgcucucgcu gccuaagcga   120
cggcuagucu gucagaccgg gaccgcccuc gacccggacu cuggcaucag cuagagggau   180
caaccgauga guucggucgc gggacucguc gggacaccaa cagcgacugg gaucgucauc   240
cuggcuaguu cgcgugacca ggagauccga gcagaggcau agcgaacugc gcacggagaa   300
gccuugaggg aaugccgua                                                319

<210> SEQ ID NO 190
```

```
<211> LENGTH: 320
<212> TYPE: DNA
<213> ORGANISM: Mycobacterium chelonae

<400> SEQUENCE: 190
acagcgagtc tcgacttaag ggaagcgtgc cggtgcaggc aagagaccac cgtaagcgtc      60
attgcaacca attaagcgcc gattctcatc agcgcgacta cgcactcgct gcctaagcga     120
ctgcgtgtct gtcagaccgg gagcgccctc agcccggacc ctggcatcag ctagagggac     180
aaactacggg ttcggtcgcg ggacccgtag ggacatcaaa cagcgactgg gatcgtcatc     240
tcggcttgtt cgcgggaccg agagatccaa gtagaggcat agcgaactgc gcacggagaa     300
gccttaatga acggccgttg                                                 320

<210> SEQ ID NO 191
<211> LENGTH: 320
<212> TYPE: RNA
<213> ORGANISM: Mycobacterium chelonae

<400> SEQUENCE: 191
acagcgaguc ucgacuuaag ggaagcgugc cggugcaggc aagagaccac cguaagcguc      60
auugcaacca auuaagcgcc gauucucauc agcgcgacua cgcacucgcu gccuaagcga     120
cugcgugucu gucagaccgg gagcgcccuc agcccggacc cuggcaucag cuagagggac     180
aaacuacggg uucggucgcg ggacccguag ggacaucaaa cagcgacugg gaucgucauc     240
ucggcuuguu cgcgggaccg agagauccaa guagaggcau agcgaacugc gcacggagaa     300
gccuuaauga acggccguug                                                 320

<210> SEQ ID NO 192
<211> LENGTH: 320
<212> TYPE: DNA
<213> ORGANISM: Mycobacterium szulgai

<400> SEQUENCE: 192
acttcgcgca tcgaatcaag ggaagcgtgc cggtgcaggc aagagaccac cgtaagcgtc      60
gttgcaacca attaagcgcc gagaacactc agcgcgactt cgctctcgct gcctaagcga     120
cagcaagtcc gtcagaccgg gaaagccctc gacccggacc ctggcgtcat ctagagggat     180
ccaccggtga gttcggtcgc gggactcatc gggacaccaa cagcgactgg gatcgtcatc     240
ctggctagtt cgcgtgacca ggagatccga gtagagacat agcgaactgc gcacggagaa     300
gccttgaggg aatgccgtag                                                 320

<210> SEQ ID NO 193
<211> LENGTH: 320
<212> TYPE: RNA
<213> ORGANISM: Mycobacterium szulgai

<400> SEQUENCE: 193
acuucgcgca ucgaaucaag ggaagcgugc cggugcaggc aagagaccac cguaagcguc      60
guugcaacca auuaagcgcc gagaacacuc agcgcgacuu cgcucucgcu gccuaagcga     120 cagcaaguccc gucagaccgg gaaagcccuc gacccggacc cuggcgucau cuagagggau    180
ccaccgguga guucggucgc gggacucauc gggacaccaa cagcgacugg gaucgucauc     240
cuggcuaguu cgcgugacca ggagauccga guagagacau agcgaacugc gcacggagaa     300
gccuugaggg aaugccguag                                                 320

<210> SEQ ID NO 194
```

```
<211> LENGTH: 320
<212> TYPE: DNA
<213> ORGANISM: Mycobacterium malmoense

<400> SEQUENCE: 194
acttcgcgca tcgaatcaag ggaagcgtgc cggtgcaggc aagagaccac cgtaagcgtc      60
gttgcaacca tataagcgcc gtttcaacac agcgcgacta cgctctcgct gcctaagcga     120
cagctagtcc gtcagaccgg gaacgccctc gacccgagc ctggcgtcag ctggagggat      180
ccaccggtga gtccggtcgc gggactcatc gggacataca cagcgactgg gatcgtcatc     240
ctggctggtt cgcgtgaccg ggagatccga gcagaggcat agcgaactgc gcacggagaa     300
gccttgaggg aatgccgtag                                                 320

<210> SEQ ID NO 195
<211> LENGTH: 320
<212> TYPE: RNA
<213> ORGANISM: Mycobacterium malmoense

<400> SEQUENCE: 195
acuucgcgca ucgaaucaag ggaagcgugc cggugcaggc aagagaccac cguaagcguc      60
guugcaacca uauaagcgcc guuucaacac agcgcgacua cgcucucgcu gccuaagcga     120
cagcuagucc gucagaccgg gaacgcccuc gacccgagc cuggcgucag cuggagggau      180
ccaccgguga guccggucgc gggacucauc gggacauaca cagcgacugg gaucgucauc     240
cuggcugguu cgcgugaccg ggagauccga gcagaggcau agcgaacugc gcacggagaa     300
gccuugaggg aaugccguag                                                 320

<210> SEQ ID NO 196
<211> LENGTH: 321
<212> TYPE: DNA
<213> ORGANISM: Mycobacterium flavescens

<400> SEQUENCE: 196
acttcgagcg tcgaatcaag ggaagcgtgc cggtgcaggc aagagaccac cgtaagcgtc      60
gttgcaacca attaagcgcc gattccaatc agcgcgacta cgcactcgct gcctaagcga     120
ctgcgtgtct gtcagcccgg gagagccctc gacccggtgt ctggcatcag ctagagggat     180
aaaccggtgg gtccggtcgc gggactcatc gggacatcaa acagcgactg gatcgtcat     240 cctgacttgt tcgcgtgatc aggagatccg agtagagaca tagcgaactg cgcacggaga    300
agccttgagg gaacgccgta g                                               321

<210> SEQ ID NO 197
<211> LENGTH: 321
<212> TYPE: RNA
<213> ORGANISM: Mycobacterium flavescens

<400> SEQUENCE: 197
acuucgagcg ucgaaucaag ggaagcgugc cggugcaggc aagagaccac cguaagcguc      60
guugcaacca auuaagcgcc gauuccaauc agcgcgacua cgcacucgcu gccuaagcga     120
cugcgugucu gucagcccgg gagagcccuc gacccggugu cuggcaucag cuagagggau     180
aaaccggugg guccggucgc gggacucauc gggacaucaa acagcgacug gaucgucau     240 ccugacuugu ucgcgugauc aggagauccg aguagagaca uagcgaacug cgcacggaga    300
agccuugagg gaacgccgua g                                               321

<210> SEQ ID NO 198
```

```
<211> LENGTH: 320
<212> TYPE: DNA
<213> ORGANISM: Mycobacterium marinum

<400> SEQUENCE: 198
acttcgcgca tcgaatcaag ggaagcgtgc cggtgcaggc aagagaccac cgtaagcgtc      60
gatgcaacta gataagcgcc gattcacatc agcgcgacta cgctctcgct gcctaagcga     120
cggctagtct gtcggaccgg gaacgccctc gccccggacc ccggcatcag ctagagggat     180
caaccgatga gttcggtcgc ggggctcatc gggacatcaa cagcgactgg gatcgtcatc     240
ctggctagtt cgcgtgacca ggagatccga gcagagacct agcggactgc gcacggagaa     300
gccttgaggg aatgccgtag                                                  320

<210> SEQ ID NO 199
<211> LENGTH: 320
<212> TYPE: RNA
<213> ORGANISM: Mycobacterium marinum

<400> SEQUENCE: 199
acuucgcgca ucgaaucaag ggaagcgugc cggugcaggc aagagaccac cguaagcguc      60
gaugcaacua gauaagcgcc gauucacauc agcgcgacua cgcucucgcu gccuaagcga     120
cggcuagucu gucggaccgg gaacgcccuc gccccggacc ccggcaucag cuagagggau     180
caaccgauga guucggucgc ggggcucauc gggacaucaa cagcgacugg gaucgucauc     240
cuggcuaguu cgcgugacca ggagauccga gcagagaccu agcggacugc gcacggagaa     300
gccuugaggg aaugccguag                                                  320

<210> SEQ ID NO 200
<211> LENGTH: 319
<212> TYPE: DNA
<213> ORGANISM: Mycobacterium microti

<400> SEQUENCE: 200
acttcgcgca tcgaatcaag ggaagcgtgc cggtgcaggc aagagaccac cgtaagcgtc      60
gttgcgacca aataagcgcc gattcacatc agcgcgacta cgctctcgct gcctaagcga     120
cggctagtct gtcagaccgg gaacgccctc ggcccggacc ctggcatcag ctagagggat     180
ccaccgatga gtccggtcgc gggactcctc gggacagcca cagcgactgg gatcgtcatc     240
tcggctagtt cgcgtgaccg ggagatccga gcagaggcat agcgaactgc gcacggagaa     300
gccttgaggg aatgccgta                                                   319

<210> SEQ ID NO 201
<211> LENGTH: 319
<212> TYPE: RNA
<213> ORGANISM: Mycobacterium microti

<400> SEQUENCE: 201
acuucgcgca ucgaaucaag ggaagcgugc cggugcaggc aagagaccac cguaagcguc      60
guugcgacca aauaagcgcc gauucacauc agcgcgacua cgcucucgcu gccuaagcga     120
cggcuagucu gucagaccgg gaacgcccuc ggcccggacc cuggcaucag cuagagggau     180
ccaccgauga guccggucgc gggacuccuc gggacagcca cagcgacugg gaucgucauc     240
ucggcuaguu cgcgugaccg ggagauccga gcagaggcau agcgaacugc gcacggagaa     300
gccuugaggg aaugccgua                                                   319

<210> SEQ ID NO 202
```

<211> LENGTH: 321
<212> TYPE: DNA
<213> ORGANISM: Mycobacterium smegmatis

<400> SEQUENCE: 202
acttcgagca tcgaatccag ggaagcgtgc cggtgcaggc aagagaccac cgtaagcgtc    60
gttgcaacca attaagcgcc gattccaatc agcgcgacta cgccctcgct gcctaagcga   120
cggctggtct gtcagaccgg gagtgccctc ggcccggatc ctggcatcag ctagagggac   180
ccacccacgg gttcggtcgc gggacctgtg gggacatcaa acagcgactg ggatcgtcat   240
ctcggcttgt tcgtgtgacc gggagatccg agtagagaca tagcgaactg cgcacggaga   300
agcctcgagg acatgccgta g                                             321

<210> SEQ ID NO 203
<211> LENGTH: 321
<212> TYPE: RNA
<213> ORGANISM: Mycobacterium smegmatis

<400> SEQUENCE: 203
acuucgagca ucgaauccag ggaagcgugc cggugcaggc aagagaccac cguaagcguc    60
guugcaacca auuaagcgcc gauuccaauc agcgcgacua cgcccucgcu gccuaagcga   120
cggcuggucu gucagaccgg gagugcccuc ggcccggauc cuggcaucag cuagagggac   180
ccacccacgg guucggucgc gggaccugug gggacaucaa acagcgacug ggaucgucau   240
cucggcuugu ucgugugacc gggagauccg aguagagaca uagcgaacug cgcacggaga   300
agccucgagg acaugccgua g                                             321

<210> SEQ ID NO 204
<211> LENGTH: 320
<212> TYPE: DNA
<213> ORGANISM: Mycobacterium xenopi

<400> SEQUENCE: 204
acttcgcgca tcgaatcaag ggaagcgtgc cggtgcaggc aagagaccac cgtaagcgtc    60
gttgcaacta aataagcgcc gattcacatc agcgcgacta cgctctcgct gcctaagcga   120
cagctagtcc gtcaggccgg gagttccctc gacccggatc ctggcgtcag ctagagggat   180
ccaccgatgg gttcggtcgc gggacccatc gggacaccac acagcgactg ggatcgccgt   240
cccggctagt tcgcgagacc gggagatccg agtaagggca aagcgaactg cgcacggaga   300
agccttgagg gtatgccgta                                               320

<210> SEQ ID NO 205
<211> LENGTH: 320
<212> TYPE: RNA
<213> ORGANISM: Mycobacterium xenopi

<400> SEQUENCE: 205
acuucgcgca ucgaaucaag ggaagcgugc cggugcaggc aagagaccac cguaagcguc    60
guugcaacua aauaagcgcc gauucacauc agcgcgacua cgcucucgcu gccuaagcga   120
cagcuagucc gucaggccgg gaguucccuc gacccggauc cuggcgucag cuagagggau   180
ccaccgaugg guucggucgc gggacccauc gggacaccac acagcgacug ggaucgccgu   240
cccggcuagu ucgcgagacc gggagauccg aguaagggca aagcgaacug cgcacggaga   300
agccuugagg guaugccgua                                               320

<210> SEQ ID NO 206

-continued

```
<211> LENGTH: 320
<212> TYPE: DNA
<213> ORGANISM: Mycobacterium intracellulare

<400> SEQUENCE: 206
acttcgcgca tcgaatcaag ggaagcgtgc cggtgcaggc aaccgaccac cgtaagcgtc      60
gttgcaaaca gataagcgcc gattcacatc agcgcgacta cgctctcgct gcctaagcga     120
cagctagtcc gtcagaccgg gaacgccctc gacccggagc ctggcgtcag ctagagggat     180
ccaccgatga gtccggtcgc gggacttatc gggacaccaa cagcgactgg gatcgtcatc     240
tcggcttgtt cgcgtgaccg ggagatccga gtagaggcat agcgaactgc gcacggagaa     300
gtcttgaggg aatgccgtag                                                 320

<210> SEQ ID NO 207
<211> LENGTH: 320
<212> TYPE: RNA
<213> ORGANISM: Mycobacterium intracellulare

<400> SEQUENCE: 207
acuucgcgca ucgaaucaag ggaagcgugc cggugcaggc aaccgaccac cguaagcguc      60
guugcaaaca gauaagcgcc gauucacauc agcgcgacua cgcucucgcu gccuaagcga     120
cagcuagucc gucagaccgg gaacgcccuc gacccggagc cuggcgucag cuagagggau     180
ccaccgauga guccggucgc gggacuuauc gggacaccaa cagcgacugg gaucgucauc     240
ucggcuuguu cgcgugaccg ggagauccga guagaggcau agcgaacugc gcacggagaa     300
gucuugaggg aaugccguag                                                 320

<210> SEQ ID NO 208
<211> LENGTH: 320
<212> TYPE: DNA
<213> ORGANISM: Mycobacterium scrofulaceum

<400> SEQUENCE: 208
acatcgcgca tcgaatcaag ggaagcgtgc cggtgcaggc aagagaccac cgtaagcgtc      60
gttgcaacca attaagcgcc gattcacatc agcgcgacta cgctctcgct gcctaagcga     120
cagctagtcc gtcagaccgg gaaagccctc gacccggagc ctggcgtcag ctagagggat     180
caaccgatga gttcggtcgc gggactcatc gggacaccaa cagcgactgg gatcgtcatc     240
ctggctagtc cgcgtgacca ggagatccga gcagaggcat agcggactgc gcacggagaa     300
gtcttgaggg aatgccgttg                                                 320

<210> SEQ ID NO 209
<211> LENGTH: 320
<212> TYPE: RNA
<213> ORGANISM: Mycobacterium scrofulaceum

<400> SEQUENCE: 209
acaucgcgca ucgaaucaag ggaagcgugc cggugcaggc aagagaccac cguaagcguc      60
guugcaacca auuaagcgcc gauucacauc agcgcgacua cgcucucgcu gccuaagcga     120
cagcuagucc gucagaccgg gaaagcccuc gacccggagc cuggcgucag cuagagggau     180
caaccgauga guucggucgc gggacucauc gggacaccaa cagcgacugg gaucgucauc     240
cuggcuaguc cgcgugacca ggagauccga gcagaggcau agcggacugc gcacggagaa     300
gucuugaggg aaugccguug                                                 320

<210> SEQ ID NO 210
```

```
<211> LENGTH: 326
<212> TYPE: DNA
<213> ORGANISM: Nocardia asteroides

<400> SEQUENCE: 210
actgtgtgcg ccgaggtagg ggaagcgtgt cggtgcaggc tggagaccac cgttaagcgt     60
cgcggcaacc aattaagcgc cgattccaat cagcgcgact acgccctcgc tgcctgatca    120
gcgacggcta gctgtcggcc cgggttgtgt tcccgaaccc ggatgccggc atcatctcag    180
ggaactcacc gtgttcgccg gtcgcggacg gacacgggac agcaaacagc gactgggatc    240
gtcatctcgg cttgttcgcg tgaccgggag atccaagtag agacatagcg gactgcacac    300
ggagaagccc tactgactcg acacag                                         326

<210> SEQ ID NO 211
<211> LENGTH: 325
<212> TYPE: RNA
<213> ORGANISM: Nocardia asteroides

<400> SEQUENCE: 211
acugugugcg ccgagguagg ggaagcgugu cggugcaggc uggagaccac cguuaagcgu     60
cgcggcaacc aauuaagcgc cgauuccaau cagcgcgacu acgcccucgc ugccugauca    120
gcgacggcua gcugucggcc cgguugugu ucccgaaccc ggaugccggc aucaucucag    180
ggaacucacc guguucgccg gucgcggacg gacacgggac agcaaacagc gacugggauc    240
gucaucucgg cuuguucgcg ugaccgggag auccaaguag agacauagcg gcugcacacg    300
gagaagcccu acugacucga cacag                                          325

<210> SEQ ID NO 212
<211> LENGTH: 314
<212> TYPE: DNA
<213> ORGANISM: Salmonella enteritidis

<400> SEQUENCE: 212
acgggatttg cgaaacccaa ggtgcatgcc gaggggcggt tggcctcgta aaagccgca      60 aaaaatagt cgcaaacgac gaaacctacg ctttagcagc ttaataacct gcttagagcc    120
ctctctccct agcctccgct cttaggacgg ggatcaagag aggtcaaacc caaagagat    180 cgcgtggatg ccctgcctgg ggttgaagcg ttaaaacgaa tcaggctagt ctggtagtgg    240
cgtgtccgtc cgcaggtgcc aggcgaatgt aaagactgac taagcatgta gtaccgagga    300
tgtaggaatt tcgg                                                      314

<210> SEQ ID NO 213
<211> LENGTH: 314
<212> TYPE: RNA
<213> ORGANISM: Salmonella enteritidis

<400> SEQUENCE: 213
acgggauuug cgaaacccaa ggugcaugcc gaggggcggu uggccucgua aaagccgca      60 aaaaauagu cgcaaacgac gaaaccuacg cuuuagcagc uuaauaaccu gcuuagagcc    120 cucucuccu agccuccgcu cuuaggacgg ggaucaagag aggucaaacc caaagagau    180 cgcguggaug cccugccugg gguugaagcg uuaaaacgaa ucaggcuagu cugguagugg    240
cguguccguc cgcaggugcc aggcgaaugu aaagacugac uaagcaugua guaccgagga    300
uguaggaauu ucgg                                                      314

<210> SEQ ID NO 214
```

```
<211> LENGTH: 313
<212> TYPE: DNA
<213> ORGANISM: Staphylococcus epidermidis (NCTC 11047)

<400> SEQUENCE: 214 acagggtcc  cccgagctta  ttaagcgtgt  cggagggttg  gctccgtcat  caacacattt      60
cggttaaata  taactgacaa  atcaaacaat  aatttcgcag  tagctgcgta  atagccactg    120
catcgcctaa  cagcatctcc  tacgtgctgt  taacgcgatt  caaccctagt  aggatatgct    180
aaacactgcc  gcttgaagtc  tgtttagatg  aaatataatc  aagctagtat  catgttggtt    240
gtttattgct  tagcatgatg  cgaaaattat  caataaacta  cacacgtaga  aagatttgta    300
tcaggacctc  tgg                                                           313

<210> SEQ ID NO 215
<211> LENGTH: 313
<212> TYPE: RNA
<213> ORGANISM: Staphylococcus epidermidis (NCTC 11047)

<400> SEQUENCE: 215
acaggguucc  cccgagcuua  uuaagcgugu  cggagggguug  gcuccgucau  caacacauuu     60
cgguuaaaua  uaacugacaa  aucaaacaau  aauuucgcag  uagcugcgua  auagccacug    120
caucgccuaa  cagcaucucc  uacgugcugu  uaacgcgauu  caacccuagu  aggauaugcu    180
aaacacugcc  gcuugaaguc  uguuuagaug  aaauauaauc  aagcuaguau  cauguugguu    240
guuuauugcu  uagcaugaug  cgaaaauuau  caauaaacua  cacacguaga  aagauuugua    300
ucaggaccuc  ugg                                                           313

<210> SEQ ID NO 216
<211> LENGTH: 302
<212> TYPE: DNA
<213> ORGANISM: Streptococcus agalactiae (NCTC 8181)

<400> SEQUENCE: 216
acaggcatta  tgaggtatat  tttgcgactc  atcggcagat  gtaaaatgcc  agttaaatat      60
aactgcaaaa  aatacaaatt  cttacgcatt  agctgcctaa  aaaacagcct  gcgtgatctt    120
cacaagattg  tttgcgtttt  gctagaaggt  cttatttatc  agcaaactac  gtttggctac    180
tgtctagtta  gttaaaaaga  gatttataga  ctcgctatgt  gagggcttga  gttatgtgtc    240
atcacctagt  taaatcaata  cataacctat  agttgtagac  aaatatatta  gcagatgttt    300
gg                                                                        302

<210> SEQ ID NO 217
<211> LENGTH: 302
<212> TYPE: RNA
<213> ORGANISM: Streptococcus agalactiae (NCTC 8181)

<400> SEQUENCE: 217
acaggcauua  ugagguauau  uuugcgacuc  aucggcagau  guaaaaugcc  aguuaaauau      60
aacugcaaaa  aauacaaauu  cuuacgcauu  agcugccuaa  aaaacagccu  gcgugaucuu    120
cacaagauug  uuugcguuuu  gcuagaaggu  cuuauuuauc  agcaaacuac  guuuggcuac    180
ugucuaguua  guuaaaaaga  gauuuauaga  cucgcuaugu  gagggcuuga  guuaugugue    240 aucaccuagu  uaaaucaaua  cauaaccuau  aguuguagac  aaauauauua  gcagauguuu    300
gg                                                                        302

<210> SEQ ID NO 218
```

```
<211> LENGTH: 21
<212> TYPE: DNA
<213> ORGANISM: Artificial Sequence
<220> FEATURE:
<223> OTHER INFORMATION: Description of Artificial Sequence: Salmonella
      genus specificic probe

<400> SEQUENCE: 218
cgaatcaggc tagtctggta g                                              21

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probe for detection of
      tuberculosis complex

<400> SEQUENCE: 219
actcctcggg acarccacag cga                                            23

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probes for detection of M.avium
      and M. paratuberculosis sequences

<400> SEQUENCE: 220
gttgcaaata gataagcgcc                                                20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe for detection of M. avium
      and M. paratuberculosis sequences

<400> SEQUENCE: 221
tccgtcagcc cgggaacgcc                                                20

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide probe used in determination of
      tmRNA integrity after heat killing treatment of
      Listeria cells

<400> SEQUENCE: 222
ttttgttttt ctttgcca                                                  18

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide probe used in determination of
      tmRNA integrity after heat killing treatment of
      Escherichia coli cells

<400> SEQUENCE: 223
```

```
agttttcgtc gtttgcga                                                    18

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence:
      Degenerative oligonucleotide primer for amplification of all
      mycobacterial sequences

<400> SEQUENCE: 224
caggcaashg accaccgtaa                                                  20

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence:
      Degenerative oligonucleotide primers for amplification of all
      mycobacterial sequences

<400> SEQUENCE: 225
ggatctccyg rtcwcrcgra cwa                                              23

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer for amplification of M.
      avium and M. paratuberculosis sequences

<400> SEQUENCE: 226
tgccggtgca ggcaactg                                                    18

<210> SEQ ID NO 227
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer for amplification of M.
      avium and M. paratuberculosis sequences

<400> SEQUENCE: 227
cacgcgaaca agccagga                                                    18

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probe for the detection of
      Listeria ssrA gene sequences

<400> SEQUENCE: 228
cattaaactt tagcaaggaa gtg                                              23

<210> SEQ ID NO 229
<211> LENGTH: 228
<212> TYPE: DNA
<213> ORGANISM: Listeria monocytogenes

<400> SEQUENCE: 229
```

```
caaagaaaaa caaaacctag ctttcgctgc ctaataagca gtagcatagc tgatcctccg      60
tgcatcgccc atgtgctacg gtaagggtct cactctaagt gggctacact agttaatctc     120
cgtctgaggt taaatagaag agcttaatca gactagctga atggaagcct gttaccgggc     180
cgatgtttat gcgaaatgct aatacggtga ctacgctcgt agatattt                  228
```

```
<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<221> NAME/KEY: misc_feature
<222> LOCATION: (4)..(4)
<223> OTHER INFORMATION: n is a or c
<220> FEATURE:
<221> NAME/KEY: misc_feature
<222> LOCATION: (5)..(5)
<223> OTHER INFORMATION: n is c or t
<220> FEATURE:
<221> NAME/KEY: misc_feature
<222> LOCATION: (11)..(11)
<223> OTHER INFORMATION: n is a or t

<400> SEQUENCE: 230
gggnntacgg nttcgac                                                     17

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<221> NAME/KEY: misc_feature
<222> LOCATION: (5)..(5)
<223> OTHER INFORMATION: n is a or g
<220> FEATURE:
<221> NAME/KEY: misc_feature
<222> LOCATION: (13)..(13)
<223> OTHER INFORMATION: n is a or g
<220> FEATURE:
<221> NAME/KEY: misc_feature
<222> LOCATION: (14)..(14)
<223> OTHER INFORMATION: n is c or g

<400> SEQUENCE: 231
gggantcgaa ccnngtcc                                                    18

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 232
ggggctgatt ctggattcga c                                                21

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide primer
```

-continued

<400> SEQUENCE: 233
ggagttgaac ccccgtccg                                                19

<210> SEQ ID NO 234
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 234
tggtggagcc ggggg                                                    15

<210> SEQ ID NO 235
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 235
agcgacttgg cttc                                                     14

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 236
tacatgctta gcaaagatga                                               20

<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<221> NAME/KEY: misc_feature
<222> LOCATION: (9)..(9)
<223> OTHER INFORMATION: n is c or g
<220> FEATURE:
<221> NAME/KEY: misc_feature
<222> LOCATION: (16)..(16)
<223> OTHER INFORMATION: n is c or t

<400> SEQUENCE: 237
ggagatggng ggaatnga                                                 18

<210> SEQ ID NO 238
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 238
tggtggagat gacggga                                                  17

<210> SEQ ID NO 239

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 239
ggggatgtag aggttttg                                                       18
```

The invention claimed is:

1. A method of assaying a sample for a prokaryotic or eukaryotic organism which comprises contacting the sample with a nucleic acid sequence which is complementary to a target region of an ssrA gene or a fragment thereof;
   detecting and identifying nucleic acid sequences in the sample that bind to the complementary nucleic acid sequence; and
   correlating the nucleic acid sequences in the sample that bind to the complementary nucleic acid sequence to the presence and/or amount of one or more prokaryotic or eukaryotic organisms by comparing the detected nucleic acid sequences to one or more sequences contained in a database of known ssrA genes that includes the gene of the nucleic acid to be detected or by comparing the binding of the nucleic acids in the sample to the binding of one or more known control nucleic acid sequences to the complementary nucleic acid sequence.

2. The method according to claim 1, wherein a fragment of the ssrA gene molecule corresponding to a region of high homology from the 5' end of the ssrA gene is used as a universal target region.

3. The method according to claim 1, wherein a fragment of the ssrA gene molecule corresponding to a region of high homology from the 3' end of ssrA gene is used as a universal target region.

4. The method according to claim 1, wherein a fragment of the ssrA gene molecule corresponding to a region of low homology is used as a target region in a nucleic acid probe assay to distinguish between species.

5. The method according to claim 1, wherein a fragment of the ssrA gene molecule corresponding to a region of low homology is used as a target region for the generation of a genus specific probe.

6. A method of assaying for a prokaryotic or eukaryotic organism which comprises
   contacting the sample with a nucleic acid sequence which is complementary to a target region of a tmRNA, an RNA transcript of the ssrA gene, or a fragment thereof;
   detecting and identifying nucleic acid sequences in the sample that bind to the complementary nucleic acid sequence; and
   correlating the nucleic acid sequences in the sample that bind to the complementary nucleic acid sequence to one or more prokaryotic or eukaryotic organisms by comparing the detected nucleic acid sequences to one or more sequences contained in a database of known ssrA genes that includes the gene of the nucleic acid sequences detected or by comparing the binding of the nucleic acids in the sample to the binding of one or more known control nucleic acid sequences to the complementary nucleic acid sequence.

7. The method according to claim 6, wherein a fragment of a tmRNA molecule corresponding to a region of high homology from the 5' end of the tmRNA is used as a universal target region.

8. The method according to claim 6, wherein a fragment of a tmRNA molecule corresponding to a region of high homology from the 3' end of the tmRNA is used as a universal target region.

9. The method according to claim 6, wherein a fragment of a tmRNA corresponding to a region of low homology is used as a target region in a nucleic acid probe assay to distinguish between species.

10. The method according to claim 6, wherein a fragment of a tmRNA corresponding to a region of low homology is used as a target region for the generation of a genus specific probe.

11. The method according to claim 1 or 6, wherein said complementary nucleic acid sequence is a primer to be used in an amplification procedure.

12. The method according to claim 11, wherein a product of the amplification procedure is used as a target region in a nucleic acid probe assay.

13. The method according to claim 6, wherein a cDNA transcript of a tmRNA molecule is used as a probe in a nucleic acid hybridisation assay.

14. The method according to claim 1 or 6, where the assay is carried out in vitro.

15. The method according to claim 1 or 6, where the assay is carried out in situ.

16. A method of distinguishing between living and dead prokaryotic or eukaryotic organisms with the method of claim 6, further comprising analyzing binding activity of the complementary nucleic acid sequence to target region in the sample wherein a decrease in binding activity indicates a loss of organism viability.

17. The method according to claim 1 or 6, wherein the assay has a multiple probe format for broad scale detection and/or identification of prokaryotic or eukaryotic organisms.

18. The method according to claim 17, wherein an ssrA gene probe or a tmRNA transcript probe is linked to a microarray gene chip system for the broad scale high throughput detection and identification of prokaryotic or eukaryotic organisms.

19. The method according to claim 1 or 6, wherein the complementary nucleic acid is used as a probe or primers in an assay to detect prokaryotic or eukaryotic organisms in a sample of matter.

20. The method according to claim 1 or 6, wherein a fragment of the ssrA gene or the tmRNA transcript is used in an assay to obtain a DNA profile of a prokaryotic or eukaryotic organism and, thereby, distinguish between strains of the same species.

21. A method of designing an agent directed against infectious prokaryotic or eukaryotic organisms for therapeutic purposes which comprises
   identifying an ssrA gene or tmRNA sequence with the assay of claim 1 or claim 6 and designing a therapeutic agent which inhibits the function of the ssrA gene or tmRNA based on the identified sequence.

22. A method of monitoring a drug therapy against infections agents which comprises
comparing the amount or presence of the ssrA gene or fragment thereof, tmRNA, RNA transcript of the ssrA gene, or fragment thereof detected and identified in the assay of claim 1 or claim 6, which is performed prior to administration of the drug therapy to the amount or presence the ssrA gene or fragment thereof, tmRNA, RNA transcript of the ssrA gene, or fragment thereof detected and identified in the assay of claim 1 or claim 6, which is performed after administration of the drug therapy.

23. A method of monitoring the viability and level of health-promoting organisms in the gastrointestinal tract, which comprises
obtaining a sample from the gastrointestinal tract
determining the presence or amount of one or more health-promoting organisms in the sample with the method of claim 1 or claim 6.

24. The method according to claim 1 or 6, which further comprises quantifying the amount of prokaryotic or eukaryotic organisms detected and identified in the sample.

25. The method according to claim 1 or 6, wherein a database of ssrA gene sequences is used to identify a prokaryotic or eukaryotic organism.

26. A method of assaying a sample for a prokaryotic or eukaryotic organism which comprises
contacting the sample with a nucleic acid sequence which is complementary to a target region of an ssrA gene or a fragment thereof;
detecting and identifying nucleic acid sequences in the sample that bind to the complementary nucleic acid sequence; and
correlating the nucleic acid sequences in the sample that bind to the complementary nucleic acid sequence to the presence and/or amount of one or more prokaryotic or eukaryotic organisms,
wherein said sample is selected from the group consisting of food samples, environmental samples, plant samples and animal samples.

27. The assay according to claim 26, wherein said environmental sample is selected from the group consisting of air, water, marine, and soil.

28. The method according to claim 26, wherein said sample is a human or animal sample and is a tissue sample from the respiratory tract, the uro-genital tract, the gastrointestinal tract or is a body fluid sample.

29. The method according to claim 28, wherein the body fluid sample is blood, a blood fraction, sputum or cerebrospinal fluid.

* * * * *